United States Patent
Bhanot et al.

(10) Patent No.: US 8,933,213 B2
(45) Date of Patent: Jan. 13, 2015

(54) ANTISENSE MODULATION OF FIBROBLAST GROWTH FACTOR RECEPTOR 4 EXPRESSION

(71) Applicant: Isis Pharmaceuticals, Inc., Carlsbad, CA (US)

(72) Inventors: Sanjay Bhanot, Carlsbad, CA (US); Xing Xian Yu, Carlsbad, CA (US); Michael L. McCaleb, La Jolla, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 13/631,437

(22) Filed: Sep. 28, 2012

(65) Prior Publication Data
US 2013/0281509 A1    Oct. 24, 2013

Related U.S. Application Data

(63) Continuation of application No. 13/525,197, filed on Jun. 15, 2012, now abandoned.

(60) Provisional application No. 61/497,921, filed on Jun. 16, 2011.

(51) Int. Cl.
| | | |
|---|---|---|
| C07H 21/04 | (2006.01) | |
| A61K 31/711 | (2006.01) | |
| A61K 45/06 | (2006.01) | |
| C12N 15/113 | (2010.01) | |

(52) U.S. Cl.
CPC ............. *C07H 21/04* (2013.01); *A61K 31/711* (2013.01); *A61K 45/06* (2013.01); *C12N 15/1138* (2013.01); *C12N 2310/11* (2013.01); *C12N 2310/315* (2013.01); *C12N 2310/323* (2013.01); *C12N 2310/3231* (2013.01); *C12N 2310/3341* (2013.01); *C12N 2310/341* (2013.01); *C12N 2310/346* (2013.01)
USPC ........................................... 536/24.5; 514/44

(58) Field of Classification Search
CPC combination set(s) only.
See application file for complete search history.

(56) References Cited

U.S. PATENT DOCUMENTS

| | | | |
|---|---|---|---|
| 5,801,154 A | 9/1998 | Baracchini et al. | |
| 6,582,908 B2 | 6/2003 | Fodor et al. | |
| 8,486,904 B2 * | 7/2013 | Bhanot et al. ............... | 514/44 A |
| 2001/0053519 A1 | 12/2001 | Fodor et al. | |
| 2002/0001825 A1 | 1/2002 | Itoh | |
| 2003/0212024 A1 | 11/2003 | Keating et al. | |
| 2003/0228597 A1 | 12/2003 | Cowsert et al. | |
| 2004/0006005 A1 | 1/2004 | Bhanot et al. | |
| 2004/0009154 A1 | 1/2004 | Khan et al. | |
| 2005/0048494 A1 | 3/2005 | Wang | |
| 2005/0053976 A1 | 3/2005 | Baker et al. | |
| 2005/0246794 A1 | 11/2005 | Khvorova et al. | |
| 2007/0248605 A1 | 10/2007 | Hestir et al. | |
| 2010/0143386 A1 | 6/2010 | Ullrich et al. | |
| 2010/0292140 A1 | 11/2010 | Bhanot et al. | |

FOREIGN PATENT DOCUMENTS

| | | |
|---|---|---|
| EP | 0420081 | 4/1991 |
| EP | 1202065 | 5/2002 |
| WO | WO 94/15945 | 7/1994 |
| WO | WO 99/53927 | 10/1999 |
| WO | WO 00/44882 | 8/2000 |
| WO | WO 00/71129 | 11/2000 |
| WO | WO 01/18210 | 3/2001 |
| WO | WO 01/49849 | 7/2001 |
| WO | WO 01/70977 | 9/2001 |
| WO | WO 01/88103 | 11/2001 |
| WO | WO 03/004602 | 1/2003 |
| WO | WO 03/035065 | 5/2003 |
| WO | WO 03/035664 | 5/2003 |
| WO | WO 03/099796 | 12/2003 |
| WO | WO/2004/001059 | 12/2003 |
| WO | WO 2004/003179 | 1/2004 |
| WO | WO 2004/006005 | 1/2004 |
| WO | WO 2004/041277 | 5/2004 |
| WO | WO 2005/037235 | 4/2005 |
| WO | WO 2005/076998 | 8/2005 |
| WO | WO 2005/076999 | 8/2005 |
| WO | WO 2006/044531 | 4/2006 |
| WO | WO 2009/046141 | 4/2009 |

OTHER PUBLICATIONS

Armstrong et al., "Localization of the fibroblast growth factor receptor-4 gene to chromosome region 5q33-qter." Genes Chromosomes Cancer (1992) 4(1):94-98.
Avraham et al., "Mapping of murine fibroblast growth factor receptors refines regions of homology between mouse and human chromosomes." Genomics (1994) 21(3):656-658.
Bange et al., "Cancer progression and tumor cell motility are associated with the FGFR4 Arg(388) allele." Cancer Res. (2002) 62(3):840-847.
Branch et al., "A good antisense molecule is hard to find," TIBS (1998) 23:45-50.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Collins et al., "Mas musculus fibroblast growth factor receptor 4." NCBI GenBank Entry, Sep. 1, 2006 retrieved from the internet URL: <http://www.ncbi.nlm.nih.gov/entrez/viewer.fcgi?val=BC033313> see definition and sequence origin.
Cosic et al., "In vitro inhibition of the actions of basic FGF by a novel 16 amino acid peptide" Mol. Cell Biochem. (1994) 130:1-9.

(Continued)

*Primary Examiner* — Kimberly Chong
(74) *Attorney, Agent, or Firm* — Knobbe, Martens, Olson & Bear LLP

(57) ABSTRACT

Provided herein are methods, compounds, and compositions for reducing expression of fibroblast growth factor receptor 4 (FGFR4) mRNA and protein in an animal. Such methods, compounds, and compositions are useful to treat, prevent, delay, or ameliorate a metabolic disease, or a symptom thereof.

9 Claims, No Drawings

(56) References Cited

OTHER PUBLICATIONS

Crooke et al., "Basic Principles of Antisense Therapeutics" Antisense Research and Application (1998) Chapter 1:1-50.
Dailey et al., "Mechanisms underlying differential responses to FGF signaling." Cytokine Growth Factor Rev. (2005) 16(2):233-247.
Eswarakumar et al., "Cellular signaling by fibroblast growth factor receptors." Cytokine Growth Factor Rev. (2005) 16(2):139-149.
Expert Panel on Detection, Evaluation, and Treatment of High Blood Cholesterol in Adults "Executive Summary of the Third Report of the National Cholesterol Education Program (NCEP) Expert Panel on Detection, Evaluation, and Treatment of High Blood Cholesterol in Adults (Adult Treatment Panel III)" JAMA (2001) 285:2486-2497.
Garcia et al., "Growth Factor Regulation of Uncoupling Protein-1 mRNA Expression in Brown Adipocytes" Am. J. Physiol. Cell Physiol. (2002) 282:C105-C112.
Gautschi et al., "Activity of a novel bcl-2/bcl-xL-bispecific antisense oligonucleotide against tumors of diverse histologic origins." J. Natl. Cancer Inst. (2001) 93(6):463-471.
Holtrich et al., "Two additional protein-tyrosine kinases expressed in human lung: fourth member of the fibroblast growth factor receptor family and an intracellular protein-tyrosine kinase." PNAS (1991) 88(23):10411-10415.
Huang et al., "FGFR4 prevents hyperlipidemia and insulin resistance but underlies high-fat diet induced fatty liver." Diabetes (2007) 56(10):2501-2510.
Hutley et al., "Human adipose tissue endothelial cells promote preadipocyte proliferation." Am. J. Physiol. Endocrinol. Metab. (2001) 281(5):E1037-1044.
Hutley et al., "Fibroblast growth factor 1: a key regulator of human adipogenesis." Diabetes (2004) 53(12):3097-3106.
Jaye et al., "Fibroblast growth factor receptor tyrosine kinases: molecular analysis and signal transduction." Biochim. Biophys. Acta (1992) 1135(2):185-199.
Kawaguchi et al., "De novo adipogenesis in mice at the site of injection of basement membrane and basic fibroblast growth factor" PNAS (1998) 95:1062-1066.
Klagsbrun et al., "A dual receptor system is required for basic fibroblast growth factor activity." Cell (1991) 67(2):229-231.
Kostrzewa et al., "Genomic structure and complete sequence of the human FGFR4 gene." Mammalian Genome (1998) 9(2):131-135.
Krieger-Brauer et al., "Antagonistic effects of different members of the fibroblast and platelet-derived growth factor families on adipose conversion and NADPH-dependent H2O2 generation in 3T2 L1-cells" Biochem. J. (1995) 307:549-556.
Maher et al., "Comparative hybrid arrest by tandem antisense oligodeoxyribonucleotides or oligodeoxyribonucleoside methylphosphonates in a cell-free system." Nuc. Acid. Res. (1988) 16(8):3341-3358.
Mohammadi et al., "Structures of the tyrosine kinase domain of fibroblast growth factor receptor in complex with inhibitors." Science (1997) 276:955-960.

Nawano et al., "Hyperglycemia contributes insulin resistance in hepatic and adipose tissue but not skeletal muscle of ZDF rats." Am. J. Physiol. Endocrinol. Metab. (2000) 278(3):E535-543.
New England Biolabs 1998/99 Catalog (cover page and pp. 121 and 284).
Ozawa et al., "Growth factors and their receptors in pancreatic cancer." Teratog. Carcinog. Mutagen. (2001) 21(1):27-44.
Patel et al., "Essential role of fibroblast growth factor signaling in preadipoctye differentiation." J Clin Endocrinol Metab. (2005) 90(2):1226-1232.
Powers et al., "Fibroblast growth factors, their eceptors and signaling." Endocr. Relat. Cancer (2000) 7(3):165-197.
Prusty et al., "Activation of MEK/ERK Signaling Promotes Adipogenesis by Enhancing Peroxisome Proliferator-activated Receptor y (PPARy) and C/EBPa Gene Expression during the Differentiation of 3T3-L1 Preadipocytes" J. Biol. Chem. (2002) 277(48):46226-46232.
Reynolds et al., "Rational siRNA design for RNA interference" Nature Biotechnology (2004) 22(3):326-330.
Sakaue et al., "Requirement of Fibroblast Growth Factor 10 in Development of White Adipose Tissue" Genes & Development (2002) 16:908-912.
Sanghvi et al., "Heterocyclic Base Modifications in Nucleic Acids and Their Applications in Antisense Oligonucleotides" Antisense Research and Applications (1993) pp. 273-288.
Sindelka et al., "Association of obesity, diabetes, serum lipids and blood pressure regulates insulin action." Physiol. Res. (2002) 51(1):85-91.
Sorisky, "From Preadipocyte to Adipocyte: Differentiation-Directed Signals of Insulin from the Cell Surface to the Nucleus" Critical Reviews in Clinical Laboratory Sciences (1999) 36(1):1-34.
Varzaneh et al., "Extracellular matrix components secreted by microvascular endothelial cells stimulate preadipocyte differentiation in vitro." Metabolism (1994) 43(7):906-912.
Woolf et al., "Specificity of antisense oligonucleotides in vivo." PNAS (1992) 89(16):7305-7309.
Yu et al., "Decreased adiposity and improved insulin selectivity in obese mice after suppression of hepatic and adipose tissue FGFR4 expression" 68th Annual Meeting of the American Diabetes Association (2008) Abstract 1708-P, Retrieved from the Internet: URL: http://professional.diabetes.org/Abstracts_Display.aspx?TYP=1 &CID=70680.
European Search Report for application EP 08835484.0 dated Mar. 9, 2012.
Supplementary Partial European Search Report for application EP 03735152 dated Jul. 6, 2006.
International Search Report for application PCT/AU03/00826 dated Sep. 17, 2003.
International Search Report for application PCT/AU05/000008 dated Feb. 25, 2005.
International Search Report for application PCT/US08/78497 dated Mar. 16, 2009.
International Search Report for application PCT/US12/42813 dated Jan. 16, 2013.

* cited by examiner

ANTISENSE MODULATION OF FIBROBLAST GROWTH FACTOR RECEPTOR 4 EXPRESSION

RELATED APPLICATIONS

This application is a continuation of U.S. patent application Ser. No. 13/525,197, filed Jun. 15, 2012, which claims priority under 35 U.S.C. §119(e) to U.S. Provisional Patent Application No. 61/497,921, filed Jun. 16, 2011, each of which is incorporated herein by reference in its entirety.

SEQUENCE LISTING

The present application is being filed along with a Sequence Listing in electronic format. The Sequence Listing is provided as a file entitled BIOL0157USC1SEQ.txt created Sep. 28, 2012, which is 144 Kb in size. The information in the electronic format of the sequence listing is incorporated herein by reference in its entirety.

FIELD

Provided herein are methods, compounds, and compositions for reducing expression of fibroblast growth factor receptor 4 (FGFR4) mRNA and protein in an animal. Such methods, compounds, and compositions are useful, for example, to treat, prevent, delay or ameliorate diseases associated with metabolic disorders, particularly disorders associated with obesity.

BACKGROUND

Obesity is considered a long-term metabolic disease. There are several serious medical sequelae related to obesity. There are over 1 billion overweight individuals worldwide with 100 million clinically obese. The increasing health care costs of treating obesity related diseases in the US alone are estimated at over $100 billion annually. Current methods for treating obesity include behavioral modification, diet, surgery (gastroplasty), administering pharmaceutical agents that block appetite stimulating signals or absorption of nutrients (fat), and administering agents that increase thermogenesis or fat metabolism. Some of these methods have disadvantages in that they rely on patient resolve, are invasive, or have unwanted side effects. An understanding of the mechanisms by which obesity is regulated may provide important therapeutic information.

Obesity is frequently associated with insulin resistance and together constitutes risk factors for later development of type 2 diabetes and cardiovascular diseases. Insulin resistance occurs well before development of type 2 diabetes, and insulin is overproduced to compensate for the insulin resistance and to maintain normal glucose levels. Type 2 diabetes ensues, as the pancreas can no longer produce enough insulin to maintain normal glucose levels. Early stages of type 2 diabetes are associated with elevated levels of insulin but as the disease progresses the pancreas may fail to produce insulin, resulting in increased blood glucose levels. Diabetes is a significant risk factor for both heart disease and stroke and is the leading cause of blindness and end-stage renal failure.

Diabetes is a disorder characterized by hyperglycemia due to deficient insulin action that may result from reduced insulin production or insulin resistance or both. Diabetes mellitus is a polygenic disorder affecting a significant portion of the people in the world. It is divided into two types. In type I diabetes, or insulin-dependent diabetes mellitus (IDDM), patients produce little or no insulin, the hormone that regulates glucose utilization. In type 2 diabetes, or noninsulin-dependent diabetes mellitus (NIDDM), patients often have plasma insulin levels that are the same compared to nondiabetic humans; however, these patients have developed a resistance to the insulin stimulating effect of glucose and lipid metabolism in the main insulin-sensitive tissues, i.e., muscle, liver and adipose tissues, and the plasma insulin levels are insufficient to overcome the pronounced insulin resistance. Additionally, glucotoxicity, which results from long-term hyperglycemia, induces tissue-dependent insulin resistance (Nawano et al., *Am. J. Physiol. Endocrinol. Metab.*, 278, E535-543) exacerbating the disease. Type 2 diabetes accounts for over 90% of all diabetes cases. It is a metabolic disorder characterized by hyperglycemia leading to secondary complications such as neuropathy, nephropathy, retinopathy, hypertriglyceridemia, obesity, and other cardiovascular diseases generally referred to as metabolic syndrome.

Metabolic syndrome is a combination of medical disorders that increase one's risk for cardiovascular disease and diabetes. The symptoms, including high blood pressure, high triglycerides, decreased HDL and obesity, tend to appear together in some individuals. Metabolic syndrome is known under various other names, such as (metabolic) syndrome X, insulin resistance syndrome or Reaven's syndrome.

Diabetes and obesity (sometimes now collectively referred to as "diabesity") are interrelated in that obesity is known to exacerbate the pathology of diabetes and greater than 60% of diabetics are obese. Most human obesity is associated with insulin resistance and leptin resistance. In fact, it has been suggested that obesity may have an even greater impact on insulin action than diabetes itself (Sindelka et al., *Physiol Res.*, 51, 85-91). Additionally, several compounds on the market for the treatment of diabetes are known to induce weight gain, a very undesirable side effect to the treatment of this disease. Therefore, a compound that has the potential to treat both diabetes and obesity would provide a significant improvement over current treatments.

Fibroblast growth factor receptor 4 (also known as FGF receptor-4, TKF; tyrosine kinase related to fibroblast growth factor receptor; hydroxyaryl-protein kinase; tyrosylprotein kinase; Fgfr4; FGFR-4; FGFR4; CD334, FGFR4_HUMAN and JTK2) has high affinity for the acidic and/or basic fibroblast growth factors. (Armstrong et al., *Genes Chromosomes Cancer*, 4, 94-98).

Although FGFRs generally have been shown to have wide distribution throughout the body, to date, FGFR4 has only been found in a few tissues. Among a wide variety of cells and tissues tested, including human lymphocytes and macrophages, FGFR4 was found to be expressed in the lung and in some tumors of lung origin as well as in malignancies not derived from lung tissues. (Holtrich et al., *Proc. Nat. Acad. Sci.*, 88, 10411-10415). FGFR4 has also been found to be expressed in the liver and in adipose tissues. (Patel et al., *JCEM*, 90(2), 1226-1232). FGFR4 has also been found to be expressed in certain carcinoma cell lines. (Bane et al., *Cancer Res.*, 62, 840-847).

Additionally, FGFR4 has been shown to play a role in systemic lipid and glucose homeostasis. FGFR4-deficient mice on a normal diet exhibited features of metabolic syndrome that include increase mass of insulin resistance, in addition to hypercholesterolemia. FGFR4 deficiency was shown to alleviate high-fat diet-induced fatty liver in a certain obese mouse model, which is also a correlate of metabolic syndrome. Restoration of FGFR4, specifically in hepatocytes of FGFR4 deficient mice, decrease plasma lipid level and restored the high fat diet-induced fatty liver but failed to restore glucose tolerance and sensitivity to insulin. (Huang et al., *Diabetes*, 56, 2501-2510).

Antisense inhibition of FGFR4 provides a unique advantage over traditional small molecule inhibitors in that antisense inhibitors do not rely on competitive binding of the compound to the protein and inhibit activity directly by reducing the expression of FGFR4. A representative United States patent that teaches FGFR4 antisense inhibitors includes U.S. Pat. Publication No. US2010/0292140, of which is herein incorporated by reference in its entirety. Antisense technology is emerging as an effective means for reducing the expression of certain gene products and may therefore prove to be uniquely useful in a number of therapeutic, diagnostic, and research applications for the modulation of FGFR4.

There is a currently a lack of acceptable options for treating metabolic disorders. It is therefore an object herein to provide compounds and methods for the treatment of such diseases and disorder. This invention relates to the discovery of novel, highly potent inhibitors of FGFR4 gene expression.

All documents, or portions of documents, cited in this application, including, but not limited to, patents, patent applications, articles, books, and treatises, are hereby expressly incorporated-by-reference for the portions of the document discussed herein, as well as in their entirety.

SUMMARY

Provided herein are methods, compounds, and compositions for modulating expression of FGFR4 and treating, preventing, delaying or ameliorating diseases associated with metabolic disorders, particularly disorders associated with obesity and/or a symptom thereof.

DETAILED DESCRIPTION

It is to be understood that both the foregoing general description and the following detailed description are exemplary and explanatory only and are not restrictive described herein, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

DEFINITIONS

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques can be used for chemical synthesis, and chemical analysis. Where permitted, all documents, or portions of documents, cited in this application, including, but not limited to, all patents, applications, published applications and other journal publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O($CH_2$)$_2$—$OCH_3$) refers to an O-methoxy-ethyl modification of the 2' position of a furosyl ring. A 2'-O-methoxyethyl modified sugar is a modified sugar.

"2'-O-methoxyethyl nucleotide" means a nucleotide comprising a 2'-O-methoxyethyl modified sugar moiety.

"3' target site" refers to the nucleotide of a target nucleic acid which is complementary to the 3'-most nucleotide of a particular antisense compound.

"5' target site" refers to the nucleotide of a target nucleic acid which is complementary to the 5'-most nucleotide of a particular antisense compound.

"5-methylcytosine" means a cytosine modified with a methyl group attached to the 5' position. A 5-methylcytosine is a modified nucleobase.

"About" means within ±10% of a value. For example, if it is stated, "a marker may be increased by about 50%", it is implied that the marker may be increased between 45%-55%.

"Active pharmaceutical agent" means the substance or substances in a pharmaceutical composition that provide a therapeutic benefit when administered to an individual. For example, in certain embodiments an antisense oligonucleotide targeted to FGFR4 is an active pharmaceutical agent.

"Active target region" or "target region" means a region to which one or more active antisense compounds is targeted. "Active antisense compounds" means antisense compounds that reduce target nucleic acid levels or protein levels.

"Adipogenesis" means the development of fat cells from preadipocytes. "Lipogenesis" means the production or formation of fat, either fatty degeneration or fatty infiltration.

"Adipose tissue" or "body fat" or "fat depot" is loose connective tissue composed of adipocytes. Two types of adipose tissue exist: white adipose tissue (WAT) and brown adipose tissue (BAT).

"Adiposity" or "Obesity" refers to the state of being obese or an excessively high amount of body fat or adipose tissue in relation to lean body mass. The amount of body fat includes concern for both the distribution of fat throughout the body and the size and mass of the adipose tissue deposits. Body fat distribution can be estimated by skin-fold measures, waist-to-hip circumference ratios, or techniques such as ultrasound, computed tomography, or magnetic resonance imaging. According to the Center for Disease Control and Prevention, individuals with a body mass index (BMI) of 30 or more are considered obese. The term "Obesity" as used herein includes conditions where there is an increase in body fat beyond the physical requirement as a result of excess accumulation of adipose tissue in the body. The term "obesity" includes, but is not limited to, the following conditions: adult-onset obesity; alimentary obesity; endogenous or inflammatory obesity; endocrine obesity; familial obesity; hyperinsulinar obesity; hyperplastic-hypertrophic obesity; hypogonadal obesity; hypothyroid obesity; lifelong obesity; morbid obesity and exogenous obesity.

"Administered concomitantly" refers to the co-administration of two agents in any manner in which the pharmacological effects of both are manifest in the patient at the same time.

Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing an agent to an animal, and includes, but is not limited to, administering by a medical professional and self-administering.

"Agent" means an active substance that can provide a therapeutic benefit when administered to an animal. "First Agent" means a therapeutic compound provided herein. For example, a first agent can be an antisense oligonucleotide targeting FGFR4. "Second agent" means a second therapeutic compound described herein (e.g. a second antisense oligonucleotide targeting FGFR4) and/or a non-FGFR4 therapeutic compound.

"Amelioration" refers to a lessening of at least one indicator, sign, or symptom of an associated disease, disorder, or condition. The severity of indicators can be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furosyl ring modified by the bridging of two non-geminal ring atoms. A bicyclic sugar is a modified sugar.

"Bicyclic nucleic acid" or "BNA" refers to a nucleoside or nucleotide wherein the furanose portion of the nucleoside or nucleotide includes a bridge connecting two carbon atoms on the furanose ring, thereby forming a bicyclic ring system.

"Biomarker" is meant to designate a gene or protein or protein fragment which is indicative of the effect of an FGFR4 inhibitor. That means the "biomarker" is used as a detection agent.

"Cap structure" or "terminal cap moiety" means chemical modifications, which have been incorporated at either terminus of an antisense compound.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-β-methoxyethyl modifications.

"Chimeric antisense compound" means an antisense compound that has at least two chemically distinct regions.

"Co-administration" means administration of two or more agents to an individual. The two or more agents can be in a single pharmaceutical composition, or can be in separate pharmaceutical compositions. Each of the two or more agents can be administered through the same or different routes of administration. Co-administration encompasses parallel or sequential administration.

"Cholesterol" is a sterol molecule found in the cell membranes of all animal tissues. Cholesterol must be transported in an animal's blood plasma by lipoproteins including very low density lipoprotein (VLDL), intermediate density lipoprotein (IDL), low density lipoprotein (LDL), and high density lipoprotein (HDL). "Plasma cholesterol" refers to the sum of all lipoproteins (VDL, IDL, LDL, HDL) esterified and/or non-esterified cholesterol present in the plasma or serum.

"Complementarity" means the capacity for pairing between nucleobases of a first nucleic acid and a second nucleic acid.

"cEt" or "constrained ethyl" means a bicyclic sugar moiety comprising a bridge connecting the 4'-carbon and the 2'-carbon, wherein the bridge has the formula: 4'-CH($CH_3$)—O-2'.

"Constrained ethyl nucleoside" (also cEt nucleoside) means a nucleoside comprising a bicyclic sugar moiety comprising a 4'-CH($CH_3$)—O-2' bridge.

"Contiguous nucleobases" means nucleobases immediately adjacent to each other.

"Deoxyribonucleotide" means a nucleotide having a hydrogen at the 2' position of the sugar portion of the nucleotide. Deoxyribonucleotides may be modified with any of a variety of substituents.

"Diabetes mellitus" or "diabetes" is a syndrome characterized by disordered metabolism and abnormally high blood sugar (hyperglycemia) resulting from insufficient levels of insulin or reduced insulin sensitivity. The characteristic symptoms are excessive urine production (polyuria) due to high blood glucose levels, excessive thirst and increased fluid intake (polydipsia) attempting to compensate for increased urination, blurred vision due to high blood glucose effects on the eye's optics, unexplained weight loss, and lethargy.

"Diabetic dyslipidemia" or "type 2 diabetes with dyslipidemia" means a condition characterized by Type 2 diabetes, reduced HDL-C, elevated triglycerides, and elevated small, dense LDL particles.

"Diluent" means an ingredient in a composition that lacks pharmacological activity, but is pharmaceutically necessary or desirable. For example, the diluent in an injected composition can be a liquid, e.g. saline solution.

"Dyslipidemia" refers to a disorder of lipid and/or lipoprotein metabolism, including lipid and/or lipoprotein overproduction or deficiency. Dyslipidemias may be manifested by elevation of lipids such as cholesterol and triglycerides as well as lipoproteins such as low-density lipoprotein (LDL) cholesterol.

"Dosage unit" means a form in which a pharmaceutical agent is provided, e.g. pill, tablet, or other dosage unit known in the art. In certain embodiments, a dosage unit is a vial containing lyophilized antisense oligonucleotide. In certain embodiments, a dosage unit is a vial containing reconstituted antisense oligonucleotide.

"Dose" means a specified quantity of a pharmaceutical agent provided in a single administration, or in a specified time period. In certain embodiments, a dose can be administered in one, two, or more boluses, tablets, or injections. For example, in certain embodiments where subcutaneous administration is desired, the desired dose requires a volume not easily accommodated by a single injection, therefore, two or more injections can be used to achieve the desired dose. In certain embodiments, the pharmaceutical agent is administered by infusion over an extended period of time or continuously. Doses can be stated as the amount of pharmaceutical agent per hour, day, week, or month.

"Effective amount" or "therapeutically effective amount" means the amount of active pharmaceutical agent sufficient to effectuate a desired physiological outcome in an individual in need of the agent. The effective amount can vary among individuals depending on the health and physical condition of the individual to be treated, the taxonomic group of the individuals to be treated, the formulation of the composition, assessment of the individual's medical condition, and other relevant factors.

"Fibroblast growth factor 4" or "FGFR4" means any nucleic acid or protein of FGFR4.

"FGFR4 expression" means the level of mRNA transcribed from the gene encoding FGFR4 or the level of protein translated from the mRNA. FGFR4 expression can be determined by art known methods such as a Northern or Western blot.

"FGFR4 nucleic acid" means any nucleic acid encoding FGFR4. For example, in certain embodiments, a FGFR4 nucleic acid includes a DNA sequence encoding FGFR4, a RNA sequence transcribed from DNA encoding FGFR4 (including genomic DNA comprising introns and exons), and a mRNA sequence encoding FGFR4. "FGFR4 mRNA" means a mRNA encoding a FGFR4 protein.

"Fully complementary" or "100% complementary" means each nucleobase of a nucleobase sequence of a first nucleic acid has a complementary nucleobase in a second nucleobase sequence of a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region can be referred to as a "gap segment" and the external regions can be referred to as "wing segments."

"Gap-widened" means a chimeric antisense compound having a gap segment of 12 or more contiguous 2'-deoxyribonucleosides positioned between and immediately adjacent to 5' and 3' wing segments having from one to six nucleosides.

"Glucose" is a monosaccharide used by cells as a source of energy and inflammatory intermediate. "Plasma glucose" refers to glucose present in the plasma.

"Hybridization" means the annealing of complementary nucleic acid molecules. In certain embodiments, complementary nucleic acid molecules include an antisense compound and a target nucleic acid.

"Hyperlipidemia" or "hyperlipemia" is a condition characterized by elevated serum lipids or circulating (plasma) lipids. This condition manifests an abnormally high concentration of fats. The lipid fractions in the circulating blood are cholesterol, low density lipoproteins, very low density lipoproteins and triglycerides.

"Hypertriglyceridemia" means a condition characterized by elevated triglyceride levels.

"Identifying" or "selecting an animal with metabolic" means identifying or selecting a subject having been diagnosed with a metabolic disease, or a metabolic disorder; or, identifying or selecting a subject having any symptom of a metabolic disease, including, but not limited to, metabolic syndrome, hyperglycemia, hypertriglyceridemia, hypertension increased insulin resistance, decreased insulin sensitivity, above normal body weight, and/or above normal body fat or any combination thereof. Such identification may be accomplished by any method, including but not limited to, standard clinical tests or assessments, such as measuring serum or circulating (plasma) blood-glucose, measuring serum or circulating (plasma) triglycerides, measuring blood-pressure, measuring body fat, measuring body weight, and the like.

"Immediately adjacent" means there are no intervening elements between the immediately adjacent elements.

"Individual" or "subject" or "animal" means a human or non-human animal selected for treatment or therapy.

"Inhibiting the expression or activity" refers to a reduction or blockade of the expression or activity of a RNA or protein and does not necessarily indicate a total elimination of expression or activity.

"Insulin resistance" is defined as the condition in which normal amounts of insulin are inadequate to produce a normal insulin response from fat, muscle and liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often leads to metabolic syndrome and type 2 diabetes.

"Insulin sensitivity" is a measure of how effectively an individual processes glucose. An individual having high insulin sensitivity effectively processes glucose whereas an individual with low insulin sensitivity does not effectively process glucose.

"Internucleoside linkage" refers to the chemical bond between nucleosides.

"Intravenous administration" means administration into a vein.

"Linked nucleosides" means adjacent nucleosides which are bonded together.

"Lipid-lowering therapy" or "lipid lowering agent" means a therapeutic regimen provided to a subject to reduce one or more lipids in a subject. In certain embodiments, a lipid-lowering therapy is provided to reduce one or more of ApoB, total cholesterol, LDL-C, VLDL-C, IDL-C, non-HDL-C, triglycerides, small dense LDL particles, and Lp(a) in a subject. Examples of lipid-lowering therapy include statins, fibrates, and MTP inhibitors.

"Major risk factors" refers to factors that contribute to a high risk for a particular disease or condition. In certain embodiments, major risk factors for coronary heart disease include, without limitation, cigarette smoking, hypertension, low HDL-C, family history of coronary heart disease, age, and other factors disclosed herein.

"Metabolic disease" or "metabolic disorder" refers to a condition characterized by an alteration or disturbance in metabolic function. "Metabolic" and "metabolism" are terms well known in the art and generally include the whole range of biochemical processes that occur within a living organism. Metabolic diseases or disorders include, but are not limited to, obesity, diabetes, hyperglycemia, prediabetes, non-alcoholic fatty liver disease (NAFLD), metabolic syndrome, insulin resistance, diabetic dyslipidemia, or hypertriglyceridemia or a combination thereof.

"Metabolic syndrome" means a condition characterized by a clustering of lipid and non-lipid cardiovascular risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL. These determinants can be readily measured in clinical practice (JAMA, 2001, 285: 2486-2497).

"Mismatch" or "non-complementary nucleobase" refers to the case when a nucleobase of a first nucleic acid is not capable of pairing with the corresponding nucleobase of a second or target nucleic acid.

"Mixed dyslipidemia" means a condition characterized by elevated cholesterol and elevated triglycerides.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleoside" means a nucleoside having, independently, a modified sugar moiety or modified nucleobase.

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising at least one modified nucleotide.

"Modified sugar" refers to a substitution or change from a natural sugar.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Non-alcoholic fatty liver disease" or "NAFLD" means a condition characterized by fatty inflammation of the liver that is not due to excessive alcohol use (for example, alcohol consumption of over 20 g/day). In certain embodiments, NAFLD is related to insulin resistance and the metabolic syndrome. NAFLD encompasses a disease spectrum ranging from simple triglyceride accumulation in hepatocytes (hepatic steatosis) to hepatic steatosis with inflammation (steatohepatitis), fibrosis, and cirrhosis.

"Nonalcoholic steatohepatitis" (NASH) occurs from progression of NAFLD beyond deposition of triglycerides. A "second hit" capable of inducing necrosis, inflammation, and fibrosis is required for development of NASH. Candidates for the second-hit can be grouped into broad categories: factors causing an increase in oxidative stress and factors promoting expression of proinflammatory cytokines "Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA). A nucleic acid can also comprise a combination of these elements in a single molecule.

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics e.g. non furanose sugar units.

"Nucleotide" means a nucleoside having a phosphate group covalently linked to the sugar portion of the nucleoside.

"Nucleotide mimetic" includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage).

"Oligomeric compound" or "oligomer" refers to a polymeric structure comprising two or more sub-structures and capable of hybridizing to a region of a nucleic acid molecule. In certain embodiments, oligomeric compounds are oligonucleosides. In certain embodiments, oligomeric compounds are oligonucleotides. In certain embodiments, oligomeric compounds are antisense compounds. In certain embodiments, oligomeric compounds are antisense oligonucleotides. In certain embodiments, oligomeric compounds are chimeric oligonucleotides.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration. Administration can be continuous, or chronic, or short or intermittent.

"Peptide" means a molecule formed by linking at least two amino acids by amide bonds. Peptide refers to polypeptides and proteins.

"Pharmaceutical agent" means a substance that provides a therapeutic benefit when administered to an individual. For example, in certain embodiments, an antisense oligonucleotide targeted to FGFR4 is pharmaceutical agent.

"Pharmaceutical composition" means a mixture of substances suitable for administering to an individual. For example, a pharmaceutical composition can comprise one or more active agents and a sterile aqueous solution.

"Pharmaceutically acceptable carrier" means a medium or diluent that does not interfere with the structure of the oligonucleotide. Certain, of such carries enable pharmaceutical compositions to be formulated as, for example, tablets, pills, dragees, capsules, liquids, gels, syrups, slurries, suspension and lozenges for the oral ingestion by a subject. For example, a pharmaceutically acceptable carrier can be a sterile aqueous solution.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum can indicate liver toxicity or liver function abnormality. For example, increased bilirubin can indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e. under physiological conditions in the case of in vivo assays and therapeutic treatments.

"Statin" means an agent that inhibits the activity of HMG-CoA reductase.

"Subcutaneous administration" means administration just below the skin.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of an agent that provides a therapeutic benefit to an individual.

"Therapeutic lifestyle change" means dietary and lifestyle changes intended to lower fat/adipose tissue mass and/or cholesterol. Such change can reduce the risk of developing heart disease, and may includes recommendations for dietary intake of total daily calories, total fat, saturated fat, polyunsaturated fat, monounsaturated fat, carbohydrate, protein, cholesterol, insoluble fiber, as well as recommendations for physical activity.

"Triglyceride" or "TG" means a lipid or neutral fat consisting of glycerol combined with three fatty acid molecules.

"Type 2 diabetes," (also known as "type 2 diabetes mellitus" or "diabetes mellitus, type 2", and formerly called "diabetes mellitus type 2", "non-insulin-dependent diabetes (NIDDM)", "obesity related diabetes", or "adult-onset diabetes") is a metabolic disorder that is primarily characterized by insulin resistance, relative insulin deficiency, and hyperglycemia.

"Treat" refers to administering a pharmaceutical composition to an animal to effect an alteration or improvement of a disease, disorder, or condition.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

Certain Embodiments

Certain embodiments provide methods, compounds, and compositions for inhibiting FGFR4 expression.

Certain embodiments provide antisense compounds targeted to a FGFR4 nucleic acid. In certain embodiments, the FGFR4 nucleic acid is any of the sequences set forth in GENBANK Accession No. NM_002011.3 (incorporated herein as SEQ ID NO: 1), GENBANK Accession No: NT_023133.11 truncated from nucleosides 21323018 to 21335213 (incorporated herein as SEQ ID NO: 2); and GENBANK Accession No. AB209631.1 (incorporated herein as SEQ ID NO: 3); and GENBANK Accession No NM_022963.2 (incorporated herein as SEQ ID NO: 4). In certain embodiments, FGFR4 has the rhesus monkey sequence as set forth in GENBANK Accession No. NW_001121000.1 truncated from nucleosides 3094000 to 3109000 (SEQ ID NO: 5). In certain embodiments, FGFR4 has the murine sequence as set forth in GENBANK Accession No. BC033313.1 (SEQ ID NO: 6).

In certain embodiments, the compounds or compositions provided herein comprise a modified oligonucleotide consisting of 12 to 30 nucleosides having a nucleobase sequence complementary to an equal length portion of any of SEQ ID NOs: 1-6.

In certain embodiments, the compounds or compositions provided herein comprise a modified oligonucleotide consisting of 12 to 30 nucleosides having a nucleobase sequence complementary to an equal length portion of any of SEQ ID NOs: 1-4.

In certain embodiments, the compounds or compositions provided herein consist of 12 to 30 linked nucleosides and have a nucleobase sequence comprising at least 8, 9, 10, 11, 12, 13, 14, 15, 16, 17, 18, 19, or 20 contiguous nucleobases of any of SEQ ID NOs: 7-322.

In certain embodiments, the compounds or compositions provided herein can consist of 12 to 30 linked nucleosides and have a nucleobase sequence comprising at least 8, 9, 10, 11, 12, 13, 14, 15, 16, 17, 18, 19, or 20 contiguous nucleobases of any of SEQ ID NOs: 16, 17, 45, 46, 70, 72, or 138.

In certain embodiments, the compound or composition provided herein is or comprises ISIS NOs: 463588, 463589, 463690, 463691, 463835, 463837, or 464225.

In certain embodiments, the compounds or compositions provided herein consist of 12 to 30 linked nucleosides and have a nucleobase sequence comprising at least 8, 9, 10, 11, 12, 13, 14, 15, 16, 17, 18, 19, or 20 contiguous nucleobases of SEQ ID NO: 16.

In certain embodiments, the compounds or compositions provided herein consist of 12 to 30 linked nucleosides and have a nucleobase sequence comprising at least 8, 9, 10, 11, 12, 13, 14, 15, 16, 17, 18, 19, or 20 contiguous nucleobases of SEQ ID NO: 45.

In certain embodiments, the compound or composition is or comprises ISIS NO: 463588.

In certain embodiments, the compound or composition is or comprises ISIS NO: 463690.

In certain embodiments, the compounds or compositions provided herein comprise a modified oligonucleotide consisting of 15 to 30 nucleosides having a nucleobase sequence complementary to an equal length portion of any of SEQ ID NOs: 1-4.

In certain embodiments, the compounds or compositions provided herein consist of 15 to 30 linked nucleosides and have a nucleobase sequence comprising at least 8, 9, 10, 11, 12, 13, 14, 15, 16, 17, 18, 19, or 20 contiguous nucleobases of any of SEQ ID NOs: 7-322.

In certain embodiments, the compounds or compositions provided herein consist of 15 to 30 linked nucleosides and have a nucleobase sequence comprising at least 8, 9, 10, 11, 12, 13, 14, 15, 16, 17, 18, 19, or 20 contiguous nucleobases of any of SEQ ID NOs: 16, 17, 45, 46, 70, 72, or 138.

In certain embodiments, the compound or composition provided herein is or comprises ISIS NOs: 463588, 463589, 463690, 463691, 463835, 463837, or 464225.

In certain embodiments, the compounds or compositions provided herein consist of 15 to 30 linked nucleosides and have a nucleobase sequence comprising at least 8, 9, 10, 11, 12, 13, 14, 15, 16, 17, 18, 19, or 20 contiguous nucleobases of SEQ ID NO: 16.

In certain embodiments, the compounds or compositions provided herein consist of 15 to 30 linked nucleosides and have a nucleobase sequence comprising at least 8, 9, 10, 11, 12, 13, 14, 15, 16, 17, 18, 19, or 20 contiguous nucleobases of SEQ ID NO: 45.

In certain embodiments, the compound or composition provided herein is or comprise ISIS NO: 463588.

In certain embodiments, the compound or composition provided herein is or comprise ISIS NO: 463690.

In certain embodiments, the compounds or compositions provided herein comprise a modified oligonucleotide consisting of 18 to 21 nucleosides having a nucleobase sequence complementary to an equal length portion of any of SEQ ID NOs: 1-4.

In certain embodiments, the compounds or compositions provided herein comprise a modified oligonucleotide consisting of 18 to 21 linked nucleosides and have a nucleobase sequence comprising at least 8, 9, 10, 11, 12, 13, 14, 15, 16, 17, 18, 19, or 20 contiguous nucleobases of any of SEQ ID NOs: 7-322.

In certain embodiments, the compounds or compositions provided herein comprise a modified oligonucleotide consisting of 18 to 21 linked nucleosides and have a nucleobase sequence comprising at least 8, 9, 10, 11, 12, 13, 14, 15, 16, 17, 18, 19, or 20 contiguous nucleobases of any of SEQ ID NOs: 16, 17, 45, 46, 70, 72, or 138

In certain embodiments, the compounds or compositions provided herein comprise a modified oligonucleotide consisting of 18 to 21 linked nucleosides and have a nucleobase sequence comprising at least 8, 9, 10, 11, 12, 13, 14, 15, 16, 17, 18, 19, or 20 contiguous nucleobases of SEQ ID NO: 16.

In certain embodiments, the compounds or compositions provided herein comprise a modified oligonucleotide consisting of 18 to 21 linked nucleosides and have a nucleobase sequence comprising at least 8, 9, 10, 11, 12, 13, 14, 15, 16, 17, 18, 19, or 20 contiguous nucleobases of SEQ ID NO: 45.

In certain embodiments, the compounds or compositions provided herein comprise a modified oligonucleotide consisting of 20 to 35 nucleosides having a nucleobase sequence complementary to an equal length portion of any of SEQ ID NOs: 1-4.

In certain embodiments, the compounds or compositions provided herein comprise a modified oligonucleotide consisting of 20 to 35 linked nucleosides and have a nucleobase sequence comprising at least 8, 9, 10, 11, 12, 13, 14, 15, 16, 17, 18, 19, or 20 contiguous nucleobases of SEQ ID NOs: 7-322.

In certain embodiments, the compounds or compositions provided herein comprise a modified oligonucleotide consisting of 20 to 35 linked nucleosides and have a nucleobase sequence comprising at least 8, 9, 10, 11, 12, 13, 14, 15, 16, 17, 18, 19, or 20 contiguous nucleobases of SEQ ID NOs: 16, 17, 45, 46, 70, 72, or 138.

In certain embodiments, the compounds or compositions provided herein can consist of 20 to 35 linked nucleosides and have a nucleobase sequence comprising at least 8, 9, 10, 11, 12, 13, 14, 15, 16, 17, 18, 19, or 20 contiguous nucleobases of SEQ ID NO: 16.

In certain embodiments, the compounds or compositions provided herein can consist of 20 to 35 linked nucleosides and have a nucleobase sequence comprising at least 8, 9, 10, 11, 12, 13, 14, 15, 16, 17, 18, 19, or 20 contiguous nucleobases of SEQ ID NO: 45.

In certain embodiments, the compounds or compositions provided herein comprise a modified oligonucleotide consisting of 20 to 30 nucleosides having a nucleobase sequence complementary to an equal length portion of any of SEQ ID NOs: 1-4.

In certain embodiments, the compounds or compositions provided herein comprise a modified oligonucleotide consisting of 20 to 30 linked nucleosides and have a nucleobase sequence comprising at least 8, 9, 10, 11, 12, 13, 14, 15, 16, 17, 18, 19, or 20 contiguous nucleobases of SEQ ID NOs: 7-322.

In certain embodiments, the compounds or compositions provided herein comprise a modified oligonucleotide consisting of 20 to 30 linked nucleosides and have a nucleobase sequence comprising at least 8, 9, 10, 11, 12, 13, 14, 15, 16, 17, 18, 19, or 20 contiguous nucleobases of SEQ ID NOs: 16, 17, 45, 46, 70, 72, or 138.

In certain embodiments, the compounds or compositions provided herein comprise a modified oligonucleotide consisting of 20 to 30 linked nucleosides and have a nucleobase sequence comprising at least 8, 9, 10, 11, 12, 13, 14, 15, 16, 17, 18, 19, or 20 contiguous nucleobases of SEQ ID NO: 16.

In certain embodiments, the compounds or compositions provided herein comprise a modified oligonucleotide consisting of 20 to 30 linked nucleosides and have a nucleobase sequence comprising at least 8, 9, 10, 11, 12, 13, 14, 15, 16, 17, 18, 19, or 20 contiguous nucleobases of SEQ ID NO: 45.

In certain embodiments, the compounds or compositions provided herein comprise a modified oligonucleotide consisting of 20 to 25 nucleosides having a nucleobase sequence complementary to an equal length portion of any of SEQ ID NOs: 1-4.

In certain embodiments, the compounds or compositions provided herein comprise a modified oligonucleotide consisting of 20 to 25 linked nucleosides and have a nucleobase sequence comprising at least 8, 9, 10, 11, 12, 13, 14, 15, 16, 17, 18, 19, or 20 contiguous nucleobases of SEQ ID NOs: 7-322.

In certain embodiments, the compounds or compositions provided herein comprise a modified oligonucleotide consisting of 20 to 25 linked nucleosides and have a nucleobase sequence comprising at least 8, 9, 10, 11, 12, 13, 14, 15, 16, 17, 18, 19, or 20 contiguous nucleobases of SEQ ID NO: 16, 17, 45, 46, 70, 72, or 138.

In certain embodiments, the compounds or compositions provided herein comprise a modified oligonucleotide consisting of 20 to 25 linked nucleosides and have a nucleobase sequence comprising at least 8, 9, 10, 11, 12, 13, 14, 15, 16, 17, 18, 19, or 20 contiguous nucleobases of SEQ ID NO: 16.

In certain embodiments, the compounds or compositions provided herein comprise a modified oligonucleotide consisting of 20 to 25 linked nucleosides and have a nucleobase sequence comprising at least 8, 9, 10, 11, 12, 13, 14, 15, 16, 17, 18, 19, or 20 contiguous nucleobases of SEQ ID NO: 45.

In certain embodiments, the compounds or compositions described herein comprise a modified oligonucleotide consisting of 20 to 24 nucleosides having a nucleobase sequence complementary to an equal length portion of any of SEQ ID NOs: 1-4.

In certain embodiments, the compounds or compositions provided herein comprise a modified oligonucleotide consisting of 20 to 24 linked nucleosides and have a nucleobase sequence comprising at least 8, 9, 10, 11, 12, 13, 14, 15, 16, 17, 18, 19, or 20 contiguous nucleobases of SEQ ID NOs: 7-322.

In certain embodiments, the compounds or compositions provided herein comprise a modified oligonucleotide consisting of 20 to 24 linked nucleosides and have a nucleobase sequence comprising at least 8, 9, 10, 11, 12, 13, 14, 15, 16, 17, 18, 19, or 20 contiguous nucleobases of SEQ ID NO: 16, 17, 45, 46, 70, 72, or 138.

In certain embodiments, the compounds or compositions provided herein comprise a modified oligonucleotide consisting of 20 to 24 linked nucleosides and have a nucleobase sequence comprising at least 8, 9, 10, 11, 12, 13, 14, 15, 16, 17, 18, 19, or 20 contiguous nucleobases of SEQ ID NO: 16.

In certain embodiments, the compounds or compositions provided herein comprise a modified oligonucleotide consisting of 20 to 24 linked nucleosides and have a nucleobase sequence comprising at least 8, 9, 10, 11, 12, 13, 14, 15, 16, 17, 18, 19, or 20 contiguous nucleobases of SEQ ID NO: 45.

In certain embodiments, the compounds or compositions provided herein comprise a modified oligonucleotide consisting of 20 to 23 nucleosides having a nucleobase sequence complementary to an equal length portion of any of SEQ ID NOs: 1-4.

In certain embodiments, the compounds or compositions provided herein comprise a modified oligonucleotide consisting of 20 to 23 linked nucleosides and have a nucleobase sequence comprising at least 8, 9, 10, 11, 12, 13, 14, 15, 16, 17, 18, 19, or 20 contiguous nucleobases of SEQ ID NOs: 7-322.

In certain embodiments, the compounds or compositions provided herein comprise a modified oligonucleotide consisting of 20 to 23 linked nucleosides and have a nucleobase sequence comprising at least 8, 9, 10, 11, 12, 13, 14, 15, 16, 17, 18, 19, or 20 contiguous nucleobases of SEQ ID NO: 16, 17, 45, 46, 70, 72, or 138.

In certain embodiments, the compounds or compositions provided herein comprise a modified oligonucleotide consisting of 20 to 23 linked nucleosides and have a nucleobase sequence comprising at least 8, 9, 10, 11, 12, 13, 14, 15, 16, 17, 18, 19, or 20 contiguous nucleobases of SEQ ID NO: 16.

In certain embodiments, the compounds or compositions provided herein comprise a modified oligonucleotide consisting of 20 to 23 linked nucleosides and have a nucleobase sequence comprising at least 8, 9, 10, 11, 12, 13, 14, 15, 16, 17, 18, 19, or 20 contiguous nucleobases of SEQ ID NO: 45.

In certain embodiments, the compounds or compositions provided herein comprise a modified oligonucleotide consisting of 20 to 22 nucleosides having a nucleobase sequence complementary to an equal length portion of any of SEQ ID NOs: 1-4.

In certain embodiments, the compounds or compositions provided herein comprise a modified oligonucleotide consisting of 20 to 22 linked nucleosides and have a nucleobase sequence comprising at least 8, 9, 10, 11, 12, 13, 14, 15, 16, 17, 18, 19, or 20 contiguous nucleobases of SEQ ID NOs: 7-322.

In certain embodiments, the compounds or compositions provided herein comprise a modified oligonucleotide consisting of 20 to 22 linked nucleosides and have a nucleobase sequence comprising at least 8, 9, 10, 11, 12, 13, 14, 15, 16, 17, 18, 19, or 20 contiguous nucleobases of SEQ ID NO: 16, 17, 45, 46, 70, 72, or 138.

In certain embodiments, the compounds or compositions provided herein comprise a modified oligonucleotide consisting of 20 to 22 linked nucleosides and have a nucleobase sequence comprising at least 8, 9, 10, 11, 12, 13, 14, 15, 16, 17, 18, 19, or 20 contiguous nucleobases of SEQ ID NO: 16.

In certain embodiments, the compounds or compositions provided herein comprise a modified oligonucleotide consisting of 20 to 22 linked nucleosides and have a nucleobase sequence comprising at least 8, 9, 10, 11, 12, 13, 14, 15, 16, 17, 18, 19, or 20 contiguous nucleobases of SEQ ID NO: 45.

In certain embodiments, the compounds or compositions provided herein comprise a modified oligonucleotide consisting of 20 to 21 nucleosides having a nucleobase sequence complementary to an equal length portion of any of SEQ ID NOs: 1-4.

In certain embodiments, the compounds or compositions provided herein comprise a modified oligonucleotide consisting of 20 to 21 linked nucleosides and having a nucleobase sequence complementary to an equal length portion of any of SEQ ID NOs: 1-4.

In certain embodiments, the compounds or compositions provided herein comprise a modified oligonucleotide consisting of 20 to 21 linked nucleosides and have a nucleobase sequence comprising at least 8, 9, 10, 11, 12, 13, 14, 15, 16, 17, 18, 19, or 20 contiguous nucleobases of SEQ ID NOs: 7-322.

In certain embodiments, the compounds or compositions provided herein comprise a modified oligonucleotide consisting of 20 to 21 linked nucleosides and have a nucleobase sequence comprising at least 8, 9, 10, 11, 12, 13, 14, 15, 16, 17, 18, 19, or 20 contiguous nucleobases of SEQ ID NO: 16, 17, 45, 46, 70, 72, or 138.

In certain embodiments, the compounds or compositions provided herein comprise a modified oligonucleotide consisting of 20 to 21 linked nucleosides and have a nucleobase sequence comprising at least 8, 9, 10, 11, 12, 13, 14, 15, 16, 17, 18, 19, or 20 contiguous nucleobases of SEQ ID NO: 16.

In certain embodiments, the compounds or compositions provided herein comprise a modified oligonucleotide consisting of 20 to 21 linked nucleosides and have a nucleobase sequence comprising at least 8, 9, 10, 11, 12, 13, 14, 15, 16, 17, 18, 19, or 20 contiguous nucleobases of SEQ ID NO: 45.

In certain embodiments, the compounds or compositions provided herein comprise a modified oligonucleotide consisting of 20 nucleosides having a nucleobase sequence complementary to an equal length portion of any of SEQ ID NOs: 1-4.

In certain embodiments, the compounds or compositions provided herein comprise a modified oligonucleotide consisting of 20 linked nucleosides and have a nucleobase sequence comprising at least 8, 9, 10, 11, 12, 13, 14, 15, 16, 17, 18, 19, or 20 contiguous nucleobases of SEQ ID NOs: 7-322.

In certain embodiments, the compounds or compositions provided herein comprise a modified oligonucleotide consisting of 20 linked nucleosides and have a nucleobase sequence comprising at least 8, 9, 10, 11, 12, 13, 14, 15, 16, 17, 18, 19, or 20 contiguous nucleobases of SEQ ID NO: 16, 17, 45, 46, 70, 72, or 138.

In certain embodiments, the compounds or compositions provided herein comprise a modified oligonucleotide consisting of 20 linked nucleosides and have a nucleobase sequence comprising at least 8, 9, 10, 11, 12, 13, 14, 15, 16, 17, 18, 19, or 20 contiguous nucleobases of SEQ ID NO: 16.

In certain embodiments, the compounds or compositions provided herein comprise a modified oligonucleotide consisting of 20 linked nucleosides and have a nucleobase sequence comprising at least 8, 9, 10, 11, 12, 13, 14, 15, 16, 17, 18, 19, or 20 contiguous nucleobases of SEQ ID NO: 45.

In certain embodiments, the compounds or compositions provided herein comprise a salt of the modified oligonucleotide.

In certain embodiments, the compounds or compositions provided herein further comprise a pharmaceutically acceptable carrier or diluent.

In certain embodiments, the nucleobase sequence of the modified oligonucleotide is at least 70%, 75%, 80%, 85%, 90%, 95%, 96%, 97%, 98%, 99% or 100% complementary to any one of SEQ ID NOs: 1-4 as measured over the entirety of the modified oligonucleotide.

In certain embodiments, the nucleobase sequence of the modified oligonucleotide has at least 70%, 75%, 80%, 85%, 90%, 95%, 96%, 97%, 98%, 99% or 100% identity to any one of SEQ ID NOs: 7-322 as measured over the entirety of the modified oligonucleotide.

In certain embodiments, the nucleobase sequence of the modified oligonucleotide has at least 70%, 75%, 80%, 85%, 90%, 95%, 96%, 97%, 98%, 99% or 100% identity to any one of SEQ ID NOs: 16, 17, 45, 46, 70, 72, or 138 as measured over the entirety of the modified oligonucleotide.

In certain embodiments, the nucleobase sequence of the modified oligonucleotide has at least 70%, 75%, 80%, 85%, 90%, 95%, 96%, 97%, 98%, 99% or 100% identity to SEQ ID NO: 16 as measured over the entirety of the modified oligonucleotide.

In certain embodiments, the nucleobase sequence of the modified oligonucleotide has at least 70%, 75%, 80%, 85%, 90%, 95%, 96%, 97%, 98%, 99% or 100% identity to SEQ ID NO: 45 as measured over the entirety of the modified oligonucleotide.

In certain embodiments, antisense compounds or modified oligonucleotides targets a region of a FGFR4 nucleic acid. In certain embodiments, such compounds or oligonucleotides targeted to a region of a FGFR4 nucleic acid have a contiguous nucleobase portion that is complementary to an equal length nucleobase portion of the region. For example, the portion can be at least an 8, 9, 10, 11, 12, 13, 14, 15, 16, 17, 18, 19 or 20 contiguous nucleobases portion complementary to an equal length portion of a region recited herein. In certain embodiments, such compounds or oligonucleotide target the following nucleotide regions of SEQ ID NO: 1: 160-179, 191-210, 191-211, 191-212, 191-213, 192-211, 192-212, 192-213, 193-212, 193-213, 194-213, 196-215, 196-216, 197-216, 200-219, 202-221, 202-222, 203-222, 290-310, 290-309, 290-311, 290-312, 290-312, 291-310, 291-311, 291-312, 292-311, 292-312, 293-312, 309-328, 332-351, 338-357, 338-358, 339-358, 347-366, 349-368, 357-376, 368-387, 368-388, 368-389, 368-390, 368-391, 369-380, 369-389, 369-390, 369-391, 370-389, 370-390, 370-391, 371-390, 371-391, 372-391, 388-407, 388-408, 389-408, 392-411, 404-423, 431-450, 431-451, 432-451, 443-462, 443-463, 444-463, 601-620, 624-643, 734-753, 757-806, 787-807, 788-807, 790-809, 790-810, 791-810, 970-989, 1024-1043, 1024-1044, 1024-1045, 1024-1046, 1024-1047, 1024-1048, 1024-1105, 1025-1044, 1025-1045, 1025-1046, 1025-1047, 1025-1048, 1026-1045, 1026-1046, 1026-1047, 1026-1048, 1027-1046, 1027-1047, 1027-1048, 1028-1047, 1028-1048, 1029-1048, 1031-1050, 1031-1051, 1032-1051, 1084-1103, 1084-1105, 1086-1105, 1097-1116, 1097-1117, 1097-1122, 1100-1119, 1100-1120, 1100-1121, 1100-1122, 1101-1120, 1101-1121, 1101-1122, 1102-1121, 1102-1122, 1103-1122, 1105-1124, 1105-1125, 1106-1125, 1110-1029, 1110-1130, 1111-1130, 1115-1134, 1185-1204, 1255-1274, 1290-1309, 1290-1310, 1291-1310, 1301-1320, 1417-1436, 1468-1487, 1468-1488, 1469-1488, 1559-1578, 1562-1581, 1564-1583, 1619-1638, 2325-2344, 2325-2345, 2326-2345, 2438-2457, 2812-2831, 2816-2835, 2816-2836, 2816-2837, 2816-2838, 2817-2836, 2817-2837, 2817-2838, 2818-2837, 2818-2838, 2819-2838, 2822-2481, 2822-2842, 2822-2843, 2822-2844, 2823-2842, 2823-2843, 2823-2844, 2824-2843, 2824-2844, 2825-2844, 2951-2970, 2951-2971, 2951-2972, 2951-2973, 2951-2974, 2951-2975, 2951-3000, 2952-2971, 2952-2972, 2952-2973, 2952-2974, 2952-2975, 2953-2972, 2953-2973, 2953-2974, 2953-2975, 2954-2973, 2954-2974, 2954-2975, 2955-2974, 2955-2975, 2956-2975.

In certain embodiments, antisense compounds or modified oligonucleotides targets a region of a FGFR4 nucleic acid. In certain embodiments, such compounds or oligonucleotides targeted to a region of a FGFR4 nucleic acid have a contiguous nucleobase portion that is complementary to an equal length nucleobase portion of the region. For example, the portion can be at least an 8, 9, 10, 11, 12, 13, 14, 15, 16, 17, 18, 19 or 20 contiguous nucleobases portion complementary to an equal length portion of a region recited herein. In certain embodiments, such compounds or oligonucleotide target the following nucleotide regions of SEQ ID NO: 2: 3165-3184, 3196-3215, 3197-3216, 3196-3217, 3196-3218, 3197-3216, 3197-3217, 3197-3218, 3198-3217, 3198-3218, 3199-3218, 3201-3220, 3201-3221, 3202-3221, 3205-3224, 3207-3226, 3207-3227, 3208-3227, 3991-4011, 3991-4010, 3991-4012, 3991-4013, 3992-4011, 3992-4012, 3992-4013, 3993-4012, 3993-4013, 3994-4013, 4010-4029, 4033-4052, 4039-4058, 4039-4059, 4040-4059, 4048-4067, 4050-4069, 4058-4077, 4069-4088, 4069-4089, 4069-4091, 4069-4091, 4069-4092, 4070-4091, 4070-4090, 4070-4091, 4070-4092, 4071-4090, 4071-4091, 4071-4092, 4072-4091, 4072-4092, 4073-4092, 4089-4108, 4089-4109, 4090-4109, 4093-4112, 4105-4124, 4132-4151, 4132-4152, 4133-4152, 4144-4163, 4144-4164, 4145-4164, 4506-4522, 4528-4547, 4638-4657, 5268-5290, 5271-5291, 5272-5291, 5274-5293, 5274-5294, 5275-5294, 5966-5985, 6020-6039, 6020-6040, 6020-6041, 6020-6042, 6020-6043, 6020-6044, 6020-6235, 6021-6040, 6021-6041, 6021-6042, 6021-6043, 6021-6044, 6022-6041, 6022-6042, 6022-6043, 6022-6044, 6023-6042, 6023-6043, 6023-6044, 6024-6043, 6024-6044, 6025-6044, 6027-6046, 6027-6047, 6028-6047, 6214-6235, 6214-6233, 6214-6235, 6216-6235, 6227-6246, 6227-6247, 6227-6252, 6230-6249, 6230-6250, 6230-6251, 6230-6252, 6231-6250, 6231-6251, 6231-6252, 6232-6251, 6232-6252, 6233-6252, 6235-6254, 6235-6255, 6236-6255, 6241-6260, 6245-6264, 6315-6334, 6784-6803, 6974-6993, 7025-7044, 7025-7045, 7026-7045, 7059-7081, 7221-7240, 7223-7242, 7278-7297, 10866-10885, 10866-10866, 10867-10886, 11108-11127, 11482-11501, 11486-11505, 11486-11506, 11486-11507, 11486-11508, 11487-11506, 11487-11507, 11487-11508, 11488-11507, 11488-11508, 11489-11508, 11492-11511, 11492-11512, 11492-11513, 11492-1151, 11493-11512, 11493-11513, 11493-11514, 11494-11513, 11494-11514, 11495-11514, 11621-11640, 11621-11641, 11621-11642, 11621-11643, 11621-11644, 11621-11645, 11621-11670, 11622-11641, 11622-

11642, 11622-11643, 11622-11644, 11622-11645, 11623-11642, 11623-11643, 11623-11644, 11623-11645, 11624-11643, 11624-11644, 11624-11645, 11625-11644, 11625-11645, 11626-11645.

Certain embodiments provide compounds comprising a modified oligonucleotide consisting of 20 linked nucleosides wherein the linked nucleosides comprise at least an 8 contiguous nucleobase portion that is complementary to an equal length nucleobase portion within the region selected from nucleotides 191-210 or 369-388 of SEQ ID NO: 1. In certain embodiments, the modified oligonucleotide has at least a 9, at least a 10, at least an 11, at least a 12, at least a 13, at least a 14, at least a 15, at least a 16, at least a 17, at least an 18, at least 19 or at least a 20 contiguous nucleobase portion of which is complementary to an equal length portion within the region selected from nucleotides 191-210 or 369-388 of SEQ ID NO: 1. In certain embodiments, the modified oligonucleotide is 90%, 95%, 99%, or 100% complementary to a nucleic acid encoding human FGFR4, eg. SEQ ID No: 1.

Certain embodiments provide compounds comprising a modified oligonucleotide consisting of 20 linked nucleosides wherein the linked nucleosides comprise at least an 8 contiguous nucleobase portion that is complementary to an equal length nucleobase portion within the region selected from nucleotides 3196-3215 or 4070-4089 of SEQ ID NO: 2. In certain embodiments, the modified oligonucleotide has at least a 9, at least a 10, at least an 11, at least a 12, at least a 13, at least a 14, at least a 15, at least a 16, at least a 17, at least an 18, at least 19 or at least a 20 contiguous nucleobase portion of which is complementary to an equal length portion within the region selected from nucleotides 3196-3215 or 4070-4089 of SEQ ID NO: 2. In certain embodiments, the modified oligonucleotide is 90%, 95%, 99%, or 100% complementary to a nucleic acid encoding human FGFR4, eg. SEQ ID No: 2.

Certain embodiments provide compounds comprising a modified oligonucleotide consisting of 20 linked nucleosides 60% complementary within the region selected from nucleotides 191-210, 193-212, 369-388, 370-389, 788-807, 790-809 and 2954-2973 of SEQ ID NO: 1.

Certain embodiments provide compounds comprising a modified oligonucleotide consisting of 20 linked nucleosides 60% complementary within the region selected from nucleotides 3196-3215, 3198-3217, 4070-4089, 4071-4090, 5272-5291, 5274-5293, and 11624-11643 of SEQ ID NO: 2.

Certain embodiments provide compounds comprising a modified oligonucleotide consisting of 20 linked nucleosides 70% complementary within the region selected from nucleotides 191-210, 193-212, 369-388, 370-389, 188-807, 790-809 and 2954-2973 of SEQ ID NO: 1.

Certain embodiments provide compounds comprising a modified oligonucleotide consisting of 20 linked nucleosides 70% complementary within the region selected from nucleotides 3196-3215, 3198-3217, 4070-4089, 4071-4090, 5272-5291, 5274-5293, and 11624-11643 of SEQ ID NO: 2.

Certain embodiments provide compounds comprising a modified oligonucleotide consisting of 20 linked nucleosides 80% complementary within the region selected from nucleotides 191-210, 193-212, 369-388, 370-389, 188-807, 790-809 and 2954-2973 of SEQ ID NO: 1.

Certain embodiments provide compounds comprising a modified oligonucleotide consisting of 20 linked nucleosides 80% complementary within the region selected from nucleotides 3196-3215, 3198-3217, 4070-4089, 4071-4090, 5272-5291, 5274-5293, and 11624-11643 of SEQ ID NO: 2.

Certain embodiments provide compounds comprising a modified oligonucleotide consisting of 20 linked nucleosides 90% complementary within the region selected from nucleotides 191-210, 193-212, 369-388, 370-389, 188-807, 790-809 and 2954-2973 of SEQ ID NO: 1.

Certain embodiments provide compounds comprising a modified oligonucleotide consisting of 20 linked nucleosides 90% complementary within the region selected from nucleotides 3196-3215, 3198-3217, 4070-4089, 4071-4090, 5272-5291, 5274-5293, and 11624-11643 of SEQ ID NO: 2.

Certain embodiments provide compounds comprising a modified oligonucleotide consisting of 20 linked nucleosides 95% complementary within the region selected from nucleotides 191-210, 193-212, 369-388, 370-389, 188-807, 790-809 and 2954-2973 of SEQ ID NO: 1.

Certain embodiments provide compounds comprising a modified oligonucleotide consisting of 20 linked nucleosides 95% complementary within the region selected from nucleotides 3196-3215, 3198-3217, 4070-4089, 4071-4090, 5272-5291, 5274-5293, and 11624-11643 of SEQ ID NO: 2.

Certain embodiments provide compounds comprising a modified oligonucleotide consisting of 20 linked nucleosides 99% complementary within the region selected from nucleotides 191-210, 193-212, 369-388, 370-389, 188-807, 790-809 and 2954-2973 of SEQ ID NO: 1.

Certain embodiments provide compounds comprising a modified oligonucleotide consisting of 20 linked nucleosides 99% complementary within the region selected from nucleotides 3196-3215, 3198-3217, 4070-4089, 4071-4090, 5272-5291, 5274-5293, and 11624-11643 of SEQ ID NO: 2.

Certain embodiments provide compounds comprising a modified oligonucleotide consisting of 20 linked nucleosides 100% complementary within the region selected from nucleotides 191-210, 193-212, 369-388, 370-389, 188-807, 790-809 and 2954-2973 of SEQ ID NO: 1.

Certain embodiments provide compounds comprising a modified oligonucleotide consisting of 20 linked nucleosides 100% complementary within the region selected from nucleotides 3196-3215, 3198-3217, 4070-4089, 4071-4090, 5272-5291, 5274-5293, and 11624-11643 of SEQ ID NO: 2.

Certain embodiments provide compounds comprising a modified oligonucleotide consisting of 20 linked nucleosides 60% complementary within nucleotides 191-210 of SEQ ID NO: 1.

Certain embodiments provide compounds comprising a modified oligonucleotide consisting of 20 linked nucleosides 60% complementary within the region selected from nucleotides 3196-3215 of SEQ ID NO: 2.

Certain embodiments provide compounds comprising a modified oligonucleotide consisting of 20 linked nucleosides 70% complementary within nucleotides 191-210 of SEQ ID NO: 1.

Certain embodiments provide compounds comprising a modified oligonucleotide consisting of 20 linked nucleosides 70% complementary within the region selected from nucleotides 3196-3215 of SEQ ID NO: 2.

Certain embodiments provide compounds comprising a modified oligonucleotide consisting of 20 linked nucleosides 80% complementary within nucleotides 191-210 of SEQ ID NO: 1.

Certain embodiments provide compounds comprising a modified oligonucleotide consisting of 20 linked nucleosides 80% complementary within the region selected from nucleotides 3196-3215 of SEQ ID NO: 2.

Certain embodiments provide compounds comprising a modified oligonucleotide consisting of 20 linked nucleosides 90% complementary within nucleotides 191-210 of SEQ ID NO: 1.

Certain embodiments provide compounds comprising a modified oligonucleotide consisting of 20 linked nucleosides 90% complementary within the region selected from nucleotides 3196-3215 of SEQ ID NO: 2.

Certain embodiments provide compounds comprising a modified oligonucleotide consisting of 20 linked nucleosides 95% complementary within nucleotides 191-210 of SEQ ID NO: 1.

Certain embodiments provide compounds comprising a modified oligonucleotide consisting of 20 linked nucleosides 95% complementary within the region selected from nucleotides 3196-3215 of SEQ ID NO: 2.

Certain embodiments provide compounds comprising a modified oligonucleotide consisting of 20 linked nucleosides 99% complementary within nucleotides 191-210 of SEQ ID NO: 1.

Certain embodiments provide compounds comprising a modified oligonucleotide consisting of 20 linked nucleosides 99% complementary within the region selected from nucleotides 3196-3215 of SEQ ID NO: 2.

Certain embodiments provide compounds comprising a modified oligonucleotide consisting of 20 linked nucleosides 100% complementary within nucleotides 191-210 of SEQ ID NO: 1.

Certain embodiments provide compounds comprising a modified oligonucleotide consisting of 20 linked nucleosides 100% complementary within the region selected from nucleotides 3196-3215 of SEQ ID NO: 2.

Certain embodiments provide compounds comprising a modified oligonucleotide consisting of 20 linked nucleosides 60% complementary within nucleotides 369-388 of SEQ ID NO: 1.

Certain embodiments provide compounds comprising a modified oligonucleotide consisting of 20 linked nucleosides 60% complementary within nucleotides 4070-4089 of SEQ ID NO: 2.

Certain embodiments provide compounds comprising a modified oligonucleotide consisting of 20 linked nucleosides 70% complementary within nucleotides 369-388 of SEQ ID NO: 1.

Certain embodiments provide compounds comprising a modified oligonucleotide consisting of 20 linked nucleosides 70% complementary within nucleotides 4070-4089 of SEQ ID NO: 2.

Certain embodiments provide compounds comprising a modified oligonucleotide consisting of 20 linked nucleosides 80% complementary within nucleotides 369-388 of SEQ ID NO: 1.

Certain embodiments provide compounds comprising a modified oligonucleotide consisting of 20 linked nucleosides 80% complementary within nucleotides 4070-4089 of SEQ ID NO: 2.

Certain embodiments provide compounds comprising a modified oligonucleotide consisting of 20 linked nucleosides 90% complementary within nucleotides 369-388 of SEQ ID NO: 1.

Certain embodiments provide compounds comprising a modified oligonucleotide consisting of 20 linked nucleosides 90% complementary within nucleotides 4070-4089 of SEQ ID NO: 2.

Certain embodiments provide compounds comprising a modified oligonucleotide consisting of 20 linked nucleosides 95% complementary within nucleotides 369-388 of SEQ ID NO: 1.

Certain embodiments provide compounds comprising a modified oligonucleotide consisting of 20 linked nucleosides 95% complementary within nucleotides 4070-4089 of SEQ ID NO: 2.

Certain embodiments provide compounds comprising a modified oligonucleotide consisting of 20 linked nucleosides 99% complementary within nucleotides 369-388 of SEQ ID NO: 1.

Certain embodiments provide compounds comprising a modified oligonucleotide consisting of 20 linked nucleosides 99% complementary within nucleotides 4070-4089 of SEQ ID NO: 2.

Certain embodiments provide compounds comprising a modified oligonucleotide consisting of 20 linked nucleosides 100% complementary within nucleotides 369-388 of SEQ ID NO: 1.

Certain embodiments provide compounds comprising a modified oligonucleotide consisting of 20 linked nucleosides 99% complementary within nucleotides 4070-4089 of SEQ ID NO: 2.

In certain embodiments, such compounds or oligonucleotides targeted to a region of a FGFR4 nucleic acid have a contiguous nucleobase portion that is complementary to an equal length nucleobase portion of the region 191-210 or 369-388 of SEQ ID NO: 1.

In certain embodiments, such compounds or oligonucleotides targeted to a region of a FGFR4 nucleic acid have a contiguous nucleobase portion that is complementary to an equal length nucleobase portion of the region 3196-3215 or 4070-4089 of SEQ ID NO: 2.

In certain embodiments, the following nucleotide regions of SEQ ID NO: 1, when targeted by antisense compounds or oligonucleotides, displays at least 65% inhibition: 160-179, 191-210, 191-211, 191-212, 191-213, 192-211, 192-212, 192-213, 193-212, 193-213, 194-213, 196-215, 196-216, 197-216, 200-219, 202-221, 202-222, 203-222, 290-210, 290-309, 290-311, 290-312, 290-312, 291-310, 291-311, 291-312, 292-311, 292-312, 293-312, 309-328, 332-351, 338-357, 338-358, 339-358, 347-366, 349-368, 357-376, 368-387, 368-388, 368-389, 368-390, 368-391, 369-380, 369-389, 369-390, 369-391, 370-389, 370-390, 370-391, 371-390, 371-391, 372-391, 388-407, 388-408, 389-408, 392-411, 404-423, 431-450, 431-451, 432-451, 443-462, 443-463, 444-463, 601-620, 624-643, 734-753, 767-806, 787-807, 788-807, 790-809, 790-810, 791-810, 970-989, 1024-1043, 1024-1044, 1024-1045, 1024-1046, 1024-1047, 1024-1048, 1024-1105, 1025-1044, 1025-1045, 1025-1046, 1025-1047, 1025-1048, 1026-1045, 1026-1046, 1026-1047, 1026-1048, 1027-1046, 1027-1047, 1027-1048, 1028-1047, 1028-1048, 1029-1048, 1031-1050, 1031-1051, 1032-1051, 1074-1051, 1084-1103, 1084-1105, 1086-1105, 1097-1116, 1097-1117, 1097-1122, 1100-1119, 1100-1119, 1100-1120, 1100-1121, 1100-1122, 1101-1120, 1101-1121, 1101-1122, 1102-1121, 1102-1122, 1103-1122, 1105-1124, 1105-1125, 1106-1125, 1110-1029, 1110-1130, 1111-1130, 1115-1134, 1185-1204, 1255-1274, 1290-1309, 1290-1310, 1291-1310, 1301-1320, 1417-1436, 1468-1487, 1468-1488, 1469-1488, 1559-1578, 1562-1581, 1564-1583, 1619-1638, 2325-2344, 2325-2345, 2326-2345, 2438-2457, 2812-2831, 2816-2835, 2816-2836, 2816-2837, 2816-2838, 2817-2836, 2817-2837, 2817-2838, 2818-2837, 2818-2838, 2819-2838, 2822-2481, 2822-2842, 2822-2843, 2822-2844, 2822-2844, 2823-2842, 2823-2843, 2823-2844, 2824-2843, 2824-2844, 2825-2844, 2951-2970, 2951-2971, 2951-2972, 2951-2973, 2951-2974, 2951-2975, 2951-2975, 2951-3000, 2952-2971, 2952-2972, 2952-2973, 2952-2974, 2952-2975, 2953-2972, 2953-2973, 2953-2974, 2953-2975, 2954-2973, 2954-2974, 2954-2975, 2955-2974, 2955-2975, and 2956-2975.

In certain embodiments, the following nucleotide regions of SEQ ID NO: 2, when targeted by antisense compounds or oligonucleotides, displays at least 65% inhibition: 3165-

3184, 3196-3215, 3196-3216, 3196-3217, 3196-3218, 3197-3216, 3197-3217, 3197-3218, 3198-3217, 3198-3218, 3199-3218, 3201-3220, 3201-3221, 3202-3221, 3205-3224, 3207-3226, 3207-3227, 3208-3227, 3991-4011, 3991-4010, 3991-4012, 3991-4013, 3991-4014, 3992-4011, 3992-4012, 3992-4013, 3993-4012, 3993-4013, 3994-4013, 4010-4029, 4033-4052, 4039-4058, 4039-4059, 4040-4059, 4048-4067, 4050-4069, 4058-4077, 4069-4088, 4069-4089, 4069-4090, 4069-4091, 4069-4092, 4070-380, 4070-4090, 4070-4091, 4070-4092, 4071-4090, 4071-4091, 4071-4092, 4072-4091, 4072-4092, 4073-4092, 4089-4108, 4089-4109, 4090-4109, 4093-4112, 4105-4124, 4132-4151, 4132-4152, 4133-4152, 4144-4163, 4144-4164, 4145-4164, 4506-4522, 4528-4547, 4638-4657, 5268-5290, 5271-5291, 5272-5291, 5274-5293, 5274-5294, 5275-5294, 5966-5985, 6020-6039, 6020-6040, 6020-6041, 6020-6042, 6020-6043, 6020-6044, 6020-6045, 6021-6040, 6021-6041, 6021-6042, 6021-6043, 6021-6044, 6022-6041, 6022-6042, 6022-6043, 6022-6044, 6023-6042, 6023-6043, 6023-6047, 6024-6043, 6024-6044, 6025-6044, 6027-6046, 6027-6047, 6028-6047, 6214-6235, 6214-6233, 6214-6235, 6216-6235, 6227-6246, 6227-6247, 6227-6252, 6230-6249, 6230-6249, 6230-6250, 6230-6251, 6230-6252, 6231-6250, 6231-6251, 6231-6252, 6232-6251, 6232-6252, 6233-6252, 6235-6254, 6235-6255, 6236-6255, 6230-6260, 6241-6260, 6245-6264, 6315-6334, 6784-6803, 6974-6993, 7025-7044, 7025-7045, 7026-7045, 7221-7240, 7223-7242, 7278-7297, 10866-10885, 10866-10886, 10867-10886, 11008-11127, 11482-11501, 11486-11505, 11486-11506, 11486-11507, 11486-11508, 11487-11506, 11487-11507, 11487-11508, 11488-11507, 11488-11508, 11489-11508, 11492-11511, 11492-11512, 11492-11513, 11492-11514, 11493-11512, 11493-11513, 11493-11514, 11494-11513, 11494-11514, 11495-11514, 11621-11640, 11621-11641, 11621-11642, 11621-11643, 11621-11644, 11621-11645, 11621-11670, 11622-11641, 11622-11642, 11622-11643, 11622-11644, 11622-11645, 11623-11642, 11623-11643, 11623-11644, 11623-1645, 11624-11643, 11624-11644, 11624-11645, 11625-11644, 11625-11645, and 11626-11645.

In certain embodiments, the nucleobase sequences recited in the following SEQ ID NOs of SEQ ID NO: 1, when targeted by antisense compounds or oligonucleotides, displays at least 65% inhibition: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 59, 61, 62, 64, 65, 66, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, and 116.

In certain embodiments, the nucleobase sequences recited in the following SEQ ID NOs of SEQ ID NO: 1, when targeted by antisense compounds or oligonucleotides, displays at least 70% inhibition: 7, 14, 15, 16, 17, 18, 19, 20, 22, 23, 24, 27, 28, 29, 30, 32, 33, 34, 35, 38, 39, 43, 44, 45, 46, 47, 48, 49, 50, 51, 54, 59, 61, 64, 69, 70, 72, 73, 75, 77, 78, 79, 80, 81, 82, 83, 85, 86, 87, 89, 90, 91, 92, 94, 97, 98, 103, 105, 106, 111, 112, 113, and 116.

In certain embodiments, the nucleobase sequences recited in the following SEQ ID NOs of SEQ ID NO: 1, when targeted by antisense compounds or oligonucleotides, displays at least 75% inhibition: 7, 14, 16, 17, 22, 24, 28, 29, 30, 32, 33, 34, 39, 43, 44, 45, 46, 47, 49, 50, 59, 61, 69, 70, 72, 73, 75, 77, 78, 79, 80, 83, 85, 89, 90, 91, 92, 105, 106, 111, and 112.

In certain embodiments, the nucleobase sequences recited in the following SEQ ID NOs of SEQ ID NO: 1, when targeted by antisense compounds or oligonucleotides, displays at least 80% inhibition: 7, 14, 16, 17, 28, 29, 33, 39, 45, 47, 49, 50, 72, 80, 90, 91, and 106.

In certain embodiments, the nucleobase sequences recited in the following SEQ ID NOs of SEQ ID NO: 1, when targeted by antisense compounds or oligonucleotides, displays at least 85% inhibition 7, 14, 16, 29, 45, 50, 80, 90, and 91.

In certain embodiments, the following nucleotide regions of SEQ ID NOs: 1 or 2, when targeted by antisense compounds or oligonucleotides, displays at least 65% inhibition: 908-927, 992-1011, 1138-1157, 1138-1161, 1142-1161, 1345-1364, 1386-1405, 1386-1413, 1394-1413, 1461-1480, 1461-1482, 1461-1484, 1461-1486, 1461-1490, 1463-1482, 1463-1484, 1463-1486, 1463-1490, 1465-1484, 1465-1486, 1465-1490, 1467-1486, 1467-1490, 1471-1490, 1542-1561, 1941-1960, 1941-1962, 1941-1964, 1943-1962, 1943-1964, 1945-1964, 2053-2072, 2104-2123, 2104-2125, 2104-2127, 2104-2129, 2104-2131, 2104-2133, 2104-2135, 2104-2137, 2106-2125, 2106-2127, 2106-2129, 2106-2131, 2106-2133, 2106-2135, 2106-2137, 2108-2127, 2108-2129, 2108-2131, 2108-2133, 2108-2135, 2108-2137, 2110-2129, 2110-2131, 2110-2133, 2110-2135, 2110-2137, 2112-2131, 2112-2133, 2112-2135, 2112-2137, 2114-2133, 2114-2135, 2114-2137, 2116-2135, 2116-2137, 2118-2137, 2271-2290, 2838-2857, 3122-3141, 3122-3144, 3125-3144, 3165-3184, 3325-3344, 3325-3346, 3325-3348, 3325-3350, 3325-3352, 3325-3354, 3325-3356, 3325-3358, 3325-3360, 3325-3362, 3325-3362, 3327-3346, 3327-3346, 3327-3348, 3327-3350, 3327-3352, 3327-3354, 3327-3356, 3327-3358, 3327-3360, 3327-3362, 3329-3348, 3329-3348, 3329-3350, 3329-3352, 3329-3354, 3329-3356, 3329-3358, 3329-3360, 3329-3362, 3331-3350, 3331-3352, 3331-3354, 3331-3356, 3331-3358, 3331-3360, 3331-3362, 3333-3352, 3333-3354, 3333-3356, 3333-3358, 3333-3360, 3333-3362, 3335-3354, 3335-3356, 3335-3358, 3335-3360, 3335-3362, 3337-3356, 3337-3358, 3337-3360, 3337-3362, 3339-3358, 3339-3360, 3339-3362, 3341-3360, 3341-3362, 3343-3362, 3386-3405, 3386-3413, 3386-3417, 3386-3419, 3386-3423, 3386-3427, 3386-3434, 3386-3434, 3394-3413, 3394-3417, 3394-3423, 3394-3427, 3394-3434, 3398-3417, 3398-3419, 3398-3423, 3398-3427, 3398-3434, 3400-3419, 3400-3423, 3400-3427, 3400-3434, 3404-3423, 3404-3427, 3404-3434, 3408-3427, 3408-3434, 3415-3434, 3445-3464, 3445-3466, 3445-3468, 3445-3470, 3447-3466, 3447-3468, 3447-3470, 3449-3468, 3449-3470, 3451-3470, 3499-3518, 3571-3590, 3571-3592, 3571-3594, 3571-3596, 3571-3598, 3573-3592, 3573-3594, 3573-3596, 3573-3598, 3575-3594, 3575-3596, 3575-3598, 3577-3596, 3577-3598, 3579-3598, 3772-3791, 3772-3793, 3772-3795, 3772-3797, 3772-3801, 3772-3807, 3772-3817, 3774-3793, 3774-3795, 3774-3797, 3776-3795, 3776-3797, 3778-3797, 3782-3801, 3782-3817, 3788-3807, 3788-3817, 3798-3817, 3993-4012, 4799-4818, 7684-7703, 7690-7709, 7692-7711.

In certain embodiments, the nucleobase sequences recited in the following SEQ ID NOs of SEQ ID NOs: 1 or 2, when targeted by antisense compounds or oligonucleotides, displays at least 65% inhibition: 29, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, and 235.

In certain embodiments, the nucleobase sequences recited in the following SEQ ID NOs of SEQ ID NOs: 1 or 2, when targeted by antisense compounds or oligonucleotides, displays at least 70% inhibition: 29, 117, 119, 120, 122, 126, 127, 128, 129, 130, 131, 132, 133, 134, 135, 136, 137, 138, 139, 140, 141, 142, 145, 146, 147, 150, 151, 152, 153, 154, 155, 156, 157, 158, 160, 161, 162, 163, 164, 165, 166, 167, 169, 170, 171, 174, 180, 183, 184, 185, 186, 187, 188, 189, 190, 193, 195, 198, 199, 200, 201, 202, 203, 206, 207, 208, 209, 210, 211, 213, 214, 215, 216, 217, 218, 219, 220, 221, 222, 223, 225, 226, 227, 228, 229, 231, 233, 234, and 235.

In certain embodiments, the nucleobase sequences recited in the following SEQ ID NOs of SEQ ID NOs: 1 or 2, when targeted by antisense compounds or oligonucleotides, displays at least 75% inhibition: 29, 117, 120, 128, 129, 131, 132, 133, 135, 136, 137, 138, 139, 140, 141, 146, 152, 153, 154, 155, 156, 160, 161, 162, 163, 164, 165, 166, 167, 169, 174, 180, 186, 187, 188, 198, 199, 201, 202, 207, 208, 209, 213, 214, 215, 216, 217, 219, 220, 221, 223, 225, 227, 228, 229, 231, 233, and 235.

In certain embodiments, the nucleobase sequences recited in the following SEQ ID NOs of SEQ ID NOs: 1 or 2, when targeted by antisense compounds or oligonucleotides, displays at least 80% inhibition: 29, 117, 131, 132, 133, 135, 136, 137, 138, 140, 141, 152, 153, 154, 155, 156, 160, 162, 163, 164, 174, 186, 187, 188, 199, 201, 202, 207, 208, 213, 214, 215, 216, 217, 219, 220, 221, 223, 227, 229, 231, and 233.

In certain embodiments, the nucleobase sequences recited in the following SEQ ID NOs of SEQ ID NOs: 1 or 2, when targeted by antisense compounds or oligonucleotides, displays at least 85% inhibition: 29, 117, 132, 135, 136, 140, 141, 154, 156, 163, 164, 187, 188, 199, 201, 215, 216, 217, 219, 220, 221, 223, 227, 229, 231, and 233.

In certain embodiments, the following nucleotide regions of SEQ ID NOs: 1 or 2 or 3, when targeted by antisense compounds or oligonucleotides, displays at least 65% inhibition: 101-120, 101-122, 101-124, 101-125, 101-126, 101-127, 102-126, 103-122, 103-124, 103-125, 103-126, 103-127, 105-124, 105-125, 105-127, 106-125, 106-126, 106-127, 107-126, 107-127, 108-127, 1122-1141, 1165-1184, 1193-1218, 1198-1217, 1199-1218, 1323-1342, 1323-1344, 1323-1346, 1323-1347, 1323-1352, 1325-1344, 1325-1346, 1325-1347, 1327-1346, 1327-1347, 1328-1347, 1333-1352, 1333-1354, 1333-1354, 1333-1356, 1333-1358, 1333-1360, 1335-1354, 1335-1356, 1335-1358, 1335-1360, 1337-1356, 1337-1358, 1337-1360, 1339-1358, 1339-1360, 1341-1360, 1392-1411, 1392-1417, 1393-1412, 1394-1413, 1394-1415, 1394-1417, 1396-1415, 1396-1417, 1398-1417, 1413-1432, 1413-1433, 1413-1434, 1414-1433, 1414-1434, 1415-1434, 1445-1464, 1445-1466, 1445-1468, 1445-1470, 1445-1471, 1447-1466, 1447-1468, 1447-1470, 1447-1471, 1449-1468, 1449-1470, 1449-1471, 1451-1470, 1451-1471, 1452-1471, 1462-1481, 1462-1481, 1462-1482, 1462-1483, 1462-1484, 1462-1485, 1462-1487, 1463-1482, 1463-1482, 1463-1483, 1463-1484, 1463-1485, 1463-1487, 1464-1483, 1464-1484, 1464-1485, 1464-1487, 1465-1484, 1465-1485, 1465-1487, 1466-1485, 1466-1487, 1468-1487, 1501-1521, 1501-1522, 1503-1522, 1569-1588, 1569-1589, 1569-1590, 1569-1591, 1569-1592, 1569-1593, 1569-1594, 1569-1596, 1569-1598, 1570-1589, 1570-1590, 1570-1591, 1570-1592, 1570-1593, 1570-1594, 1570-1596, 1570-1598, 1571-1590, 1571-1591, 1571-1591, 1571-1592, 1571-1593, 1571-1593, 1571-1594, 1571-1594, 1571-1596, 1571-1596, 1571-1598, 1571-1598, 1572-1591, 1572-1592, 1572-1593, 1572-1594, 1572-1596, 1572-1598, 1573-1592, 1573-1593, 1573-1594, 1573-1596, 1573-1598, 1574-1593, 1574-1594, 1574-1596, 1574-1598, 1575-1594, 1575-1596, 1575-1598, 1577-1596, 1577-1598, 1579-1598, 1778-1797, 1778-1799, 1778-1805, 1778-1809, 1778-1811, 1778-1821, 1780-1799, 1786-1805, 1790-1809, 1790-1811, 1790-1821, 1792-1811, 1792-1821, 1802-1821, 1944-1963, 1996-2015, 2053-2072, 2074-2093, 2418-2437, 4988-5007, 5120-5139, 5121-5140, 5121-5146, 5122-5141, 5122-5142, 5122-5143, 5122-5144, 5122-5146, 5123-5142, 5123-5143, 5123-5144, 5123-5146, 5124-5143, 5124-5144, 5124-5144, 5124-5146, 5125-5146, 5127-5146, 5150-5169, 5150-5170, 5150-5171, 5151-5170, 5151-5171, 5152-5171, 7801-7820, 7801-7822, 7803-7822.

In certain embodiments, the nucleobase sequences recited in the following SEQ ID NOs of SEQ ID NOs: 1 or 2 or 3, when targeted by antisense compounds or oligonucleotides, displays at least 65% inhibition: 29, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, and 322.

In certain embodiments, the nucleobase sequences recited in the following SEQ ID NOs of SEQ ID NOs: 1 or 2 or 3, when targeted by antisense compounds or oligonucleotides, displays at least 70% inhibition: 29, 239, 240, 241, 242, 243, 244, 245, 247, 249, 250, 251, 252, 253, 254, 255, 256, 257, 258, 259, 260, 261, 262, 263, 264, 265, 266, 268, 269, 270, 271, 272, 274, 275, 276, 277, 278, 279, 280, 282, 283, 284, 285, 286, 287, 288, 289, 290, 291, 294, 295, 296, 297, 298, 299, 300, 301, 304, 305, 306, 307, 308, 309, 310, 311, 312, 313, 314, 315, 317, 319, 320, and 322.

In certain embodiments, the nucleobase sequences recited in the following SEQ ID NOs of SEQ ID NOs: 1 or 2 or 3, when targeted by antisense compounds or oligonucleotides, displays at least 75% inhibition: 29, 239, 240, 241, 242, 243, 244, 245, 247, 250, 251, 252, 253, 254, 255, 256, 257, 258, 259, 260, 261, 262, 264, 266, 269, 271, 272, 274, 275, 276, 277, 278, 279, 283, 284, 286, 287, 288, 291, 298, 299, 300, 305, 306, 307, 308, 309, 310, 312, 313, 315, 317, 319, and 320.

In certain embodiments, the nucleobase sequences recited in the following SEQ ID NOs of SEQ ID NOs: 1 or 2 or 3, when targeted by antisense compounds or oligonucleotides, displays at least 80% inhibition: 29, 241, 242, 243, 244, 245, 247, 250, 253, 254, 255, 256, 259, 260, 261, 262, 264, 266, 271, 272, 274, 276, 278, 283, 284, 286, 287, 299, 300, 305, 306, 307, 308, 310, 312, 313, 317, and 320.

In certain embodiments, the nucleobase sequences recited in the following SEQ ID NOs of SEQ ID NOs: 1 or 2 or 3, when targeted by antisense compounds or oligonucleotides, displays at least 85% inhibition: 29, 241, 242, 243, 244, 247, 254, 256, 259, 260, 264, 272, 278, 299, 300, 305, 306, 307, 308, 310, 317, and 320.

In certain embodiments, the following antisense compounds target a region of SEQ ID NO: 1, a nucleic acid encoding human FGFR4, and demonstrate at least 65% inhibition of a FGFR4 mRNA: ISIS NOs: 299005, 299010, 299018, 299022, 299024, 299025, 299028, 299029, 299030, 463588, 463589, 463590, 463592, 463593, 463594, 463596, 463598, 463599, 463601, 463625, 463627, 463628, 463629, 463630, 463636, 463645, 463648, 463654, 463655, 463656, 463657, 463670, 463672, 463673, 463677, 463678, 463679, 463689, 463690, 463691, 463692, 463693, 463708, 463709, 463712, 463717, 463718, 463724, 463733, 463734, 463735, 463751, 463763, 463770, 463774, 463791, 463805, 463832, 463834, 463835, 463836, 463837, 463838, 463860, 463861, 463871, 463874, 463875, 463876, 463877, 463878, 463880, 463882, 463883, 463884, 463893, 463894, 463906, 463907, 463908, 463909, 463910, 463912, 463913, 463918, 463919, 463922, 463937, 463938, 463947, 463967, 463994, 464002, 464004, 464013, 464014, 464015, 464030, 464033, 464037, 464038, 464041, 464043, 464046, 464048, and 464049.

In certain embodiments, the following antisense compounds target a region of SEQ ID NO: 1, a nucleic acid encoding human FGFR4 and demonstrate at least 70% inhibition of a FGFR4 mRNA: ISIS NOs: 299005, 299029, 299030, 463588, 463589, 463590, 463592, 463593, 463596, 463598, 463599, 463627, 463628, 463629, 463630, 463645, 463648, 463654, 463655, 463670, 463672, 463679, 463689, 463690, 463691, 463692, 463693, 463708, 463709, 463712, 463724, 463751, 463763, 463774, 463834, 463835, 463837, 463838, 463861, 463874, 463875, 463876, 463877, 463878, 463880, 463882, 463884, 463893, 463894, 463907, 463908, 463909, 463910, 463913, 463922, 463937, 464002, 464013, 464014, 464038, 464041, 464043, and 464049.

In certain embodiments, the following antisense compounds target a region of SEQ ID NO: 1, a nucleic acid encoding human FGFR4 and demonstrate at least 75% inhibition of a FGFR4 mRNA: ISIS NOs: 299005, 299029, 463588, 463589, 463596, 463599, 463628, 463629, 463630, 463645, 463648, 463654, 463672, 463679, 463689, 463690, 463691, 463692, 463708, 463709, 463751, 463763, 463834, 463835, 463837, 463838, 463861, 463874, 463875, 463876, 463877, 463882, 463884, 463907, 463908, 463909, 463910, 464013, 464014, 464038, and 464041.

In certain embodiments, the following antisense compounds target a region of SEQ ID NO: 1, a nucleic acid encoding human FGFR4 and demonstrate at least 80% inhibition of a FGFR4 mRNA: ISIS NOs: 299005, 299029, 463588, 463589, 463628, 463629, 463648, 463672, 463690, 463692, 463708, 463709, 463837, 463877, 463908, 463909, and 464014.

In certain embodiments, the following antisense compounds target a region of SEQ ID NO: 1, a nucleic acid encoding human FGFR4 and demonstrate at least 85% inhibition of a FGFR4 mRNA: ISIS NOs: 299005, 299029, 463588, 463629, 463690, 463709, 463877, 463908, and 463909.

In certain embodiments, the following antisense compounds target a region of SEQ ID NOs:1 or 2, a nucleic acid encoding human FGFR4, and demonstrate at least 65% inhibition of a FGFR4 mRNA: ISIS NOs: 463629, 299004, 464138, 464139, 464167, 464168, 464170, 464173, 299055, 464181, 464203, 464207, 464208, 464209, 464210, 464213, 464214, 464215, 464216, 464222, 464223, 464224, 464225, 464226, 464227, 464228, 464238, 464239, 464254, 464258, 464266, 464268, 464269, 464270, 464278, 464280, 464284, 464285, 464286, 464287, 464288, 464290, 464291, 464292, 464298, 464299, 464300, 464308, 464309, 464310, 464311, 464333, 464342, 464425, 464428, 464429, 464430, 464433, 464449, 464453, 464568, 464569, 464575, 464576, 464579, 464581, 464582, 464584, 464585, 464586, 464587, 464588, 464589, 464590, 464591, 464593, 464617, 464622, 464623, 464657, 464658, 464677, 464682, 464683, 464684, 464685, 464686, 464687, 464688, 464689, 464692, 464696, 464698, 464699, 464701, 464703, 464705, 464706, 464707, 464708, 464709, 464710, 464711, 464716, 464717, 464718, 464719, 464720, 464726, 464727, 464728, 464729, 464730, 464732, 464734, 464735, 464736, 464740, 464800, and 464801.

In certain embodiments, the following antisense compounds target a region of SEQ ID NOs: 1 or 2, a nucleic acid encoding human FGFR4 and demonstrate at least 70% inhibition of a FGFR4 mRNA: ISIS NOs: 463629, 299004, 464138, 464139, 464168, 464203, 464207, 464208, 464209, 464210, 464213, 464214, 464215, 464216, 464222, 464223, 464224, 464225, 464226, 464227, 464228, 464238, 464258, 464266, 464268, 464278, 464280, 464284, 464285, 464286, 464287, 464288, 464290, 464291, 464298, 464299, 464300, 464308, 464309, 464310, 464311, 464333, 464425, 464428, 464429, 464449, 464579, 464584, 464585, 464586, 464587, 464588, 464589, 464590, 464591, 464622, 464657, 464682, 464683, 464684, 464685, 464686, 464687, 464692, 464696, 464698, 464699, 464701, 464703, 464706, 464707, 464708, 464709, 464710, 464711, 464716, 464717, 464718, 464719, 464720, 464727, 464728, 464729, 464730, 464732, 464735, 464740, 464800, and 464801.

In certain embodiments, the following antisense compounds target a region of SEQ ID NOs: 1 or 2, a nucleic acid encoding human FGFR4 and demonstrate at least 75% inhibition of a FGFR4 mRNA: ISIS NOs: 463629, 299004, 464139, 464208, 464209, 464213, 464214, 464215, 464222, 464223, 464224, 464225, 464226, 464227, 464228, 464266, 464284, 464285, 464286, 464287, 464288, 464298, 464299, 464300, 464308, 464309, 464310, 464311, 464333, 464425, 464449, 464579, 464587, 464588, 464589, 464682, 464683, 464685, 464686, 464696, 464698, 464699, 464706, 464707, 464708, 464709, 464710, 464716, 464717, 464718, 464720, 464727, 464729, 464730, 464732, 464735, 464740, and 464801.

In certain embodiments, the following antisense compounds target a region of SEQ ID NOs: 1 or 2, a nucleic acid encoding human FGFR4 and demonstrate at least 80% inhibition of a FGFR4 mRNA: ISIS NOs: 463629, 299004, 464213, 464214, 464215, 464222, 464223, 464224, 464225, 464227, 464228, 464284, 464285, 464286, 464287, 464288, 464298, 464300, 464308, 464309, 464449, 464587, 464588, 464589, 464683, 464685, 464686, 464696, 464698, 464706, 464707, 464708, 464709, 464710, 464716, 464717, 464718, 464720, 464729, 464732, 464735, and 464740.

In certain embodiments, the following antisense compounds target a region of SEQ ID NOs: 1 or 2, a nucleic acid encoding human FGFR4 and demonstrate at least 85% inhibition of a FGFR4 mRNA: ISIS NOs: 463629, 299004, 464214, 464222, 464223, 464227, 464228, 464286, 464288, 464308, 464309, 464588, 464589, 464683, 464685, 464708, 464709, 464710, 464716, 464717, 464718, 464720, 464729, 464732, 464735, and 464740.

In certain embodiments, the following antisense compounds target a region of SEQ ID NOs:1 or 2 or 3, a nucleic acid encoding human FGFR4, and demonstrate at least 65% inhibition of a FGFR4 mRNA: ISIS NOs: 463629, 479530, 479532, 479533, 479534, 479535, 479536, 479537, 479538, 479539, 479540, 479541, 479542, 479543, 479544, 479545, 479546, 479547, 479548, 479549, 479550, 479551, 479552, 479553, 479554, 479555, 479556, 479557, 479558, 479560, 479561, 479562, 479564, 479565, 479566, 479567, 479568, 479569, 479570, 479572, 479573, 479574, 479576, 479577, 479582, 479583, 479584, 479585, 479594, 479596, 479597, 479608, 479613, 479614, 479622, 479625, 479626, 479641, 479682, 479689, 479690, 479691, 479692, 479693, 479694, 479696, 479697, 479698, 479699, 479703, 479704, 479705, 479706, 479716, 479721, 479722, 479725, 479731, 479732, 479736, 479737, 479738, 479739, 479740, and 479741.

In certain embodiments, the following antisense compounds target a region of SEQ ID NOs: 1 or 2 or 3, a nucleic acid encoding human FGFR4 and demonstrate at least 70% inhibition of a FGFR4 mRNA: ISIS NOs: 463629, 479530, 479532, 479533, 479534, 479535, 479536, 479537, 479539, 479541, 479542, 479543, 479544, 479545, 479546, 479547, 479548, 479549, 479550, 479551, 479552, 479553, 479554, 479555, 479556, 479557, 479558, 479561, 479562, 479564, 479565, 479566, 479568, 479569, 479570, 479572, 479573, 479574, 479576, 479582, 479583, 479584, 479585, 479594, 479596, 479597, 479608, 479613, 479614, 479626, 479641, 479682, 479689, 479690, 479691, 479692, 479693, 479697, 479698, 479699, 479703, 479704, 479705, 479706, 479716, 479721, 479722, 479725, 479731, 479736, 479738, 479739, and 479741.

In certain embodiments, the following antisense compounds target a region of SEQ ID NOs: 1 or 2 or 3, a nucleic acid encoding human FGFR4 and demonstrate at least 75% inhibition of a FGFR4 mRNA: ISIS NOs: 463629, 479530, 479532, 479533, 479534, 479535, 479536, 479537, 479539, 479542, 479543, 479544, 479545, 479546, 479547, 479548, 479549, 479550, 479551, 479552, 479553, 479554, 479556, 479558, 479562, 479565, 479566, 479568, 479569, 479570, 479572, 479573, 479574, 479583, 479584, 479594, 479596, 479597, 479614, 479690, 479691, 479692, 479698, 479699, 479703, 479704, 479705, 479706, 479721, 479722, 479731, 479736, 479738, and 479739.

In certain embodiments, the following antisense compounds target a region of SEQ ID NOs: 1 or 2 or 3, a nucleic acid encoding human FGFR4 and demonstrate at least 80% inhibition of a FGFR4 mRNA: ISIS NOs: 463629, 479533, 479534, 479535, 479536, 479537, 479539, 479542, 479545, 479546, 479547, 479548, 479551, 479552, 479553, 479554, 479556, 479558, 479565, 479566, 479568, 479570, 479573, 479583, 479584, 479594, 479596, 479691, 479692, 479698, 479699, 479703, 479704, 479706, 479721, 479722, 479736, and 479739.

In certain embodiments, the following antisense compounds target a region of SEQ ID NOs: 1 or 2 or 3, a nucleic acid encoding human FGFR4 and demonstrate at least 85% inhibition of a FGFR4 mRNA: ISIS NOs: 463629, 479533, 479534, 479535, 479536, 479539, 479546, 479548, 479551, 479552, 479556, 479566, 479573, 479691, 479692, 479698, 479699, 479703, 479704, 479706, 479736, and 479739.

In certain embodiments, the compounds provided herein have a greater therapeutic potential than ISIS NO: 299005. In certain embodiments, the compounds provided herein have better in vivo inhibition over ISIS NO: 299005. In certain embodiments, the compounds provided herein have a better tolerability profile than ISIS NO: 299005.

In certain embodiments, the compound provided herein consists of a single-stranded modified oligonucleotide.

In certain embodiments, the modified oligonucleotide consists of 8, 9, 10, 11, 12, 13, 14, 15, 16, 17, 18, 19, 20, 21, 22, 23, 24, 25, 26, 27, 28, 29, 30, 31, 32, 33, 34 or 35 linked nucleosides. In certain embodiments, the modified oligonucleotide consists of 20 linked nucleosides. In certain embodiments, the modified oligonucleotide consists of 19 linked nucleosides. In certain embodiments, the modified oligonucleotide consists of 18 linked nucleosides. In certain embodiments, the modified oligonucleotide consists of 17 linked nucleosides. In certain embodiments, the modified oligonucleotide consists of 16 linked nucleosides.

In certain embodiments, at least one internucleoside linkage of the modified oligonucleotide is a modified internucleoside linkage. In certain embodiments, each internucleoside linkage is a phosphorothioate internucleoside linkage.

In certain embodiments, at least one nucleoside of said modified oligonucleotide comprises a modified nucleobase. In certain embodiments, the modified nucleobase is a 5-methylcytosine.

In certain embodiments, the modified oligonucleotide comprises: a) a gap segment consisting of linked deoxynucleosides; b) a 5' wing segment consisting of linked nucleosides; and c) a 3' wing segment consisting of linked nucleosides. The gap segment is positioned between the 5' wing segment and the 3' wing segment and each nucleoside of each wing segment comprises a modified sugar.

In certain embodiments, the modified oligonucleotide consists of 20 linked nucleosides, the gap segment consisting of ten linked deoxynucleosides, the 5' wing segment consisting of five linked nucleosides, the 3' wing segment consisting of five linked nucleosides, each nucleoside of each wing segment comprises a 2'-O-methoxyethyl modified sugar, each internucleoside linkage is a phosphorothioate linkage and each cytosine is a 5-methylcytosine.

In certain embodiments, the modified oligonucleotide consists of 17 linked nucleosides, the gap segment consisting of ten linked deoxynucleosides, the 5' wing segment consisting of three linked nucleosides, the 3' wing segment consisting of four linked nucleosides, each nucleoside of each wing segment comprises a 2'-O-methoxyethyl modified sugar, each internucleoside linkage is a phosphorothioate linkage and each cytosine is a 5-methylcytosine.

In certain embodiments, the compounds or compositions provided herein comprise a modified oligonucleotide consisting of 20 linked nucleosides having a nucleobase sequence comprising at least 8 contiguous nucleobases complementary to an equal length portion of any of SEQ ID NOs: 1-4, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 20 linked nucleosides having a nucleobase sequence comprising at least 8 contiguous nucleobases complementary to an equal length portion of any of SEQ ID NO: 1, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 20 linked nucleosides having a nucleobase sequence comprising at least 19 contiguous nucleobases of SEQ ID NOs: 7-322 wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 20 linked nucleosides having a nucleobase sequence comprising at least 19 contiguous nucleobases of SEQ ID NOs: 16, 17, 45, 46, 70, 72, or 138, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 20 linked nucleosides having a nucleobase sequence comprising at least 19 contiguous nucleobases of SEQ ID NO: 16, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 20 linked nucleosides having a nucleobase sequence comprising at least 19 contiguous nucleobases of SEQ ID NO: 45, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 20 linked nucleosides having a nucleobase sequence comprising at least 20 contiguous nucleobases of SEQ ID NOs: 7-322, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 20 linked nucleosides having a nucleobase sequence comprising at least 20 contiguous nucleobases of SEQ ID NOs: 16, 17, 45, 46, 70, 72, or 138, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine. In certain embodiments, the compound or composition comprises the compound of any of ISIS NOs: 463588, 463589, 463690, 463691, 463835, 463837, or 464225.

In certain embodiments, the compounds or compositions provided herein comprise a modified oligonucleotide consisting of 20 linked nucleosides having a nucleobase sequence comprising at least 20 contiguous nucleobases of SEQ ID NO: 16, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine. In certain embodiments, the compound or composition comprises the compound of ISIS NO: 463588.

In certain embodiments, the compounds or compositions provided herein comprise a modified oligonucleotide consisting of 20 linked nucleosides having a nucleobase sequence comprising at least 20 contiguous nucleobases of SEQ ID NO: 45, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine. In certain embodiments, the compound or composition comprises the compound of ISIS NO: 463690.

Certain embodiments provide methods, compounds, and compositions for inhibiting FGFR4 expression.

Certain embodiments provide a method of reducing FGFR4 expression in an animal comprising administering to the animal a compound as described herein. In certain embodiments, the compound comprises a modified oligonucleotide 12 to 30 linked nucleosides in length targeted to FGFR4. In certain embodiments, the compound comprises a modified oligonucleotide 15 to 30 linked nucleosides in length targeted to FGFR4. In certain embodiments, the compound comprises a modified oligonucleotide 18 to 21 linked nucleosides in length targeted to FGFR4. In certain embodiments, the compound comprises a modified oligonucleotide 20 to 35 linked nucleosides in length targeted to FGFR4. In certain embodiments, the compound comprises a modified oligonucleotide 20 to 25 linked nucleosides in length targeted to FGFR4. In certain embodiments, the compound comprises a modified oligonucleotide 20 to 24 linked nucleosides in length targeted to FGFR4. In certain embodiments, the compound comprises a modified oligonucleotide 20 to 23 linked nucleosides in length targeted to FGFR4. In certain embodiments, the compound comprises a modified oligonucleotide 20 to 22 linked nucleosides in length targeted to FGFR4. In certain embodiments, the compound comprises a modified oligonucleotide 20 to 21 linked nucleosides in length targeted to FGFR4. In certain embodiments, the compound comprises a modified oligonucleotide 20 linked nucleosides in length targeted to FGFR4.

Certain embodiments provide a method of preventing, ameliorating or treating a metabolic disease in an animal comprising administering to the animal a compound as described herein. In certain embodiments, the compound comprises a modified oligonucleotide 12 to 30 linked nucleosides in length targeted to FGFR4. In certain embodiments, the compound comprises a modified oligonucleotide 20 linked nucleosides in length targeted to FGFR4. Examples of metabolic diseases or disorders include, but are not limited to obesity, diabetes, hyperglycemia, prediabetes, non-alcoholic fatty liver disease (NAFLD), metabolic syndrome, insulin resistance, diabetic dyslipidemia, or hypertriglyceridemia or a combination thereof.

Certain embodiments provide a compound as described herein for use in preventing, ameliorating or treating a metabolic disease in an animal. In certain embodiments, the compound comprises a modified oligonucleotide 12 to 30 linked nucleosides in length targeted to FGFR4. In certain embodiments, the compound comprises a modified oligonucleotide 20 linked nucleosides in length targeted to FGFR4. Examples of metabolic diseases or disorders include, but are not limited to obesity, diabetes, hyperglycemia, prediabetes, non-alcoholic fatty liver disease (NAFLD), metabolic syndrome, insulin resistance, diabetic dyslipidemia, or hypertriglyceridemia or a combination thereof.

Certain embodiments provide use of a compound as described herein in the manufacture of a medicament for preventing, ameliorating or treating a metabolic disease in an animal. In certain embodiments, the compound comprises a modified oligonucleotide 12 to 30 linked nucleosides in length targeted to FGFR4. In certain embodiments, the compound comprises a modified oligonucleotide 20 linked nucleosides in length targeted to FGFR4. Examples of metabolic diseases or disorders include, but are not limited to obesity, diabetes, hyperglycemia, prediabetes, non-alcoholic fatty liver disease (NAFLD), metabolic syndrome, insulin resistance, diabetic dyslipidemia, or hypertriglyceridemia or a combination thereof.

Certain embodiments provide a method of preventing, ameliorating or treating obesity in an animal comprising administering to the animal a compound as described herein. In certain embodiments, the compound comprises a modified oligonucleotide 12 to 30 linked nucleosides in length targeted to FGFR4. In certain embodiments, the compound comprises a modified oligonucleotide 20 linked nucleosides in length targeted to FGFR4. In certain embodiments, the compound or composition comprises the compound of ISIS NOs: 463588, 463589, 463690, 463691, 463835, 463837, or 464225. In certain embodiments, the compound or composition comprises the compound of ISIS NO: 463588. In certain embodiments, the compound or composition comprises the compound of ISIS NO: 463690.

Certain embodiments provide a compound as described herein for use in preventing, ameliorating or treating obesity in an animal. In certain embodiments, the compound comprises a modified oligonucleotide 12 to 30 linked nucleosides in length targeted to FGFR4. In certain embodiments, the compound comprises a modified oligonucleotide 20 linked nucleosides in length targeted to FGFR4. In certain embodiments, the compound or composition comprises the compound of ISIS NOs: 463588, 463589, 463690, 463691, 463835, 463837, or 464225. In certain embodiments, the compound or composition comprises the compound of ISIS NO: 463588. In certain embodiments, the compound or composition comprises the compound of ISIS NO: 463690.

Certain embodiments provide use of a compound as described herein in the manufacture of a medicament for preventing, ameliorating or treating obesity in an animal. In certain embodiments, the compound comprises a modified oligonucleotide 12 to 30 linked nucleosides in length targeted to FGFR4. In certain embodiments, the compound comprises a modified oligonucleotide 20 linked nucleosides in length targeted to FGFR4. In certain embodiments, the compound or composition comprises the compound of ISIS NOs: 463588, 463589, 463690, 463691, 463835, 463837, or 464225. In certain embodiments, the compound or composition comprises the compound of ISIS NO: 463588. In certain embodiments, the compound or composition comprises the compound of ISIS NO: 463690.

Certain embodiments provide a method of reducing body weight in an animal comprising administering to the animal a compound as described herein. In certain embodiments, the compound comprises a modified oligonucleotide 12 to 30 linked nucleosides in length targeted to FGFR4. In certain embodiments, the compound comprises a modified oligonucleotide 20 linked nucleosides in length targeted to FGFR4. In certain embodiments, reduction of body weight in an animal prevents, ameliorates or treats a metabolic disease. In certain embodiments, reduction of body weight in an animal prevents, ameliorates or treats diabetes. In certain embodiments, reduction of body weight in an animal prevents, ameliorates or treats obesity. In certain embodiments, reduction of body weight in an animal prevents, ameliorates or treats metabolic syndrome. In certain embodiments, reduction of body weight in an animal prevents, ameliorates or treats insulin resistance. In certain embodiments, reduction of body weight in an animal prevents, ameliorates or treats hyperglycemia. In certain embodiments, reduction of body weight in an animal prevents, ameliorates or treats NAFLD. In certain embodiments, reduction of body weight in an animal prevents, ameliorates or treats diabetic dyslipidemia. In certain embodiments, the body weight is reduced by at least 5%, 10%, 20%, 30%, 35%, 40%, 45%, 50%, 55%, 60%, 65%, 70%, 75%, 80%, 85%, 90%, 95% or 100%.

Certain embodiments provide a compound as described herein for use in reducing body weight in an animal. In certain embodiments, the compound comprises a modified oligonucleotide 12 to 30 linked nucleosides in length targeted to FGFR4. In certain embodiments, the compound comprises a modified oligonucleotide 20 linked nucleosides in length targeted to FGFR4. In certain embodiments, reduction of body weight in an animal prevents, ameliorates or treats a metabolic disease. In certain embodiments, reduction of body weight in an animal prevents, ameliorates or treats diabetes. In certain embodiments, reduction of body weight in an animal prevents, ameliorates or treats obesity. In certain embodiments, reduction of body weight in an animal prevents, ameliorates or treats metabolic syndrome. In certain embodiments, reduction of body weight in an animal prevents, ameliorates or treats insulin resistance. In certain embodiments, reduction of body weight in an animal prevents, ameliorates or treats hyperglycemia. In certain embodiments, reduction of body weight in an animal prevents, ameliorates or treats NAFLD. In certain embodiments, reduction of body weight in an animal prevents, ameliorates or treats diabetic dyslipidemia. In certain embodiments, the body weight is reduced by at least 5%, 10%, 20%, 30%, 35%, 40%, 45%, 50%, 55%, 60%, 65%, 70%, 75%, 80%, 85%, 90%, 95% or 100%.

Certain embodiments provide use of a compound as described herein in the manufacture of a medicament for reducing body weight in an animal. In certain embodiments, the compound comprises a modified oligonucleotide 12 to 30 linked nucleosides in length targeted to FGFR4. In certain embodiments, the compound comprises a modified oligonucleotide 20 linked nucleosides in length targeted to FGFR4. In certain embodiments, reduction of body weight in an animal prevents, ameliorates or treats a metabolic disease. In certain embodiments, reduction of body weight in an animal prevents, ameliorates or treats diabetes. In certain embodiments, reduction of body weight in an animal prevents, ameliorates or treats obesity. In certain embodiments, reduction of body weight in an animal prevents, ameliorates or treats metabolic syndrome. In certain embodiments, reduction of body weight in an animal prevents, ameliorates or treats insulin resistance. In certain embodiments, reduction of body weight in an animal prevents, ameliorates or treats hyperglycemia. In certain embodiments, reduction of body weight in an animal prevents, ameliorates or treats NAFLD. In certain embodiments, reduction of body weight in an animal prevents, ameliorates or treats diabetic dyslipidemia. In certain embodiments, the body weight is reduced by at least 5%, 10%, 20%, 30%, 35%, 40%, 45%, 50%, 55%, 60%, 65%, 70%, 75%, 80%, 85%, 90%, 95% or 100%.

Certain embodiments provide a method of reducing adipose tissue in an animal comprising administering to the animal a compound as described herein. In certain embodiments, the compound comprises a modified oligonucleotide 12 to 30 linked nucleosides in length targeted to FGFR4. In certain embodiments, the compound comprises a modified oligonucleotide 20 linked nucleosides in length targeted to FGFR4. In certain embodiments, reduction in adiposity in an animal prevents, ameliorates or treats a metabolic disease. In certain embodiments, reduction in adiposity in an animal prevents, ameliorates or treats diabetes. In certain embodiments, reduction in adiposity in an animal prevents, ameliorates or treats obesity. In certain embodiments, reduction in adiposity in an animal prevents, ameliorates or treats metabolic syndrome. In certain embodiments, reduction in adiposity in an animal prevents, ameliorates or treats insulin resistance. In certain embodiments, reduction in adiposity in an animal prevents, ameliorates or treats hyperglycemia. In certain embodiments, reduction in adiposity in an animal prevents, ameliorates or treats NAFLD. In certain embodiments, reduction in adiposity in an animal prevents, ameliorates or treats diabetic dyslipidemia. In certain embodiments, adiposity is reduced by at least 5%, 10%, 20%, 30%, 35%, 40%, 45%, 50%, 55%, 60%, 65%, 70%, 75%, 80%, 85%, 90%, 95% or 100%.

Certain embodiments provide a compound as described herein for use in reducing adipose tissue in an animal. In certain embodiments, the compound comprises a modified oligonucleotide 12 to 30 linked nucleosides in length targeted to FGFR4. In certain embodiments, the compound comprises a modified oligonucleotide 20 linked nucleosides in length targeted to FGFR4. In certain embodiments, reduction in adiposity in an animal prevents, ameliorates or treats a metabolic disease. In certain embodiments, reduction in adiposity in an animal prevents, ameliorates or treats diabetes. In certain embodiments, reduction in adiposity in an animal prevents, ameliorates or treats obesity. In certain embodiments, reduction in adiposity in an animal prevents, ameliorates or treats metabolic syndrome. In certain embodiments, reduction in adiposity in an animal prevents, ameliorates or treats insulin resistance. In certain embodiments, reduction in adiposity in an animal prevents, ameliorates or treats hyperglycemia. In certain embodiments, reduction in adiposity in an animal prevents, ameliorates or treats NAFLD. In certain embodiments, reduction in adiposity in an animal prevents, ameliorates or treats diabetic dyslipidemia. In certain embodiments, adiposity is reduced by at least 5%, 10%, 20%, 30%, 35%, 40%, 45%, 50%, 55%, 60%, 65%, 70%, 75%, 80%, 85%, 90%, 95% or 100%.

Certain embodiments provide use of a compound as described herein in the manufacture of a medicament for reducing adipose tissue in an animal. In certain embodiments, the compound comprises a modified oligonucleotide 12 to 30 linked nucleosides in length targeted to FGFR4. In certain embodiments, the compound comprises a modified oligonucleotide 20 linked nucleosides in length targeted to FGFR4. In certain embodiments, reduction in adiposity in an animal prevents, ameliorates or treats a metabolic disease. In certain embodiments, reduction in adiposity in an animal prevents, ameliorates or treats diabetes. In certain embodiments, reduction in adiposity in an animal prevents, ameliorates or treats obesity. In certain embodiments, reduction in adiposity in an animal prevents, ameliorates or treats metabolic syndrome. In certain embodiments, reduction in adiposity in an animal prevents, ameliorates or treats insulin resistance. In certain embodiments, reduction in adiposity in an animal prevents, ameliorates or treats hyperglycemia. In certain embodiments, reduction in adiposity in an animal prevents, ameliorates or treats NAFLD. In certain embodiments, reduction in adiposity in an animal prevents, ameliorates or treats diabetic dyslipidemia. In certain embodiments, adiposity is reduced by at least 5%, 10%, 20%, 30%, 35%, 40%, 45%, 50%, 55%, 60%, 65%, 70%, 75%, 80%, 85%, 90%, 95% or 100%.

Certain embodiments provide a method of increasing fatty acid oxidation in an animal comprising administering to the animal a compound as described herein. In certain embodiments, the compound comprises a modified oligonucleotide 12 to 30 linked nucleosides in length targeted to FGFR4. In certain embodiments, the compound comprises a modified oligonucleotide 20 linked nucleosides in length targeted to FGFR4. In certain embodiments, increasing fatty acid oxidation in an animal prevents, ameliorates or treats a metabolic disease. In certain embodiments, increasing fatty acid oxidation in an animal prevents, ameliorates or treats diabetes. In certain embodiments, increasing fatty acid oxidation an animal prevents, ameliorates or treats obesity. In certain embodiments, increasing fatty acid oxidation in an animal prevents, ameliorates or treats metabolic syndrome. In certain embodiments, increasing fatty acid oxidation in an animal prevents, ameliorates or treats insulin resistance. In certain embodiments, increasing fatty acid oxidation in an animal prevents, ameliorates or treats hyperglycemia. In certain embodiments, increasing fatty acid oxidation in an animal prevents, ameliorates or treats NAFLD. In certain embodiments, increasing fatty acid oxidation prevents, ameliorates or treats diabetic dyslipidemia. In certain embodiments, the fatty acid oxidation is increased by at least 5%, 10%, 20%, 30%, 35%, 40%, 45%, 50%, 55%, 60%, 65%, 70%, 75%, 80%, 85%, 90%, 95% or 100%.

Certain embodiments provide a compound as described herein for use in increasing fatty acid oxidation in an animal. In certain embodiments, the compound comprises a modified oligonucleotide 12 to 30 linked nucleosides in length targeted to FGFR4. In certain embodiments, the compound comprises a modified oligonucleotide 20 linked nucleosides in length targeted to FGFR4. In certain embodiments, increasing fatty acid oxidation in an animal prevents, ameliorates or treats a metabolic disease. In certain embodiments, increasing fatty acid oxidation in an animal prevents, ameliorates or treats diabetes. In certain embodiments, increasing fatty acid oxidation an animal prevents, ameliorates or treats obesity. In certain embodiments, increasing fatty acid oxidation in an animal prevents, ameliorates or treats metabolic syndrome. In certain embodiments, increasing fatty acid oxidation in an animal prevents, ameliorates or treats insulin resistance. In certain embodiments, increasing fatty acid oxidation in an animal prevents, ameliorates or treats hyperglycemia. In certain embodiments, increasing fatty acid oxidation in an animal prevents, ameliorates or treats NAFLD. In certain embodiments, increasing fatty acid oxidation prevents, ameliorates or treats diabetic dyslipidemia. In certain embodiments, the fatty acid oxidation is increased by at least 5%, 10%, 20%, 30%, 35%, 40%, 45%, 50%, 55%, 60%, 65%, 70%, 75%, 80%, 85%, 90%, 95% or 100%.

Certain embodiments provide use of a compound as described herein in the manufacture of a medicament for increasing fatty acid oxidation in an animal. In certain embodiments, the compound comprises a modified oligonucleotide 12 to 30 linked nucleosides in length targeted to FGFR4. In certain embodiments, the compound comprises a modified oligonucleotide 20 linked nucleosides in length targeted to FGFR4. In certain embodiments, increasing fatty acid oxidation in an animal prevents, ameliorates or treats a metabolic disease. In certain embodiments, increasing fatty acid oxidation in an animal prevents, ameliorates or treats diabetes. In certain embodiments, increasing fatty acid oxidation an animal prevents, ameliorates or treats obesity. In certain embodiments, increasing fatty acid oxidation in an animal prevents, ameliorates or treats metabolic syndrome. In certain embodiments, increasing fatty acid oxidation in an animal prevents, ameliorates or treats insulin resistance. In certain embodiments, increasing fatty acid oxidation in an animal prevents, ameliorates or treats hyperglycemia. In certain embodiments, increasing fatty acid oxidation in an animal prevents, ameliorates or treats NAFLD. In certain embodiments, increasing fatty acid oxidation prevents, ameliorates or treats diabetic dyslipidemia. In certain embodiments, the fatty acid oxidation is increased by at least 5%, 10%, 20%, 30%, 35%, 40%, 45%, 50%, 55%, 60%, 65%, 70%, 75%, 80%, 85%, 90%, 95% or 100%.

Certain embodiments provide a method of reducing glucose levels in an animal comprising administering to the animal a compound as described herein. In certain embodiments, the compound comprises a modified oligonucleotide 12 to 30 linked nucleosides in length targeted to FGFR4. In certain embodiments, the compound comprises a modified oligonucleotide 20 linked nucleosides in length targeted to FGFR4. In certain embodiments, reduction of glucose levels in an animal prevents, ameliorates or treats a metabolic disease. In certain embodiments, reduction of glucose levels in an animal prevents, ameliorates or treats diabetes. In certain embodiments, reduction of glucose levels in an animal prevents, ameliorates or treats obesity. In certain embodiments, reduction of glucose levels in an animal prevents, ameliorates or treats metabolic syndrome. In certain embodiments, reduction of glucose levels in an animal prevents, ameliorates or treats insulin resistance. In certain embodiments, reduction of glucose levels in an animal prevents, ameliorates or treats hyperglycemia. In certain embodiments, reduction of glucose levels in an animal prevents, ameliorates or treats NAFLD. In certain embodiments, reduction of glucose levels in an animal prevents, ameliorates or treats diabetic dyslipidemia. In certain embodiments, the glucose level is reduced by at least 5%, 10%, 20%, 30%, 35%, 40%, 45%, 50%, 55%, 60%, 65%, 70%, 75%, 80%, 85%, 90%, 95% or 100%.

Certain embodiments provide a compound as described herein for use in reducing glucose levels in an animal. In certain embodiments, the compound comprises a modified oligonucleotide 12 to 30 linked nucleosides in length targeted to FGFR4. In certain embodiments, the compound comprises a modified oligonucleotide 20 linked nucleosides in length targeted to FGFR4. In certain embodiments, reduction of glucose levels in an animal prevents, ameliorates or treats a metabolic disease. In certain embodiments, reduction of glucose levels in an animal prevents, ameliorates or treats diabetes. In certain embodiments, reduction of glucose levels in an animal prevents, ameliorates or treats obesity. In certain embodiments, reduction of glucose levels in an animal prevents, ameliorates or treats metabolic syndrome. In certain embodiments, reduction of glucose levels in an animal prevents, ameliorates or treats insulin resistance. In certain embodiments, reduction of glucose levels in an animal prevents, ameliorates or treats hyperglycemia. In certain embodiments, reduction of glucose levels in an animal prevents, ameliorates or treats NAFLD. In certain embodiments, reduction of glucose levels in an animal prevents, ameliorates or treats diabetic dyslipidemia. In certain embodiments, the glucose level is reduced by at least 5%, 10%, 20%, 30%, 35%, 40%, 45%, 50%, 55%, 60%, 65%, 70%, 75%, 80%, 85%, 90%, 95% or 100%.

Certain embodiments provide use of a compound as described herein in the manufacture of a medicament for reducing glucose levels in an animal. In certain embodiments, the compound comprises a modified oligonucleotide 12 to 30 linked nucleosides in length targeted to FGFR4. In certain embodiments, the compound comprises a modified oligonucleotide 20 linked nucleosides in length targeted to FGFR4. In certain embodiments, reduction of glucose levels in an animal prevents, ameliorates or treats a metabolic disease. In certain embodiments, reduction of glucose levels in an animal prevents, ameliorates or treats diabetes. In certain embodiments, reduction of glucose levels in an animal prevents, ameliorates or treats obesity. In certain embodiments, reduction of glucose levels in an animal prevents, ameliorates or treats metabolic syndrome. In certain embodiments, reduction of glucose levels in an animal prevents, ameliorates or treats insulin resistance. In certain embodiments, reduction of glucose levels in an animal prevents, ameliorates or treats hyperglycemia. In certain embodiments, reduction of glucose levels in an animal prevents, ameliorates or treats NAFLD. In certain embodiments, reduction of glucose levels in an animal prevents, ameliorates or treats diabetic dyslipidemia. In certain embodiments, the glucose level is reduced by at least 5%, 10%, 20%, 30%, 35%, 40%, 45%, 50%, 55%, 60%, 65%, 70%, 75%, 80%, 85%, 90%, 95% or 100%.

In certain embodiments, FGFR4 has the sequence as set forth in any of the GENBANK Accession Numbers: GENBANK Accession No. NM_002011.3 (incorporated herein as SEQ ID NO: 1), GENBANK Accession No: NT_023133.11 truncated from nucleosides 21323018 to 21335213 (incorporated herein as SEQ ID NO: 2); GENBANK Accession No. AB209631.1 (incorporated herein as SEQ ID NO: 3); and GENBANK Accession No NM_022963.2 (incorporated herein as SEQ ID NO: 4)). In certain embodiments, FGFR4 has the human sequence as set forth in SEQ ID NOs: 1-4. In certain embodiments, FGFR4 has the rhesus monkey sequence as set forth in GENBANK Accession No. NW_001121000.1 truncated from nucleosides 3094000 to 3109000 (SEQ ID NO: 5). In certain embodiments, FGFR4 has the murine sequence as set forth in GENBANK Accession No. BC033313.1 (SEQ ID NO: 6).

In certain embodiments, the compounds or compositions provided herein comprise a salt thereof, and a pharmaceutically acceptable carrier or diluent. In certain embodiments, the composition comprises a modified oligonucleotide consisting of 20 to 35 linked nucleosides and having a nucleobase sequence comprising at least 20 contiguous nucleobases of a nucleobase sequence recited in SEQ ID NOs: 16, 17, 45, 46, 70, 72, or 138 or a salt thereof and a pharmaceutically acceptable carrier or diluent. In certain embodiments, the composition comprises a modified oligonucleotide consisting of 20 to 25 linked nucleosides and having a nucleobase sequence comprising at least 20 contiguous nucleobases of a nucleobase sequence recited in SEQ ID NOs: 16, 17, 45, 46, 70, 72, or 138 or a salt thereof and a pharmaceutically acceptable carrier or diluent. In certain embodiments, the composition comprises a modified oligonucleotide consisting of 20 linked nucleosides and having a nucleobase sequence comprising at least 20 contiguous nucleobases of a nucleobase sequence recited in SEQ ID NO: 16, 17, 45, 46, 70, 72, or 138 or a salt thereof and a pharmaceutically acceptable carrier or diluent.

In certain embodiments, the compounds or compositions provided herein comprise a salt thereof, and a pharmaceutically acceptable carrier or diluent. In certain embodiments, the composition comprises a modified oligonucleotide consisting of 20 to 35 linked nucleosides and having a nucleobase sequence comprising at least 20 contiguous nucleobases of a nucleobase sequence recited in SEQ ID NO: 16 or a salt thereof and a pharmaceutically acceptable carrier or diluent. In certain embodiments, the composition comprises a modified oligonucleotide consisting of 20 to 25 linked nucleosides and having a nucleobase sequence comprising at least 20 contiguous nucleobases of a nucleobase sequence recited in SEQ ID NO: 16 or a salt thereof and a pharmaceutically acceptable carrier or diluent. In certain embodiments, the composition comprises a modified oligonucleotide consisting of 20 linked nucleosides and having a nucleobase sequence comprising at least 20 contiguous nucleobases of a nucleobase sequence recited in SEQ ID NO: 16 or a salt thereof and a pharmaceutically acceptable carrier or diluent.

In certain embodiments, the compounds or compositions provided herein comprise a salt thereof, and a pharmaceutically acceptable carrier or diluent. In certain embodiments, the composition comprises a modified oligonucleotide consisting of 20 to 35 linked nucleosides and having a nucleobase sequence comprising at least 20 contiguous nucleobases of a nucleobase sequence recited in SEQ ID NO: 45 or a salt thereof and a pharmaceutically acceptable carrier or diluent. In certain embodiments, the composition comprises a modified oligonucleotide consisting of 20 to 25 linked nucleosides and having a nucleobase sequence comprising at least 20 contiguous nucleobases of a nucleobase sequence recited in SEQ ID NO: 45 or a salt thereof and a pharmaceutically acceptable carrier or diluent. In certain embodiments, the composition comprises a modified oligonucleotide consisting of 20 linked nucleosides and having a nucleobase sequence comprising at least 20 contiguous nucleobases of a nucleobase sequence recited in SEQ ID NO: 45 or a salt thereof and a pharmaceutically acceptable carrier or diluent.

Certain embodiments provide a method for treating an animal with a FGFR4 related disease or condition comprising: a) identifying said animal with the FGFR4 related disease or condition, and b) administering to said animal a therapeutically effective amount of a compound comprising a modified oligonucleotide consisting of 12 to 30 linked nucleosides and having a nucleobase sequence at least 90% complementary to any of SEQ ID NOs: 1-4 as measured over the entirety of said modified oligonucleotide. In certain embodiments, the therapeutically effective amount of the compound administered to the animal treats or reduces the FGFR4 related disease or condition, or a symptom thereof, in the animal. In certain embodiments, the FGFR4 related disease or condition is obesity. In certain embodiments, the FGFR4 related disease or condition is diabetes.

Certain embodiments provide a compound comprising a modified oligonucleotide consisting of 12 to 30 linked nucleosides and having a nucleobase sequence at least 90% complementary to any of SEQ ID NOs: 1-4 as measured over the entirety of said modified oligonucleotide for treating a FGFR4 related disease or condition. In certain embodiments, the FGFR4 related disease or condition is obesity. In certain embodiments, the FGFR4 related disease or condition is diabetes.

Certain embodiments provide use of a compound comprising a modified oligonucleotide consisting of 12 to 30 linked nucleosides and having a nucleobase sequence at least 90% complementary to any of SEQ ID NOs: 1-4 as measured over the entirety of said modified oligonucleotide in the preparation of a medicament for treating a FGFR4 related disease or condition. In certain embodiments, the FGFR4 related disease or condition is obesity. In certain embodiments, the FGFR4 related disease or condition is diabetes.

Certain embodiments provide a method for treating an animal with a FGFR4 related disease or condition comprising: a) identifying said animal with the FGFR4 related disease or condition, and b) administering to said animal a therapeutically effective amount of a compound comprising a modified oligonucleotide consisting of 20 linked nucleosides and having a nucleobase sequence at least 100% complementary to any of SEQ ID NOs: 1-4 as measured over the entirety of said modified oligonucleotide. In certain embodiments, the therapeutically effective amount of the compound administered to the animal treats or reduces the FGFR4 related disease or condition, or a symptom thereof, in the animal. In certain embodiments, the FGFR4 related disease or condition is obesity. In certain embodiments, the FGFR4 related disease or condition is diabetes.

Certain embodiments provide a compound comprising a modified oligonucleotide consisting of 20 linked nucleosides and having a nucleobase sequence at least 100% complementary to any of SEQ ID NOs: 1-4 as measured over the entirety of said modified oligonucleotide for treating a FGFR4 related disease or condition. In certain embodiments, the FGFR4 related disease or condition is obesity. In certain embodiments, the FGFR4 related disease or condition is diabetes.

Certain embodiments provide use of a compound comprising a modified oligonucleotide consisting of 20 linked nucleosides and having a nucleobase sequence at least 100% complementary to any of SEQ ID NOs: 1-4 as measured over the entirety of said modified oligonucleotide in the preparation of a medicament for treating a FGFR4 related disease or condition. In certain embodiments, the FGFR4 related disease or condition is obesity. In certain embodiments, the FGFR4 related disease or condition is diabetes.

Certain embodiments provide methods of treating, preventing, or ameliorating a metabolic disease. In certain embodiments the metabolic disease is obesity, diabetes, hyperglycemia, prediabetes, non-alcoholic fatty liver disease (NAFLD), metabolic syndrome, insulin resistance, diabetic dyslipidemia, or hypertriglyceridemia or a combination thereof.

Certain embodiments provide compounds described herein for treating, preventing, or ameliorating a metabolic disease. In certain embodiments the metabolic disease is obesity, diabetes, hyperglycemia, prediabetes, non-alcoholic fatty liver disease (NAFLD), metabolic syndrome, insulin resistance, diabetic dyslipidemia, or hypertriglyceridemia or a combination thereof.

Certain embodiments provide use of compounds described herein in the preparation of a medicament for treating, preventing, or ameliorating a metabolic disease. In certain embodiments the metabolic disease is obesity, diabetes, hyperglycemia, prediabetes, non-alcoholic fatty liver disease (NAFLD), metabolic syndrome, insulin resistance, diabetic dyslipidemia, or hypertriglyceridemia or a combination thereof.

Certain embodiments provide methods comprising administering to an animal a compound as described herein to an animal. In certain embodiments, the method comprises administering to an animal a modified oligonucleotide consisting of 20 to 35 linked nucleosides and having a nucleobase sequence comprising at least 20 contiguous nucleobases of a nucleobase sequence recited in SEQ ID NOs: 16, 17, 45, 46, 70, 72, or 138.

Certain embodiments provide a modified oligonucleotide consisting of 20 to 35 linked nucleosides and having a nucleobase sequence comprising at least 20 contiguous nucleobases of a nucleobase sequence recited in SEQ ID NOs: 16, 17, 45, 46, 70, 72, or 138 for treating a metabolic disease, diabetes, and/or obesity.

Certain embodiments provide use of a modified oligonucleotide consisting of 20 to 35 linked nucleosides and having a nucleobase sequence comprising at least 20 contiguous nucleobases of a nucleobase sequence recited in SEQ ID NOs: 16, 17, 45, 46, 70, 72, or 138 in the preparation of a medicament for treating metabolic disease, diabetes, and/or obesity.

Certain embodiments provide methods comprising administering to an animal a compound as described herein to an animal. In certain embodiments, the method comprises administering to an animal a modified oligonucleotide consisting of 20 to 35 linked nucleosides and having a nucleobase sequence comprising at least 20 contiguous nucleobases of a nucleobase sequence selected from among the nucleobase sequences recited in SEQ ID NO: 16.

Certain embodiments provide a modified oligonucleotide consisting of 20 to 35 linked nucleosides and having a nucleobase sequence comprising at least 20 contiguous nucleobases of a nucleobase sequence recited in SEQ ID NO: 16 for treating metabolic disease, diabetes, and/or obesity.

Certain embodiments provide use of a modified oligonucleotide consisting of 20 to 35 linked nucleosides and having a nucleobase sequence comprising at least 20 contiguous nucleobases of a nucleobase sequence recited in SEQ ID NO: 16 in the preparation of a medicament for treating metabolic disease, diabetes, and/or obesity.

Certain embodiments provide methods comprising administering to an animal a compound as described herein to an animal. In certain embodiments, the method comprises administering to an animal a modified oligonucleotide consisting of 20 to 35 linked nucleosides and having a nucleobase sequence comprising at least 20 contiguous nucleobases of a nucleobase sequence selected from among the nucleobase sequences recited in SEQ ID NO: 45.

Certain embodiments provide a modified oligonucleotide consisting of 20 to 35 linked nucleosides and having a nucleobase sequence comprising at least 20 contiguous nucleobases of a nucleobase sequence recited in SEQ ID NO: 45 for treating metabolic disease, diabetes, and/or obesity.

Certain embodiments provide use of a modified oligonucleotide consisting of 20 to 35 linked nucleosides and having a nucleobase sequence comprising at least 20 contiguous nucleobases of a nucleobase sequence recited in SEQ ID NO: 45 in the preparation of a medicament for treating metabolic disease, diabetes, and/or obesity.

Certain embodiments provide methods comprising administering to an animal a compound as described herein to an animal. In certain embodiments, the method comprises administering to an animal a modified oligonucleotide consisting of 20 to 35 linked nucleosides and having a nucleobase sequence comprising at least 20 contiguous nucleobases of a nucleobase sequence selected from among the nucleobase sequences recited in ISIS NO: 463588.

Certain embodiments provide a modified oligonucleotide consisting of 20 to 35 linked nucleosides and having a nucleobase sequence comprising at least 20 contiguous nucleobases of a nucleobase sequence of ISIS NO: 463588 for treating metabolic disease, diabetes, and/or obesity.

Certain embodiments provide use of a modified oligonucleotide consisting of 20 to 35 linked nucleosides and having a nucleobase sequence comprising at least 20 contiguous nucleobases of a nucleobase sequence of ISIS NO: 463588 in the preparation of a medicament for treating metabolic disease, diabetes, and/or obesity.

Certain embodiments provide methods comprising administering to an animal a compound as described herein to an animal. In certain embodiments, the method comprises administering to an animal a modified oligonucleotide consisting of 20 to 35 linked nucleosides and having a nucleobase sequence comprising at least 20 contiguous nucleobases of a nucleobase sequence selected from among the nucleobase sequences recited in ISIS NO: 463690.

Certain embodiments provide a modified oligonucleotide consisting of 20 to 35 linked nucleosides and having a nucleobase sequence comprising at least 20 contiguous nucleobases of a nucleobase sequence of ISIS NO: 463690 for treating metabolic disease, diabetes, and/or obesity.

Certain embodiments provide use of a modified oligonucleotide consisting of 20 to 35 linked nucleosides and having a nucleobase sequence comprising at least 20 contiguous nucleobases of a nucleobase sequence of ISIS NO: 463690 in the preparation of a medicament for treating metabolic disease, diabetes, and/or obesity.

In certain embodiments, the animal is a human.

In certain embodiments, the administering prevents, treats, ameliorates, or slows progression of a metabolic disease as described herein.

In certain embodiments, the administering prevents, treats, ameliorates, or slows progression of obesity as described herein.

In certain embodiments, the administering prevents, treats, ameliorates, or slows progression of diabetes as described herein.

In certain embodiments, the compound is co-administered with a second agent.

In certain embodiments, the compound and the second agent are administered concomitantly.

In certain embodiments, the administering is parenteral administration.

Certain embodiments further provide a method to reduce FGFR4 mRNA or protein expression in an animal comprising administering to the animal a compound or composition as described herein to reduce FGFR4 mRNA or protein expression in the animal. In certain embodiments, the animal is a human. In certain embodiments, reducing FGFR4 mRNA or protein expression prevents, treats, ameliorates, or slows progression of metabolic disease. In certain embodiments, the metabolic disease or condition is diabetes. In certain embodiments, the metabolic disease or condition is obesity.

Certain embodiments provide a method for treating a human with a metabolic disease comprising identifying the human with the disease and administering to the human a therapeutically effective amount of a compound or composition as described herein. In certain embodiments, the treatment reduces a symptom selected from the group consisting of metabolic syndrome, hyperglycemia, hypertriglyceridemia, hypertension, increased glucose levels, increased insulin resistance, decreased insulin sensitivity, above normal body weight, and/or above normal body fat or any combination thereof.

Certain embodiments provide a method for treating a human with obesity comprising identifying the human with the disease and administering to the human a therapeutically effective amount of a compound or composition as described herein. In certain embodiments, the treatment reduces a symptom selected from the group consisting of metabolic syndrome, hyperglycemia, hypertriglyceridemia, hypertension, increased glucose levels, increased insulin resistance, decreased insulin sensitivity, above normal body weight, and/or above normal body fat or any combination thereof.

Certain embodiments provide a method for treating a human with diabetes comprising identifying the human with the disease and administering to the human a therapeutically effective amount of a compound or composition as described herein. In certain embodiments, the treatment reduces a symptom selected from the group consisting of metabolic syndrome, hyperglycemia, hypertriglyceridemia, hypertension, increased glucose levels, increased insulin resistance, decreased insulin sensitivity, above normal body weight, and/or above normal body fat or any combination thereof.

Further provided is a method for reducing or preventing metabolic disease comprising administering to a human a therapeutically effective amount compound or composition as described herein, thereby reducing or preventing metabolic disease.

Further provided is a method for reducing or preventing obesity comprising administering to a human a therapeutically effective amount compound or composition as described herein, thereby reducing or preventing diabetes.

Further provided is a method for reducing or preventing diabetes comprising administering to a human a therapeutically effective amount compound or composition as described herein, thereby reducing or preventing diabetes.

Further provided is a method for ameliorating a symptom of metabolic disease, comprising administering to a human in need thereof a compound comprising a modified oligonucleotide consisting of 20 to 35 linked nucleosides, wherein said modified oligonucleotide specifically hybridizes to SEQ ID NO: 1, 2, 3, 4 or 5, thereby ameliorating a symptom of metabolic disease in the human.

Further provided is a method for ameliorating a symptom of obesity, comprising administering to a human in need thereof a compound comprising a modified oligonucleotide consisting of 20 to 35 linked nucleosides, wherein said modified oligonucleotide specifically hybridizes to SEQ ID NO: 1, 2, 3, 4 or 5, thereby ameliorating a symptom of metabolic disease in the human.

Further provided is a method for ameliorating a symptom of diabetes, comprising administering to a human in need thereof a compound comprising a modified oligonucleotide consisting of 20 to 35 linked nucleosides, wherein said modified oligonucleotide specifically hybridizes to SEQ ID NO: 1, 2, 3, 4 or 5, thereby ameliorating a symptom of metabolic disease in the human.

Further provided is a method for ameliorating a symptom of metabolic syndrome, comprising administering to a human in need thereof a compound comprising a modified oligonucleotide consisting of 12 to 30 linked nucleosides, wherein said modified oligonucleotide specifically hybridizes to SEQ ID NO: 1, 2, 3, 4 or 5, thereby ameliorating a symptom of metabolic syndrome in the human.

Further provided is a method for ameliorating a symptom of metabolic disease, comprising administering to a human in need thereof a compound comprising a modified oligonucleotide consisting of 12 to 30 linked nucleosides, wherein said modified oligonucleotide specifically hybridizes to SEQ ID NO: 1, 2, 3, 4 or 5, thereby ameliorating a symptom of metabolic disease in the human.

Further provided is a method for ameliorating a symptom of obesity, comprising administering to a human in need thereof a compound comprising a modified oligonucleotide consisting of 12 to 30 linked nucleosides, wherein said modified oligonucleotide specifically hybridizes to SEQ ID NO: 1, 2, 3, 4 or 5, thereby ameliorating a symptom of obesity in the human.

Further provided is a method for ameliorating a symptom of diabetes, comprising administering to a human in need thereof a compound comprising a modified oligonucleotide consisting of 12 to 30 linked nucleosides, wherein said modified oligonucleotide specifically hybridizes to SEQ ID NO: 1, 2, 3, 4 or 5, thereby ameliorating a symptom of diabetes in the human.

Further provided is a method for ameliorating a symptom of metabolic syndrome, comprising administering to a human in need thereof a compound comprising a modified oligonucleotide consisting of 12 to 30 linked nucleosides, wherein said modified oligonucleotide specifically hybridizes to SEQ ID NO: 1, 2, 3, 4 or 5, thereby ameliorating a symptom of metabolic syndrome in the human.

Further provided is a method for ameliorating a symptom of metabolic disease, comprising administering to a human in need thereof a compound comprising a modified oligonucleotide consisting of 20 linked nucleosides, wherein said modified oligonucleotide specifically hybridizes to SEQ ID NO: 1, 2, 3, 4 or 5, thereby ameliorating a symptom of metabolic disease in the human.

Further provided is a method for ameliorating a symptom of obesity, comprising administering to a human in need thereof a compound comprising a modified oligonucleotide consisting of 20 linked nucleosides, wherein said modified oligonucleotide specifically hybridizes to SEQ ID NO: 1, 2, 3, 4 or 5, thereby ameliorating a symptom of obesity in the human.

Further provided is a method for ameliorating a symptom of diabetes, comprising administering to a human in need thereof a compound comprising a modified oligonucleotide consisting of 20 linked nucleosides, wherein said modified oligonucleotide specifically hybridizes to SEQ ID NO: 1, 2, 3, 4 or 5, thereby ameliorating a symptom of diabetes in the human.

Further provided is a method for ameliorating a symptom of metabolic syndrome, comprising administering to a human in need thereof a compound comprising a modified oligonucleotide consisting of 20 linked nucleosides, wherein said modified oligonucleotide specifically hybridizes to SEQ ID NO: 1, 2, 3, 4 or 5, thereby ameliorating a symptom of metabolic syndrome in the human.

Further provided is a method for reducing the rate of progression of a symptom associated with metabolic disease, comprising administering to a human in need thereof a compound comprising a modified oligonucleotide consisting of 20 to 35 linked nucleosides, wherein said modified oligonucleotide specifically hybridizes to SEQ ID NO: 1, 2, 3, 4 or 5, thereby reducing the rate of progression a symptom of metabolic disease in the human.

Further provided is a method for reducing the rate of progression of a symptom associated with obesity, comprising administering to a human in need thereof a compound comprising a modified oligonucleotide consisting of 20 to 35 linked nucleosides, wherein said modified oligonucleotide specifically hybridizes to SEQ ID NO: 1, 2, 3, 4 or 5, thereby reducing the rate of progression a symptom of obesity in the human.

Further provided is a method for reducing the rate of progression of a symptom associated with diabetes, comprising administering to a human in need thereof a compound comprising a modified oligonucleotide consisting of 20 to 35 linked nucleosides, wherein said modified oligonucleotide specifically hybridizes to SEQ ID NO: 1, 2, 3, 4 or 5, thereby reducing the rate of progression a symptom of diabetes in the human.

Further provided is a method for reducing the rate of progression of a symptom associated with metabolic syndrome, comprising administering to a human in need thereof a compound comprising a modified oligonucleotide consisting of 20 to 35 linked nucleosides, wherein said modified oligonucleotide specifically hybridizes to SEQ ID NO: 1, 2, 3, 4 or 5, thereby reducing the rate of progression a symptom of metabolic syndrome in the human.

Further provided is a method for reducing the rate of progression of a symptom associated with metabolic disease, comprising administering to a human in need thereof a compound comprising a modified oligonucleotide consisting of 12 to 30 linked nucleosides, wherein said modified oligonucleotide specifically hybridizes to SEQ ID NO: 1, 2, 3, 4 or 5, thereby reducing the rate of progression a symptom of metabolic disease in the human.

Further provided is a method for reducing the rate of progression of a symptom associated with obesity, comprising administering to a human in need thereof a compound comprising a modified oligonucleotide consisting of 12 to 30 linked nucleosides, wherein said modified oligonucleotide specifically hybridizes to SEQ ID NO: 1, 2, 3, 4 or 5, thereby reducing the rate of progression a symptom of obesity in the human.

Further provided is a method for reducing the rate of progression of a symptom associated with diabetes, comprising administering to a human in need thereof a compound comprising a modified oligonucleotide consisting of 12 to 30 linked nucleosides, wherein said modified oligonucleotide specifically hybridizes to SEQ ID NO: 1, 2, 3, 4 or 5, thereby reducing the rate of progression a symptom of diabetes in the human.

Further provided is a method for reducing the rate of progression of a symptom associated with metabolic syndrome, comprising administering to a human in need thereof a compound comprising a modified oligonucleotide consisting of 12 to 30 linked nucleosides, wherein said modified oligonucleotide specifically hybridizes to SEQ ID NO: 1, 2, 3, 4 or 5, thereby reducing the rate of progression a symptom of metabolic syndrome in the human.

Further provided is a method for reducing the rate of progression of a symptom associated with metabolic disease, comprising administering to a human in need thereof a compound comprising a modified oligonucleotide consisting of 20 linked nucleosides, wherein said modified oligonucleotide specifically hybridizes to SEQ ID NO: 1, 2, 3, 4 or 5, thereby reducing the rate of progression a symptom of metabolic disease in the human.

Further provided is a method for reducing the rate of progression of a symptom associated with obesity, comprising administering to a human in need thereof a compound comprising a modified oligonucleotide consisting of 20 linked nucleosides, wherein said modified oligonucleotide specifically hybridizes to SEQ ID NO: 1, 2, 3, 4 or 5, thereby reducing the rate of progression a symptom of obesity in the human.

Further provided is a method for reducing the rate of progression of a symptom associated with diabetes, comprising administering to a human in need thereof a compound comprising a modified oligonucleotide consisting of 20 linked nucleosides, wherein said modified oligonucleotide specifically hybridizes to SEQ ID NO: 1, 2, 3, 4 or 5, thereby reducing the rate of progression a symptom of diabetes in the human.

Further provided is a method for reducing the rate of progression of a symptom associated with metabolic syndrome, comprising administering to a human in need thereof a compound comprising a modified oligonucleotide consisting of 20 linked nucleosides, wherein said modified oligonucleotide specifically hybridizes to SEQ ID NO: 1, 2, 3, 4 or 5, thereby reducing the rate of progression a symptom of metabolic syndrome in the human.

Also provided are methods and compounds for the preparation of a medicament for the treatment, prevention, or amelioration of metabolic disease.

Also provided are methods and compounds for the preparation of a medicament for the treatment, prevention, or amelioration of obesity.

Also provided are methods and compounds for the preparation of a medicament for the treatment, prevention, or amelioration of diabetes.

Also provided are methods and compounds for the preparation of a medicament for the treatment, prevention, or amelioration of metabolic syndrome.

Certain embodiments provide the use of a compound as described herein in the manufacture of a medicament for treating, ameliorating, or preventing metabolic disease.

Certain embodiments provide the use of a compound as described herein in the manufacture of a medicament for treating, ameliorating, or preventing obesity.

Certain embodiments provide the use of a compound as described herein in the manufacture of a medicament for treating, ameliorating, or preventing diabetes.

Certain embodiments provide the use of a compound as described herein in the manufacture of a medicament for treating, ameliorating, or preventing metabolic syndrome.

Certain embodiments provide a compound as described herein for use in treating, preventing, or ameliorating metabolic disease as described herein by combination therapy with an additional agent or therapy as described herein. Agents or therapies can be co-administered or administered concomitantly.

Certain embodiments provide a compound as described herein for use in treating, preventing, or ameliorating diabetes as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating metabolic disease as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating obesity as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating diabetes as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating diabetes as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating metabolic disease as described herein in a patient who is subsequently administered an additional agent or therapy as described herein.

Certain embodiments provide the use of a compound as described herein in the manufacture of a medicament for treating, preventing, or ameliorating obesity as described herein in a patient who is subsequently administered an additional agent or therapy as described herein.

Certain embodiments provide the use of a compound as described herein in the manufacture of a medicament for treating, preventing, or ameliorating diabetes as described herein in a patient who is subsequently administered an additional agent or therapy as described herein.

Certain embodiments provide the use of a compound as described herein in the manufacture of a medicament for treating, preventing, or ameliorating metabolic syndrome as described herein in a patient who is subsequently administered an additional agent or therapy as described herein.

Certain embodiments provide a kit for treating, preventing, or ameliorating metabolic disease as described herein wherein the kit comprises:
(i) a compound as described herein; and alternatively
(ii) an additional agent or therapy as described herein.

Certain embodiments provide a kit for treating, preventing, or ameliorating obesity as described herein wherein the kit comprises:
(i) a compound as described herein; and alternatively
(ii) an additional agent or therapy as described herein.

Certain embodiments provide a kit for treating, preventing, or ameliorating diabetes as described herein wherein the kit comprises:
(i) a compound as described herein; and alternatively
(ii) an additional agent or therapy as described herein.

Certain embodiments provide a kit for treating, preventing, or ameliorating metabolic syndrome as described herein wherein the kit comprises:
(i) a compound as described herein; and alternatively
(ii) an additional agent or therapy as described herein.

A kit as described herein may further include instructions for using the kit to treat, prevent, or ameliorate metabolic disease as described herein by combination therapy as described herein. In certain embodiments, the metabolic disease is obesity. In certain embodiments, the metabolic disease is diabetes.

In certain embodiments, a biomarker of the anti-obesity effect of an FGFR4 inhibitor is an increase in FGF15 and/or FGF19 protein levels. In certain embodiments, a biomarker of FGFR4 antisense oligonucleotide-caused anti-obesity effect is an increase in FGF15 and/or FGF19 gene expression levels. In certain embodiments, a biomarker of FGFR4 antisense oligonucleotide-caused anti-obesity effect is an increase in FGF15 and/or FGF19 protein levels. In certain embodiments, a biomarker of FGFR4 antisense oligonucleotide-caused anti-obesity effect is an increase in FGF15 and/or FGF19 gene expression levels. In certain embodiments, the FGF15 and/or FGF19 nucleic acid is any of the sequences set forth in GENBANK Accession No. NM_008003.2 (incorporated herein as SEQ ID NO: 345), GENBANK Accession No: XM_001100825.1 (incorporated herein as SEQ ID NO: 346); and GENBANK Accession No. NM_005117.1 (incorporated herein as SEQ ID NO: 347).

Certain embodiments provide methods of detecting the anti-obesity effect of a FGFR4 inhibitor in an animal by measuring an increase in ileum FGF15 and/or ileum FGF19 gene expression and plasma FGF15 and/or plasma FGF19 protein levels.

Certain embodiments provide methods for predicting responsiveness of an animal to an FGFR4 inhibitor by measuring an increase in ileum FGF15 and/or ileum FGF19 gene expression and plasma FGF15 and/or plasma FGF19 protein levels.

Certain embodiments provide methods of detecting the anti-obesity effect of a FGFR4 inhibitor in an animal comprising: (a) measuring FGF15 gene expression in an individual prior to administration of a FGFR4 inhibitor (b) administering an FGFR4 inhibitor (c) measuring FGF15 gene expression after administration of a FGFR4 inhibitor (d) detecting an increase of FGF15 gene expression. In certain embodiments, the FGFR4 inhibitor is a modified antisense oligonucleotide targeted to FGFR4.

Certain embodiments provide methods of detecting the anti-obesity effect of a FGFR4 inhibitor in an animal comprising: (a) measuring FGF19 gene expression in an individual prior to administration of a FGFR4 inhibitor (b) administering an FGFR4 inhibitor (c) measuring FGF19 gene expression after administration of a FGFR4 inhibitor (d) detecting an increase of FGF19 gene expression. In certain embodiments, the FGFR4 inhibitor is a modified antisense oligonucleotide targeted to FGFR4.

Certain embodiments provide methods of detecting the anti-obesity effect of a FGFR4 inhibitor in an animal comprising: (a) measuring FGF15 protein levels in an individual prior to administration of a FGFR4 inhibitor (b) administering an FGFR4 inhibitor (c) measuring FGF15 protein levels after administration of a FGFR4 inhibitor (d) detecting an increase of FGF15 protein levels. In certain embodiments, the FGFR4 inhibitor is a modified antisense oligonucleotide targeted to FGFR4.

Certain embodiments provide methods of detecting the anti-obesity effect of a FGFR4 inhibitor in an animal comprising: (a) measuring FGF19 protein levels in an individual prior to administration of a FGFR4 inhibitor (b) administering an FGFR4 inhibitor (c) measuring FGF19 protein levels after administration of a FGFR4 inhibitor (d) detecting an increase of FGF19 protein levels. In certain embodiments, the FGFR4 inhibitor is a modified antisense oligonucleotide targeted to FGFR4.

Certain embodiments provide methods for predicting responsiveness of an animal to an FGFR4 inhibitor comprising: (a) measuring FGF15 gene expression in an individual prior to administration of a FGFR4 inhibitor (b) administering an FGFR4 inhibitor (c) measuring FGF15 gene expression after administration of a FGFR4 inhibitor (d) detecting an increase of FGF15 gene expression. In certain embodiments, the FGFR4 inhibitor is a modified antisense oligonucleotide targeted to FGFR4.

Certain embodiments provide methods for predicting responsiveness of an animal to an FGFR4 inhibitor comprising: (a) measuring FGF19 gene expression in an individual prior to administration of a FGFR4 inhibitor (b) administering an FGFR4 inhibitor (c) measuring FGF19 gene expression after administration of a FGFR4 inhibitor (d) detecting an increase of FGF19 gene expression. In certain embodiments, the FGFR4 inhibitor is a modified antisense oligonucleotide targeted to FGFR4.

Certain embodiments provide methods for predicting responsiveness of an animal to an FGFR4 inhibitor comprising: (a) measuring FGF15 protein levels in an individual prior to administration of a FGFR4 inhibitor (b) administering an FGFR4 inhibitor (c) measuring FGF15 protein levels after administration of a FGFR4 inhibitor (d) detecting an increase of FGF15 protein levels. In certain embodiments, the FGFR4 inhibitor is a modified antisense oligonucleotide targeted to FGFR4.

Certain embodiments provide methods for predicting responsiveness of an animal to an FGFR4 inhibitor comprising: (a) measuring FGF19 protein levels in an individual prior to administration of a FGFR4 inhibitor (b) administering an FGFR4 inhibitor (c) measuring FGF19 protein levels after administration of a FGFR4 inhibitor (d) detecting an increase of FGF19 protein levels. In certain embodiments, the FGFR4 inhibitor is a modified antisense oligonucleotide targeted to FGFR4.

Certain embodiments provide a method for treating a metabolic disease, including obesity, diabetes, hyperglycemia, prediabetes, non-alcoholic fatty liver disease (NAFLD), metabolic syndrome, insulin resistance, diabetic dyslipidemia, or hypertriglyceridemia or a combination thereof, comprising administering a first dose of a compound or composition as described herein to a subject having a baseline level of FGF15 or FGF19 mRNA or protein in the blood or a tissue and administering one or more additional doses of the compound or composition to the subject until the level of FGF15 or FGF19 in the blood or a tissue is not increased from the baseline level by a certain extent for a certain amount of time.

In some aspects, one or more additional doses of the compound or composition described herein is administered to the subject until the level of FGF15 or FGF19 mRNA or protein in the blood or a tissue is not increased from the baseline level for at least about one week, two weeks, three weeks, four weeks, five weeks, six weeks, seven weeks, eight weeks, nine weeks, ten weeks, eleven weeks, twelve weeks, thirteen weeks, fourteen weeks, fifteen weeks, sixteen weeks, seventeen weeks, eighteen weeks, nineteen weeks, twenty weeks, twenty-one weeks, twenty-two weeks, twenty-three weeks, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, or fifty weeks.

In certain aspects, one or more additional doses of the compound or composition described herein is administered to the subject until the level of FGF15 or FGF19 mRNA or protein in the blood or a tissue is not increased from the baseline level by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103% 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, 151%, 152%, 153%, 154%, 155%, 156%, 157%, 158%, 159%, 160%, 161%, 162%, 163%, 164%, 165%, 166%, 167%, 168%, 169%, 170%, 171%, 172%, 173%, 174%, 175%, 176%, 177%, 178%, 179%, 180%, 181%, 182%, 183%, 184%, 185%, 186%, 187%, 188%, 189%, 190%, 191%, 192%, 193%, 194%, 195%, 196%, 197%, 198%, 199%, 200%, 300%, 400%, 500%, 600%, 700%, 800%, 900%, 1,000%, or any value in between any of the aforementioned percentages.

Administration of one or more additional doses of the compound or composition described herein can continue until such increases in the level of FGF15 or FGF19 mRNA or protein in the blood or a tissue relative to the baseline level does not occur for at least about one week, two weeks, three weeks, four weeks, five weeks, six weeks, seven weeks, eight weeks, nine weeks, ten weeks, eleven weeks, twelve weeks, thirteen weeks, fourteen weeks, fifteen weeks, sixteen weeks, seventeen weeks, eighteen weeks, nineteen weeks, twenty weeks, twenty-one weeks, twenty-two weeks, twenty-three weeks, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, or fifty weeks. In several aspects, each dose of compound or composition described herein can be about 50-2000 mg, about 50-400 mg, about 50-200 mg, about 50-100 mg, about 100-200 mg, or any amount in between any of the aforementioned ranges.

In certain aspects, one or more additional doses of the compound or composition described herein is administered to the subject until the level of FGF15 or FGF19 protein in the blood or a tissue is not increased from the baseline level by at least about 1 pg/mL, 5 pg/mL, 10 pg/mL, 15 pg/mL, 20 pg/mL, 25 pg/mL, 30 pg/mL, 35 pg/mL, 40 pg/mL, 45 pg/mL, 50 pg/mL, 55 pg/mL, 60 pg/mL, 65 pg/mL, 70 pg/mL, 75 pg/mL, 80 pg/mL, 85 pg/mL, 90 pg/mL, 95 pg/mL, 100 pg/mL, 105 pg/mL, 110 pg/mL, 115 pg/mL, 120 pg/mL, 125 pg/mL, 130 pg/mL, 135 pg/mL, 140 pg/mL, 145 pg/mL, 150 pg/mL, 155 pg/mL, 160 pg/mL, 165 pg/mL, 170 pg/mL, 175 pg/mL, 180 pg/mL, 185 pg/mL, 190 pg/mL, 195 pg/mL, 200 pg/mL, 205 pg/mL, 210 pg/mL, 215 pg/mL, 220 pg/mL, 225 pg/mL, 230 pg/mL, 235 pg/mL, 240 pg/mL, 245 pg/mL, 250 pg/mL, 255 pg/mL, 260 pg/mL, 265 pg/mL, 270 pg/mL, 275 pg/mL, 280 pg/mL, 290 pg/mL, 295 pg/mL, 300 pg/mL, 350 pg/mL, 400 pg/mL, 450 pg/mL, 500 pg/mL, 550 pg/mL, 600 pg/mL, 650 pg/mL, 700 pg/mL, 750 pg/mL, 800 pg/mL, 850 pg/mL, 900 pg/mL, 950 pg/mL, 1,000 pg/mL, 2,000 pg/mL, or any value in between any of the aforementioned concentrations. Administration of one or more additional doses of the compound or composition described herein can continue until such increases in the level of FGF15 or FGF19 protein in the blood or a tissue relative to the baseline level does not occur for at least about one week, two weeks, three weeks, four weeks, five weeks, six weeks, seven weeks, eight weeks, nine weeks, ten weeks, eleven weeks, twelve weeks, thirteen weeks, fourteen weeks, fifteen weeks, sixteen weeks, seventeen weeks, eighteen weeks, nineteen weeks, twenty weeks, twenty-one weeks, twenty-two weeks, twenty-three weeks, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, or fifty weeks. In several aspects, each dose of compound or composition described herein can be about 50-2000 mg, about 50-400 mg, about 50-200 mg, about 50-100 mg, about 100-200 mg, or any amount in between any of the aforementioned ranges.

It will be understood that one or more doses of the compound or composition described herein can be administered during the aforementioned time periods. For example, a subject may have been administered one or more doses of the compound or composition described herein during the at least about one week, two weeks, three weeks, four weeks, five weeks, six weeks, seven weeks, eight weeks, nine weeks, ten weeks, eleven weeks, twelve weeks, thirteen weeks, fourteen weeks, fifteen weeks, sixteen weeks, seventeen weeks, eighteen weeks, nineteen weeks, twenty weeks, twenty-one weeks, twenty-two weeks, twenty-three weeks, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, or fifty weeks. In certain embodiments, additional doses of the compound or composition described herein are administered to the subject until the level of FGF15 or FGF19 mRNA or protein in the blood or a tissue is not increased from the baseline level by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103% 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, 151%, 152%, 153%, 154%, 155%, 156%, 157%, 158%, 159%, 160%, 161%, 162%, 163%, 164%, 165%, 166%, 167%, 168%, 169%, 170%, 171%, 172%, 173%, 174%, 175%, 176%, 177%, 178%, 179%, 180%, 181%, 182%, 183%, 184%, 185%, 186%, 187%, 188%, 189%, 190%, 191%, 192%, 193%, 194%, 195%, 196%, 197%, 198%, 199%, 200%, 300%, 400%, 500%, 600%, 700%, 800%, 900%, 1,000%, or any value in between any of the aforementioned percentages in the aforementioned time periods. In several aspects, each dose of compound or composition described herein can be about 50-2000 mg, about 50-400 mg, about 50-200 mg, about 50-100 mg, about 100-200 mg, or any amount in between any of the aforementioned ranges.

Various embodiments are directed to a method of treating a metabolic disease, including obesity, diabetes, hyperglycemia, prediabetes, non-alcoholic fatty liver disease (NAFLD), metabolic syndrome, insulin resistance, diabetic dyslipidemia, or hypertriglyceridemia or a combination thereof, comprising (a) obtaining the baseline level of FGF15 or FGF19 mRNA or protein in the blood or a tissue of a subject, (b) administering to the subject a dose of a compound or composition described herein, (c) obtaining the level of FGF15 or FGF19 mRNA or protein in the blood or a tissue after the administration of the compound or composition described herein; and (d) repeating steps (b) and (c) until the level of FGF15 or FGF19 mRNA or protein in the blood or a tissue does not increase by a certain extent for a certain amount of time relative to baseline.

In several aspects, steps (b) and (c) are repeated until the level of FGF15 or FGF19 mRNA or protein in the blood or a tissue does not increase relative to baseline for at least about one week, two weeks, three weeks, four weeks, five weeks, six weeks, seven weeks, eight weeks, nine weeks, ten weeks, eleven weeks, twelve weeks, thirteen weeks, fourteen weeks, fifteen weeks, sixteen weeks, seventeen weeks, eighteen weeks, nineteen weeks, twenty weeks, twenty-one weeks, twenty-two weeks, twenty-three weeks, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, or fifty weeks. In several aspects, each dose of compound or composition described herein can be about 50-2000 mg, about 50-400 mg, about 50-200 mg, about 50-100 mg, about 100-200 mg, or any amount in between any of the aforementioned ranges.

In certain aspects, one or more additional doses of the compound or composition described herein is administered to the subject until the level of FGF15 or FGF19 protein in the blood or a tissue is not increased from the baseline level by at least about 1 pg/mL, 5 pg/mL, 10 pg/mL, 15 pg/mL, 20 pg/mL, 25 pg/mL, 30 pg/mL, 35 pg/mL, 40 pg/mL, 45 pg/mL, 50 pg/mL, 55 pg/mL, 60 pg/mL, 65 pg/mL, 70 pg/mL, 75 pg/mL, 80 pg/mL, 85 pg/mL, 90 pg/mL, 95 pg/mL, 100 pg/mL, 105 pg/mL, 110 pg/mL, 115 pg/mL, 120 pg/mL, 125 pg/mL, 130 pg/mL, 135 pg/mL, 140 pg/mL, 145 pg/mL, 150 pg/mL, 155 pg/mL, 160 pg/mL, 165 pg/mL, 170 pg/mL, 175 pg/mL, 180 pg/mL, 185 pg/mL, 190 pg/mL, 195 pg/mL, 200 pg/mL, 205 pg/mL, 210 pg/mL, 215 pg/mL, 220 pg/mL, 225 pg/mL, 230 pg/mL, 235 pg/mL, 240 pg/mL, 245 pg/mL, 250 pg/mL, 255 pg/mL, 260 pg/mL, 265 pg/mL, 270 pg/mL, 275 pg/mL, 280 pg/mL, 290 pg/mL, 295 pg/mL, 300 pg/mL, 350 pg/mL, 400 pg/mL, 450 pg/mL, 500 pg/mL, 550 pg/mL, 600 pg/mL, 650 pg/mL, 700 pg/mL, 750 pg/mL, 800 pg/mL, 850 pg/mL, 900 pg/mL, 950 pg/mL, 1,000 pg/mL, 2,000 pg/mL, or any value in between any of the aforementioned concentrations. Administration of one or more additional doses of the compound or composition described herein can continue until such increases in the level of FGF15 or FGF19 protein in the blood or a tissue relative to the baseline level does not occur for at least about one week, two weeks, three weeks, four weeks, five weeks, six weeks, seven weeks, eight weeks, nine weeks, ten weeks, eleven weeks, twelve weeks, thirteen weeks, fourteen weeks, fifteen weeks, sixteen weeks, seventeen weeks, eighteen weeks, nineteen weeks, twenty weeks, twenty-one weeks, twenty-two weeks, twenty-three weeks, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, or fifty weeks. In several aspects, each dose of compound or composition described herein can be about 50-2000 mg, about 50-400 mg, about 50-200 mg, about 50-100 mg, about 100-200 mg, or any amount in between any of the aforementioned ranges.

In certain embodiments, a method of treating a metabolic disease and/or obesity comprises (a) obtaining the baseline level of FGF15 or FGF19 mRNA or protein in the blood or a tissue of a subject, (b) administering to the subject a dose of a compound or composition described herein, (c) obtaining the level of FGF15 or FGF19 mRNA or protein in the blood or a tissue after the administration of the compound or composition described herein; and (d) repeating steps (b) and (c) until the level of FGF15 or FGF19 mRNA or protein in the blood or a tissue does not increase by about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103% 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, 151%, 152%, 153%, 154%, 155%, 156%, 157%, 158%, 159%, 160%, 161%, 162%, 163%, 164%, 165%, 166%, 167%, 168%, 169%, 170%, 171%, 172%, 173%, 174%, 175%, 176%, 177%, 178%, 179%, 180%, 181%, 182%, 183%, 184%, 185%, 186%, 187%, 188%, 189%, 190%, 191%, 192%, 193%, 194%, 195%, 196%, 197%, 198%, 199%, 200%, 300%, 400%, 500%, 600%, 700%, 800%, 900%, 1,000%, or any value in between any of the aforementioned percentages relative to baseline for at least about one week, two weeks, three weeks, four weeks, five weeks, six weeks, seven weeks, eight weeks, nine weeks, ten weeks, eleven weeks, twelve weeks, thirteen weeks, fourteen weeks, fifteen weeks, sixteen weeks, seventeen weeks, eighteen weeks, nineteen weeks, twenty weeks, twenty-one weeks, twenty-two weeks, twenty-three weeks, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, or fifty weeks. In several aspects, each dose of compound or composition described herein can be about 50-2000 mg, about 50-400 mg, about 50-200 mg, about 50-100 mg, about 100-200 mg, or any amount in between any of the aforementioned ranges.

Certain embodiments provide a method for treating a metabolic disease, including obesity, diabetes, hyperglycemia, prediabetes, non-alcoholic fatty liver disease (NAFLD), metabolic syndrome, insulin resistance, diabetic dyslipidemia, or hypertriglyceridemia or a combination thereof, comprising administering a first dose of a compound or composition as described herein to a subject having a baseline level of FGF15 or FGF19 mRNA or protein in the blood or a tissue and administering one or more additional higher doses of the compound or composition to the subject until the level of FGF15 or FGF19 in the blood or a tissue is increased from the baseline level by a certain extent for a certain amount of time. In several aspects, such method further comprises administering additional doses of the compound or composition to the subject to maintain FGF15 or FGF19 mRNA or protein in the blood or a tissue at a certain level above the baseline level. It will be understood that the one or more additional higher doses can be relative to the first dose or the most recently administered additional higher dose.

In some aspects, one or more additional higher doses of the compound or composition described herein is administered to the subject until the level of FGF15 or FGF19 mRNA or protein in the blood or a tissue is increased from the baseline level for at least about one week, two weeks, three weeks, four weeks, five weeks, six weeks, seven weeks, eight weeks, nine weeks, ten weeks, eleven weeks, twelve weeks, thirteen weeks, fourteen weeks, fifteen weeks, sixteen weeks, seventeen weeks, eighteen weeks, nineteen weeks, twenty weeks, twenty-one weeks, twenty-two weeks, twenty-three weeks, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, or fifty weeks.

In several aspects, one or more additional higher doses of the compound or composition described herein is an amount at least about 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0 fold greater than the first dose or most recently administered additional higher dose. In certain aspects, each dose of compound or composition described herein can be about 50-2000 mg, about 50-400 mg, about 50-200 mg, about 50-100 mg, about 100-200 mg, or any amount in between any of the aforementioned ranges.

In certain aspects, one or more additional higher doses of the compound or composition described herein is administered to the subject until the level of FGF15 or FGF19 mRNA or protein in the blood or a tissue is increased from the baseline level by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103% 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, 151%, 152%, 153%, 154%, 155%, 156%, 157%, 158%, 159%, 160%, 161%, 162%, 163%, 164%, 165%, 166%, 167%, 168%, 169%, 170%, 171%, 172%, 173%, 174%, 175%, 176%, 177%, 178%, 179%, 180%, 181%, 182%, 183%, 184%, 185%, 186%, 187%, 188%, 189%, 190%, 191%, 192%, 193%, 194%, 195%, 196%, 197%, 198%, 199%, 200%, 300%, 400%, 500%, 600%, 700%, 800%, 900%, 1,000%, or any value in between any of the aforementioned percentages.

Administration of one or more additional higher doses of the compound or composition described herein can continue until such increases in the level of FGF15 or FGF19 mRNA or protein in the blood or a tissue relative to the baseline level occurs for at least about one week, two weeks, three weeks, four weeks, five weeks, six weeks, seven weeks, eight weeks, nine weeks, ten weeks, eleven weeks, twelve weeks, thirteen weeks, fourteen weeks, fifteen weeks, sixteen weeks, seventeen weeks, eighteen weeks, nineteen weeks, twenty weeks, twenty-one weeks, twenty-two weeks, twenty-three weeks, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, or fifty weeks. In certain aspects, additional doses of the compound or composition can be administered to the subject to maintain FGF15 or FGF19 mRNA or protein in the blood or a tissue at a certain level above the baseline level. In several aspects, each dose of compound or composition described herein can be about 50-2000 mg, about 50-400 mg, about 50-200 mg, about 50-100 mg, about 100-200 mg, or any amount in between any of the aforementioned ranges.

In certain aspects, one or more additional higher doses of the compound or composition described herein is administered to the subject until the level of FGF15 or FGF19 protein in the blood or a tissue is increased from the baseline level by at least about 1 pg/mL, 5 pg/mL, 10 pg/mL, 15 pg/mL, 20 pg/mL, 25 pg/mL, 30 pg/mL, 35 pg/mL, 40 pg/mL, 45 pg/mL, 50 pg/mL, 55 pg/mL, 60 pg/mL, 65 pg/mL, 70 pg/mL, 75 pg/mL, 80 pg/mL, 85 pg/mL, 90 pg/mL, 95 pg/mL, 100 pg/mL, 105 pg/mL, 110 pg/mL, 115 pg/mL, 120 pg/mL, 125 pg/mL, 130 pg/mL, 135 pg/mL, 140 pg/mL, 145 pg/mL, 150 pg/mL, 155 pg/mL, 160 pg/mL, 165 pg/mL, 170 pg/mL, 175 pg/mL, 180 pg/mL, 185 pg/mL, 190 pg/mL, 195 pg/mL, 200 pg/mL, 205 pg/mL, 210 pg/mL, 215 pg/mL, 220 pg/mL, 225 pg/mL, 230 pg/mL, 235 pg/mL, 240 pg/mL, 245 pg/mL, 250 pg/mL, 255 pg/mL, 260 pg/mL, 265 pg/mL, 270 pg/mL, 275 pg/mL, 280 pg/mL, 290 pg/mL, 295 pg/mL, 300 pg/mL, 350 pg/mL, 400 pg/mL, 450 pg/mL, 500 pg/mL, 550 pg/mL, 600 pg/mL, 650 pg/mL, 700 pg/mL, 750 pg/mL, 800 pg/mL, 850 pg/mL, 900 pg/mL, 950 pg/mL, 1,000 pg/mL, 2,000 pg/mL, or any value in between any of the aforementioned concentrations. Administration of one or more additional higher doses of the compound or composition described herein can continue until such increases in the level of FGF15 or FGF19 protein in the blood or a tissue relative to the baseline level occurs for at least about one week, two weeks, three weeks, four weeks, five weeks, six weeks, seven weeks, eight weeks, nine weeks, ten weeks, eleven weeks, twelve weeks, thirteen weeks, fourteen weeks, fifteen weeks, sixteen weeks, seventeen weeks, eighteen weeks, nineteen weeks, twenty weeks, twenty-one weeks, twenty-two weeks, twenty-three weeks, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, or fifty weeks. In certain aspects, additional doses of the compound or composition can be administered to the subject to maintain FGF15 or FGF19 protein in the blood or a tissue at any of the aforementioned concentrations above the baseline level. In several aspects, each dose of compound or composition described herein can be about 50-2000 mg, about 50-400 mg, about 50-200 mg, about 50-100 mg, about 100-200 mg, or any amount in between any of the aforementioned ranges.

It will be understood that one or more higher doses of the compound or composition described herein can be administered during the aforementioned time periods. For example, a subject may have been administered one or more doses of the compound or composition described herein during the at least about one week, two weeks, three weeks, four weeks, five weeks, six weeks, seven weeks, eight weeks, nine weeks, ten weeks, eleven weeks, twelve weeks, thirteen weeks, fourteen weeks, fifteen weeks, sixteen weeks, seventeen weeks, eighteen weeks, nineteen weeks, twenty weeks, twenty-one weeks, twenty-two weeks, twenty-three weeks, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, or fifty weeks. In certain embodiments, additional higher doses of the compound or composition described herein are administered to the subject until the level of FGF15 or FGF19 mRNA or protein in the blood or a tissue is increased from the baseline level by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103% 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, 151%, 152%, 153%, 154%, 155%, 156%, 157%, 158%, 159%, 160%, 161%, 162%, 163%, 164%, 165%, 166%, 167%, 168%, 169%, 170%, 171%, 172%, 173%, 174%, 175%, 176%, 177%, 178%, 179%, 180%, 181%, 182%, 183%, 184%, 185%, 186%, 187%, 188%, 189%, 190%, 191%, 192%, 193%, 194%, 195%, 196%, 197%, 198%, 199%, 200%, 300%, 400%, 500%, 600%, 700%, 800%, 900%, 1,000%, or any value in between any of the aforementioned percentages in the aforementioned time periods. In certain aspects, additional doses of the compound or composition can be administered to the subject to maintain FGF15 or FGF19 mRNA or protein in the blood or a tissue at any of the aforementioned increased levels above the baseline level. In several aspects, each dose of compound or composition described herein can be about 50-2000 mg, about 50-400 mg, about 50-200 mg, about 50-100 mg, about 100-200 mg, or any amount in between any of the aforementioned ranges.

In certain embodiments, a method of treating a metabolic disease, including obesity, diabetes, hyperglycemia, prediabetes, non-alcoholic fatty liver disease (NAFLD), metabolic syndrome, insulin resistance, diabetic dyslipidemia, or hypertriglyceridemia or a combination thereof, comprises (a) obtaining the baseline level of FGF15 or FGF19 mRNA or protein in the blood or a tissue of a subject, (b) administering to the subject a dose of a compound or composition described herein, (c) obtaining the level of FGF15 or FGF19 mRNA or protein in the blood or a tissue after the administration of the compound or composition described herein; and (d) repeating steps (b) and (c) until the level of FGF15 or FGF19 mRNA or protein in the blood or a tissue is increased by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103% 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, 151%, 152%, 153%, 154%, 155%, 156%, 157%, 158%, 159%, 160%, 161%, 162%, 163%, 164%, 165%, 166%, 167%, 168%, 169%, 170%, 171%, 172%, 173%, 174%, 175%, 176%, 177%, 178%, 179%, 180%, 181%, 182%, 183%, 184%, 185%, 186%, 187%, 188%, 189%, 190%, 191%, 192%, 193%, 194%, 195%, 196%, 197%, 198%, 199%, 200%, 300%, 400%, 500%, 600%, 700%, 800%, 900%, 1,000%, or any value in between any of the aforementioned percentages relative to the baseline level. In certain aspects, the dose administered in step (d) can be a higher dose than previously administered until the level of FGF15 or FGF19 mRNA or protein in the blood or a tissue is increased by any of the aforementioned percentages. In certain aspects, such method further comprises administering additional doses of the compound or composition to the subject to maintain FGF15 or FGF19 mRNA or protein in the blood or a tissue at any of the aforementioned increased levels above the baseline level. In several aspects, each dose of compound or composition described herein can be about 50-2000 mg, about 50-400 mg, about 50-200 mg, about 50-100 mg, about 100-200 mg, or any amount in between any of the aforementioned ranges.

In certain embodiments, a method of treating a metabolic disease, including obesity, diabetes, hyperglycemia, prediabetes, non-alcoholic fatty liver disease (NAFLD), metabolic syndrome, insulin resistance, diabetic dyslipidemia, or hypertriglyceridemia or a combination thereof, comprises (a) obtaining the baseline level of FGF15 or FGF19 protein in the blood or a tissue of a subject, (b) administering to the subject a dose of a compound or composition described herein, (c) obtaining the level of FGF15 or FGF19 protein in the blood or a tissue after the administration of the compound or composition described herein; and (d) repeating steps (b) and (c) until the level of FGF15 or FGF19 protein in the blood or a tissue is increased by at least about 1 pg/mL, 5 pg/mL, 10 pg/mL, 15 pg/mL, 20 pg/mL, 25 pg/mL, 30 pg/mL, 35 pg/mL, 40 pg/mL, 45 pg/mL, 50 pg/mL, 55 pg/mL, 60 pg/mL, 65 pg/mL, 70 pg/mL, 75 pg/mL, 80 pg/mL, 85 pg/mL, 90 pg/mL, 95 pg/mL, 100 pg/mL, 105 pg/mL, 110 pg/mL, 115 pg/mL, 120 pg/mL, 125 pg/mL, 130 pg/mL, 135 pg/mL, 140 pg/mL, 145 pg/mL, 150 pg/mL, 155 pg/mL, 160 pg/mL, 165 pg/mL, 170 pg/mL, 175 pg/mL, 180 pg/mL, 185 pg/mL, 190 pg/mL, 195 pg/mL, 200 pg/mL, 205 pg/mL, 210 pg/mL, 215 pg/mL, 220 pg/mL, 225 pg/mL, 230 pg/mL, 235 pg/mL, 240 pg/mL, 245 pg/mL, 250 pg/mL, 255 pg/mL, 260 pg/mL, 265 pg/mL, 270 pg/mL, 275 pg/mL, 280 pg/mL, 290 pg/mL, 295 pg/mL, 300 pg/mL, 350 pg/mL, 400 pg/mL, 450 pg/mL, 500 pg/mL, 550 pg/mL, 600 pg/mL, 650 pg/mL, 700 pg/mL, 750 pg/mL, 800 pg/mL, 850 pg/mL, 900 pg/mL, 950 pg/mL, 1,000 pg/mL, 2,000 pg/mL, or any value in between any of the aforementioned concentrations. In certain aspects, the dose administered in step (d) can be a higher dose than previously administered until the level of FGF15 or FGF19 mRNA or protein in the blood or a tissue is increased by any of the aforementioned percentages. In certain aspects, such method further comprises administering additional doses of the compound or composition to the subject to maintain FGF15 or FGF19 protein in the blood or a tissue at any of the aforementioned increased concentrations above the baseline level. In several aspects, each dose of compound or composition described herein can be about 50-2000 mg, about 50-400 mg, about 50-200 mg, about 50-100 mg, about 100-200 mg, or any amount in between any of the aforementioned ranges.

The level of FGF15 or FGF19 mRNA or protein in a blood or a tissue, such as liver tissue, may be obtained by several known assays. For instance, FGF15 or FGF19 mRNA levels can be obtained by quantitative RT-PCR. FGF15 or FGF19 protein levels can be obtained, for example, by using any of a number of well recognized immunological binding assays such as, but not limited to, an enzyme linked immunosorbent assay (ELISA), which is also known as a "sandwich assay", an enzyme immunoassay, a radioimmunoassay (RIA), a fluoroimmunoassay (FIA), a chemiluminescent immunoassay (CLIA) a counting immunoassay (CIA), a filter media enzyme immunoassay (MEIA), or a fluorescence-linked immunosorbent assay (FLISA). Several commercial antibodies against FGF15 or FGF19 mRNA or protein are suitable for obtaining the level of FGF15 or FGF19 mRNA or protein in a blood or a tissue. Such commercially available antibodies can be obtained from Abcam or Santa Cruz Biotechnology, for example. FGF15 or FGF19 protein levels can be also be obtained by high performance liquid chromatography (HPLC), mass spectrometry, or surface plasmon resonance.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a FGFR4 nucleic acid is 12 to 30 nucleotides in length. In other words, antisense compounds are from 12 to 30 linked nucleobases. In other embodiments, the antisense compound comprises a modified oligonucleotide consisting of 8 to 80, 10 to 50, 15 to 30, 18 to 21, 20 to 80, 20 to 35, 20 to 30, 20 to 29, 20 to 28, 20 to 27, 20 to 26, 20 to 25, 20 to 24, 20 to 23, 20 to 22, 20 to 21 or 20 linked nucleobases. In certain such embodiments, the antisense compound comprises a modified oligonucleotide consisting of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked nucleobases in length, or a range defined by any two of the above values.

In certain embodiments, the antisense compound comprises a shortened or truncated modified oligonucleotide. The shortened or truncated modified oligonucleotide can have a single nucleoside deleted from the 5' end (5' truncation), or alternatively from the 3' end (3' truncation). A shortened or truncated oligonucleotide may have two nucleosides deleted from the 5' end, or alternatively may have two subunits deleted from the 3' end. Alternatively, the deleted nucleosides may be dispersed throughout the modified oligonucleotide, for example, in an antisense compound having one nucleoside deleted from the 5' end and one nucleoside deleted from the 3' end.

When a single additional nucleoside is present in a lengthened oligonucleotide, the additional nucleoside may be located at the 5' or 3' end of the oligonucleotide. When two or more additional nucleosides are present, the added nucleosides may be adjacent to each other, for example, in an oligonucleotide having two nucleosides added to the 5' end (5' addition), or alternatively to the 3' end (3' addition), of the oligonucleotide. Alternatively, the added nucleoside may be dispersed throughout the antisense compound, for example, in an oligonucleotide having one nucleoside added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a FGFR4 nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE and 2'-O—CH$_3$, among others), and bicyclic sugar modified nucleosides (such bicyclic sugar modified nucleosides may include those having a constrained ethyl). In certain embodiments, wings may include several modified sugar moieties, including, for example 2'-MOE and constrained ethyl. In certain embodiments, wings may include several modified and unmodified sugar moieties. In certain embodiments, wings may include various combinations of 2'-MOE nucleosides, constrained ethyl nucleosides, and 2'-deoxynucleosides.

Each distinct region may comprise uniform sugar moieties, variant, or alternating sugar moieties. The wing-gap-wing motif is frequently described as "X—Y—Z", where "X" represents the length of the 5'-wing, "Y" represents the length of the gap, and "Z" represents the length of the 3'-wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X—Y—Z" has a configuration such that the gap is positioned immediately adjacent to each of the 5'-wing and the 3' wing. Thus, no intervening nucleotides exist between the 5'-wing and gap, or the gap and the 3'-wing. Any of the antisense compounds described herein can have a gapmer motif. In certain embodiments, "X" and "Z" are the same, in other embodiments they are different. In certain embodiments, "Y" is between 8 and 15 nucleosides. X, Y, or Z can be any of 1, 2, 3, 4, 5, 6, 7, 8, 9, 10, 11, 12, 13, 14, 15, 16, 17, 18, 19, 20, 25, 30 or more nucleosides.

In certain embodiments, antisense compounds targeted to a FGFR4 nucleic acid possess a 5-10-5 gapmer motif.

In certain embodiments, antisense compounds targeted to a FGFR4 nucleic acid possess a 3-10-4 gapmer motif.

Target Nucleic Acids, Target Regions and Nucleotide Sequences

In certain embodiments, the FGFR4 nucleic acid is any of the sequences set forth in GENBANK Accession No. NM_002011.3 (incorporated herein as SEQ ID NO: 1), GENBANK Accession No: NT_023133.11 truncated from nucleosides 21323018 to 21335213 (incorporated herein as SEQ ID NO: 2); GENBANK Accession No. AB209631.1 (incorporated herein as SEQ ID NO: 3) and GENBANK Accession No NM_022963.2 (incorporated herein as SEQ ID NO: 4). In certain embodiments, FGFR4 has the rhesus monkey sequence as set forth in GENBANK Accession No. NW_001121000.1 truncated from nucleosides 3094000 to 3109000 (SEQ ID NO: 5). In certain embodiments, FGFR4 has the murine sequence as set forth in GENBANK Accession No. BC033313.1 (SEQ ID NO: 6).

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for FGFR4 can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in FGFR4 mRNA levels are indicative of inhibition of FGFR4 expression. Reductions in levels of a FGFR4 protein are also indicative of inhibition of target mRNA expression. Further, phenotypic changes are indicative of inhibition of FGFR4 expression. In certain embodiments, reduced glucose levels, reduced lipid levels, and reduced body weight can be indicative of inhibition of FGFR4 expression. In certain embodiments, amelioration of symptoms associated with metabolic disease can be indicative of inhibition of FGFR4 expression. In certain embodiments, amelioration of symptoms associated with diabetes can be indicative of inhibition of FGFR4 expression. In certain embodiments, reduction of insulin resistance is indicative of inhibition of FGFR4 expression. In certain embodiments, reduction of diabetes biomarkers can be indicative of inhibition of FGFR4 expression. In certain embodiments, reduction of FGFR4 expression is accompanied by an increase in FGF15 and/or FGF19 gene expression and/or an increase in FGF15 and/or FGF19 protein levels. In certain embodiments, reduction of FGFR4 expression is accompanied by an increase in ileum FGF15 and/or ileum FGF19 gene expression and plasma FGF15 and/or plasma FGF19 protein levels. Therefore, certain embodiments provide methods of measuring reduction of FGFR expression by measuring an increase in ileum FGF15 and/or ileum FGF19 gene expression and plasma FGF15 and/or plasma FGF19 protein levels.

In certain embodiments, a biomarker of the anti-obesity effect of an FGFR4 inhibitor is an increase in FGF15 and/or FGF19 gene expression levels. In certain embodiments, a biomarker of the anti-obesity effect of an FGFR4 inhibitor is an increase in FGF15 and/or FGF19 protein levels. In certain embodiments, a biomarker of FGFR4 antisense oligonucleotide-caused anti-obesity effect is an increase in FGF15 and/or FGF19 gene expression levels. In certain embodiments, a biomarker of FGFR4 antisense oligonucleotide-caused anti-obesity effect is an increase in FGF15 and/or FGF19 protein levels. In certain embodiments, a biomarker of FGFR4 antisense oligonucleotide-caused anti-obesity effect is an increase in FGF15 and/or FGF19 gene expression levels.

Certain embodiments provide methods of detecting the anti-obesity effect of a FGFR4 inhibitor in an animal by measuring an increase in ileum FGF15 and/or ileum FGF19 gene expression and plasma FGF15 and/or plasma FGF19 protein levels.

Certain embodiments provide methods of detecting the anti-obesity effect of a FGFR4 inhibitor in an animal comprising: (a) measuring FGF15 gene expression in an individual prior to administration of a FGFR4 inhibitor (b) administering an FGFR4 inhibitor (c) measuring FGF15 gene expression after administration of a FGFR4 inhibitor (d) detecting an increase of FGF15 gene expression. In certain embodiments, the FGFR4 inhibitor is a modified antisense oligonucleotide targeted to FGFR4.

Certain embodiments provide methods of detecting the anti-obesity effect of a FGFR4 inhibitor in an animal comprising: (a) measuring FGF19 gene expression in an individual prior to administration of a FGFR4 inhibitor (b) administering an FGFR4 inhibitor (c) measuring FGF19 gene expression after administration of a FGFR4 inhibitor (d) detecting an increase of FGF19 gene expression. In certain embodiments, the FGFR4 inhibitor is a modified antisense oligonucleotide targeted to FGFR4.

Certain embodiments provide methods of detecting the anti-obesity effect of a FGFR4 inhibitor in an animal comprising: (a) measuring FGF15 protein levels in an individual prior to administration of a FGFR4 inhibitor (b) administering an FGFR4 inhibitor (c) measuring FGF15 protein levels after administration of a FGFR4 inhibitor (d) detecting an increase of FGF15 protein levels. In certain embodiments, the FGFR4 inhibitor is a modified antisense oligonucleotide targeted to FGFR4.

Certain embodiments provide methods of detecting the anti-obesity effect of a FGFR4 inhibitor in an animal comprising: (a) measuring FGF19 protein levels in an individual prior to administration of a FGFR4 inhibitor (b) administering an FGFR4 inhibitor (c) measuring FGF19 protein levels after administration of a FGFR4 inhibitor (d) detecting an increase of FGF19 protein levels. In certain embodiments, the FGFR4 inhibitor is a modified antisense oligonucleotide targeted to FGFR4.

Certain embodiments provide methods for predicting responsiveness of an animal to an FGFR4 inhibitor comprising: (a) measuring FGF15 gene expression in an individual prior to administration of a FGFR4 inhibitor (b) administering an FGFR4 inhibitor (c) measuring FGF15 gene expression after administration of a FGFR4 inhibitor (d) detecting an increase of FGF15 gene expression. In certain embodiments, the FGFR4 inhibitor is a modified antisense oligonucleotide targeted to FGFR4.

Certain embodiments provide methods for predicting responsiveness of an animal to an FGFR4 inhibitor comprising: (a) measuring FGF19 gene expression in an individual prior to administration of a FGFR4 inhibitor (b) administering an FGFR4 inhibitor (c) measuring FGF19 gene expression after administration of a FGFR4 inhibitor (d) detecting an increase of FGF19 gene expression. In certain embodiments, the FGFR4 inhibitor is a modified antisense oligonucleotide targeted to FGFR4.

Certain embodiments provide methods for predicting responsiveness of an animal to an FGFR4 inhibitor by measuring an increase in ileum FGF15 and/or ileum FGF19 gene expression and plasma FGF15 and/or plasma FGF19 protein levels.

Certain embodiments provide methods for predicting responsiveness of an animal to an FGFR4 inhibitor comprising: (a) measuring FGF15 protein levels in an individual prior to administration of a FGFR4 inhibitor (b) administering an FGFR4 inhibitor (c) measuring FGF15 protein levels after administration of a FGFR4 inhibitor (d) detecting an increase of FGF15 protein levels. In certain embodiments, the FGFR4 inhibitor is a modified antisense oligonucleotide targeted to FGFR4.

Certain embodiments provide methods for predicting responsiveness of an animal to an FGFR4 inhibitor comprising: (a) measuring FGF19 protein levels in an individual prior to administration of a FGFR4 inhibitor (b) administering an FGFR4 inhibitor (c) measuring FGF19 protein levels after administration of a FGFR4 inhibitor (d) detecting an increase of FGF19 protein levels. In certain embodiments, the FGFR4 inhibitor is a modified antisense oligonucleotide targeted to FGFR4.

Hybridization

In some embodiments, hybridization occurs between an antisense compound disclosed herein and a FGFR4 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a FGFR4 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a FGFR4 nucleic acid).

An antisense compound may hybridize over one or more segments of a FGFR4 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a FGFR4 nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. As such, an antisense compound which is 18 nucleobases in length having 4 (four) non-complementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, antisense compound may be fully complementary to a FGFR4 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a FGFR4 nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a FGFR4 nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 12 nucleobase portion of a target segment. In certain embodiments, the antisense compounds are complementary to at least a 13 nucleobase portion of a target segment. In certain embodiments, the antisense compounds are complementary to at least a 14 nucleobase portion of a target segment. In certain embodiments, the antisense compounds are complementary to at least a 15 nucleobase portion of a target segment. In certain embodiments, the antisense compounds are complementary to at least a 16 nucleobase portion of a target segment. In certain embodiments, the antisense compounds are complementary to at least a 17 nucleobase portion of a target segment. In certain embodiments, the antisense compounds are complementary to at least a 18 nucleobase portion of a target segment. In certain embodiments, the antisense compounds are complementary to at least a 19 nucleobase portion of a target segment. In certain embodiments, the antisense compounds are complementary to at least a 20 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 91%, 92%, 93%, 94%, 95%, 96%, 97%, 98%, 99% or 100% identical to one or more of the antisense compounds or SEQ ID NOs, or a portion thereof, disclosed herein.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a FGFR4 nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds provided herein can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise a chemically modified ribofuranose ring moiety. Examples of chemically modified ribofuranose rings include, without limitation, addition of substitutent groups (including 5' and 2' substituent groups); bridging of non-geminal ring atoms to form bicyclic nucleic acids (BNA); replacement of the ribosyl ring oxygen atom with S, N(R), or C(R1)(R)2 (R=H, $C_1$-$C_{12}$ alkyl or a protecting group); and combinations thereof. Examples of chemically modified sugars include, 2'-F-5'-methyl substituted nucleoside (see, PCT International Application WO 2008/101157, published on Aug. 21, 2008 for other disclosed 5',2'-bis substituted nucleosides), replacement of the ribosyl ring oxygen atom with S with further substitution at the 2'-position (see, published U.S. Patent Application US2005/0130923, published on Jun. 16, 2005), or, alternatively, 5'-substitution of a BNA (see, PCT International Application WO 2007/134181, published on Nov. 22, 2007, wherein LNA is substituted with, for example, a 5'-methyl or a 5'-vinyl group).

Examples of nucleosides having modified sugar moieties include, without limitation, nucleosides comprising 5'-vinyl, 5'-methyl (R or S), 4'-S, 2'-F, 2'-OCH$_3$, and 2'-O(CH$_2$)2OCH$_3$ substituent groups. The substituent at the 2' position can also be selected from allyl, amino, azido, thio, O-allyl, O—C$_1$-C$_{10}$ alkyl, OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl.

As used herein, "bicyclic nucleosides" refer to modified nucleosides comprising a bicyclic sugar moiety. Examples of bicyclic nucleosides include, without limitation, nucleosides comprising a bridge between the 4' and the 2' ribosyl ring atoms. In certain embodiments, antisense compounds provided herein include one or more bicyclic nucleosides wherein the bridge comprises a 4' to 2' bicyclic nucleoside. Examples of such 4' to 2' bicyclic nucleosides, include, but are not limited to, one of the formulae: 4'-(CH$_2$)—O-2' (LNA); 4'-(CH$_2$)—S-2; 4'-(CH$_2$)$_2$—O-2' (ENA); 4'-CH(CH$_3$)—O-2' and 4'-C—H(CH$_2$OCH$_3$)—O-2', and analogs thereof (see, U.S. Pat. No. 7,399,845, issued on Jul. 15, 2008); 4'-C(CH$_3$)(CH$_3$)—O-2', and analogs thereof (see, published PCT International Application WO2009/006478, published Jan. 8, 2009); 4'-CH$_2$—N(OCH$_3$)-2', and analogs thereof (see, published PCT International Application WO2008/150729, published Dec. 11, 2008); 4'-CH$_2$—O—N(CH$_3$)-2' (see, published U.S. Patent Application US2004/0171570, published Sep. 2, 2004); 4'-CH$_2$—N(R)—O-2', wherein R is H, C$_1$-C$_{12}$ alkyl, or a protecting group (see, U.S. Pat. No. 7,427,672, issued on Sep. 23, 2008); 4'-CH$_2$—C(H)(CH$_3$)-2' (see, Chattopadhyaya, et al., *J. Org. Chem.*, 2009, 74, 118-134); and 4'-CH$_2$—C(=CH$_2$)-2', and analogs thereof (see, published PCT International Application WO 2008/154401, published on Dec. 8, 2008). Also see, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 6,670,461, 7,053,207, 6,268,490, 6,770,748, 6,794,499, 7,034,133, 6,525,191, 7,399,845; published PCT International applications WO 2004/106356, WO 94/14226, WO 2005/021570, and WO 2007/134181; U.S. Patent Publication Nos. US2004/0171570, US2007/0287831, and US2008/0039618; and U.S. patent Ser. Nos. 12/129,154, 60/989,574, 61/026,995, 61/026,998, 61/056,564, 61/086,231, 61/097,787, and 61/099,844; and PCT International Application Nos. PCT/US2008/064591, PCMS2008/066154, and PCT/US2008/068922. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

In certain embodiments, the bridge of a bicyclic sugar moiety is, —[C(R$_a$)(R$_b$)]$_a$—, —[C(R$_a$)(R$_b$)]—O—, —C(R$_a$R$_b$)—N(R)—O— or, —C(R$_a$R$_b$)—O—N(R)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2', and 4'-CH$_2$—N(R)—O-2'-, wherein each R is, independently, H, a protecting group, or C$_1$-C$_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include, but are not limited to, (A) α-L-Methyleneoxy (4'-CH$_2$—O-2') BNA (B) β-D-Methyleneoxy (4'-CH$_2$—O-2') BNA, (C) Ethyleneoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, (F) Methyl(methyleneoxy) (4'-CH(CH$_3$)—O-2') BNA, (G) methylene-thio (4'-CH$_2$—S-2') BNA, (H) methylene-amino (4'-CH2-N(R)-2') BNA, (I) methyl carbocyclic (4'-CH$_2$—CH(CH$_3$)-2') BNA, and (J) propylene carbocyclic (4'-(CH$_2$)$_3$-2') BNA as depicted below.

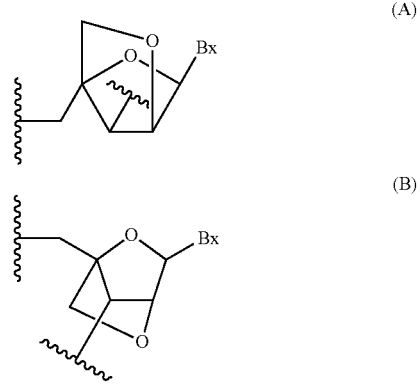

(C) 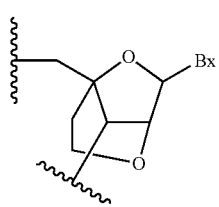

(D) 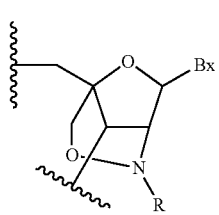

(E) 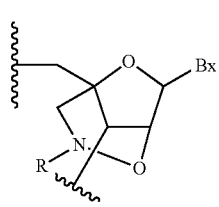

(F) 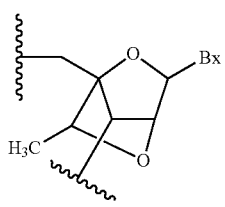

(G) 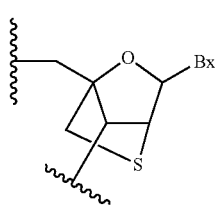

(H) 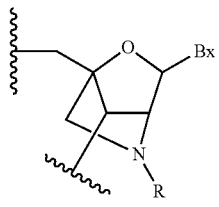

(I) 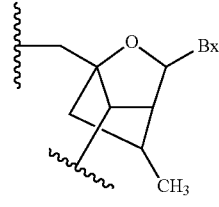

(J) 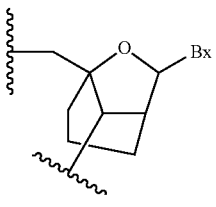

wherein Bx is the base moiety and R is, independently, H, a protecting group or $C_1$-$C_{12}$ alkyl.

In certain embodiments, bicyclic nucleoside having Formula I:

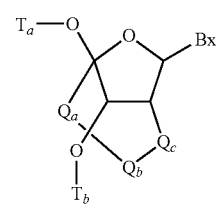

I wherein:
Bx is a heterocyclic base moiety;
—$Q_a$-$Q_b$-$Q_c$- is —$CH_2$—$N(R_c)$—$CH_2$—, —$C(=O)$—$N(R_c)$—$CH_2$—, —$CH_2$—$O$—$N(R_c)$—, —$CH_2$—$N(R_c)$—$O$—, or —$N(R_c)$—$O$—$CH_2$;
$R_c$ is $C_1$-$C_{12}$ alkyl or an amino protecting group; and
$T_a$ and $T_b$ are each, independently, H, a hydroxyl protecting group, a conjugate group, a reactive phosphorus group, a phosphorus moiety, or a covalent attachment to a support medium.

In certain embodiments, bicyclic nucleoside having Formula II:

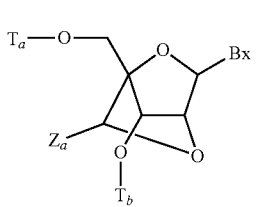

II wherein:
Bx is a heterocyclic base moiety;
$T_a$ and $T_b$ are each, independently, H, a hydroxyl protecting group, a conjugate group, a reactive phosphorus group, a phosphorus moiety, or a covalent attachment to a support medium;
$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol, or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_eC(=X)NJ_cJ_d$, wherein each $J_c$, $J_d$, and $J_e$ is, independently, H, $C_1$-$C_6$ alkyl, or substituted $C_1$-$C_6$ alkyl and X is O or $NJ_c$.

In certain embodiments, bicyclic nucleoside having Formula III:

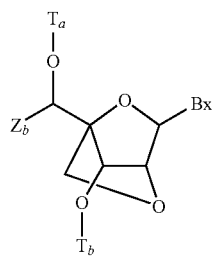

wherein:
Bx is a heterocyclic base moiety;
$T_a$ and $T_b$ are each, independently, H, a hydroxyl protecting group, a conjugate group, a reactive phosphorus group, a phosphorus moiety, or a covalent attachment to a support medium;
$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, or substituted acyl (C(=O)—).

In certain embodiments, bicyclic nucleoside having Formula IV:

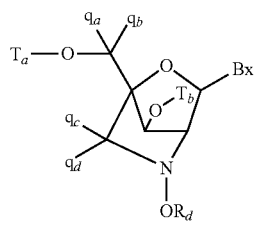

wherein:
Bx is a heterocyclic base moiety;
$T_a$ and $T_b$ are each, independently H, a hydroxyl protecting group, a conjugate group, a reactive phosphorus group, a phosphorus moiety, or a covalent attachment to a support medium;
$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl;
each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl, or substituted $C_1$-$C_6$ aminoalkyl;

In certain embodiments, bicyclic nucleoside having Formula V:

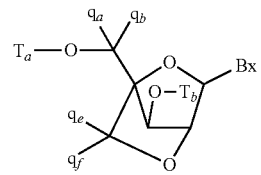

wherein:
Bx is a heterocyclic base moiety;
$T_a$ and $T_b$ are each, independently, H, a hydroxyl protecting group, a conjugate group, a reactive phosphorus group, a phosphorus moiety, or a covalent attachment to a support medium;
$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, O(=O)$J_j$, O—C(=O)—$NJ_jJ_k$, N(H)C(=NH)$NJ_jJ_k$, N(H)C(=O)$NJ_jJ_k$ or N(H)C(=S)$NJ_jJ_k$;
or $q_e$ and $q_f$ together are =C($q_g$)($q_h$);
$q_g$ and $q_h$ are each, independently, H, halogen, $C_1$-$C_{12}$ alkyl, or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine, and uracil, along with their oligomerization, and nucleic acid recognition properties have been described (see, e.g., Koshkin et al., *Tetrahedron*, 1998, 54, 3607-3630). BNAs and preparation thereof are also described in WO 98/39352 and WO 99/14226.

Analogs of methyleneoxy (4'-$CH_2$—O-2') BNA, methyleneoxy (4'-$CH_2$—O-2') BNA, and 2'-thio-BNAs, have also been prepared (see, e.g., Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (see, e.g., Wengel et al., WO 99/14226). Furthermore, synthesis of 2'-amino-BNA, a novel comformationally restricted high-affinity oligonucleotide analog, has been described in the art (see, e.g., Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleoside having Formula VI:

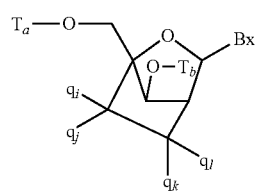

wherein:
Bx is a heterocyclic base moiety;
$T_a$ and $T_b$ are each, independently, H, a hydroxyl protecting group, a conjugate group, a reactive phosphorus group, a phosphorus moiety, or a covalent attachment to a support medium;
each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$, or N(H)C(=S)$NJ_jJ_k$; and $q_i$ and $q_j$ or $q_l$ and $q_k$ together are =C($q_g$)($q_h$), wherein $q_g$ and $q_k$ are each, independently, H, halogen, $C_1$-$C_{12}$ alkyl, or substituted $C_1$-$C_{12}$ alkyl.

One carbocyclic bicyclic nucleoside having a 4'-($CH_2$)$_3$-2' bridge and the alkenyl analog, bridge 4'-CH=CH—$CH_2$-2', have been described (see, e.g., Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting the 2' carbon atom and the 4'carbon atom.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)_nNH_2$, $O(CH_2)_nCH_3$, $O(CH_2)_nONH_2$, $OCH_2C(=O)N(H)CH_3$, and $O(CH_2)_nON[(CH_2)_nCH_3]_2$, where n and m are from 1 to about 10. Other 2'-substituent groups can also be selected from: $C_1$-$C_{12}$ alkyl; substituted alkyl; alkenyl; alkynyl; alkaryl; aralkyl; O-alkaryl or O-aralkyl; SH; $SCH_3$; OCN; Cl; Br; CN; $CF_3$; $OCF_3$; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving pharmacokinetic properties; and a group for improving the pharmacodynamic properties of an antisense compound, and other substituents having similar properties. In certain embodiments, modified nucleosides comprise a 2'-MOE side chain (see, e.g., Baker et al., J. Biol. Chem., 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (see, e.g., Martin, P., *Helv. Chim. Acta,* 1995, 78, 486-504; Altmann et al., *Chimia,* 1996, 50, 168-176; Altmann et al., *Biochem. Soc. Trans.,* 1996, 24, 630-637; and Altmann et al., *Nucleosides Nucleotides,* 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), or those compounds having Formula X:

Formula X:

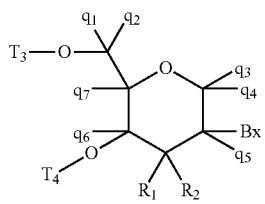

wherein independently for each of said at least one tetrahydropyran nucleoside analog of Formula X:
Bx is a heterocyclic base moiety;
$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;
$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and
one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S, or $NJ_1$, and each $J_1$, $J_2$, and $J_3$ is, independently, H or $C_1$-$C_6$ alkyl.

In certain embodiments, the modified THP nucleosides of Formula X are provided wherein $q_m$, $q_n$, $q_p$, $q_r$, $q_s$, $q_t$, and $q_u$ are each H. In certain embodiments, at least one of $q_m$, $q_n$, $q_p$, $q_r$, $q_s$, $q_t$, and $q_u$ is other than H. In certain embodiments, at least one of $q_m$, $q_n$, $q_p$, $q_r$, $q_s$, $q_t$, and $q_u$ is methyl. In certain embodiments, THP nucleosides of Formula X are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring and nucleosides with non-bridging 2' substituents, such as allyl, amino, azido, thio, O-allyl, O—$C_1$-$C_{10}$ alkyl, —$OCF_3$, O—$(CH_2)_2$—O—$CH_3$, 2'—$O(CH_2)_2SCH_3$, O—$(CH_2)_2$—O—$N(R_m)(R_n)$, or O—$CH_2$—$C(=O)$—$N(R_m)(R_n)$, where each $R_m$ and $R_n$ is, independently, H or substituted or unsubstituted $C_1$-$C_{10}$ alkyl. 2'-modified nucleosides may further comprise other modifications, for example, at other positions of the sugar and/or at the nucleobase.

As used herein, "2'-F" refers to a sugar comprising a fluoro group at the 2' position.

As used herein, "2'-OMe" or "2'-OCH_3" or "2'-O-methyl" each refers to a sugar comprising an —$OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see, e.g., review article: Leumann, J. C, *Bioorganic & Medicinal Chemistry,* 2002, 10, 841-854). Such ring systems can undergo various additional substitutions to enhance activity.

Methods for the preparations of modified sugars are well known to those skilled in the art.

In nucleotides having modified sugar moieties, the nucleobase moieties (natural, modified, or a combination thereof) are maintained for hybridization with an appropriate nucleic acid target.

In certain embodiments, antisense compounds comprise one or more nucleotides having modified sugar moieties. In certain embodiments, the modified sugar moiety is 2'-MOE. In certain embodiments, the 2'-MOE modified nucleotides are arranged in a gapmer motif. In certain embodiments, the modified sugar moiety is a cEt. In certain embodiments, the cEt modified nucleotides are arranged throughout the wings of a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional unmodified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to a FGFR4 nucleic acid comprise one or more modified nucleobases. In certain embodiments, gap-widened antisense oligonucleotides targeted to a FGFR4 nucleic acid comprise one or more modified nucleobases. In certain embodiments, the modified nucleobase is 5-methylcytosine. In certain embodiments, each cytosine is a 5-methylcytosine.

Compositions and Methods for Formulating Pharmaceutical Compositions

Antisense oligonucleotides may be admixed with pharmaceutically acceptable active or inert substance for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compound targeted to a FGFR4 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a FGFR4 nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

Pharmaceutically acceptable salts of the compounds described herein may be prepared by methods well-known in the art. For a review of pharmaceutically acceptable salts, see Stahl and Wermuth, Handbook of Pharmaceutical Salts: Properties, Selection and Use (Wiley-VCH, Weinheim, Germany, 2002). Sodium salts of antisense oligonucleotides are useful and are well accepted for therapeutic administration to humans. Accordingly, in one embodiment the compounds described herein are in the form of a sodium salt.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of FGFR4 nucleic acids can be tested in vitro in a variety of cell types. Cell types used for such analyses are available from commercial vendors (e.g. American Type Culture Collection, Manassus, Va.; Zen-Bio, Inc., Research Triangle Park, N.C.; Clonetics Corporation, Walkersville, Md.) and cells are cultured according to the vendor's instructions using commercially available reagents (e.g. Invitrogen Life Technologies, Carlsbad, Calif.). Illustrative cell types include, but are not limited to, HepG2 cells and primary hepatocytes.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluence in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE 2000® (Invitrogen, Carlsbad, Calif.). Antisense oligonucleotide is mixed with LIPOFECTAMINE 2000® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 ug/mL per 100 nM antisense oligonucleotide.

Another reagent used to introduce antisense oligonucleotides into cultured cells includes Cytofectin® (Invitrogen, Carlsbad, Calif.). Antisense oligonucleotide is mixed with Cytofectin® in OPTI-MEMO 1 reduced serum medium (Invitrogen, Carlsbad, Calif.) to achieve the desired concentration of antisense oligonucleotide and a Cytofectin® concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE2000®, Lipofectin or Cytofectin. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL® Reagent (Invitrogen, Carlsbad, Calif.) according to the manufacturer's recommended protocols.

Analysis of Inhibition of Target Levels or Expression

Inhibition of levels or expression of a FGFR4 nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT, real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN® (Invitrogen, Inc. Carlsbad, Calif.). Cyclophilin A expression is quantified by real time PCR, by being run simultaneously with the target, multiplexing, or separately. Total RNA is quantified using RIBOGREEN® RNA quantification reagent (Invitrogen, Inc. Eugene, Oreg.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems) is used to measure RIBOGREEN® fluorescence.

Probes and primers are designed to hybridize to a FGFR4 nucleic acid. Methods for designing real-time PCR probes and primers are well known in the art, and may include the use of software such as PRIMER EXPRESS® Software (Applied Biosystems, Foster City, Calif.).

Analysis of Protein Levels

Antisense inhibition of FGFR4 nucleic acids can be assessed by measuring FGFR4 protein levels. Protein levels of FGFR4 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of human and rat FGFR4 are commercially available.

In Vivo Testing of Antisense Compounds

Antisense compounds, for example, antisense oligonucleotides, are tested in animals to assess their ability to inhibit expression of FGFR4 and produce phenotypic changes. Testing may be performed in normal animals, or in experimental disease models. For administration to animals, antisense oligonucleotides are formulated in a pharmaceutically acceptable diluent, such as phosphate-buffered saline. Administration includes parenteral routes of administration. Following a period of treatment with antisense oligonucleotides, RNA is isolated from tissue and changes in FGFR4 nucleic acid expression are measured. Changes in FGFR4 protein levels are also measured.

Certain Indications

In certain embodiments, provided herein are methods of treating an individual comprising administering one or more pharmaceutical compositions as described herein. In certain embodiments, the individual has a metabolic disease.

As shown in the examples below, compounds targeted to FGFR4, as described herein, have been shown to reduce the severity of physiological symptoms of a metabolic disease, including obesity or adiposity, metabolic syndrome, diabetes mellitus, insulin resistance, diabetic dyslipidemia, and hypertriglyceridemia. In certain of the experiments, the compounds reduced body weight, e.g., the animals continued to experience symptoms, but the symptoms were less severe compared to untreated animals. In certain of the experiments, the compounds reduced body fat, e.g., the animals continued to experience symptoms, but the symptoms were less severe compared to untreated animals. In certain of the experiments, the compounds reduced adipose tissue, e.g., the animals continued to experience symptoms, but the symptoms were less severe compared to untreated animals. In other of the experiments, however, the compounds appear to reduce the symptoms of obesity; e.g., animals treated for a longer period of time experienced less severe symptoms than those administered the compounds for a shorter period of time. In other of the experiments, however, the compounds appear to reduce the symptoms of diabetes; e.g., animals treated for a longer period of time experienced less severe symptoms than those administered the compounds for a shorter period of time. In other of the experiments, however, the compounds appear to inhibit weight gain; e.g., animals treated for a longer period of time experienced less severe symptoms than those administered the compounds for a shorter period of time. In other of the experiments, however, the compounds appear to reduce glucose levels; e.g., animals treated for a longer period of time experienced less severe symptoms than those administered the compounds for a shorter period of time. In other of the experiments, however, the compounds appear to increase fatty acid oxidation; e.g., animals treated for a longer period of time experienced less severe symptoms than those administered the compounds for a shorter period of time. The ability of the compounds exemplified below to restore function therefore demonstrates that symptoms of the disease may be reversed by treatment with a compound as described herein.

Obesity is characterized by numerous physical and physiological symptoms. Any symptom known to one of skill in the art to be associated with obesity can be ameliorated or otherwise modulated as set forth above in the methods described above. In certain embodiments, the symptom is a physical symptom selected from the group consisting of increased adipose tissue mass or weight, increased weight gain, increased fat pad weight, imbalance with caloric intake and energy expenditure, increase in body fat, increase in body mass, having a body mass index (BMI) of 30 or higher, increase in body frame, increased sweating, sleep apnea, difficulty in sleeping, inability to cope with sudden physical activity, lethargy, back and joint problems, increase in breathlessness, increase in breast region adiposity, increase in abdomen size or fat, extreme hunger, or extreme fatigue.

In certain embodiments, the symptom is a physiological symptom selected from the group consisting of high blood pressure, hypertension, high cholesterol levels, type 2 diabetes, stroke, cardiac insufficiency, heart disease, coronary artery obstruction, breast cancer in women, gastro-oesophageal reflux disease, hip and knee arthrosis, and reduced life expectancy.

In certain embodiments, the physical symptom is excess body weight. In certain embodiments, the symptom is excess fat mass. In certain embodiments, the symptom is a body mass index of 30 or higher. In certain embodiments, the symptom is breathlessness. In certain embodiments, the symptom is increased sweating. In certain embodiments, the symptom is sleep apnea. In certain embodiments, the symptom is difficulty in sleeping. In certain embodiments, the symptom is inability to cope with sudden physical activity. In certain embodiments, the symptom is lethargy. In certain embodiments, the symptom is back and joint problems.

In certain embodiments, the physiological symptom is high blood pressure. In certain embodiments, the symptom is hypertension. In certain embodiments, the symptom is high cholesterol levels. In certain embodiments, the symptom is type 2 diabetes. In certain embodiments, the symptom is stroke. In certain embodiments, the symptom is cardiac insufficiency. In certain embodiments, the symptom is heart disease. In certain embodiments, the symptom is coronary artery obstruction. In certain embodiments, the symptom is breast cancer in women. In certain embodiments, the symptom is gastro-oesophageal reflux disease. In certain embodiments, the symptom is hip and knee arthrosis. In certain embodiments, the symptom is reduced life expectancy.

Diabetes mellitus is characterized by numerous physical and physiological symptoms. Any symptom known to one of skill in the art to be associated with Type 2 diabetes can be ameliorated or otherwise modulated as set forth above in the methods described above. In certain embodiments, the symptom is a physical symptom selected from the group consisting of increased glucose levels, increased weight gain, frequent urination, unusual thirst, extreme hunger, extreme fatigue, blurred vision, frequent infections, tingling or numbness at the extremities, dry and itchy skin, weight loss, slow-healing sores, and swollen gums.

In certain embodiments, the symptom is a physiological symptom selected from the group consisting of increased insulin resistance, increased glucose levels, increased fat mass, decreased metabolic rate, decreased glucose clearance, decreased glucose tolerance, decreased insulin sensitivity, decreased hepatic insulin sensitivity, increased adipose tissue size and weight, increased body fat, and increased body weight.

In certain embodiments, the physical symptom is increased weight gain. In certain embodiments, the symptom is frequent urination. In certain embodiments, the symptom is unusual thirst. In certain embodiments, the symptom is extreme hunger. In certain embodiments, the symptom is extreme fatigue. In certain embodiments, the symptom is blurred vision. In certain embodiments, the symptom is frequent infections. In certain embodiments, the symptom is tingling or numbness at the extremities. In certain embodiments, the symptom is dry and itchy skin. In certain embodiments, the symptom is weight loss. In certain embodiments, the symptom is slow-healing sores. In certain embodiments, the symptom is swollen gums. In certain embodiments, the symptom is increased insulin resistance. In certain embodiments, the symptom is increased fat mass. In certain embodiments, the symptom is decreased metabolic rate. In certain embodiments, the symptom is decreased glucose clearance. In certain embodiments, the symptom is decreased glucose tolerance. In certain embodiments, the symptom is decreased insulin sensitivity. In certain embodiments, the symptom is decreased hepatic insulin sensitivity. In certain embodiments, the symptom is increased adipose tissue size and weight. In certain embodiments, the symptom is increased body fat. In certain embodiments, the symptom is increased body weight.

In certain embodiments, provided are methods of treating an individual comprising administering one or more pharmaceutical compositions as described herein. In certain embodiments, the individual has metabolic related disease.

In certain embodiments, administration of an antisense compound targeted to a FGFR4 nucleic acid results in reduction of FGFR4 expression by at least about 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to FGFR4 are used for the preparation of a medicament for treating a patient suffering or susceptible to a metabolic disease.

In certain embodiments, the methods described herein include administering a compound comprising a modified oligonucleotide having a contiguous nucleobases portion as described herein of a sequence recited in SEQ ID NO: 16.

In certain embodiments, the methods described herein include administering a compound comprising a modified oligonucleotide having a contiguous nucleobases portion as described herein of a sequence recited in SEQ ID NO: 45.

Administration

In certain embodiments, the compounds and compositions as described herein may be administered in a number of ways depending upon whether local or systemic treatment is desired and upon the area to be treated. Administration may be topical, pulmonary, e.g., by inhalation or insufflation of powders or aerosols, including by nebulizer; intratracheal, intranasal, epidermal and transdermal, oral or parenteral. The compounds and compositions as described herein can be administered directly to a tissue or organ.

In certain embodiments, the compounds and compositions as described herein are administered parenterally. "Parenteral administration" means administration through injection or infusion. Parenteral administration includes subcutaneous administration, intravenous administration, intramuscular administration, intraarterial administration, intraperitoneal administration, or intracranial administration, e.g. intracerebral administration, intrathecal administration, intraventricular administration, ventricular administration, intracerebroventricular administration, cerebral intraventricular administration or cerebral ventricular administration. Administration can be continuous, or chronic, or short or intermittent.

In certain embodiments, parenteral administration is by injection. The injection can be delivered with a syringe or a pump. In certain embodiments, the injection is a bolus injection. In certain embodiments, the injection is administered directly to a tissue or organ.

In certain embodiments, the compounds and compositions as described herein are administered parenterally.

In certain embodiments, parenteral administration is subcutaneous.

In further embodiments, the formulation for administration is the compounds described herein and saline.

In certain embodiments, an antisense oligonucleotide is delivered by injection or infusion once every month, every two months, every 90 days, every 3 months, every 6 months, twice a year or once a year.

Certain Combination Therapies

In certain embodiments, one or more pharmaceutical compositions described herein are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions as described herein. In certain embodiments, one or more pharmaceutical compositions are co-administered with another pharmaceutical agent to treat an undesired effect of that other pharmaceutical agent. In certain embodiments, one or more pharmaceutical compositions are co-administered with another pharmaceutical agent to produce a combinational effect. In certain embodiments, one or more pharmaceutical compositions are co-administered with another pharmaceutical agent to produce a synergistic effect.

In certain embodiments, a first agent and one or more second agents are administered at the same time. In certain embodiments, the first agent and one or more second agents are administered at different times. In certain embodiments, the first agent and one or more second agents are prepared together in a single pharmaceutical formulation. In certain embodiments, the first agent and one or more second agents are prepared separately.

In certain embodiments, the second compound is administered prior to administration of a pharmaceutical composition described herein. In certain embodiments, the second compound is administered following administration of a pharmaceutical composition described herein. In certain embodiments, the second compound is administered at the same time as a pharmaceutical composition described herein. In certain embodiments, the dose of a co-administered second compound is the same as the dose that would be administered if the second compound was administered alone. In certain embodiments, the dose of a co-administered second compound is lower than the dose that would be administered if the second compound was administered alone. In certain embodiments, the dose of a co-administered second compound is greater than the dose that would be administered if the second compound was administered alone.

In certain embodiments, the co-administration of a second compound enhances the effect of a first compound, such that co-administration of the compounds results in an effect that is greater than the effect of administering the first compound alone. In certain embodiments, the co-administration results in effects that are additive of the effects of the compounds when administered alone. In certain embodiments, the co-administration results in effects that are supra-additive of the effects of the compounds when administered alone. In certain embodiments, the first compound is an antisense compound. In certain embodiments, the second compound is an antisense compound.

In certain embodiments the FGFR4 antisense oligonucleotide is delivered concomitant with delivery of the second agent. Alternatively, delivery can be in the same formulation or can be administered separately. In certain embodiments, FGFR4 antisense oligonucleotide is administered prior to the treatment with the second agents. In a certain embodiment, the FGFR4 antisense oligonucleotide is administered after treatment with an obesity inducing drug or agent is ceased.

In certain embodiments, second agents include, but are not limited to, a glucose-lowering agent. The glucose lowering agent can include, but is not limited to, a therapeutic lifestyle change, PPAR agonist, a dipeptidyl peptidase (IV) inhibitor, a GLP-1 analog, insulin or an insulin analog, an insulin secretagogue, a SGLT2 inhibitor, a human amylin analog, a biguanide, an alpha-glucosidase inhibitor, or a combination thereof. The glucose-lowering agent can include, but is not limited to metformin, sulfonylurea, rosiglitazone, meglitinide, thiazolidinedione, alpha-glucosidase inhibitor or a combination thereof. The sulfonylurea can be acetohexamide, chlorpropamide, tolbutamide, tolazamide, glimepiride, a glipizide, a glyburide, or a gliclazide. The meglitinide can be nateglinide or repaglinide. The thiazolidinedione can be pioglitazone or rosiglitazone. The alpha-glucosidase can be acarbose or miglitol.

In some embodiments, the glucose-lowering therapeutic is a GLP-1 analog. In some embodiments, the GLP-1 analog is exendin-4 or liraglutide.

In other embodiments, the glucose-lowering therapeutic is a sulfonylurea. In some embodiments, the sulfonylurea is acetohexamide, chlorpropamide, tolbutamide, tolazamide, glimepiride, a glipizide, a glyburide, or a gliclazide.

In some embodiments, the glucose-lowering drug is a biguanide. In some embodiments, the biguanide is metformin, and in some embodiments, blood glucose levels are decreased without increased lactic acidosis as compared to the lactic acidosis observed after treatment with metformin alone.

In some embodiments, the glucose-lowering drug is a meglitinide. In some embodiments, the meglitinide is nateglinide or repaglinide.

In some embodiments, the glucose-lowering drug is a thiazolidinedione. In some embodiments, the thiazolidinedione is pioglitazone, rosiglitazone, or troglitazone. In some embodiments, blood glucose levels are decreased without greater weight gain than observed with rosiglitazone treatment alone.

In some embodiments, the glucose-lowering drug is an alpha-glucosidase inhibitor. In some embodiments, the alpha-glucosidase inhibitor is acarbose or miglitol.

In a certain embodiment, a co-administered glucose-lowering agent is ISIS 113715.

In a certain embodiment, glucose-lowering therapy is therapeutic lifestyle change.

In certain embodiments, second agents include, but are not limited to, lipid-lowering agents. The lipid-lowering agent can include, but is not limited to atorvastatin, simvastatin, rosuvastatin, and ezetimibe. In certain such embodiments, the lipid-lowering agent is administered prior to administration of a pharmaceutical composition described herein. In certain such embodiments, the lipid-lowering agent is administered following administration of a pharmaceutical composition described herein. In certain such embodiments the lipid-lowering agent is administered at the same time as a pharmaceutical composition described herein. In certain such embodiments the dose of a co-administered lipid-lowering agent is the same as the dose that would be administered if the lipid-lowering agent was administered alone. In certain such embodiments the dose of a co-administered lipid-lowering agent is lower than the dose that would be administered if the lipid-lowering agent was administered alone. In certain such embodiments the dose of a co-administered lipid-lowering agent is greater than the dose that would be administered if the lipid-lowering agent was administered alone.

In certain embodiments, a co-administered lipid-lowering agent is a HMG-CoA reductase inhibitor. In certain such embodiments the HMG-CoA reductase inhibitor is a statin. In certain such embodiments the statin is selected from atorvastatin, simvastatin, pravastatin, fluvastatin, and rosuvastatin.

In certain embodiments, a co-administered lipid-lowering agent is a cholesterol absorption inhibitor. In certain such embodiments, cholesterol absorption inhibitor is ezetimibe.

In certain embodiments, a co-administered lipid-lowering agent is a co-formulated HMG-CoA reductase inhibitor and cholesterol absorption inhibitor. In certain such embodiments the co-formulated lipid-lowering agent is ezetimibe/simvastatin.

In certain embodiments, a co-administered lipid-lowering agent is a microsomal triglyceride transfer protein inhibitor (MTP inhibitor).

In certain embodiments, a co-administered lipid-lowering agent is an oligonucleotide targeted to ApoB.

In certain embodiments, second agents include, but are not limited to an anti-obesity drug or agent. Such anti-obesity agents include but are not limited to Orlistat, Sibutramine, or Rimonabant, and may be administered as described above as adipose or body weight lowering agents. In certain embodiments, the antisense compound may be co-administered with appetite suppressants. Such appetite suppressants include but are not limited to diethylpropion tenuate, mazindol, orlistat, phendimetrazine, phentermine, and sibutramine and may be administered as described herein. In certain embodiment, the anti-obesity agents are CNS based such as, but not limited to, sibutramine or GLP-1 based such as, but not limited to, liraglutide.

In certain embodiments, second agents include, but are not limited to an antipsychotic drug or agent. Such antipsychotic agents therapeutics may be administered as described above to reduce metabolic abnormalities associated with treatment with antipsychotic agents. In a particular embodiment administering of the FGFR4 antisense compound results in increased metabolic rate or decreasing adiposity or decreasing body weight or all three without affecting the CNS effects of the psychotherapeutic agent Due to the ability of FGFR4 antisense oligonucleotides to increase metabolic rate and insulin sensitivity and reduce adiposity and weight gain, these compounds can be administered to reduce metabolic abnormalities associated with treatment with antipsychotic agents. In certain embodiments the FGFR4 antisense oligonucleotide is delivered in a method of reducing metabolic abnormalities associated with the therapeutic use of psychotherapeutic agents. Such weight inducing antipsychotic agents include, but are not limited to clozapine, olanzapine, aripiprazole, risperidone and ziprasidone.

Further provided is a method of administering an antisense compound targeted to a FGFR4 nucleic acid via injection and further including administering a topical steroid at the injection site.

Further examples of pharmaceutical agents that may be co-administered with a pharmaceutical composition of the present invention include, but are not limited to, corticosteroids, including but not limited to prednisone; immunoglobulins, including, but not limited to intravenous immunoglobulin (IVIg); analgesics (e.g., acetaminophen); anti-inflammatory agents, including, but not limited to nonsteroidal anti-inflammatory drugs (e.g., ibuprofen, COX-1 inhibitors, and COX-2, inhibitors); salicylates; antibiotics; antivirals; antifungal agents; antidiabetic agents (e.g., biguanides, glucosidase inhibitors, insulins, sulfonylureas, and thiazolidenediones); adrenergic modifiers; diuretics; hormones (e.g., anabolic steroids, androgen, estrogen, calcitonin, progestin, somatostan, and thyroid hormones); immunomodulators; muscle relaxants; antihistamines; osteoporosis agents (e.g., biphosphonates, calcitonin, and estrogens); prostaglandins, antineoplastic agents; psychotherapeutic agents; sedatives; poison oak or poison sumac products; antibodies; and vaccines.

In certain embodiments, the pharmaceutical compositions of the present invention may be administered in conjunction with a lipid-lowering therapy. In certain such embodiments, a lipid-lowering therapy is therapeutic lifestyle change. In certain such embodiments, a lipid-lowering therapy is LDL apheresis.

Formulations

The compounds provided herein may also be admixed, conjugated or otherwise associated with other molecules, molecule structures or mixtures of compounds, as for example, liposomes, receptor-targeted molecules, or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds provided herein encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds provided herein: i.e., salts that retain the desired biological activity of the parent compound and do not impart undesired toxicological effects thereto. The term "pharmaceutically acceptable salt" includes a salt prepared from pharmaceutically acceptable non-toxic acids or bases, including inorganic or organic acids and bases. For oligonucleotides, preferred examples of pharmaceutically acceptable salts and their uses are further described in U.S. Pat. No. 6,287,860, which is incorporated herein in its entirety. Sodium salts have been shown to be suitable forms of oligonucleotide drugs.

The term "pharmaceutically acceptable derivative" encompasses, but is not limited to, pharmaceutically acceptable salts, solvates, hydrates, esters, prodrugs, polymorphs, isomers, isotopically labeled variants of the compounds described herein.

The present invention also includes pharmaceutical compositions and formulations which include the antisense compounds provided herein. The pharmaceutical compositions described herein may be administered in a number of ways depending upon whether local or systemic treatment is desired and upon the area to be treated. Administration may be parenteral. Parenteral administration includes intravenous, intraarterial, subcutaneous, intraperitoneal or intramuscular injection or infusion; or intracranial, e.g., intracerebral administration, intrathecal administration, intraventricular administration, ventricular administration, intracerebroventricular administration, cerebral intraventricular administration or cerebral ventricular administration.

Parenteral administration, is preferred to target FGFR4 expression in the liver and plasma. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations described herein, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions described herein may be formulated into any of many possible dosage forms such as, but not limited to, tablets, capsules, gel capsules, liquid syrups, soft gels, suppositories, and enemas. The compositions described herein may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions described herein include, but are not limited to, solutions, emulsions, foams and liposome-containing formulations. The pharmaceutical compositions and formulations described herein may comprise one or more penetration enhancers, carriers, excipients or other active or inactive ingredients.

Emulsions are typically heterogenous systems of one liquid dispersed in another in the form of droplets usually exceeding 0.1 μm in diameter. Emulsions may contain additional components in addition to the dispersed phases, and the active drug which may be present as a solution in the aqueous phase, oily phase or itself as a separate phase. Microemulsions are included as an embodiment described herein. Emulsions and their uses are well known in the art and are further described in U.S. Pat. No. 6,287,860, which is incorporated herein in its entirety.

Formulations include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Liposomes and their uses are further described in U.S. Pat. No. 6,287,860, which is incorporated herein in its entirety.

In another embodiment, formulations include saline formulations. In certain embodiments, a formulation consists of the compounds described herein and saline. In certain embodiments, a formulation consists essentially of the compounds described herein and saline. In certain embodiments, the saline is pharmaceutically acceptable grade saline. In certain embodiments, the saline is buffered saline. In certain embodiments, the saline is phosphate buffered saline (PBS).

In certain embodiments, a formulation excludes liposomes. In certain embodiments, the formulation excludes sterically stabilized liposomes. In certain embodiments, a formulation excludes phospholipids. In certain embodiments, the formulation consists essentially of the compounds described herein and saline and excludes liposomes.

The pharmaceutical formulations and compositions may also include surfactants. Surfactants and their uses are further described in U.S. Pat. No. 6,287,860, which is incorporated herein in its entirety.

In one embodiment, the present invention employs various penetration enhancers to affect the efficient delivery of nucleic acids, particularly oligonucleotides. Penetration enhancers and their uses are further described in U.S. Pat. No. 6,287,860, which is incorporated herein in its entirety.

One of skill in the art will recognize that formulations are routinely designed according to their intended use, i.e. route of administration.

Formulations for topical administration include those in which the oligonucleotides provided herein are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

Compositions and formulations for parenteral administration, including intravenous, intraarterial, subcutaneous, intraperitoneal, intramuscular injection or infusion, or intracranial may include sterile aqueous solutions which may also contain buffers, diluents and other suitable additives such as, but not limited to, penetration enhancers, carrier compounds and other pharmaceutically acceptable carriers or excipients.

Certain embodiments provided herein provide pharmaceutical compositions containing one or more oligomeric compounds and one or more other chemotherapeutic agents which function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds provided herein, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions provided herein. Combinations of antisense compounds and other non-antisense drugs are also within the scope of this invention. Two or more combined compounds may be used together or sequentially.

In another related embodiment, compositions provided herein may contain one or more antisense compounds, particularly oligonucleotides, targeted to a first nucleic acid and one or more additional antisense compounds targeted to a second nucleic acid target. Alternatively, compositions provided herein may contain two or more antisense compounds targeted to different regions of the same nucleic acid target. Numerous examples of antisense compounds are known in the art. Two or more combined compounds may be used together or sequentially.

Dosing

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Optimum dosages may vary depending on the relative potency of individual oligonucleotides, and can generally be estimated based on $EC_{50}$s found to be effective in in vitro and in vivo animal models. In general, dosage is from 0.01 µg to 100 g per kg of body weight, and may be given once or more daily, weekly, monthly or yearly, or at desired intervals. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily.

While the present invention has been described with specificity in accordance with certain of its preferred embodiments, the following examples serve only to illustrate the invention and are not intended to limit the same. Each of the references, GENBANK accession numbers, and the like recited in the present application is incorporated herein by reference in its entirety.

Certain Compounds

About one thousand four hundred and fifty four newly designed and previously disclosed antisense compounds of various lengths, motifs and backbone composition were tested for their effect on human FGFR4 mRNA in vitro in several cell types. The new compounds were compared with nine previously designed compounds, including ISIS 299005, ISIS 299010, ISIS 299018, ISIS 299022, ISIS 299024, ISIS 299025, ISIS 299028, ISIS 299029, and ISIS 299030 which have previously been determined to be some of the most potent antisense compounds in vitro (see e.g., U.S. Patent Publication No. US2010/0292140). Of the one thousand four hundred and fifty four newly designed and the nine previously designed antisense compounds, fifty three compounds were selected for further study based on in vitro potency. The selected compounds were tested for dose dependent inhibition in HepG2 (Examples 8 and 9).

Certain oligonucleotides were then tested for tolerability in a CD1 mouse model, as well as a Sprague-Dawley rat model. The oligonucleotides tested for tolerability include oligonucleotides, ISIS 299005 (SEQ ID NO: 7), ISIS 463588 (SEQ ID NO: 16), ISIS 463589 (SEQ ID NO: 17), ISIS 463628 (SEQ ID NO: 28), ISIS 463690 (SEQ ID NO: 45), ISIS 463691 (SEQ ID NO: 46), ISIS 463835 (SEQ ID NO: 70), ISIS 463837 (SEQ ID NO: 72), ISIS 464222 (SEQ ID NO: 135), ISIS 464225 (SEQ ID NO: 138), ISIS 464228 (SEQ ID NO: 141), ISIS 464286 (SEQ ID NO: 154), ISIS 464308 (SEQ ID NO: 163), ISIS 464449 (SEQ ID NO: 174), ISIS 464587 (SEQ ID NO: 186), ISIS 464588 (SEQ ID NO: 187), ISIS 464589 (SEQ ID NO: 188), ISIS 464718 (SEQ ID NO: 221), ISIS 479533 (SEQ ID NO: 241), ISIS 479551 (SEQ ID NO: 259), ISIS 479691 (SEQ ID NO: 299), ISIS 479692 (SEQ ID NO: 300), ISIS 479698 (SEQ ID NO: 305), ISIS 479699 (SEQ ID NO: 306), ISIS 479703 (SEQ ID NO: 307), ISIS 479704 (SEQ ID NO: 308), ISIS 479706 (SEQ ID NO: 310), and ISIS 479736 (SEQ ID NO: 317). By virtue of their complementary sequence, the compounds are complementary to the regions 192-211, 191-210, 193-212, 291-310, 369-388, 370-389, 788-807, 790-809, 2951-2970, 2954-2973, and 2981-3000 of SEQ ID NO: 1; 11621-11640, 11624-11643, 11651-11670, 1463-1482, 3325-3344, 7802-7821, 2110-2129, 2112-2131, 2114-2133, 3575-3594, 2111-2130, 3570-3589, 11623-11639, 11624-11640, 11652-11668, 11653-11669, 2113-2129, 2114-2130, 2116-2132, and 3571-3587 of SEQ ID NO: 2; and 103-122, 1569-1588, 5122-5138, 5123-5139, 5151-5167, 5152-5168, 105-121, 106-122, 108-124, and 1570-1586 of SEQ ID NO: 3.

In the in vivo models, the liver function markers, such as alanine transaminase, aspartate transaminase and bilirubin, and kidney function markers, such as BUN and creatinine were measured. (Example 11).

Eight oligonucleotides having a nucleobase sequence of a sequence recited in SEQ ID NO: 7 (ISIS 299005), 16 (ISIS 463588), 17 (ISIS 463589), 45 (ISIS 463690), 46 (ISIS 463691), 70 (ISIS 463835), 72 (ISIS 463837) and 138 (ISIS 464225) were tested. By virtue of their complementary sequence, the compounds are complementary to the regions 192-211, 191-210, 193-212, 369-388, 370-389, 788-807, 790-809, and 2954-2973 of SEQ ID NO: 1. In certain embodiments, the compounds targeting the listed regions, as further described herein, comprise a modified oligonucleotide having some nucleobase portion of the sequence recited in the SEQ ID NOs, as further described herein. In certain embodiments, the compounds targeting the listed regions or having a nucleobase portion of a sequence recited in the listed SEQ ID NOs can be of various length, as further described herein, and can have one of various motifs, as further described herein. In certain embodiments, a compound targeting a region or having a nucleobase portion of a sequence recited in the listed SEQ ID NOs has the specific length and motif, as indicated by the ISIS NOs: 299005, 463588, 463589, 463690, 463691, 463835, 463837, and 464225.

These eight compounds, ISIS 299005 (SEQ ID NO: 7), ISIS 463588 (SEQ ID NO: 16), ISIS 463589 (SEQ ID NO: 17), ISIS 463690 (SEQ ID NO: 45), ISIS 463691 (SEQ ID NO: 46), ISIS 463835 (SEQ ID NO: 70), ISIS 463837 (SEQ ID NO: 72), and ISIS 464225 (SEQ ID NO: 138), were assayed for long-term effects on tolerability in a CD/1GS rat model for 13 weeks (Example 12). Body weights and organ weights, the liver function markers, such as alanine transaminase, aspartate transaminase and bilirubin, and kidney function markers, such as BUN and creatinine were measured. The eight compounds were also tested for their viscosity. (Example 14)

ISIS 463588, ISIS 463589, and ISIS 463690 which demonstrated very good tolerability in all three in vivo models, were tested for their half-life in CD1 mouse liver (Example 13).

These eight compounds, ISIS 299005 (SEQ ID NO: 7), ISIS 463588 (SEQ ID NO: 16), ISIS 463589 (SEQ ID NO: 17), ISIS 463690 (SEQ ID NO: 45), ISIS 463691 (SEQ ID NO: 46), ISIS 463835 (SEQ ID NO: 70), ISIS 463837 (SEQ ID NO: 72), and ISIS 464225 (SEQ ID NO: 138), were tested for efficacy, pharmacokinetic profile and tolerability in cynomolgus monkeys (Example 15). The inhibition studies in these monkeys indicated that treatment with some of these compounds caused reduction of FGFR4 mRNA in the liver tissues. Specifically, treatment with ISIS 463588 caused significantly greater reduction of FGFR4 mRNA in liver and kidney tissues, respectively compared to treatment with the previously disclosed compound, ISIS 299005. It was noted that ISIS 463588 caused the highest reduction of FGFR4 mRNA compared to the PBS control, irrespective of the primer probe set used. Hence, in terms of potency, treatment with ISIS 463588 was the most effective in the monkey study. Treatment with ISIS 463690 also caused a greater reduction of FGFR4 mRNA in liver and kidney tissues, respectively compared to treatment with the previously disclosed compound, ISIS 299005.

FGF19 has been known to reduce adiposity and improve insulin sensitivity in transgenic mice (Fu, L. et al., Endocrinology. 145: 2594-2603, 2004). FGF19 is also characterized as a high affinity ligand for FGFR4 (Xie, M.-H. et al., Cytokine. 11: 729-735, 1999). However, treating mice with FGF19 protein induces hepatocyte proliferation consistent with the increased hepatocyte proliferation and liver tumor formation observed in FGF19 transgenic mice (Wu, X. et al., JBC 285 (8): 5165-5170, 2010). Leptin is a hormone which has been found to be present at very high levels in obese individuals compared to normal-weight individuals (Considine, R. V. et al., N. Engl. J. Med. 334: 292-295, 1996). Evaluation of FGF19 mRNA and plasma levels demonstrated the significant increase in FGF19 mRNA and protein levels in all the treatment groups. Specifically, monkeys treated with ISIS 463588 had the most significant increase in FGF19 levels. Evaluation of leptin plasma levels demonstrated a significant decrease in monkeys treated with ISIS 463588 or ISIS 463690. Tolerability studies in cynomolgus monkeys (Example 15) were conducted after treatment with the ISIS oligonucleotides. This included measurement plasma levels of liver metabolites, kidney metabolites, pro-inflammatory factors, such as C-reactive protein, complement C3 and cytokines. The results indicated that treatment with the ISIS oligonucleotides in Example 15 remained within acceptable levels for antisense oligonucleotides and were therefore tolerable to the monkeys. In particular, treatment with ISIS 463588 was very well-tolerated in this model.

Pharmacokinetic studies of the three most well-tolerated ISIS oligonucleotides, ISIS 463588, ISIS 463589, and ISIS 463690, was also performed in the monkeys and indicated that the pharmacokinetics of all three were optimal.

Hence, the in vivo studies, particularly in the cynomolgus monkeys, indicate that ISIS 463588, ISIS 463589, and ISIS 463690, were a more potent oligonucleotide compared to ISIS 299005 and was also considerably more tolerable.

Accordingly, provided herein are antisense compounds with any one or more of the improved characteristics. In a certain embodiments, provided herein are compounds comprising a modified oligonucleotide as further described herein targeted to or specifically hybridizable with the region of nucleotides of SEQ ID NO: 1.

In certain embodiments, the compounds as described herein are efficacious by virtue of having at least one of an in vitro $IC_{50}$ of less than 1.5 µM, less than 1.4 µM, less than 1.3 µM, less than 1.2 µM, less than 1.1 µM, less than 1.0 µM, less than 0.9 µM, less than 0.8 µM, less than 0.7 µM, less than 0.6 µM when delivered to a HepG2 cell line using electroporation as described in Example 8. In certain embodiments, the compounds as described herein are efficacious in vivo, as demonstrated by decreasing the levels of FGFR4 mRNA by 60%, 65%, 70%, 75% or 80%. In further embodiments, the compounds are efficacious in vivo, as demonstrated by increasing the levels of FGF15 and FGF19 mRNA and protein by 100%, 200%, 300%, 400%, 500%, 600%, 700%, 800%, 900%, or 1000%. In other embodiments, the compounds are efficacious in vivo, as demonstrated by decreasing plasma levels of leptin by 30%, 35%, or 40%.

In certain embodiments, the compounds as described herein are highly tolerable, as demonstrated by having at least one of an increase an ALT or AST value of no more than 4 fold, 3 fold, or 2 fold over saline treated animals; or an increase in liver, spleen or kidney weight of no more than 30%, 20%, 15%, 12%, 10%, 5% or 2%.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1

Antisense Inhibition of Human Fibroblast Growth Factor Receptor (FGFR4) in HepG2 Cells Antisense oligonucleotides were designed targeting a FGFR4 nucleic acid and were tested for their effects on FGFR4 mRNA in vitro. Cultured HepG2 cells at a density of 20,000 cells per well were transfected using electroporation with 4,500 nM antisense oligonucleotide. After a treatment period of approximately 24 hours, RNA was isolated from the cells and FGFR4 mRNA levels were measured by quantitative real-time PCR. Human primer probe set RTS3232 (forward sequence TCATCAACGGCAGCAGCTT, designated herein as SEQ ID NO: 327; reverse sequence AGCTATTGATGTCTGCAGTCTTTAGG, designated herein as SEQ ID NO: 328; probe sequence AGCCGACGGTTTCCCCTATGTGCA, designated herein as SEQ ID NO: 329) was used to measure mRNA levels. FGFR4 mRNA levels were adjusted according to total RNA content, as measured by RIBOGREEN®. Results are presented as percent inhibition of FGFR4, relative to untreated control cells. A total of 458 oligonucleotides were tested. Only those oligonucleotides demonstrating greater than 65% inhibition in vitro or which were used in subsequent assays are shown in Table 1.

Some of the antisense oligonucleotides were also tested with an additional primer probe set RTS1325 (forward sequence TTGCTGTGCCGTGTCCAA, designated herein as SEQ ID NO: 330; reverse sequence TCCAAGAAGCCGAGCAGAAC, designated herein as SEQ ID NO: 331; probe sequence AGCTGCCGTGCCTGTGTCCTGAT, designated herein as SEQ ID NO: 332). 'n/a' indicates that particular antisense oligonucleotide was not tested with RTS 1325.

The newly designed chimeric antisense oligonucleotides in Table 1 were designed as 5-10-5 MOE gapmers. The gapmers are 20 nucleosides in length, wherein the central gap segment comprises of ten 2'-deoxynucleosides and is flanked by wing segments on the 5' and 3' directions comprising five nucleosides each. Each nucleotide in the 5' wing segment and each nucleotide in the 3' wing segment has a 2'-MOE modification. The internucleoside linkages throughout each gapmer are phosphorothioate (P=S) linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted in the human gene sequence. Each gapmer listed in Table 1 is targeted to the human FGFR4 mRNA, designated herein as SEQ ID NO: 1 (GENBANK Accession No. NM_002011.3).

TABLE 1

Inhibition of human FGFR4 mRNA levels by chimeric antisense oligonucleotides targeted to SEQ ID NO: 1

| Start Site | Stop Site | Sequence | ISIS No | % inhibition (RTS3232) | % inhibition (RTS1325) | SEQ ID NO |
|---|---|---|---|---|---|---|
| 192 | 211 | GGCACACTCAGCAGGACCCC | 299005 | 85 | n/a | 7 |
| 304 | 323 | AGGCTGCCCAAGGGCTACTG | 299010 | 65 | n/a | 8 |
| 597 | 616 | GTCCAGTAGGGTGCTTGCTG | 299018 | 68 | n/a | 9 |
| 727 | 746 | CCCATGAAAGGCCTGTCCAT | 299022 | 68 | n/a | 10 |
| 757 | 776 | GCGCAGCCGAATGCCTCCAA | 299024 | 68 | 65 | 11 |
| 785 | 804 | TCTCCATCACGAGACTCCAG | 299025 | 65 | 59 | 12 |
| 969 | 988 | TACACCTTGCACAGCAGCTC | 299028 | 68 | 66 | 13 |
| 1027 | 1046 | GCTGCTGCCGTTGATGACGA | 299029 | 91 | 61 | 14 |
| 1032 | 1051 | CCGAAGCTGCTGCCGTTGAT | 299030 | 72 | 19 | 15 |
| 191 | 210 | GCACACTCAGCAGGACCCCC | 463588 | 87 | n/a | 16 |
| 193 | 212 | AGGCACACTCAGCAGGACCC | 463589 | 83 | n/a | 17 |
| 194 | 213 | CAGGCACACTCAGCAGGACC | 463590 | 72 | n/a | 18 |
| 196 | 215 | CCCAGGCACACTCAGCAGGA | 463592 | 73 | n/a | 19 |

TABLE 1 -continued

Inhibition of human FGFR4 mRNA levels by chimeric antisense oligonucleotides targeted to SEQ ID NO: 1

| Start Site | Stop Site | Sequence | ISIS No | % inhibition (RTS3232) | % inhibition (RTS1325) | SEQ ID NO |
|---|---|---|---|---|---|---|
| 197 | 216 | GCCCAGGCACACTCAGCAGG | 463593 | 71 | n/a | 20 |
| 198 | 217 | GGCCCAGGCACACTCAGCAG | 463594 | 69 | n/a | 21 |
| 200 | 219 | GAGGCCCAGGCACACTCAGC | 463596 | 78 | n/a | 22 |
| 202 | 221 | TGGAGGCCCAGGCACACTCA | 463598 | 72 | n/a | 23 |
| 203 | 222 | CTGGAGGCCCAGGCACACTC | 463599 | 78 | n/a | 24 |
| 205 | 224 | GACTGGAGGCCCAGGCACAC | 463601 | 69 | n/a | 25 |
| 287 | 306 | CTGTCAGCTCCTGCTCTTGC | 463625 | 65 | n/a | 26 |
| 290 | 309 | CTACTGTCAGCTCCTGCTCT | 463627 | 74 | n/a | 27 |
| 291 | 310 | GCTACTGTCAGCTCCTGCTC | 463628 | 82 | n/a | 28 |
| 292 | 311 | GGCTACTGTCAGCTCCTGCT | 463629 | 93 | n/a | 29 |
| 293 | 312 | GGGCTACTGTCAGCTCCTGC | 463630 | 75 | n/a | 30 |
| 299 | 318 | GCCCAAGGGCTACTGTCAGC | 463636 | 69 | n/a | 31 |
| 309 | 328 | CGCACAGGCTGCCCAAGGGC | 463645 | 75 | n/a | 32 |
| 332 | 351 | GCTCAGCCCGCCCACAGCAC | 463648 | 81 | n/a | 33 |
| 338 | 357 | CACCACGCTCAGCCCGCCCA | 463654 | 77 | n/a | 34 |
| 339 | 358 | CCACCACGCTCAGCCCGCCC | 463655 | 73 | n/a | 35 |
| 340 | 359 | GCCACCACGCTCAGCCCGCC | 463656 | 69 | n/a | 36 |
| 341 | 360 | GGCCACCACGCTCAGCCCGC | 463657 | 65 | n/a | 37 |
| 347 | 366 | ACCAGTGGCCACCACGCTCA | 463670 | 73 | n/a | 38 |
| 349 | 368 | GTACCAGTGGCCACCACGCT | 463672 | 81 | n/a | 39 |
| 350 | 369 | TGTACCAGTGGCCACCACGC | 463673 | 69 | n/a | 40 |
| 355 | 374 | CTCCTTGTACCAGTGGCCAC | 463677 | 67 | n/a | 41 |
| 356 | 375 | CCTCCTTGTACCAGTGGCCA | 463678 | 66 | n/a | 42 |
| 357 | 376 | CCCTCCTTGTACCAGTGGCC | 463679 | 76 | n/a | 43 |
| 368 | 387 | CCAGGCGACTGCCCTCCTTG | 463689 | 76 | n/a | 44 |
| 369 | 388 | GCCAGGCGACTGCCCTCCTT | 463690 | 85 | n/a | 45 |
| 370 | 389 | TGCCAGGCGACTGCCCTCCT | 463691 | 78 | n/a | 46 |
| 371 | 390 | GTGCCAGGCGACTGCCCTCC | 463692 | 81 | n/a | 47 |
| 372 | 391 | GGTGCCAGGCGACTGCCCTC | 463693 | 70 | n/a | 48 |
| 388 | 407 | CCGTACACGGCCAGCAGGTG | 463708 | 80 | n/a | 49 |
| 389 | 408 | CCCGTACACGGCCAGCAGGT | 463709 | 85 | n/a | 50 |
| 392 | 411 | AGCCCCGTACACGGCCAGCA | 463712 | 73 | n/a | 51 |
| 397 | 416 | CCTCCAGCCCCGTACACGGC | 463717 | 66 | n/a | 52 |
| 398 | 417 | CCCTCCAGCCCCGTACACGG | 463718 | 66 | n/a | 53 |
| 404 | 423 | GGCGGCCCCTCCAGCCCCGT | 463724 | 70 | n/a | 54 |
| 414 | 433 | GCAATCTCTAGGCGGCCCCT | 463733 | 65 | n/a | 55 |
| 415 | 434 | GGCAATCTCTAGGCGGCCCC | 463734 | 69 | n/a | 56 |

TABLE 1 -continued

Inhibition of human FGFR4 mRNA levels by chimeric antisense oligonucleotides targeted to SEQ ID NO: 1

| Start Site | Stop Site | Sequence | ISIS No | % inhibition (RTS3232) | % inhibition (RTS1325) | SEQ ID NO |
|---|---|---|---|---|---|---|
| 416 | 435 | TGGCAATCTCTAGGCGGCCC | 463735 | 67 | n/a | 57 |
| 431 | 450 | CCTCAGGTAGGAAGCTGGCA | 463750 | 56 | n/a | 58 |
| 432 | 451 | TCCTCAGGTAGGAAGCTGGC | 463751 | 76 | n/a | 59 |
| 443 | 462 | AGCGGCCAGCATCCTCAGGT | 463762 | 58 | n/a | 60 |
| 444 | 463 | TAGCGGCCAGCATCCTCAGG | 463763 | 77 | n/a | 61 |
| 599 | 618 | GTGTCCAGTAGGGTGCTTGC | 463770 | 66 | n/a | 62 |
| 601 | 620 | GTGTGTCCAGTAGGGTGCTT | 463771 | 32 | n/a | 63 |
| 624 | 643 | AGTTTCTTCTCCATGCGCTG | 463774 | 72 | n/a | 64 |
| 717 | 736 | GCCTGTCCATCCTTAAGCCA | 463791 | 68 | n/a | 65 |
| 732 | 751 | TTCTCCCCATGAAAGGCCTG | 463805 | 65 | n/a | 66 |
| 734 | 753 | GGTTCTCCCCATGAAAGGCC | 463807 | 60 | n/a | 67 |
| 784 | 803 | CTCCATCACGAGACTCCAGT | 463832 | 65 | 76 | 68 |
| 787 | 806 | GCTCTCCATCACGAGACTCC | 463834 | 78 | 59 | 69 |
| 788 | 807 | CGCTCTCCATCACGAGACTC | 463835 | 78 | 67 | 70 |
| 789 | 808 | ACGCTCTCCATCACGAGACT | 463836 | 69 | 66 | 71 |
| 790 | 809 | CACGCTCTCCATCACGAGAC | 463837 | 80 | 75 | 72 |
| 791 | 810 | CCACGCTCTCCATCACGAGA | 463838 | 76 | 67 | 73 |
| 968 | 987 | ACACCTTGCACAGCAGCTCC | 463860 | 66 | 67 | 74 |
| 970 | 989 | GTACACCTTGCACAGCAGCT | 463861 | 76 | 74 | 75 |
| 1021 | 1040 | GCCGTTGATGACGATGTGCT | 463871 | 65 | 46 | 76 |
| 1024 | 1043 | GCTGCCGTTGATGACGATGT | 463874 | 77 | 52 | 77 |
| 1025 | 1044 | TGCTGCCGTTGATGACGATG | 463875 | 78 | 42 | 78 |
| 1026 | 1045 | CTGCTGCCGTTGATGACGAT | 463876 | 78 | 10 | 79 |
| 1028 | 1047 | AGCTGCTGCCGTTGATGACG | 463877 | 90 | 54 | 80 |
| 1029 | 1048 | AAGCTGCTGCCGTTGATGAC | 463878 | 73 | 22 | 81 |
| 1031 | 1050 | CGAAGCTGCTGCCGTTGATG | 463880 | 74 | 3 | 82 |
| 1084 | 1103 | GCTATTGATGTCTGCAGTCT | 463882 | 76 | 67 | 83 |
| 1085 | 1104 | AGCTATTGATGTCTGCAGTC | 463883 | 68 | 56 | 84 |
| 1086 | 1105 | GAGCTATTGATGTCTGCAGT | 463884 | 75 | 61 | 85 |
| 1097 | 1116 | CCTCCACCTCTGAGCTATTG | 463893 | 74 | 73 | 86 |
| 1098 | 1117 | ACCTCCACCTCTGAGCTATT | 463894 | 71 | 71 | 87 |
| 1099 | 1118 | GACCTCCACCTCTGAGCTAT | 463906 | 66 | 55 | 88 |
| 1100 | 1119 | GGACCTCCACCTCTGAGCTA | 463907 | 77 | 90 | 89 |
| 1101 | 1120 | AGGACCTCCACCTCTGAGCT | 463908 | 89 | 47 | 90 |
| 1102 | 1121 | CAGGACCTCCACCTCTGAGC | 463909 | 89 | 74 | 91 |
| 1103 | 1122 | ACAGGACCTCCACCTCTGAG | 463910 | 79 | 55 | 92 |
| 1105 | 1124 | GTACAGGACCTCCACCTCTG | 463912 | 69 | 75 | 93 |

TABLE 1 -continued

Inhibition of human FGFR4 mRNA levels by chimeric antisense oligonucleotides targeted to SEQ ID NO: 1

| Start Site | Stop Site | Sequence | ISIS No | % inhibition (RTS3232) | % inhibition (RTS1325) | SEQ ID NO |
|---|---|---|---|---|---|---|
| 1106 | 1125 | GGTACAGGACCTCCACCTCT | 463913 | 71 | 73 | 94 |
| 1111 | 1130 | CCGCAGGTACAGGACCTCCA | 463918 | 67 | 72 | 95 |
| 1112 | 1131 | TCCGCAGGTACAGGACCTCC | 463919 | 65 | 37 | 96 |
| 1115 | 1134 | CGTTCCGCAGGTACAGGACC | 463922 | 70 | 72 | 97 |
| 1185 | 1204 | GCAGACTGGTAGGAGAGGCC | 463937 | 74 | 82 | 98 |
| 1186 | 1205 | GGCAGACTGGTAGGAGAGGC | 463938 | 66 | 7 | 99 |
| 1214 | 1233 | GGTCCTCCTCTGGCAGCACC | 463947 | 68 | 55 | 100 |
| 1301 | 1320 | GCAGGAGCACAGCCAAGGCC | 463967 | 67 | 77 | 101 |
| 1329 | 1348 | GCCTGCCCTCGATACAGCCC | 463994 | 68 | n/a | 102 |
| 1417 | 1436 | GCCTGACTCCAGGGAGAACT | 464002 | 73 | n/a | 103 |
| 1419 | 1438 | GAGCCTGACTCCAGGGAGAA | 464004 | 68 | n/a | 104 |
| 1468 | 1487 | GGAGGAGAGACGCACGCCTC | 464013 | 77 | n/a | 105 |
| 1469 | 1488 | TGGAGGAGAGACGCACGCCT | 464014 | 82 | n/a | 106 |
| 1470 | 1489 | CTGGAGGAGAGACGCACGCC | 464015 | 68 | n/a | 107 |
| 1502 | 1521 | GACTCACGAGGCCGGCGAGC | 464030 | 68 | n/a | 108 |
| 1505 | 1524 | CTAGACTCACGAGGCCGGCG | 464033 | 68 | n/a | 109 |
| 1558 | 1577 | CCCAAGCACCAGCCTGTCCC | 464037 | 67 | n/a | 110 |
| 1559 | 1578 | TCCCAAGCACCAGCCTGTCC | 464038 | 79 | n/a | 111 |
| 1562 | 1581 | GCTTCCCAAGCACCAGCCTG | 464041 | 75 | n/a | 112 |
| 1564 | 1583 | GGGCTTCCCAAGCACCAGCC | 464043 | 74 | n/a | 113 |
| 1616 | 1635 | CCATGCCAAAGGCCTCTGCA | 464046 | 65 | n/a | 114 |
| 1618 | 1637 | GTCCATGCCAAAGGCCTCTG | 464048 | 68 | n/a | 115 |
| 1619 | 1638 | GGTCCATGCCAAAGGCCTCT | 464049 | 73 | n/a | 116 |

Example 2

Dose-Dependent Antisense Inhibition of Human FGFR4 in HepG2 Cells

Gapmers from Example 1 exhibiting significant in vitro inhibition of human FGFR4 were tested at various doses in HepG2 cells. Cells were plated at a density of 20,000 cells per well and transfected using electroporation with 0.6 nM, 1.3 nM, 2.5 nM, 5.0 nM, and 10.0 µM concentrations of antisense oligonucleotide, as specified in Table 2. After a treatment period of approximately 16 hours, RNA was isolated from the cells and FGFR4 mRNA levels were measured by quantitative real-time PCR. Human FGFR4 primer probe set RTS3232 was used to measure mRNA levels. FGFR4 mRNA levels were adjusted according to total RNA content, as measured by RIBOGREEN®. Results are presented as percent inhibition of FGFR4, relative to untreated control cells.

The half maximal inhibitory concentration ($IC_{50}$) of each oligonucleotide is also presented in Table 2 and was calculated by plotting the concentrations of oligonucleotides used versus the percent inhibition of FGFR4 mRNA expression achieved at each concentration, and noting the concentration of oligonucleotide at which 50% inhibition of FGFR4 mRNA expression was achieved compared to the control. As illustrated in Table 2, FGFR4 mRNA levels were significantly reduced in a dose-dependent manner in antisense oligonucleotide treated cells.

TABLE 2

Dose-dependent antisense inhibition of human FGFR4 in HepG2 cells using electroporation

| ISIS No | 0.6 µM | 1.3 µM | 2.5 µM | 5.0 µM | 10.0 µM | $IC_{50}$ (µM) |
|---|---|---|---|---|---|---|
| 299005 | 45 | 63 | 77 | 92 | 95 | 0.7 |
| 463588 | 43 | 66 | 86 | 90 | 97 | 0.6 |
| 463589 | 41 | 67 | 85 | 92 | 95 | 0.6 |
| 463628 | 55 | 68 | 87 | 94 | 92 | 0.3 |
| 463629 | 25 | 40 | 63 | 76 | 91 | 1.8 |
| 463648 | 36 | 51 | 71 | 85 | 96 | 1.1 |
| 463672 | 19 | 46 | 74 | 90 | 96 | 1.5 |
| 463690 | 30 | 66 | 86 | 94 | 97 | 0.9 |

TABLE 2-continued

Dose-dependent antisense inhibition of human FGFR4 in HepG2 cells using electroporation

| ISIS No | 0.6 µM | 1.3 µM | 2.5 µM | 5.0 µM | 10.0 µM | IC$_{50}$ (µM) |
|---|---|---|---|---|---|---|
| 463691 | 31 | 50 | 78 | 89 | 96 | 1.1 |
| 463692 | 33 | 56 | 75 | 90 | 94 | 1.1 |
| 463708 | 11 | 45 | 63 | 77 | 94 | 1.9 |
| 463709 | 35 | 50 | 73 | 86 | 96 | 1.1 |
| 463750 | 24 | 42 | 54 | 80 | 93 | 1.8 |
| 463762 | 57 | 76 | 90 | 95 | 98 | <0.6 |
| 463771 | 53 | 44 | 66 | 83 | 88 | 1.4 |
| 463807 | 13 | 36 | 56 | 87 | 96 | 2.0 |
| 463834 | 32 | 44 | 68 | 90 | 97 | 1.3 |
| 463835 | 37 | 59 | 82 | 91 | 97 | 0.9 |
| 463837 | 28 | 61 | 77 | 92 | 97 | 1.1 |
| 463838 | 29 | 50 | 72 | 88 | 95 | 1.3 |
| 463861 | 44 | 52 | 78 | 90 | 97 | 0.8 |
| 463893 | 29 | 33 | 65 | 84 | 95 | 1.6 |
| 464013 | 27 | 34 | 50 | 75 | 86 | 2.1 |
| 464014 | 16 | 33 | 55 | 78 | 90 | 2.1 |
| 464038 | 37 | 55 | 74 | 90 | 96 | 1.0 |

Example 3

Antisense Inhibition of Human Fibroblast Growth Factor Receptor (FGFR4) in HepG2 Cells Additional antisense oligonucleotides were designed targeting a FGFR4 nucleic acid and were tested for their effects on FGFR4 mRNA in vitro. Some of the antisense oligonucleotides described in Example 1 were also included in the assay for comparison. Cultured HepG2 cells at a density of 20,000 cells per well were transfected using electroporation with 4,500 nM antisense oligonucleotide. After a treatment period of approximately 24 hours, RNA was isolated from the cells and FGFR4 mRNA levels were measured by quantitative real-time PCR. Human primer probe set RTS3232 was used to measure mRNA levels. FGFR4 mRNA levels were adjusted according to total RNA content, as measured by RIBOGREEN®. Results are presented as percent inhibition of FGFR4, relative to untreated control cells. A total of 772 oligonucleotides were tested. Only those oligonucleotides demonstrating greater than 65% inhibition are shown in Tables 3 and 4.

The newly designed chimeric antisense oligonucleotides in Table 3 were designed as 5-10-5 MOE gapmers. The gapmers are 20 nucleosides in length, wherein the central gap segment comprises of ten 2'-deoxynucleosides and is flanked by wing segments on the 5' and 3' directions comprising five nucleosides each. Each nucleotide in the 5' wing segment and each nucleotide in the 3' wing segment has a 2'-MOE modification. The internucleoside linkages throughout each gapmer are phosphorothioate (P=S) linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted in the human gene sequence.

Each gapmer listed in Table 3 is targeted to either the human FGFR4 mRNA, designated herein as SEQ ID NO: 1 (GENBANK Accession No. NM_002011.3) or the human FGFR4 genomic sequence, designated herein as SEQ ID NO: 2 (GENBANK Accession No: NT_023133.11 truncated from nucleosides 21323018 to 21335213), or both. Some of the antisense oligonucleotides were designed to target variant gene sequences and are listed in Table 4. Each gapmer in Table 4 is listed to either SEQ ID NO: 3 (GENBANK Accession No. AB209631.1)

TABLE 3

Inhibition of human FGFR4 mRNA levels by chimeric antisense oligonucleotides targeted to SEQ ID NO: 1 and SEQ ID NO: 2

| Start Site on SEQ ID NO: 1 | Stop Site on SEQ ID NO: 1 | ISIS No | Sequence | % inhibition | Start Site on SEQ ID NO: 2 | Stop Site on SEQ ID NO: 2 | SEQ ID NO |
|---|---|---|---|---|---|---|---|
| 160 | 179 | 299004 | CAGCAGCCGCATCTCCTTCT | 88 | 3165 | 3184 | 117 |
| 2497 | 2516 | 299055 | GCTGAAGACAGAATCGCTGG | 65 | 11167 | 11186 | 118 |
| 292 | 311 | 463629 | GGCTACTGTCAGCTCCTGCT | 87 | 3993 | 4012 | 29 |
| 2325 | 2344 | 464138 | CAGCACTCACGCATCAGCCC | 72 | 10866 | 10885 | 119 |
| 2326 | 2345 | 464139 | CCAGCACTCACGCATCAGCC | 75 | 10867 | 10886 | 120 |
| 2437 | 2456 | 464167 | GGGTCCGAAGGTCAGGCGGA | 68 | 11107 | 11126 | 121 |
| 2438 | 2457 | 464168 | AGGGTCCGAAGGTCAGGCGG | 70 | 11108 | 11127 | 122 |
| 2440 | 2459 | 464170 | ATAGGGTCCGAAGGTCAGGC | 67 | 11110 | 11129 | 123 |
| 2443 | 2462 | 464173 | GGAATAGGGTCCGAAGGTCA | 69 | 11113 | 11132 | 124 |
| 2582 | 2601 | 464181 | GTGCCTGCACAGCCTTGAGC | 66 | 11252 | 11271 | 125 |
| 2812 | 2831 | 464203 | TCTCCAGCCAGGCTCAGCCA | 72 | 11482 | 11501 | 126 |
| 2816 | 2835 | 464207 | CAGCTCTCCAGCCAGGCTCA | 72 | 11486 | 11505 | 127 |
| 2817 | 2836 | 464208 | GCAGCTCTCCAGCCAGGCTC | 78 | 11487 | 11506 | 128 |
| 2818 | 2837 | 464209 | AGCAGCTCTCCAGCCAGGCT | 79 | 11488 | 11507 | 129 |

TABLE 3 -continued

Inhibition of human FGFR4 mRNA levels by chimeric antisense
oligonucleotides targeted to SEQ ID NO: 1 and SEQ ID NO: 2

| Start Site on SEQ ID NO: 1 | Stop Site on SEQ ID NO: 1 | ISIS No | Sequence | % inhibition | Start Site on SEQ ID NO: 2 | Stop Site on SEQ ID NO: 2 | SEQ ID NO |
|---|---|---|---|---|---|---|---|
| 2819 | 2838 | 464210 | TAGCAGCTCTCCAGCCAGGC | 70 | 11489 | 11508 | 130 |
| 2822 | 2841 | 464213 | GCATAGCAGCTCTCCAGCCA | 82 | 11492 | 11511 | 131 |
| 2823 | 2842 | 464214 | AGCATAGCAGCTCTCCAGCC | 85 | 11493 | 11512 | 132 |
| 2824 | 2843 | 464215 | TAGCATAGCAGCTCTCCAGC | 84 | 11494 | 11513 | 133 |
| 2825 | 2844 | 464216 | TTAGCATAGCAGCTCTCCAG | 72 | 11495 | 11514 | 134 |
| 2951 | 2970 | 464222 | CCAGCTTCTCTGGGCTCAGG | 88 | 11621 | 11640 | 135 |
| 2952 | 2971 | 464223 | TCCAGCTTCTCTGGGCTCAG | 86 | 11622 | 11641 | 136 |
| 2953 | 2972 | 464224 | TTCCAGCTTCTCTGGGCTCA | 81 | 11623 | 11642 | 137 |
| 2954 | 2973 | 464225 | CTTCCAGCTTCTCTGGGCTC | 82 | 11624 | 11643 | 138 |
| 2955 | 2974 | 464226 | GCTTCCAGCTTCTCTGGGCT | 79 | 11625 | 11644 | 139 |
| 2956 | 2975 | 464227 | GGCTTCCAGCTTCTCTGGGC | 87 | 11626 | 11645 | 140 |
| 2981 | 3000 | 464228 | ACGCCATTTGCTCCTGTTTT | 89 | 11651 | 11670 | 141 |
| n/a | n/a | 464238 | TGCGAATCAATGGGTCCCGA | 73 | 908 | 927 | 142 |
| n/a | n/a | 464239 | GGTGCGAATCAATGGGTCCC | 67 | 910 | 929 | 143 |
| n/a | n/a | 464254 | CCGCCGGCGCGAAGACAGCC | 66 | 984 | 1003 | 144 |
| n/a | n/a | 464258 | CATCTCTGCCGCCGGCGCGA | 71 | 992 | 1011 | 145 |
| n/a | n/a | 464266 | CTGACCGCTGACCGACCACC | 76 | 1138 | 1157 | 146 |
| n/a | n/a | 464268 | GCTGCTGACCGCTGACCGAC | 73 | 1142 | 1161 | 147 |
| n/a | n/a | 464269 | CTGCCCTGATATCAGAGTCC | 65 | 1180 | 1199 | 148 |
| n/a | n/a | 464270 | GGCTGCCCTGATATCAGAGT | 65 | 1182 | 1201 | 149 |
| n/a | n/a | 464278 | CTCAGATACTGCTGTCTCTG | 71 | 1345 | 1364 | 150 |
| n/a | n/a | 464280 | TGCCCATCCCTCTGTGCCCC | 72 | 1386 | 1405 | 151 |
| n/a | n/a | 464284 | TGCTCTCTTGCCCATCCCTC | 82 | 1394 | 1413 | 152 |
| n/a | n/a | 464285 | CTCTTTGGTCACACCGTCTG | 82 | 1461 | 1480 | 153 |
| n/a | n/a | 464286 | ATCTCTTTGGTCACACCGTC | 90 | 1463 | 1482 | 154 |
| n/a | n/a | 464287 | CTATCTCTTTGGTCACACCG | 82 | 1465 | 1484 | 155 |
| n/a | n/a | 464288 | GCCTATCTCTTTGGTCACAC | 88 | 1467 | 1486 | 156 |
| n/a | n/a | 464290 | CGCTGCCTATCTCTTTGGTC | 70 | 1471 | 1490 | 157 |
| n/a | n/a | 464291 | AGCTTGCAAGCCCTTAATGG | 70 | 1542 | 1561 | 158 |
| n/a | n/a | 464292 | CCAGCTTGCAAGCCCTTAAT | 69 | 1544 | 1563 | 159 |
| n/a | n/a | 464298 | ACCTTCATCTTCCAGCAGAG | 80 | 1941 | 1960 | 160 |
| n/a | n/a | 464299 | CAACCTTCATCTTCCAGCAG | 76 | 1943 | 1962 | 161 |
| n/a | n/a | 464300 | TTCAACCTTCATCTTCCAGC | 81 | 1945 | 1964 | 162 |
| n/a | n/a | 464308 | CAGCTTTGCTCAGCCCAGCA | 90 | 3325 | 3344 | 163 |
| n/a | n/a | 464309 | TCCAGCTTTGCTCAGCCCAG | 87 | 3327 | 3346 | 164 |
| n/a | n/a | 464310 | TTTCCAGCTTTGCTCAGCCC | 78 | 3329 | 3348 | 165 |

TABLE 3 -continued

Inhibition of human FGFR4 mRNA levels by chimeric antisense
oligonucleotides targeted to SEQ ID NO: 1 and SEQ ID NO: 2

| Start Site on SEQ ID NO: 1 | Stop Site on SEQ ID NO: 1 | ISIS No | Sequence | % inhibition | Start Site on SEQ ID NO: 2 | Stop Site on SEQ ID NO: 2 | SEQ ID NO |
|---|---|---|---|---|---|---|---|
| n/a | n/a | 464311 | CCTTTCCAGCTTTGCTCAGC | 78 | 3331 | 3350 | 166 |
| n/a | n/a | 464333 | CCAGGTCCACAGTCCAGGGC | 75 | 4799 | 4818 | 167 |
| n/a | n/a | 464342 | ACTTGCCAGAGAGTAGCAGA | 66 | 4836 | 4855 | 168 |
| n/a | n/a | 464425 | GCCATAGCACCTCCTCCAGG | 75 | 7684 | 7703 | 169 |
| n/a | n/a | 464428 | CCCAATGCCATAGCACCTCC | 73 | 7690 | 7709 | 170 |
| n/a | n/a | 464429 | GTCCCAATGCCATAGCACCT | 70 | 7692 | 7711 | 171 |
| n/a | n/a | 464430 | TAGTCCCAATGCCATAGCAC | 65 | 7694 | 7713 | 172 |
| n/a | n/a | 464433 | TTCTATTAGTCCCAATGCCA | 69 | 7700 | 7719 | 173 |
| n/a | n/a | 464449 | GTCACTTGCCAGGGTCAGGA | 81 | 7802 | 7821 | 174 |
| n/a | n/a | 464453 | GCTCAGAAGTCACTTGCCAG | 68 | 7810 | 7829 | 175 |
| n/a | n/a | 464568 | GTCCATCTGGCTTCCCCTGC | 68 | 2031 | 2050 | 176 |
| n/a | n/a | 464569 | CAGTCCATCTGGCTTCCCCT | 68 | 2033 | 2052 | 177 |
| n/a | n/a | 464575 | CCACTCCACTTCCAGTCCAT | 65 | 2045 | 2064 | 178 |
| n/a | n/a | 464576 | TGCCACTCCACTTCCAGTCC | 68 | 2047 | 2066 | 179 |
| n/a | n/a | 464579 | GGTCACTGCCACTCCACTTC | 78 | 2053 | 2072 | 180 |
| n/a | n/a | 464581 | CCTTGGTCACTGCCACTCCA | 68 | 2057 | 2076 | 181 |
| n/a | n/a | 464582 | GGAAGCCTATCACACCTCCT | 67 | 2080 | 2099 | 182 |
| n/a | n/a | 464584 | GTGTCTCTGGATCTACCCTG | 71 | 2104 | 2123 | 183 |
| n/a | n/a | 464585 | TGGTGTCTCTGGATCTACCC | 74 | 2106 | 2125 | 184 |
| n/a | n/a | 464586 | ACTGGTGTCTCTGGATCTAC | 72 | 2108 | 2127 | 185 |
| n/a | n/a | 464587 | GCACTGGTGTCTCTGGATCT | 83 | 2110 | 2129 | 186 |
| n/a | n/a | 464588 | TGGCACTGGTGTCTCTGGAT | 88 | 2112 | 2131 | 187 |
| n/a | n/a | 464589 | GGTGGCACTGGTGTCTCTGG | 88 | 2114 | 2133 | 188 |
| n/a | n/a | 464590 | TGGGTGGCACTGGTGTCTCT | 74 | 2116 | 2135 | 189 |
| n/a | n/a | 464591 | TATGGGTGGCACTGGTGTCT | 74 | 2118 | 2137 | 190 |
| n/a | n/a | 464593 | GGCCTATGGGTGGCACTGGT | 68 | 2122 | 2141 | 191 |
| n/a | n/a | 464617 | GTCAGGCTGTGATGTACACA | 69 | 2261 | 2280 | 192 |
| n/a | n/a | 464622 | TGCTGTTACTGTCAGGCTGT | 73 | 2271 | 2290 | 193 |
| n/a | n/a | 464623 | GCCAGTCACCTCTGGTTCGG | 68 | 2292 | 2311 | 194 |
| n/a | n/a | 464657 | AGCAGTTTTGGGATTCTITT | 72 | 2838 | 2857 | 195 |
| n/a | n/a | 464658 | AAAGCAGTTTTGGGATTCTT | 67 | 2840 | 2859 | 196 |
| n/a | n/a | 464677 | TCCAAGTCCCTGGCCAGGCT | 65 | 2993 | 3012 | 197 |
| n/a | n/a | 464682 | ATCCTTTCCAGCTTTGCTCA | 78 | 3333 | 3352 | 198 |
| n/a | n/a | 464683 | GGATCCTTTCCAGCTTTGCT | 90 | 3335 | 3354 | 199 |
| n/a | n/a | 464684 | AAGGATCCTTTCCAGCTTTG | 72 | 3337 | 3356 | 200 |
| n/a | n/a | 464685 | GCAAGGATCCTTTCCAGCTT | 88 | 3339 | 3358 | 201 |

TABLE 3 -continued

Inhibition of human FGFR4 mRNA levels by chimeric antisense
oligonucleotides targeted to SEQ ID NO: 1 and SEQ ID NO: 2

| Start Site on SEQ ID NO: 1 | Stop Site on SEQ ID NO: 1 | ISIS No | Sequence | % inhibition | Start Site on SEQ ID NO: 2 | Stop Site on SEQ ID NO: 2 | SEQ ID NO |
|---|---|---|---|---|---|---|---|
| n/a | n/a | 464686 | GGGCAAGGATCCTTTCCAGC | 82 | 3341 | 3360 | 202 |
| n/a | n/a | 464687 | CTGGGCAAGGATCCTTTCCA | 71 | 3343 | 3362 | 203 |
| n/a | n/a | 464688 | GCCTGGGCAAGGATCCTTTC | 69 | 3345 | 3364 | 204 |
| n/a | n/a | 464689 | GTGGTTGAGCCCTGCCCTGC | 67 | 3380 | 3399 | 205 |
| n/a | n/a | 464692 | GTCTCAGTGGTTGAGCCCTG | 71 | 3386 | 3405 | 206 |
| n/a | n/a | 464696 | CTGACTGAGTCTCAGTGGTT | 82 | 3394 | 3413 | 207 |
| n/a | n/a | 464698 | GGCACTGACTGAGTCTCAGT | 84 | 3398 | 3417 | 208 |
| n/a | n/a | 464699 | CAGGCACTGACTGAGTCTCA | 79 | 3400 | 3419 | 209 |
| n/a | n/a | 464701 | AAGCCAGGCACTGACTGAGT | 72 | 3404 | 3423 | 210 |
| n/a | n/a | 464703 | CTGGAAGCCAGGCACTGACT | 70 | 3408 | 3427 | 211 |
| n/a | n/a | 464705 | GCTTGCTGGAAGCCAGGCAC | 67 | 3413 | 3432 | 212 |
| n/a | n/a | 464706 | ATGCTTGCTGGAAGCCAGGC | 80 | 3415 | 3434 | 213 |
| n/a | n/a | 464707 | GTCCTCTCTCGCAGACACAG | 84 | 3445 | 3464 | 214 |
| n/a | n/a | 464708 | CAGTCCTCTCTCGCAGACAC | 86 | 3447 | 3466 | 215 |
| n/a | n/a | 464709 | GCCAGTCCTCTCTCGCAGAC | 86 | 3449 | 3468 | 216 |
| n/a | n/a | 464710 | AGGCCAGTCCTCTCTCGCAG | 90 | 3451 | 3470 | 217 |
| n/a | n/a | 464711 | GAGCTCACCACCAGCTCTGC | 70 | 3499 | 3518 | 218 |
| n/a | n/a | 464716 | GCTGCCTGGACCTCCTAGGT | 90 | 3571 | 3590 | 219 |
| n/a | n/a | 464717 | ATGCTGCCTGGACCTCCTAG | 85 | 3573 | 3592 | 220 |
| n/a | n/a | 464718 | ACATGCTGCCTGGACCTCCT | 89 | 3575 | 3594 | 221 |
| n/a | n/a | 464719 | ACACATGCTGCCTGGACCTC | 73 | 3577 | 3596 | 222 |
| n/a | n/a | 464720 | CCACACATGCTGCCTGGACC | 88 | 3579 | 3598 | 223 |
| n/a | n/a | 464726 | GCAAATGCCACACTCTTGGG | 67 | 3770 | 3789 | 224 |
| n/a | n/a | 464727 | GGGCAAATGCCACACTCTTG | 78 | 3772 | 3791 | 225 |
| n/a | n/a | 464728 | CAGGGCAAATGCCACACTCT | 71 | 3774 | 3793 | 226 |
| n/a | n/a | 464729 | CCCAGGGCAAATGCCACACT | 87 | 3776 | 3795 | 227 |
| n/a | n/a | 464730 | CACCCAGGGCAAATGCCACA | 78 | 3778 | 3797 | 228 |
| n/a | n/a | 464732 | GCCACACCCAGGGCAAATGC | 87 | 3782 | 3801 | 229 |
| n/a | n/a | 464734 | GGATGCCACACCCAGGGCAA | 66 | 3786 | 3805 | 230 |
| n/a | n/a | 464735 | GCGGATGCCACACCCAGGGC | 87 | 3788 | 3807 | 231 |
| n/a | n/a | 464736 | CTGCGGATGCCACACCCAGG | 67 | 3790 | 3809 | 232 |
| n/a | n/a | 464740 | GCCACATGCTGCGGATGCCA | 88 | 3798 | 3817 | 233 |
| n/a | n/a | 464800 | GGACTTCCCACCAACTGCCT | 71 | 3122 | 3141 | 234 |
| n/a | n/a | 464801 | GCTGGACTTCCCACCAACTG | 77 | 3125 | 3144 | 235 |

TABLE 4

Inhibition of human FGFR4 mRNA levels by chimeric antisense oligonucleotides targeted to SEQ ID NO: 3

| Target Start Site | Sequence | ISIS No | % inhibition | SEQ ID NO |
|---|---|---|---|---|
| 1502 | CAAGGAGCTCACCACCAGCT | 464713 | 83 | 236 |
| 1504 | GGCAAGGAGCTCACCACCAG | 464714 | 76 | 237 |
| 1506 | CAGGCAAGGAGCTCACCACC | 464715 | 69 | 238 |

Example 4

Dose-Dependent Antisense Inhibition of Human FGFR4 in HepG2 Cells

Gapmers from Example 3 which caused significant inhibition of FGFR4 mRNA were further tested at various doses in HepG2 cells. Cells were plated at a density of 20,000 cells per well and transfected using electroporation with 0.6 µM, 1.3 µM, 2.5 µM, 5.0 µM, and 10.0 µM concentrations of antisense oligonucleotide, as specified in Table 5. After a treatment period of approximately 16 hours, RNA was isolated from the cells and FGFR4 mRNA levels were measured by quantitative real-time PCR. Human FGFR4 primer probe set RTS3232 was used to measure mRNA levels. FGFR4 mRNA levels were adjusted according to total RNA content, as measured by RIBOGREEN®. Results are presented as percent inhibition of FGFR4, relative to untreated control cells.

The half maximal inhibitory concentration (IC$_{50}$) of each oligonucleotide is also presented in Table 5. As illustrated in Table 5, FGFR4 mRNA levels were significantly reduced in a dose-dependent manner in antisense oligonucleotide treated cells.

TABLE 5

Dose-dependent antisense inhibition of human FGFR4 in HepG2 cells using electroporation

| ISIS No | 0.6 µM | 1.3 µM | 2.5 µM | 5.0 µM | 10.0 µM | IC$_{50}$ (µM) |
|---|---|---|---|---|---|---|
| 299004 | 20 | 44 | 73 | 87 | 96 | 1.5 |
| 463629 | 23 | 54 | 80 | 87 | 96 | 1.0 |
| 464138 | 0 | 32 | 57 | 84 | 91 | 2.3 |
| 464208 | 28 | 37 | 58 | 76 | 87 | 1.8 |
| 464209 | 22 | 30 | 64 | 79 | 80 | 2.0 |
| 464213 | 21 | 40 | 54 | 79 | 90 | 1.9 |
| 464214 | 14 | 31 | 55 | 84 | 93 | 2.1 |
| 464215 | 35 | 38 | 67 | 85 | 94 | 1.4 |
| 464222 | 29 | 53 | 73 | 89 | 93 | 1.2 |
| 464223 | 16 | 0 | 63 | 76 | 88 | 3.2 |
| 464225 | 36 | 43 | 74 | 85 | 88 | 1.2 |
| 464227 | 29 | 56 | 64 | 86 | 90 | 1.3 |
| 464228 | 52 | 76 | 82 | 91 | 92 | 0.3 |
| 464284 | 21 | 44 | 67 | 83 | 91 | 1.6 |
| 464285 | 27 | 36 | 57 | 81 | 93 | 1.9 |
| 464286 | 35 | 47 | 70 | 89 | 95 | 1.2 |
| 464287 | 26 | 50 | 68 | 85 | 90 | 1.4 |
| 464288 | 19 | 49 | 55 | 83 | 90 | 1.7 |
| 464300 | 25 | 34 | 47 | 75 | 93 | 2.1 |
| 464308 | 35 | 57 | 77 | 94 | 97 | 1.0 |
| 464309 | 4 | 25 | 65 | 89 | 95 | 2.1 |
| 464425 | 2 | 31 | 52 | 71 | 81 | 2.7 |
| 464449 | 32 | 59 | 78 | 88 | 95 | 1.0 |
| 464587 | 25 | 52 | 75 | 88 | 91 | 1.3 |
| 464588 | 26 | 74 | 84 | 93 | 93 | 1.0 |
| 464589 | 29 | 62 | 83 | 90 | 93 | 1.0 |
| 464683 | 10 | 35 | 50 | 71 | 90 | 2.4 |
| 464685 | 14 | 42 | 42 | 62 | 88 | 2.6 |
| 464686 | 12 | 44 | 66 | 81 | 95 | 1.8 |
| 464696 | 22 | 43 | 68 | 85 | 94 | 1.6 |
| 464698 | 12 | 10 | 20 | 44 | 71 | 5.9 |
| 464706 | 16 | 52 | 46 | 84 | 92 | 1.8 |
| 464707 | 26 | 40 | 69 | 84 | 93 | 1.5 |
| 464708 | 18 | 46 | 57 | 84 | 94 | 1.7 |
| 464709 | 6 | 14 | 32 | 58 | 84 | 3.7 |
| 464710 | 12 | 30 | 44 | 65 | 86 | 2.7 |
| 464713 | 9 | 28 | 47 | 78 | 92 | 2.4 |
| 464716 | 21 | 45 | 64 | 86 | 93 | 1.6 |
| 464717 | 13 | 37 | 57 | 86 | 94 | 2.0 |
| 464718 | 22 | 56 | 80 | 93 | 97 | 1.2 |
| 464720 | 15 | 33 | 49 | 77 | 92 | 2.2 |
| 464729 | 15 | 20 | 35 | 69 | 84 | 3.0 |
| 464732 | 19 | 55 | 73 | 85 | 93 | 1.4 |
| 464735 | 27 | 45 | 62 | 89 | 94 | 1.5 |
| 464740 | 10 | 44 | 65 | 82 | 89 | 1.9 |
| 464801 | 17 | 53 | 56 | 81 | 92 | 1.7 |

Example 5

Dose-Dependent Antisense Inhibition of Human FGFR4 in HepG2 Cells

Gapmers from the studies described above which caused significant inhibition of FGFR4 mRNA were further tested at various doses in HepG2 cells. Cells were plated at a density of 20,000 cells per well and transfected using electroporation with 0.3 µM, 0.6 µM, 1.3 µM, 2.5 µM, 5.0 µM, and 10.0 µM concentrations of antisense oligonucleotide, as specified in Table 6. After a treatment period of approximately 16 hours, RNA was isolated from the cells and FGFR4 mRNA levels were measured by quantitative real-time PCR. Human FGFR4 primer probe set RTS3232 was used to measure mRNA levels. FGFR4 mRNA levels were adjusted according to total RNA content, as measured by RIBOGREEN®. Results are presented as percent inhibition of FGFR4, relative to untreated control cells.

The half maximal inhibitory concentration (IC$_{50}$) of each oligonucleotide is also presented in Table 6. As illustrated in Table 6, FGFR4 mRNA levels were significantly reduced in a dose-dependent manner in antisense oligonucleotide treated cells.

TABLE 6

Dose-dependent antisense inhibition of human FGFR4 in HepG2 cells using electroporation

| ISIS No | 0.3 µM | 0.6 µM | 1.3 µM | 2.5 µM | 5.0 µM | 10.0 µM | IC$_{50}$ (µM) |
|---|---|---|---|---|---|---|---|
| 299004 | 0 | 20 | 14 | 49 | 70 | 89 | 2.5 |
| 299005 | 7 | 25 | 52 | 76 | 92 | 96 | 1.3 |
| 463588 | 26 | 22 | 43 | 84 | 94 | 98 | 1.3 |
| 463589 | 13 | 24 | 52 | 74 | 92 | 95 | 1.3 |
| 463628 | 27 | 45 | 57 | 76 | 94 | 95 | 0.8 |
| 463629 | 24 | 36 | 67 | 85 | 93 | 96 | 0.9 |
| 463648 | 14 | 21 | 38 | 54 | 75 | 90 | 1.9 |
| 463672 | 8 | 28 | 41 | 57 | 86 | 95 | 1.6 |
| 463690 | 22 | 17 | 59 | 74 | 91 | 97 | 1.3 |
| 463691 | 10 | 24 | 45 | 60 | 86 | 87 | 1.6 |
| 463692 | 0 | 10 | 33 | 56 | 76 | 92 | 2.2 |
| 463709 | 12 | 22 | 36 | 66 | 85 | 95 | 1.6 |
| 463762 | 0 | 22 | 16 | 29 | 0 | 84 | >10.0 |
| 463771 | 0 | 29 | 38 | 49 | 66 | 89 | 2.2 |
| 463834 | 14 | 24 | 43 | 52 | 79 | 94 | 1.7 |
| 463835 | 18 | 35 | 40 | 58 | 82 | 94 | 1.4 |

TABLE 6-continued

Dose-dependent antisense inhibition of human FGFR4 in HepG2 cells using electroporation

| ISIS No | 0.3 µM | 0.6 µM | 1.3 µM | 2.5 µM | 5.0 µM | 10.0 µM | IC$_{50}$ (µM) |
|---|---|---|---|---|---|---|---|
| 463837 | 8 | 22 | 53 | 73 | 89 | 97 | 1.4 |
| 463838 | 12 | 23 | 44 | 56 | 77 | 91 | 1.7 |
| 463861 | 25 | 41 | 41 | 61 | 76 | 90 | 1.3 |
| 463907 | 0 | 25 | 51 | 68 | 84 | 95 | 1.6 |
| 463909 | 19 | 39 | 54 | 82 | 93 | 97 | 1.0 |
| 464038 | 8 | 22 | 36 | 44 | 72 | 89 | 2.2 |

Example 6

Dose-Dependent Antisense Inhibition of Human FGFR4 in HepG2 Cells

Gapmers from the study described in Example 4 exhibiting significant in vitro inhibition of FGFR4 mRNA were selected and tested at various doses in HepG2 cells. Cells were plated at a density of 20,000 cells per well and transfected using electroporation with 0.6 µM, 1.3 µM, 2.5 µM, 5.0 µM and 10.0 µM concentrations of antisense oligonucleotide, as specified in Table 7. After a treatment period of approximately 16 hours, RNA was isolated from the cells and FGFR4 mRNA levels were measured by quantitative real-time PCR. Human FGFR4 primer probe set RTS3232 was used to measure mRNA levels. FGFR4 mRNA levels were adjusted according to total RNA content, as measured by RIBOGREEN®. Results are presented as percent inhibition of FGFR4, relative to untreated control cells.

The half maximal inhibitory concentration (IC$_{50}$) of each oligonucleotide is also presented in Table 7. As illustrated in Table 7, FGFR4 mRNA levels were significantly reduced in a dose-dependent manner in antisense oligonucleotide treated cells.

TABLE 7

Dose-dependent antisense inhibition of human FGFR4 in HepG2 cells using electroporation

| ISIS No | 0.6 µM | 1.3 µM | 2.5 µM | 5.0 µM | 10.0 µM | IC$_{50}$ (µM) |
|---|---|---|---|---|---|---|
| 463629 | 44 | 73 | 86 | 96 | 98 | <0.6 |
| 464222 | 40 | 65 | 81 | 88 | 96 | 0.7 |
| 464225 | 47 | 76 | 84 | 92 | 86 | <0.6 |
| 464228 | 56 | 80 | 86 | 92 | 95 | <0.6 |
| 464284 | 24 | 47 | 62 | 78 | 90 | 1.6 |
| 464286 | 23 | 60 | 73 | 86 | 93 | 1.2 |
| 464287 | 19 | 62 | 69 | 89 | 91 | 1.3 |
| 464308 | 38 | 54 | 78 | 90 | 96 | 1.0 |
| 464449 | 27 | 69 | 80 | 91 | 94 | 0.9 |
| 464587 | 24 | 68 | 74 | 88 | 91 | 1.1 |
| 464588 | 42 | 75 | 81 | 88 | 92 | <0.6 |

TABLE 7-continued

Dose-dependent antisense inhibition of human FGFR4 in HepG2 cells using electroporation

| ISIS No | 0.6 µM | 1.3 µM | 2.5 µM | 5.0 µM | 10.0 µM | IC$_{50}$ (µM) |
|---|---|---|---|---|---|---|
| 464589 | 36 | 69 | 78 | 90 | 92 | 0.8 |
| 464716 | 52 | 60 | 75 | 90 | 95 | 0.6 |
| 464718 | 38 | 61 | 76 | 91 | 95 | 0.9 |
| 464732 | 30 | 39 | 65 | 85 | 94 | 1.5 |

Example 7

Antisense Inhibition of Human Fibroblast Growth Factor Receptor (FGFR4) in HepG2 Cells Additional antisense oligonucleotides were designed targeting a FGFR4 nucleic acid and were tested for their effects on FGFR4 mRNA in vitro. ISIS 463629 and ISIS 463762 were also included in the assay for comparison. Cultured HepG2 cells at a density of 20,000 cells per well were transfected using electroporation with 4,500 nM antisense oligonucleotide. After a treatment period of approximately 24 hours, RNA was isolated from the cells and FGFR4 mRNA levels were measured by quantitative real-time PCR. Human primer probe set RTS3232 was used to measure mRNA levels. FGFR4 mRNA levels were adjusted according to total RNA content, as measured by RIBOGREEN®. Results are presented as percent inhibition of FGFR4, relative to untreated control cells. A total of 230 oligonucleotides were tested. Only those oligonucleotides demonstrating greater than 65% inhibition are shown in Table 8.

The newly designed chimeric antisense oligonucleotides in Table 8 were designed as 5-10-5 MOE gapmers or 3-10-4 MOE gapmers. The 5-10-5 gapmers are 20 nucleosides in length, wherein the central gap segment comprises of ten 2'-deoxynucleosides and is flanked by wing segments on the 5' and 3' directions comprising five nucleosides each. The 3-10-4 gapmers are 17 nucleosides in length, wherein the central gap segment comprises of ten 2'-deoxynucleosides and is flanked by a wing segment in the 5' direction comprising three nucleosides and a wing segment in the 3' direction comprising four nucleosides. Each nucleotide in the 5' wing segment and each nucleotide in the 3' wing segment has a 2'-MOE modification. The internucleoside linkages throughout each gapmer are phosphorothioate (P=S) linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted in the human gene sequence.

Each gapmer listed in Table 8 is targeted to either the human FGFR4 mRNA, designated herein as SEQ ID NO: 1 (GENBANK Accession No. NM_002011.3) or the human FGFR4 genomic sequence, designated herein as SEQ ID NO: 2 (GENBANK Accession No: NT_023133.11 truncated from nucleosides 21323018 to 21335213), or SEQ ID NO: 3 (GENBANK Accession No. AB209631.1), or all three.

TABLE 8

Inhibition of human FGFR4 mRNA levels by chimeric antisense oligonucleotides targeted to SEQ ID NO: 1, SEQ ID NO: 2 and SEQ ID NO: 3

| Start Site on SEQ ID NO: 1 | Start Site on SEQ ID NO: 2 | Start Site on SEQ ID NO: 3 | Motif | Sequence | ISIS No | % inhibition | SEQ ID NO |
|---|---|---|---|---|---|---|---|
| 292 | 3993 | 1996 | 5-10-5 | GGCTACTGTCAGCTCCTGCT | 463629 | 93 | 29 |
| 118 | 3123 | 1122 | 5-10-5 | TGGACTTCCCACCAACTGCC | 479530 | 77 | 239 |

TABLE 8 -continued

Inhibition of human FGFR4 mRNA levels by chimeric antisense oligonucleotides targeted to SEQ ID NO: 1, SEQ ID NO: 2 and SEQ ID NO: 3

| Start Site on SEQ ID NO: 1 | Start Site on SEQ ID NO: 2 | Start Site on SEQ ID NO: 3 | Motif | Sequence | ISIS No | % inhibition | SEQ ID NO |
|---|---|---|---|---|---|---|---|
| n/a | 2109 | 101 | 5-10-5 | CACTGGTGTCTCTGGATCTA | 479532 | 78 | 240 |
| n/a | 2111 | 103 | 5-10-5 | GGCACTGGTGTCTCTGGATC | 479533 | 89 | 241 |
| n/a | 2113 | 105 | 5-10-5 | GTGGCACTGGTGTCTCTGGA | 479534 | 92 | 242 |
| n/a | 2115 | 107 | 5-10-5 | GGGTGGCACTGGTGTCTCTG | 479535 | 88 | 243 |
| n/a | 3334 | 1333 | 5-10-5 | GATCCTTTCCAGCTTTGCTC | 479536 | 91 | 244 |
| n/a | 3336 | 1335 | 5-10-5 | AGGATCCTTTCCAGCTTTGC | 479537 | 84 | 245 |
| n/a | 3338 | 1337 | 5-10-5 | CAAGGATCCTTTCCAGCTTT | 479538 | 65 | 246 |
| n/a | 3340 | 1339 | 5-10-5 | GGCAAGGATCCTTTCCAGCT | 479539 | 88 | 247 |
| n/a | 3342 | 1341 | 5-10-5 | TGGGCAAGGATCCTTTCCAG | 479540 | 68 | 248 |
| n/a | 3393 | 1392 | 5-10-5 | TGACTGAGTCTCAGTGGTTG | 479541 | 71 | 249 |
| n/a | 3395 | 1394 | 5-10-5 | ACTGACTGAGTCTCAGTGGT | 479542 | 80 | 250 |
| n/a | 3397 | 1396 | 5-10-5 | GCACTGACTGAGTCTCAGTG | 479543 | 76 | 251 |
| n/a | 3399 | 1398 | 5-10-5 | AGGCACTGACTGAGTCTCAG | 479544 | 77 | 252 |
| n/a | 3414 | 1413 | 5-10-5 | TGCTTGCTGGAAGCCAGGCA | 479545 | 83 | 253 |
| n/a | 3446 | 1445 | 5-10-5 | AGTCCTCTCTCGCAGACACA | 479546 | 88 | 254 |
| n/a | 3448 | 1447 | 5-10-5 | CCAGTCCTCTCTCGCAGACA | 479547 | 80 | 255 |
| n/a | 3450 | 1449 | 5-10-5 | GGCCAGTCCTCTCTCGCAGA | 479548 | 92 | 256 |
| n/a | 3502 | 1501 | 5-10-5 | AAGGAGCTCACCACCAGCTC | 479549 | 76 | 257 |
| n/a | n/a | 1503 | 5-10-5 | GCAAGGAGCTCACCACCAGC | 479550 | 79 | 258 |
| n/a | 3570 | 1569 | 5-10-5 | CTGCCTGGACCTCCTAGGTC | 479551 | 95 | 259 |
| n/a | 3572 | 1571 | 5-10-5 | TGCTGCCTGGACCTCCTAGG | 479552 | 85 | 260 |
| n/a | 3574 | 1573 | 5-10-5 | CATGCTGCCTGGACCTCCTA | 479553 | 80 | 261 |
| n/a | 3576 | 1575 | 5-10-5 | CACATGCTGCCTGGACCTCC | 479554 | 80 | 262 |
| n/a | 3578 | 1577 | 5-10-5 | CACACATGCTGCCTGGACCT | 479555 | 71 | 263 |
| n/a | 3580 | 1579 | 5-10-5 | ACCACACATGCTGCCTGGAC | 479556 | 87 | 264 |
| n/a | 3775 | 1778 | 5-10-5 | CCAGGGCAAATGCCACACTC | 479557 | 71 | 265 |
| n/a | 3777 | 1780 | 5-10-5 | ACCCAGGGCAAATGCCACAC | 479558 | 83 | 266 |
| n/a | 3783 | 1786 | 5-10-5 | TGCCACACCCAGGGCAAATG | 479560 | 67 | 267 |
| n/a | 3787 | 1790 | 5-10-5 | CGGATGCCACACCCAGGGCA | 479561 | 70 | 268 |
| n/a | 3789 | 1792 | 5-10-5 | TGCGGATGCCACACCCAGGG | 479562 | 78 | 269 |
| n/a | 3799 | 1802 | 5-10-5 | AGCCACATGCTGCGGATGCC | 479564 | 71 | 270 |
| n/a | 1393 | n/a | 5-10-5 | GCTCTCTTGCCCATCCCTCT | 479565 | 81 | 271 |
| n/a | 1462 | n/a | 5-10-5 | TCTCTTTGGTCACACCGTCT | 479566 | 90 | 272 |
| n/a | 1464 | n/a | 5-10-5 | TATCTCTTTGGTCACACCGT | 479567 | 67 | 273 |
| n/a | 1466 | n/a | 5-10-5 | CCTATCTCTTTGGTCACACC | 479568 | 83 | 274 |
| n/a | 1468 | n/a | 5-10-5 | TGCCTATCTCTTTGGTCACA | 479569 | 76 | 275 |

TABLE 8 -continued

Inhibition of human FGFR4 mRNA levels by chimeric antisense oligonucleotides targeted to SEQ ID NO: 1, SEQ ID NO: 2 and SEQ ID NO: 3

| Start Site on SEQ ID NO: 1 | Start Site on SEQ ID NO: 2 | Start Site on SEQ ID NO: 3 | Motif | Sequence | ISIS No | % inhibition | SEQ ID NO |
|---|---|---|---|---|---|---|---|
| n/a | 1944 | n/a | 5-10-5 | TCAACCTTCATCTTCCAGCA | 479570 | 80 | 276 |
| n/a | 3324 | 1323 | 5-10-5 | AGCTTTGCTCAGCCCAGCAG | 479572 | 75 | 277 |
| n/a | 3326 | 1325 | 5-10-5 | CCAGCTTTGCTCAGCCCAGC | 479573 | 85 | 278 |
| n/a | 3328 | 1327 | 5-10-5 | TTCCAGCTTTGCTCAGCCCA | 479574 | 79 | 279 |
| n/a | 7801 | n/a | 5-10-5 | TCACTTGCCAGGGTCAGGAG | 479576 | 70 | 280 |
| n/a | 7803 | n/a | 5-10-5 | AGTCACTTGCCAGGGTCAGG | 479577 | 65 | 281 |
| n/a | 1462 | n/a | 3-10-4 | CTTTGGTCACACCGTCT | 479582 | 74 | 282 |
| n/a | 1463 | n/a | 3-10-4 | TCTTTGGTCACACCGTC | 479583 | 84 | 283 |
| n/a | 1464 | n/a | 3-10-4 | CTCTTTGGTCACACCGT | 479584 | 82 | 284 |
| n/a | 1465 | n/a | 3-10-4 | TCTCTTTGGTCACACCG | 479585 | 71 | 285 |
| n/a | 3326 | 1325 | 3-10-4 | GCTTTGCTCAGCCCAGC | 479594 | 80 | 286 |
| n/a | 3328 | 1327 | 3-10-4 | CAGCTTTGCTCAGCCCA | 479596 | 81 | 287 |
| n/a | 3329 | 1328 | 3-10-4 | CCAGCTTTGCTCAGCCC | 479597 | 78 | 288 |
| 161 | 3166 | 1165 | 3-10-4 | GCAGCCGCATCTCCTTC | 479608 | 70 | 289 |
| 194 | 3199 | 1198 | 3-10-4 | GCACACTCAGCAGGACC | 479613 | 72 | 290 |
| 195 | 3200 | 1199 | 3-10-4 | GGCACACTCAGCAGGAC | 479614 | 78 | 291 |
| 349 | 4050 | 2053 | 3-10-4 | CCAGTGGCCACCACGCT | 479622 | 67 | 292 |
| 369 | 4070 | 2073 | 3-10-4 | AGGCGACTGCCCTCCTT | 479625 | 68 | 293 |
| 370 | 4071 | 2074 | 3-10-4 | CAGGCGACTGCCCTCCT | 479626 | 71 | 294 |
| 602 | 4506 | 2418 | 3-10-4 | GTGTCCAGTAGGGTGCT | 479641 | 70 | 295 |
| 2819 | 11489 | 4988 | 3-10-4 | CAGCTCTCCAGCCAGGC | 479682 | 71 | 296 |
| 2951 | 11621 | 5120 | 3-10-4 | GCTTCTCTGGGCTCAGG | 479689 | 72 | 297 |
| 2952 | 11622 | 5121 | 3-10-4 | AGCTTCTCTGGGCTCAG | 479690 | 78 | 298 |
| 2953 | 11623 | 5122 | 3-10-4 | CAGCTTCTCTGGGCTCA | 479691 | 87 | 299 |
| 2954 | 11624 | 5123 | 3-10-4 | CCAGCTTCTCTGGGCTC | 479692 | 87 | 300 |
| 2955 | 11625 | 5124 | 3-10-4 | TCCAGCTTCTCTGGGCT | 479693 | 71 | 301 |
| 2956 | 11626 | 5125 | 3-10-4 | TTCCAGCTTCTCTGGGC | 479694 | 67 | 302 |
| 2958 | 11628 | 5127 | 3-10-4 | GCTTCCAGCTTCTCTGG | 479696 | 65 | 303 |
| 2981 | 11651 | 5150 | 3-10-4 | CCATTTGCTCCTGTTTT | 479697 | 73 | 304 |
| 2982 | 11652 | 5151 | 3-10-4 | GCCATTTGCTCCTGTTT | 479698 | 88 | 305 |
| 2983 | 11653 | 5152 | 3-10-4 | CGCCATTTGCTCCTGTT | 479699 | 92 | 306 |
| n/a | 2113 | 105 | 3-10-4 | GCACTGGTGTCTCTGGA | 479703 | 88 | 307 |
| n/a | 2114 | 106 | 3-10-4 | GGCACTGGTGTCTCTGG | 479704 | 95 | 308 |
| n/a | 2115 | 107 | 3-10-4 | TGGCACTGGTGTCTCTG | 479705 | 78 | 309 |
| n/a | 2116 | 108 | 3-10-4 | GTGGCACTGGTGTCTCT | 479706 | 90 | 310 |
| n/a | 3395 | 1394 | 3-10-4 | GACTGAGTCTCAGTGGT | 479716 | 71 | 311 |

TABLE 8 -continued

Inhibition of human FGFR4 mRNA levels by chimeric antisense oligonucleotides targeted to SEQ ID NO: 1, SEQ ID NO: 2 and SEQ ID NO: 3

| Start Site on SEQ ID NO: 1 | Start Site on SEQ ID NO: 2 | Start Site on SEQ ID NO: 3 | Motif | Sequence | ISIS No | % inhibition | SEQ ID NO |
|---|---|---|---|---|---|---|---|
| n/a | 3415 | 1414 | 3-10-4 | CTTGCTGGAAGCCAGGC | 479721 | 82 | 312 |
| n/a | 3416 | 1415 | 3-10-4 | GCTTGCTGGAAGCCAGG | 479722 | 82 | 313 |
| n/a | 3446 | 1445 | 3-10-4 | CCTCTCTCGCAGACACA | 479725 | 70 | 314 |
| n/a | 3452 | 1451 | 3-10-4 | GCCAGTCCTCTCTCGCA | 479731 | 78 | 315 |
| n/a | 3453 | 1452 | 3-10-4 | GGCCAGTCCTCTCTCGC | 479732 | 69 | 316 |
| n/a | 3571 | 1570 | 3-10-4 | GCCTGGACCTCCTAGGT | 479736 | 97 | 317 |
| n/a | 3572 | 1571 | 3-10-4 | TGCCTGGACCTCCTAGG | 479737 | 69 | 318 |
| n/a | 3573 | 1572 | 3-10-4 | CTGCCTGGACCTCCTAG | 479738 | 76 | 319 |
| n/a | 3574 | 1573 | 3-10-4 | GCTGCCTGGACCTCCTA | 479739 | 88 | 320 |
| n/a | 3575 | 1574 | 3-10-4 | TGCTGCCTGGACCTCCT | 479740 | 66 | 321 |
| n/a | 3576 | 1575 | 3-10-4 | ATGCTGCCTGGACCTCC | 479741 | 72 | 322 |

Example 8

Dose-Dependent Antisense Inhibition of Human FGFR4 in HepG2 Cells

Gapmers from Examples 5, 6 and 7 exhibiting significant in vitro inhibition of FGFR4 mRNA were further selected and tested at various doses in HepG2 cells. Cells were plated at a density of 20,000 cells per well and transfected using electroporation with 0.6 µM, 1.3 µM, 2.5 µM, 5.0 µM, and 10.0 µM concentrations of antisense oligonucleotide, as specified in Table 9. After a treatment period of approximately 16 hours, RNA was isolated from the cells and FGFR4 mRNA levels were measured by quantitative real-time PCR. Human FGFR4 primer probe set RTS3232 was used to measure mRNA levels. FGFR4 mRNA levels were adjusted according to total RNA content, as measured by RIBOGREEN®. Results are presented as percent inhibition of FGFR4, relative to untreated control cells.

The half maximal inhibitory concentration ($IC_{50}$) of each oligonucleotide is also presented in Table 9. As illustrated in Table 9, FGFR4 mRNA levels were significantly reduced in a dose-dependent manner in antisense oligonucleotide treated cells.

TABLE 9

Dose-dependent antisense inhibition of human FGFR4 in HepG2 cells using electroporation

| ISIS No | 0.6 µM | 1.3 µM | 2.5 µM | 5.0 µM | 10.0 µM | $IC_{50}$ (µM) |
|---|---|---|---|---|---|---|
| 299005 | 31 | 50 | 66 | 89 | 95 | 1.3 |
| 463588 | 25 | 48 | 70 | 91 | 97 | 1.4 |
| 463589 | 33 | 46 | 69 | 87 | 96 | 1.3 |
| 463628 | 49 | 67 | 77 | 90 | 97 | <0.6 |
| 463629 | 36 | 58 | 70 | 88 | 92 | 1.6 |
| 463648 | 34 | 41 | 49 | 64 | 84 | 1.9 |
| 463672 | 16 | 34 | 68 | 84 | 94 | 1.8 |
| 463690 | 42 | 58 | 75 | 88 | 97 | 0.8 |
| 463691 | 27 | 38 | 73 | 83 | 96 | 1.5 |
| 463692 | 3 | 39 | 57 | 76 | 94 | 2.2 |
| 463709 | 22 | 43 | 64 | 82 | 95 | 1.6 |
| 463762 | 13 | 29 | 46 | 74 | 90 | 2.5 |
| 463771 | 40 | 31 | 51 | 78 | 91 | 1.7 |
| 463834 | 23 | 44 | 55 | 78 | 93 | 1.8 |
| 463835 | 30 | 39 | 65 | 83 | 95 | 1.5 |
| 463837 | 29 | 43 | 72 | 87 | 95 | 1.4 |
| 463838 | 23 | 40 | 59 | 77 | 93 | 1.8 |
| 463861 | 9 | 33 | 61 | 82 | 97 | 2.1 |
| 464038 | 19 | 25 | 42 | 61 | 88 | 2.8 |
| 464222 | 30 | 56 | 75 | 87 | 95 | 1.1 |
| 464225 | 40 | 60 | 79 | 85 | 90 | 0.8 |
| 464228 | 50 | 72 | 86 | 91 | 94 | <0.6 |
| 464284 | 30 | 52 | 59 | 84 | 90 | 1.4 |
| 464286 | 50 | 65 | 83 | 92 | 95 | <0.6 |
| 464287 | 24 | 50 | 67 | 89 | 92 | 1.4 |
| 464308 | 36 | 56 | 76 | 90 | 97 | 1.0 |
| 464449 | 44 | 73 | 85 | 93 | 95 | <0.6 |
| 464587 | 33 | 54 | 79 | 92 | 98 | 1.0 |
| 464588 | 53 | 76 | 89 | 95 | 95 | <0.6 |
| 464589 | 30 | 66 | 80 | 93 | 95 | 0.9 |
| 464716 | 33 | 41 | 69 | 86 | 95 | 1.4 |
| 464718 | 33 | 56 | 77 | 93 | 98 | 1.0 |
| 464732 | 27 | 43 | 61 | 86 | 95 | 1.6 |
| 479533 | 68 | 84 | 89 | 93 | 95 | <0.6 |
| 479534 | 67 | 74 | 92 | 95 | 97 | <0.6 |
| 479535 | 54 | 72 | 81 | 91 | 95 | <0.6 |
| 479536 | 38 | 68 | 86 | 96 | 98 | 0.7 |
| 479539 | 39 | 52 | 77 | 92 | 98 | 1.0 |
| 479546 | 32 | 70 | 78 | 91 | 98 | 0.9 |
| 479548 | 49 | 71 | 81 | 93 | 96 | <0.6 |
| 479551 | 72 | 82 | 91 | 95 | 97 | <0.6 |
| 479556 | 36 | 63 | 83 | 90 | 97 | 0.9 |

Example 9

Dose-Dependent Antisense Inhibition of Human FGFR4 in HepG2 Cells

Gapmers from Examples 7 and 8 exhibiting significant in vitro inhibition of FGFR4 mRNA were further selected and tested at various doses in HepG2 cells. Cells were plated at a density of 20,000 cells per well and transfected using electroporation with 0156 µM, 0.31 µM, 0.63 µM, 1.25 µM, 2.50 µM and 5.00 µM concentrations of antisense oligonucleotide, as specified in Table 10. After a treatment period of approximately 16 hours, RNA was isolated from the cells and FGFR4 mRNA levels were measured by quantitative real-time PCR. Human FGFR4 primer probe set RTS3232 was used to measure mRNA levels. FGFR4 mRNA levels were adjusted according to total RNA content, as measured by RIBOGREEN®. Results are presented as percent inhibition of FGFR4, relative to untreated control cells.

The half maximal inhibitory concentration ($IC_{50}$) of each oligonucleotide is also presented in Table 10. As illustrated in Table 10, FGFR4 mRNA levels were significantly reduced in a dose-dependent manner in antisense oligonucleotide treated cells.

TABLE 10

Dose-dependent antisense inhibition of human FGFR4 in HepG2 cells using electroporation

| ISIS No | 0.156 µM | 0.31 µM | 0.63 µM | 1.25 µM | 2.50 µM | 5.00 µM | $IC_{50}$ (µM) |
|---|---|---|---|---|---|---|---|
| 463629 | 19 | 30 | 48 | 66 | 84 | 91 | 0.7 |
| 479533 | 18 | 33 | 63 | 67 | 84 | 86 | 0.6 |
| 479534 | 18 | 25 | 34 | 63 | 82 | 86 | 0.9 |
| 479535 | 24 | 28 | 43 | 62 | 68 | 81 | 0.9 |
| 479536 | 25 | 28 | 29 | 62 | 78 | 90 | 0.8 |
| 479539 | 8 | 16 | 36 | 48 | 75 | 88 | 1.1 |
| 479546 | 0 | 27 | 33 | 63 | 77 | 87 | 1.1 |
| 479548 | 8 | 39 | 30 | 62 | 74 | 85 | 0.9 |
| 479551 | 27 | 44 | 59 | 80 | 86 | 89 | 0.4 |
| 479556 | 16 | 29 | 32 | 53 | 71 | 87 | 1.0 |
| 479566 | 19 | 27 | 29 | 63 | 81 | 88 | 0.9 |
| 479584 | 3 | 22 | 30 | 58 | 80 | 88 | 1.0 |
| 479596 | 4 | 20 | 32 | 54 | 71 | 88 | 1.1 |
| 479691 | 18 | 11 | 50 | 62 | 80 | 91 | 0.8 |
| 479692 | 12 | 26 | 49 | 61 | 79 | 90 | 0.8 |
| 479698 | 23 | 40 | 57 | 73 | 87 | 92 | 0.5 |
| 479699 | 17 | 37 | 60 | 76 | 90 | 93 | 0.5 |
| 479703 | 18 | 20 | 41 | 67 | 82 | 89 | 0.8 |
| 479704 | 31 | 43 | 66 | 80 | 90 | 92 | 0.4 |
| 479706 | 26 | 18 | 36 | 58 | 76 | 90 | 0.9 |
| 479736 | 36 | 48 | 71 | 86 | 93 | 94 | 0.3 |

Example 10

Tolerability of Antisense Oligonucleotides Targeting Human FGFR4 in CD1 Mice CD1® mice (Charles River, Mass.) are a multipurpose mice model, frequently utilized for safety and efficacy testing. The mice were treated with ISIS antisense oligonucleotides selected from studies described above and evaluated for changes in the levels of various markers.

Treatment

Groups of five male CD1 mice were injected subcutaneously twice a week for 6 weeks with 50 mg/kg of ISIS 299005, ISIS 463588, ISIS 463589, ISIS 463628, ISIS 463690, ISIS 463691, ISIS 463835, ISIS 463837, ISIS 464222, ISIS 464225, ISIS 464228, ISIS 464286, ISIS 464308, ISIS 464449, ISIS 464587, ISIS 464588, ISIS 464589, ISIS 464718, ISIS 479533, ISIS 479551, ISIS 479691, ISIS 479692, ISIS 479698, ISIS 479699, ISIS 479703, ISIS 479704, ISIS 479706, or ISIS 479736. One group of male CD1 mice was injected subcutaneously twice a week for 6 weeks with PBS. Mice were euthanized 48 hours after the last dose, and plasma were harvested for further analysis. Treatment with ISIS 479691 caused death of the mice and that ISIS oligonucleotide was therefore removed from further study.

Plasma Chemistry Markers

To evaluate the effect of ISIS oligonucleotides on metabolic function, plasma concentrations of transaminases, bilirubin, albumin, creatinine, and BUN were measured using an automated clinical chemistry analyzer (Hitachi Olympus AU400e, Melville, N.Y.). The transaminase levels are expressed as IU/L; the bilirubin, creatinine, and BUN levels are expressed as mg/dL; and the albumin is expressed in g/dL. The results are presented in Table 11. ISIS oligonucleotides that caused adverse changes in the levels of any of the plasma chemistry markers were excluded in further studies.

TABLE 11

ALT, AST, Bilirubin, BUN, Creatinine and Albumin levels in CD1 mouse plasma at week 6

| | ALT (IU/L) | AST (IU/L) | Bilirubin (mg/dL) | BUN (mg/dL) | Creatinine (mg/dL) | Albumin (g/dL) |
|---|---|---|---|---|---|---|
| PBS | 34 | 59 | 0.2 | 33 | 0.16 | 3.3 |
| ISIS 299005 | 50 | 72 | 0.1 | 27 | 0.12 | 2.8 |
| ISIS 463588 | 55 | 72 | 0.1 | 30 | 0.12 | 3.0 |
| ISIS 463589 | 64 | 79 | 0.2 | 28 | 0.10 | 2.7 |
| ISIS 463628 | 48 | 83 | 0.1 | 27 | 0.13 | 3.0 |
| ISIS 463690 | 71 | 93 | 0.2 | 29 | 0.13 | 3.0 |
| ISIS 463691 | 145 | 134 | 0.2 | 26 | 0.10 | 3.0 |
| ISIS 463835 | 159 | 113 | 0.2 | 26 | 0.11 | 3.0 |
| ISIS 463837 | 59 | 78 | 0.1 | 27 | 0.09 | 2.8 |
| ISIS 464222 | 559 | 564 | 0.2 | 23 | 0.09 | 2.7 |
| ISIS 464225 | 83 | 88 | 0.1 | 25 | 0.09 | 2.8 |
| ISIS 464228 | 58 | 93 | 0.1 | 29 | 0.10 | 2.8 |
| ISIS 464286 | 139 | 154 | 0.1 | 21 | 0.05 | 2.8 |
| ISIS 464308 | 2533 | 1673 | 0.2 | 28 | 0.11 | 3.3 |
| ISIS 464449 | 748 | 451 | 0.2 | 24 | 0.08 | 3.0 |
| ISIS 464587 | 183 | 159 | 0.1 | 25 | 0.11 | 3.0 |
| ISIS 464588 | 256 | 726 | 0.2 | 21 | 0.03 | 2.0 |
| ISIS 464589 | 142 | 126 | 0.2 | 27 | 0.09 | 2.9 |
| ISIS 464718 | 789 | 608 | 0.2 | 19 | 0.03 | 2.7 |
| ISIS 479533 | 61 | 76 | 0.1 | 22 | 0.09 | 2.9 |
| ISIS 479551 | 81 | 104 | 0.2 | 26 | 0.13 | 3.0 |
| ISIS 479692 | 847 | 1026 | 0.3 | 26 | 0.10 | 3.1 |
| ISIS 479698 | 92 | 133 | 0.2 | 29 | 0.12 | 2.7 |
| ISIS 479699 | 57 | 95 | 0.1 | 20 | 0.09 | 2.6 |
| ISIS 479703 | 158 | 108 | 0.1 | 23 | 0.11 | 3.0 |
| ISIS 479704 | 38 | 56 | 0.2 | 23 | 0.10 | 3.2 |
| ISIS 479706 | 700 | 642 | 0.5 | 26 | 0.12 | 3.1 |
| ISIS 479736 | 204 | 134 | 0.1 | 25 | 0.11 | 2.9 |

Example 11

Tolerability of Antisense Oligonucleotides Targeting Human FGFR4 in Sprague-Dawley Rats Sprague-Dawley rats are a multipurpose model used for safety and efficacy evaluations. The rats were treated with ISIS antisense oligonucleotides from the study described in Example 10 and evaluated for changes in the levels of various plasma chemistry markers.

Treatment

Seven week old male Sprague-Dawley rats were maintained on a 12-hour light/dark cycle and fed ad libitum with Purina normal rat chow, diet 5001. Groups of four Sprague-Dawley rats each were injected subcutaneously twice a week for 4 weeks with 50 mg/kg of ISIS 299005, ISIS 463588, ISIS 463589, ISIS 463628, ISIS 463690, ISIS 463691, ISIS 463835, ISIS 463837, ISIS 464222, ISIS 464225, ISIS 464228, ISIS 464286, ISIS 464308, ISIS 464449, ISIS 464587, ISIS 464718, ISIS 479533, ISIS 479551, ISIS 479691, ISIS 479692, ISIS 479698, ISIS 479699, ISIS 479703, ISIS 479704, ISIS 479706, or ISIS 479736. A group of rats were injected subcutaneously twice a week for 4 weeks with PBS. Forty eight hours after the last dose, rats were euthanized and plasmas were harvested for further analysis.

Liver Function

To evaluate the effect of ISIS oligonucleotides on hepatic function, plasma concentrations of transaminases were measured using an automated clinical chemistry analyzer (Hitachi Olympus AU400e, Melville, N.Y.). Plasma concentrations of ALT (alanine transaminase) and AST (aspartate transaminase) were measured and the results are presented in Table 12, expressed in IU/L. Plasma levels of bilirubin were also measured using the same clinical chemistry analyzer and the results are also presented in Table 12, expressed as mg/dL. ISIS oligonucleotides that caused adverse changes were excluded in further studies.

TABLE 12

Effect of antisense oligonucleotide treatment on ALT, AST, and Bilirubin in the liver of Sprague-Dawley rats

|  | ALT (IU/L) | AST (IU/L) | Bilirubin (g/dL) |
|---|---|---|---|
| PBS | 52 | 206 | 0.15 |
| ISIS 299005 | 72 | 387 | 0.16 |
| ISIS 463588 | 56 | 305 | 0.13 |
| ISIS 463589 | 82 | 553 | 0.15 |
| ISIS 463628 | 351 | 351 | 0.13 |
| ISIS 463690 | 81 | 367 | 0.14 |
| ISIS 463691 | 83 | 368 | 0.13 |
| ISIS 463835 | 90 | 345 | 0.13 |
| ISIS 463837 | 67 | 301 | 0.11 |
| ISIS 464222 | 231 | 322 | 0.19 |
| ISIS 464225 | 66 | 241 | 0.11 |
| ISIS 464228 | 77 | 359 | 0.57 |
| ISIS 464286 | 96 | 207 | 0.11 |
| ISIS 464308 | 59 | 295 | 0.12 |
| ISIS 464449 | 158 | 509 | 0.15 |
| ISIS 464587 | 414 | 373 | 0.29 |
| ISIS 464588 | 215 | 278 | 0.40 |
| ISIS 464589 | 282 | 482 | 0.32 |
| ISIS 464718 | 280 | 577 | 0.43 |
| ISIS 479533 | 391 | 457 | 0.29 |
| ISIS 479551 | 1360 | 1300 | 0.41 |
| ISIS 479691 | 383 | 439 | 0.35 |
| ISIS 479692 | 674 | 675 | 0.24 |
| ISIS 479698 | 354 | 775 | 0.86 |
| ISIS 479699 | 145 | 455 | 0.90 |
| ISIS 479703 | 779 | 781 | 0.54 |
| ISIS 479704 | 790 | 1243 | 0.41 |
| ISIS 479706 | 570 | 680 | 0.36 |
| ISIS 479736 | 499 | 644 | 0.24 |

Kidney Function

To evaluate the effect of ISIS oligonucleotides on kidney function, plasma concentrations of blood urea nitrogen (BUN) and creatinine were measured using an automated clinical chemistry analyzer (Hitachi Olympus AU400e, Melville, N.Y.). Results are presented in Table 13, expressed in mg/dL.

TABLE 13

Effect of antisense oligonucleotide treatment on renal function markers (mg/dL) of Sprague-Dawley rats

|  | BUN | Creatinine |
|---|---|---|
| Saline | 18 | 0.29 |
| ISIS 299005 | 20 | 0.33 |
| ISIS 463588 | 23 | 0.35 |
| ISIS 463589 | 19 | 0.32 |
| ISIS 463628 | 19 | 0.33 |
| ISIS 463690 | 19 | 0.35 |
| ISIS 463691 | 18 | 0.34 |
| ISIS 463835 | 19 | 0.34 |
| ISIS 463837 | 18 | 0.32 |
| ISIS 464222 | 21 | 0.37 |
| ISIS 464225 | 20 | 0.29 |
| ISIS 464228 | 22 | 0.32 |
| ISIS 464286 | 22 | 0.36 |
| ISIS 464308 | 18 | 0.32 |
| ISIS 464449 | 16 | 0.32 |
| ISIS 464587 | 23 | 0.38 |
| ISIS 464588 | 23 | 0.27 |
| ISIS 464589 | 24 | 0.35 |
| ISIS 464718 | 22 | 0.32 |
| ISIS 479533 | 28 | 0.31 |
| ISIS 479551 | 21 | 0.36 |
| ISIS 479691 | 29 | 0.36 |
| ISIS 479692 | 25 | 0.40 |
| ISIS 479698 | 30 | 0.34 |
| ISIS 479699 | 30 | 0.35 |
| ISIS 479703 | 28 | 0.31 |
| ISIS 479704 | 31 | 0.42 |
| ISIS 479706 | 26 | 0.38 |
| ISIS 479736 | 22 | 0.37 |

Example 12

Tolerability of Antisense Oligonucleotides Targeting Human FGFR4 in CD/IGS Rats

CD/IGS rats are a multipurpose model used for safety and efficacy evaluations. The rats were treated with ISIS antisense oligonucleotides selected from the study described in Examples 10 and 11 and evaluated for changes in the levels of various markers.

Treatment

Ten-twelve week old male CD/IGS rats were maintained on a 12-hour light/dark cycle and fed ad libitum with Purina normal rat chow, diet 5001. Groups of four CD/IGS rats each were injected subcutaneously twice a week for 12 weeks with 30 mg/kg of ISIS 299005, ISIS 463588, ISIS 463589, ISIS 463690, ISIS 463691, ISIS 463835, ISIS 463837, or ISIS 464225. A group of 6 rats was injected subcutaneously twice a week for 12 weeks with PBS and served as a control group. Urine and blood samples were collected at various time points. Forty eight hours after the last dose, body weights were taken, rats were euthanized and organs and plasma were harvested for further analysis.

Liver Function

To evaluate the effect of ISIS oligonucleotides on hepatic function, plasma concentrations of various liver function markers were measured on week 8 and week 12 using an automated clinical chemistry analyzer (Hitachi Olympus AU400e, Melville, N.Y.). Plasma concentrations of ALT (alanine transaminase) and AST (aspartate transaminase) were measured and the results are presented in Tables 14 and 15, expressed in IU/L. Plasma levels of bilirubin and BUN were also measured using the same clinical chemistry analyzer and the results are also presented in Tables 14 and 15, expressed as mg/dL. ISIS oligonucleotides that caused adverse changes in the levels of any of the markers of liver function were excluded in further studies.

TABLE 14

ALT, AST, Bilirubin and BUN of CD/IGS rats on week 8

|  | ALT (IU/L) | AST (IU/L) | Bilirubin (mg/dL) | BUN (mg/dL) |
| --- | --- | --- | --- | --- |
| PBS | 31 | 71 | 0.16 | 13.6 |
| ISIS 299005 | 60 | 121 | 0.15 | 17.4 |
| ISIS 463588 | 57 | 103 | 0.19 | 18.6 |
| ISIS 463589 | 46 | 136 | 0.14 | 16.8 |
| ISIS 463690 | 79 | 91 | 0.24 | 18.1 |
| ISIS 463691 | 80 | 93 | 0.18 | 18.8 |
| ISIS 463835 | 103 | 118 | 0.18 | 16.6 |
| ISIS 463837 | 52 | 101 | 0.14 | 20.7 |
| ISIS 464225 | 48 | 253 | 0.14 | 18.9 |

TABLE 15

ALT, AST, TBIL, and BUN levels in the liver of CD/IGS rats on week 12

|  | ALT (IU/L) | AST (IU/L) | TBIL (mg/dL) | BUN (mg/dL) |
| --- | --- | --- | --- | --- |
| PBS | 38 | 60 | 0.10 | 18.2 |
| ISIS 299005 | 79 | 150 | 0.10 | 20.0 |
| ISIS 463588 | 66 | 146 | 0.13 | 23.3 |
| ISIS 463589 | 47 | 106 | 0.10 | 18.3 |
| ISIS 463690 | 66 | 65 | 0.10 | 20.3 |
| ISIS 463691 | 72 | 68 | 0.13 | 20.3 |
| ISIS 463835 | 63 | 76 | 0.10 | 18.8 |
| ISIS 463837 | 52 | 98 | 0.10 | 21.8 |
| ISIS 464225 | 48 | 260 | 0.10 | 19.0 |

Example 13

Pharmacokinetic Measurement of Antisense Oligonucleotide in CD1 Mouse Liver

CD1 mice were treated with ISIS 463588, ISIS 463589, and ISIS 463690, and the oligonucleotide half-life as well as the elapsed time for oligonucleotide degradation and elimination from the liver was evaluated.

Treatment

Group of ten CD1 mice each were injected subcutaneously twice per week for 2 weeks (4 doses) with 50 mg/kg of ISIS 463588, ISIS 463589, or ISIS 463690. Groups of five mice each from each group were sacrificed 3 days and 56 days following the final dose. Livers were harvested for analysis.

Measurement of Oligonucleotide Concentration

The concentration of the full-length oligonucleotide as well as the total oligonucleotide concentration (including the degraded form) was measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-O-methoxyethyl modified phosphorothioate oligonucleotide, GCGTTTGCTCTTCTTCTTGCGTTTTTT, designated herein as SEQ ID NO: 323) was added prior to extraction. Tissue sample concentrations were calculated using calibration curves, with a lower limit of quantitation (LLOQ) of approximately 1.14 µg/g. Half-lives were then calculated using WinNonlin software (PHARSIGHT).

The results are presented in Table 16, expressed as µg/g liver tissue. The half-life of the ISIS oligonucleotides was calculated from these values and is also presented in Table 17. The half-life for each oligonucleotide was considered optimal.

TABLE 16

Oligonucleotide concentration of ISIS oligonucleotides in the liver of CD1 mice

|  | ISIS 463588 | ISIS 463589 | ISIS 463690 |
| --- | --- | --- | --- |
| Day 3 | 157 | 168 | 196 |
| Day 56 | 31 | 17 | 28 |

TABLE 17

Half-life of ISIS oligonucleotides in the liver of CD1 mice

| ISIS No | Days |
| --- | --- |
| 463588 | 22.4 |
| 463589 | 15.9 |
| 463690 | 18.7 |

Example 14

Measurement of Viscosity of ISIS Antisense Oligonucleotides Targeting Human FGFR4

The viscosity of the antisense oligonucleotides selected from in vivo studies described above was measured with the aim of screening out antisense oligonucleotides which have a viscosity more than 40 cP at a concentration of 165-185 mg/mL. Oligonucleotides having a viscosity greater than 40 cP would be too viscous to be administered to any subject.

ISIS oligonucleotides (32-35 mg) were weighed into a glass vial, 120 µL of water was added and the antisense oligonucleotide was dissolved into solution by heating the vial at 50° C. Part of (75 µL) the pre-heated sample was pipetted to a micro-viscometer (Cambridge). The temperature of the micro-viscometter was set to 25° C. and the viscosity of the sample was measured. Another part (20 µL) of the pre-heated sample was pipetted into 10 mL of water for UV reading at 260 nM at 85° C. (Cary UV instrument). The results are presented in Table 18 and indicate that most of the antisense oligonucleotide solutions are optimal in their viscosity under the criterion stated above.

TABLE 18

Viscosity and concentration of ISIS antisense oligonucleotides targeting human FGFR4

| ISIS No. | Viscosity (cP) | Concentration (mg/mL) |
| --- | --- | --- |
| 299005 | 44 | 174 |
| 463588 | 21 | 189 |
| 463589 | 17 | 174 |
| 463690 | 12 | 178 |
| 463691 | 9 | 194 |
| 463835 | 25 | 174 |
| 463837 | 8 | 181 |
| 464225 | 21 | 204 |

Example 15

Effect of ISIS Antisense Oligonucleotides Targeting Human FGFR4 in Cynomolgus Monkeys Chinese cynomolgus monkeys were treated with ISIS antisense oligonucleotides selected from studies described in Examples 11-14. Antisense oligonucleotide efficacy and tolerability, as well as their pharmacokinetic profile in the liver and kidney, were evaluated. The human antisense oligonucleotides tested are also cross-reactive with the rhesus genomic sequence GENBANK Accession No NW_001121000.1 truncated from nucleosides 3094000 to 3109000 (SEQ ID NO: 5). The greater the complementarity between the human oligonucleotide and the rhesus monkey sequence, the more likely the human oligonucleotide can cross-react with the rhesus monkey sequence. The start sites of each oligonucleotide to SEQ ID NO: 5 is presented in Table 19. "Target start site" indicates the 5'-most nucleotide to which the gapmer is targeted in the rhesus monkey gene sequence.

TABLE 19

Antisense oligonucleotides complementary to SEQ ID NO: 5

| Target Site | Sequence | ISIS No | Motif | SEQ ID NO |
|---|---|---|---|---|
| 4366 | GGCACACTCAGCAGGACCCC | 299005 | 5-10-5 | 7 |
| 4365 | GCACACTCAGCAGGACCCCC | 463588 | 5-10-5 | 16 |
| 4367 | AGGCACACTCAGCAGGACCC | 463589 | 5-10-5 | 17 |
| 5223 | GCCAGGCGACTGCCCTCCTT | 463690 | 5-10-5 | 45 |
| 5224 | TGCCAGGCGACTGCCCTCCT | 463691 | 5-10-5 | 46 |
| 6420 | CGCTCTCCATCACGAGACTC | 463835 | 5-10-5 | 70 |
| 6422 | CACGCTCTCCATCACGAGAC | 463837 | 5-10-5 | 72 |
| 12755 | CTTCCAGCTTCTCTGGGCTC | 464225 | 5-10-5 | 138 |

Treatment

This study was conducted at Charles River Laboratories, Nevada. Prior to the study, the monkeys were acclimated to their designated housing for at least 13 days before the start of dosing. The animals were confirmed to have at least one negative serum antibody test to simian retrovirus (SRV), as well as to other related viruses. Tuberculosis testing was also done. The animals were housed individually in stainless steel cages, as specified in the USDA Animal Welfare Act (9 CFR, Parts 1, 2, and 3). The monkeys were 2.5 to 8 years old and weighed between 2.5 and 4.0 kg. Eight groups of five randomly assigned male cynomolgus monkeys each were injected subcutaneously with ISIS oligonucleotide using a stainless steel dosing needle and syringe of appropriate size into any of six dosing sites, which were used on a rotational basis. These sites were one site each on the lateral portion of each thigh, and four separate sites on the back. The monkeys were dosed once every other day at a dose of 40 mg/kg for the first week (days 1, 3, and 5) as loading doses, and subsequently twice a week at a maintenance dose of 20 mg/kg (40 mg/kg/week) for weeks 2-13, with ISIS 299005, ISIS 463588, ISIS 463589, ISIS 463690, ISIS 463691, ISIS 463835, ISIS 463837, or ISIS 464225. A control group of 8 cynomolgus monkeys was injected with PBS subcutaneously once every other day for the first week (days 1, 3, and 5), and subsequently twice a week for weeks 2-13.

During the study period, the monkeys were observed twice daily for a sign of illness or distress. Veterinary care was available throughout the course of the study and animals were examined by the veterinary staff, as warranted for clinical signs or other changes. At the end of the study period, the animals were euthanized under deep anesthesia induced by ketamine and Beuthanasia-D®, followed by exsanguination. All organs were collected within 10 minutes of exsanguinations.

RNA Analysis

Total RNA was extracted from liver and kidney tissue for real-time PCR analysis and FGFR4 mRNA levels were measured using human primer probe set RTS3232 and the rhesus primer probe set rhFGFR4_LTS00467 (forward sequence TCATCAACGGCAGCAGCTT, designated herein as SEQ ID NO: 333; reverse sequence TGAGCTATTGATGTCTGCAGTCTTC, designated herein as SEQ ID NO: 334; probe sequence CCGACGGCTTCCCCTATGTGCA, designated herein as SEQ ID NO: 335). Results are presented as percent inhibition of FGFR4, relative to PBS control, normalized to Cyclophilin expression levels and for directly with RIBOGREEN®. As shown in Tables 20 and 21, treatment with ISIS antisense oligonucleotides resulted in significant reduction of FGFR4 mRNA in comparison to the PBS control.

TABLE 20

% Inhibition of FGFR4 mRNA in the cynomolgus monkey liver relative to the PBS control

| ISIS No | RTS3232/Ribogreen | RTS3232/Cyclophilin | rhFGFR4_LTS00467/ RIBOGREEN | rhFGFR4_LTS00467/ Cyclophilin |
|---|---|---|---|---|
| 299005 | 42 | 33 | 41 | 32 |
| 463588 | 71 | 72 | 68 | 68 |
| 463589 | 40 | 38 | 44 | 43 |
| 463690 | 64 | 67 | 58 | 61 |
| 463691 | 47 | 65 | 41 | 61 |
| 463835 | 61 | 51 | 50 | 37 |
| 463837 | 39 | 34 | 38 | 29 |
| 464225 | 65 | 64 | 61 | 60 |

TABLE 21

% Inhibition of FGFR4 mRNA in the cynomolgus monkey kidney relative to the PBS control

| ISIS No | RTS3232/Ribogreen | rhFGFR4_LTS00467/ RIBOGREEN |
|---|---|---|
| 299005 | 60 | 52 |
| 463588 | 86 | 85 |
| 463589 | 77 | 71 |

TABLE 21-continued

% Inhibition of FGFR4 mRNA in the cynomolgus monkey kidney relative to the PBS control

| ISIS No | RTS3232/Ribogreen | rhFGFR4_LTS00467/ RIBOGREEN |
|---|---|---|
| 463690 | 76 | 68 |
| 463691 | 75 | 63 |
| 463835 | 61 | 52 |
| 463837 | 54 | 49 |
| 464225 | 87 | 83 |

FGF19 and Leptin Levels

FGF19 has been known to reduce adiposity and improve insulin sensitivity in transgenic mice (Fu, L. et al., Endocrinology. 145: 2594-2603, 2004). FGF19 is also characterized as a high affinity ligand for FGFR4 (Xie, M.-H. et al., Cytokine. 11: 729-735, 1999). Leptin is a hormone which has been found to be present at very high levels in obese individuals compared to normal-weight individuals (Considine, R. V. et al., N. Engl. J. Med. 334: 292-295, 1996).

FGF19 mRNA levels were measured in ileum tissue samples by RT-PCR analysis, using the primer probe set rhFGF19_LTS00681 (forward sequence CCCCATGTGG-GAATTGATCT, designated herein as SEQ ID NO: 336; reverse sequence CATGCCTGCTTCAGTCAGTTCT, designated herein as SEQ ID NO: 337; probe sequence TTTGC-CCTTCCCAAACCCCTCCA, designated herein as SEQ ID NO: 338). The results are presented in Table 22, expressed as percent expression over the PBS control. The data indicates that treatment with any of the ISIS oligonucleotides enhanced the expression of FGF19.

The plasma samples of monkeys treated with ISIS 299005, ISIS 463588, ISIS 463589, and ISIS 463690 were assessed for FGF19 levels. The plasma samples of monkeys treated with ISIS 463588 and ISIS 463690 were assessed for leptin levels. Plasma levels of FGF19 were measured pre-dose and on days 23, 65 and 89 using an ELISA assay kit (R&D Systems). Plasma levels of leptin measured pre-dose and on days 58 and 93 using an ELISA assay kit (Alpco). Results are presented in Tables 23 and 24. The data indicates that treatment with any of the ISIS oligonucleotides increased FGF19 plasma levels and decreases leptin levels. In particular, treatment with ISIS 463588 caused the highest increase in FGF19 plasma levels compared to the PBS control as well as to the other experimental plasma samples. Treatment with ISIS 463588 caused the most significant decrease in leptin levels compared to the PBS control.

TABLE 22

Ileum FGF19 mRNA levels in the cynomolgus monkey (% expression over the PBS control)

| ISIS No | % expression |
|---|---|
| 299005 | 688 |
| 463588 | 715 |
| 463589 | 545 |
| 463690 | 1032 |
| 463691 | 477 |
| 463835 | 445 |
| 463837 | 384 |
| 464225 | 370 |

TABLE 23

Plasma FGF19 levels in the cynomolgus monkey (pg/ml)

| | Pre-dose | Day 23 | Day 65 | Day 89 |
|---|---|---|---|---|
| PBS | 106 | 79 | 104 | 84 |
| ISIS 299005 | 125 | 110 | 191 | 202 |
| ISIS 463588 | 192 | 146 | 309 | 401 |
| ISIS 463589 | 111 | 117 | 177 | 151 |
| ISIS 463690 | 184 | 154 | 287 | 266 |

TABLE 24

Plasma leptin levels in the cynomolgus monkey (ng/ml)

| | Pre-dose | Day 58 | Day 93 |
|---|---|---|---|
| PBS | 0.21 | 0.60 | 0.53 |
| ISIS 463588 | 0.15 | 0.23 | 0.26 |
| ISIS 463690 | 0.27 | 0.32 | 0.36 |

Tolerability Studies

Liver Function

To evaluate the effect of ISIS oligonucleotides on hepatic function, blood samples were collected from all the study groups. The blood samples were collected via femoral venipuncture on day 58, 48 hrs post-dosing and processed for serum. Concentrations of various metabolites were measured using an automated clinical chemistry analyzer (Hitachi Olympus AU400e, Melville, N.Y.). Plasma concentrations of ALT and AST were measured and the results are presented in Table 25, expressed in IU/L. Bilirubin is also a liver function marker, was similarly measured and is presented in Table 25, expressed in mg/dL. The results indicate that treatment with ISIS 463588, as well as several other ISIS oligonucleotides, was well tolerated in terms of the liver function of the monkeys.

TABLE 25

ALT, AST, and Bilirubin in cynomolgus monkey plasma (on day 58)

| | ALT (IU/L) | AST (IU/L) | Bilirubin (mg/dL) |
|---|---|---|---|
| PBS | 47.4 | 40.3 | 0.2 |
| ISIS 299005 | 45.2 | 37.4 | 0.2 |
| ISIS 463588 | 77.6 | 73.2 | 0.1 |
| ISIS 463589 | 33.8 | 29.8 | 0.2 |
| ISIS 463690 | 103.6 | 47.6 | 0.2 |
| ISIS 463691 | 76.2 | 72.4 | 1.8 |
| ISIS 463835 | 116.2 | 42.0 | 0.1 |
| ISIS 463837 | 121.0 | 43.2 | 0.1 |
| ISIS 464225 | 81.4 | 40.8 | 0.1 |

Kidney Function

To evaluate the effect of ISIS oligonucleotides on kidney function, blood samples were collected from all the study groups. The blood samples were collected via femoral venipuncture on day 58, 48 hrs post-dosing and processed for serum. Concentrations of BUN and creatinine were measured using an automated clinical chemistry analyzer (Hitachi Olympus AU400e, Melville, N.Y.). Results are presented in Table 26, expressed in mg/dL.

The results indicate that most of the ISIS oligonucleotides did not have any adverse effects on the kidney function. Specifically, treatment with ISIS 463588 was well tolerated in terms of the kidney function of the monkeys.

TABLE 26

Plasma BUN and creatinine levels (mg/dL) in cynomolgus monkeys on day 58

|  | BUN | Creatinine |
|---|---|---|
| PBS | 28.6 | 0.8 |
| ISIS 299005 | 24.3 | 0.7 |
| ISIS 463588 | 23.2 | 0.7 |
| ISIS 463589 | 28.7 | 0.8 |
| ISIS 463690 | 22.7 | 0.7 |
| ISIS 463691 | 16.8 | 0.5 |
| ISIS 463835 | 32.2 | 0.8 |
| ISIS 463837 | 26.7 | 0.7 |
| ISIS 464225 | 25.8 | 0.6 |

Analysis of Markers of Inflammation

To evaluate the effect of ISIS oligonucleotides on factors involved in inflammation, blood was collected from all available animals for C-reactive protein (CRP) and complement C3 analysis, as well as for measurement of cytokine and chemokine levels. The blood samples were collected via femoral venipuncture on day 93, 48 hrs post-dosing and processed for separately for serum and plasma. Serum CRP and plasma complement C3 was measured using an automated clinical chemistry analyzer (Hitachi Olympus AU400e, Melville, N.Y.). The data is presented in Tables 27 and 28, expressed in mg/dL.

For cytokine level analyses, blood (1 mL each) was collected and then centrifuged 3,000 rpm for 10 min at 2-8° C. Plasma samples of mice treated with ISIS 463588, ISIS 463589, and ISIS 463690 were sent to Aushon Biosystems Inc. (Billerica, Mass.) for measurement of chemokine and cytokine levels. Levels of IL-6, MIP-1α, IL-8, MIP-1β, MCP-1, IL-1β, and RANTES were measured using the respective cross-reacting human antibodies and IFN-γ and IL-1β were measured using the respective primate antibodies. Measurements were taken pre-dose and on day 93. The results are presented in Tables 29-36.

The data indicate that most of the ISIS oligonucleotides were not pro-inflammatory. Specifically, treatment with ISIS 463588 was well tolerated in terms of being non-pro-inflammatory in the monkeys since there were no changes in CRP, a marker of inflammation.

TABLE 27

CRP (mg/dL) in cynomolgus monkeys

|  | Pre-dose | Day 30 | Day 58 | Day 93 |
|---|---|---|---|---|
| PBS | 2.2 | 3.1 | 2.5 | 4.1 |
| ISIS 299005 | 1.0 | 1.5 | 1.2 | 1.2 |
| ISIS 463588 | 2.9 | 5.2 | 3.7 | 3.8 |
| ISIS 463589 | 1.8 | 1.9 | 2.2 | 2.4 |
| ISIS 463690 | 2.2 | 3.1 | 2.1 | 3.6 |
| ISIS 463691 | 6.3 | 5.2 | 10.3 | 2.6 |
| ISIS 463835 | 9.7 | 16.2 | 4.7 | 5.7 |
| ISIS 463837 | 2.5 | 11.4 | 2.8 | 2.9 |
| ISIS 464225 | 2.5 | 8.1 | 6.9 | 5.2 |

TABLE 28

Complement C3 (mg/dL) in cynomolgus monkeys

|  | Pre-dose | Day 30 | Day 58 | Day 93 |
|---|---|---|---|---|
| PBS | 114.3 | 109.1 | 112.5 | 113.3 |
| ISIS 299005 | 108.3 | 92.1 | 99.6 | 91.4 |
| ISIS 463588 | 106.7 | 91.9 | 94.9 | 95.7 |
| ISIS 463589 | 116.3 | 102.0 | 105.1 | 100.9 |
| ISIS 463690 | 113.3 | 89.4 | 85.6 | 78.7 |
| ISIS 463691 | 123.5 | 89.2 | 70.6 | 97.6 |
| ISIS 463835 | 105.5 | 66.2 | 66.5 | 69.0 |
| ISIS 463837 | 107.1 | 91.1 | 88.7 | 86.5 |
| ISIS 464225 | 104.7 | 91.9 | 92.7 | 80.1 |

TABLE 29

IL-6 (pg/mL) in cynomolgus monkeys

|  | Pre-dose | Day 93 |
|---|---|---|
| PBS | 1.0 | 1.0 |
| ISIS 463588 | 0.4 | 0.9 |
| ISIS 463589 | 0.5 | 2.8 |
| ISIS 463690 | 1.2 | 10.2 |

TABLE 30

IL-8 (pg/mL) in cynomolgus monkeys

|  | Pre-dose | Day 93 |
|---|---|---|
| PBS | 544 | 482 |
| ISIS 463588 | 1255 | 1159 |
| ISIS 463589 | 424 | 636 |
| ISIS 463690 | 719 | 1344 |

TABLE 31

MIP-1α (pg/mL) in cynomolgus monkeys

|  | Pre-dose | Day 93 |
|---|---|---|
| PBS | 7.6 | 8.9 |
| ISIS 463588 | 8.9 | 10.8 |
| ISIS 463589 | 7.9 | 11.2 |
| ISIS 463690 | 13.8 | 18.9 |

TABLE 32

MIP-1β (pg/mL) in cynomolgus monkeys

|  | Pre-dose | Day 93 |
|---|---|---|
| PBS | 249 | 229 |
| ISIS 463588 | 219 | 211 |
| ISIS 463589 | 175 | 196 |
| ISIS 463690 | 362 | 478 |

TABLE 33

MCP-1 (pg/mL) in cynomolgus monkeys

|  | Pre-dose | Day 93 |
|---|---|---|
| PBS | 200 | 275 |
| ISIS 463588 | 420 | 496 |
| ISIS 463589 | 343 | 363 |
| ISIS 463690 | 441 | 709 |

TABLE 34

IFN-γ (pg/mL) in cynomolgus monkeys

|  | Pre-dose | Day 93 |
|---|---|---|
| PBS | 22.1 | 25.9 |
| ISIS 463588 | 1.6 | 1.5 |
| ISIS 463589 | 10.8 | 12.3 |
| ISIS 463690 | 20.8 | 17.4 |

TABLE 35

IL-1β (pg/mL) in cynomolgus monkeys

|  | Pre-dose | Day 93 |
|---|---|---|
| PBS | 0.09 | 0.28 |
| ISIS 463588 | 0.07 | 0.08 |
| ISIS 463589 | 0.13 | 0.06 |
| ISIS 463690 | 0.20 | 0.36 |

TABLE 36

RANTES (pg/mL) in cynomolgus monkeys

|  | Pre-dose | Day 93 |
|---|---|---|
| PBS | 43339 | 48967 |
| ISIS 463588 | 45962 | 51326 |
| ISIS 463589 | 38382 | 30985 |
| ISIS 463690 | 37330 | 29209 |

Hematology

To evaluate any effect of ISIS oligonucleotides in cynomolgus monkeys on hematologic parameters, approximately 1.3 mL of blood was collected on day 93 from each of the available study animals in tubes containing $K_2$-EDTA. Samples were analyzed for red blood cell (RBC) count, white blood cells (WBC) count, individual white blood cell counts, such as that of monocytes, neutrophils, lymphocytes, as well as for platelet count, hemoglobin content and hematocrit, using an ADVIA 120 hematology analyzer (Bayer, USA). The data is presented in Tables 37 and 38.

The data indicate that most of the ISIS oligonucleotides did not have any adverse effects on the any hematologic parameters. Specifically, treatment with ISIS 463588 was well tolerated in terms of the hematologic parameters of the monkeys.

TABLE 37

Blood cells in cynomolgus monkeys

|  | RBC (× 10⁶/μL) | Platelets (× 10³/μL) | WBC (× 10³/μL) | Neutrophils (/μL) | Lymphocytes (/μL) | Monocytes (/μL) |
|---|---|---|---|---|---|---|
| PBS | 6.1 | 426 | 13.8 | 3244 | 9637 | 483 |
| ISIS 299005 | 6.2 | 348 | 13.8 | 3395 | 9378 | 549 |
| ISIS 463588 | 6.4 | 331 | 11.7 | 3081 | 7741 | 387 |
| ISIS 463589 | 5.7 | 360 | 12.3 | 3590 | 8037 | 413 |
| ISIS 463690 | 6.1 | 430 | 13.1 | 2592 | 9451 | 571 |
| ISIS 463691 | 5.3 | 494 | 17.5 | 7511 | 8534 | 1144 |
| ISIS 463835 | 5.5 | 558 | 12.7 | 3129 | 8374 | 664 |
| ISIS 463837 | 5.8 | 480 | 13.3 | 3145 | 9025 | 566 |
| ISIS 464225 | 5.9 | 429 | 13.6 | 2994 | 9349 | 762 |

TABLE 38

Hematologic parameters in cynomolgus monkeys

|  | Hemoglobin (g/dL) | HCT (%) |
|---|---|---|
| PBS | 14.2 | 45.5 |
| ISIS 299005 | 13.7 | 44.0 |
| ISIS 463588 | 13.9 | 45.4 |
| ISIS 463589 | 13.3 | 41.9 |
| ISIS 463690 | 13.8 | 44.7 |
| ISIS 463691 | 12.7 | 40.8 |
| ISIS 463835 | 12.3 | 40.0 |
| ISIS 463837 | 12.8 | 41.7 |
| ISIS 464225 | 13.1 | 42.8 |

Pharmacokinetic Studies

Measurement of Oligonucleotide Concentration

The concentration of the full-length oligonucleotide as well as the total oligonucleotide concentration (including the degraded form) was measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-O-methoxyethyl modified phosphorothioate oligonucleotide, GCGTTTGCTCTTCTTCTTGCGTTTTTT, designated herein as SEQ ID NO: 323) was added prior to extraction. Tissue sample concentrations were calculated using calibration curves, with a lower limit of quantitation (LLOQ) of approximately 1.14 μg/g. The results are presented in Table 39, expressed as μg/g tissue. The ratio of the concentrations in the kidney versus the liver was calculated and presented in Table 39. Treatment with ISIS oligonucleotides did not result in any abnormality in the ratio.

TABLE 39

Full-length oligonucleotide concentration (μg/g) in the liver and kidney of cynomolgus monkey

| ISIS No | Kidney | Liver | Kidney/Liver |
|---|---|---|---|
| 463588 | 1717 | 1033 | 1.7 |
| 463589 | 1663 | 1227 | 1.4 |
| 463690 | 1395 | 1226 | 1.1 |

Overall, the results of the study indicate that ISIS 463588 is a potent and tolerable antisense oligonucleotide for treatment of metabolic diseases, such as diabetes, obesity, insulin resistance, and insulin deficiency.

Example 16

In Vivo Effect of Antisense Inhibition of Murine FGFR4 in Diet-Induced Obesity (DIO) Mice with Caloric Restriction DIO mice are C57BL/6 mice fed a high fat diet starting from 6 weeks of age and are a standard model used for assays related to studying the effect of therapeutic agents on lowering adiposity and improving insulin sensitivity. The antisense oligonucleotide, ISIS 393250, a 5-10-5 MOE gapmer, having a sequence of 5'-GCCACATTTCCTTCCAGCTG-3 (SEQ ID NO: 324), and with a target start site of 337 on murine FGFR4 mRNA (GENBANK Accession No. BC033313.1 (SEQ ID NO: 6) was used in this assay. The effect of ISIS 393250 on a DIO model under caloric restriction was evaluated.

Treatment

Male 6 week-old C57BL/6 mice (Jackson Laboratories) were fed with 58 kcal % high-fat diet (Research diet D12330) ad lib for 4 months to induce obesity. The mice were divided into 4 groups based on body weight and body fat content. The first group of mice was treated with 25 mg/kg ISIS 393250 administered subcutaneously twice weekly for 6 weeks. The second group of mice was treated with 25 mg/kg control oligonucleotide, ISIS 141923 (CCTTCCCTGAAGGTTC-CTCC (SEQ ID NO: 325), 5-10-5 MOE gapmer with no known murine target), administered subcutaneously twice weekly for 6 weeks. Two control groups of mice were treated with PBS administered subcutaneously twice weekly for 6 weeks. After two weeks of treatment, the oligonucleotide-treated mice and one of the PBS control group mice were subjected to caloric restriction by providing 95% of the amount of food consumed daily by the FGFR4 ASO-treated mice during the first two weeks of treatment. The second PBS control group continued to be fed ad libitum with the same amount of food as in the first two weeks of treatment.

Weekly body weights were measured and body compositions were monitored at different time point with an Echo MRI Body Composition Analyzer. The mice were euthanized after 6 weeks of treatment.

RNA Analysis

RNA was extracted from the liver for RT-PCR analysis of murine FGFR4 expression. The primer probe set mFGFR4_LTS00702 (forward sequence CCCTGAGGCCA-GATACACAGATAT, designated herein as SEQ ID NO: 339; reverse sequence ACGGATGACTTGCCGATGATA, designated herein as SEQ ID NO: 340; probe sequence CTCACTGGTTCTGCTTGTGCTCCTGCT, designated herein as SEQ ID NO: 341) was used for analysis. The results indicated that treatment with ISIS 393250 reduced murine FGFR4 levels by 76%.

Body Weight and Body Composition Analysis

Weekly body weights were measured and are presented in Table 40. Body fat content data is presented in Table 41, expressed as percent of the corresponding body weight. Lean body mass is presented in Table 42, expressed in grams. White adipose tissue weight was measured after euthanizing the mice and is presented in Table 43, expressed in grams. The data indicates calorie restriction significantly lowered body weight and total body fat content. Treatment with ISIS 393250 further lowered both body weight and fat content, but had no effect on body lean mass. Treatment with ISIS 141923 had no effect. Hence, antisense inhibition of FGFR4 expression has a beneficial effect on body weight and body fat content in subjects suffering from obesity.

TABLE 40

Weekly body weights (g)

| | Calorie-restricted | Pre-dose | Week 1 | Week 2 | Week 3 | Week 4 | Week 5 | Week 6 |
|---|---|---|---|---|---|---|---|---|
| PBS | No | 51.7 | 51.1 | 52.1 | 52.6 | 53.1 | 50.6 | 53.4 |
| PBS | Yes | 50.3 | 50.4 | 51.1 | 50.0 | 47.6 | 46.0 | 45.4 |
| ISIS 141923 | Yes | 49.5 | 50.1 | 50.9 | 49.8 | 48.1 | 46.3 | 45.2 |
| ISIS 393250 | Yes | 50.5 | 50.9 | 50.9 | 48.9 | 46.7 | 44.4 | 42.1 |

TABLE 41

Body fat content (% body weight)

| | Calorie-restricted | Pre-dose | Week 2 | Week 4 | Week 6 |
|---|---|---|---|---|---|
| PBS | No | 39.5 | 39.8 | 40 | 40 |
| PBS | Yes | 38.7 | 40.2 | 39.1 | 38.3 |
| ISIS 141923 | Yes | 38.9 | 39.1 | 38.1 | 37.7 |
| ISIS 393250 | Yes | 39.4 | 38.6 | 35.3 | 31.3 |

TABLE 42

Lean body mass (g)

| | Calorie-restricted | Pre-dose | Week 2 | Week 4 | Week 6 |
|---|---|---|---|---|---|
| PBS | No | 27.8 | 28.2 | 28.2 | 28.3 |
| PBS | Yes | 27.3 | 27.5 | 25.7 | 24.5 |
| ISIS 141923 | Yes | 26.7 | 27.3 | 26 | 24.9 |
| ISIS 393250 | Yes | 27.1 | 27.8 | 25.9 | 24.8 |

TABLE 43

White adipose tissue weight (g)

| | Calorie-restricted | Epididymal | Peri-renal |
|---|---|---|---|
| PBS | No | 2.5 | 1.1 |
| PBS | Yes | 2.2 | 0.9 |
| ISIS 141923 | Yes | 2.2 | 0.9 |
| ISIS 393250 | Yes | 1.8 | 0.7 |

Metabolic Rate and Locomotor Activity Analysis

The metabolic rate was assessed by measuring the oxygen consumption and heat production of the mice. Both parameters were measured with an indirect calorimetry system (Oxymax system, Columbus Instruments). Locomotor activity was also assessed with the same instrument. Metabolic rate and locomotor activity was assessed both in darkness, when the mice are typically more active, and in light. The results are presented in Tables 44-46. The results indicate that calorie restriction reduced whole body oxygen consumption. Treatment with ISIS 393250 prevented this decrease in oxygen consumption without affecting locomotor activity. Hence, antisense inhibition of FGFR4 expression in obese subjects with a calorie-restricted diet would be beneficial as it would prevent any decline in metabolic rate in the subject.

TABLE 44

$O_2$ consumption (mL/kg lean tissue/hr)

| | Calorie-restricted | dark | light |
|---|---|---|---|
| PBS | No | 4275 | 3327 |
| PBS | Yes | 4085 | 3259 |
| ISIS 141923 | Yes | 4094 | 3258 |
| ISIS 393250 | Yes | 4268 | 3359 |

TABLE 45

Heat production (kcal/kg lean tissue/hr)

| | Calorie-restricted | dark | light |
|---|---|---|---|
| PBS | No | 19.8 | 15 |
| PBS | Yes | 19.1 | 15.1 |
| ISIS 141923 | Yes | 19.1 | 15.1 |
| ISIS 393250 | Yes | 19.7 | 15.7 |

TABLE 46

Locomotor activity (events/min)

| | Calorie-restricted | dark | light |
|---|---|---|---|
| PBS | No | 16.4 | 1.9 |
| PBS | Yes | 21.9 | 3.1 |
| ISIS 141923 | Yes | 16.1 | 2.5 |
| ISIS 393250 | Yes | 16.2 | 3 |

Example 17

In Vivo Effect of Antisense Inhibition of Murine FGFR4 in Diet-Induced Obesity (DIO) Mice with Caloric Restriction The effect of ISIS 446259 (TCCATTTCCTCAGAGGCCTC (SEQ ID NO: 326), 5-10-5 MOE gapmer, with a target start site of 407 on GENBANK Accession No. BC033313.1 (SEQ ID NO: 6)) on DIO mice under caloric restriction was evaluated.

Treatment

Male 6 week-old C57BL/6 mice (Jackson Laboratories) were fed with 58 kcal % high-fat diet Research diet D12330) ad lib for 3.5 months to induce obesity. The mice were divided into 4 groups based on body weight and body fat content. The first group of mice was treated with 25 mg/kg ISIS 446259 administered subcutaneously twice weekly for 8 weeks. The second group of mice was treated with 25 mg/kg control oligonucleotide, ISIS 141923 administered subcutaneously twice weekly for 8 weeks. Two control groups of mice were treated with PBS administered subcutaneously twice weekly for 8 weeks. After two weeks of treatment, the oligonucleotide-treated mice and one of the PBS control group mice were subjected to caloric restriction by providing 90% of the amount of food consumed daily by the FGFR4 ASO-treated mice during the first two weeks of treatment. The second PBS control group continued to be fed ad libitum with the same amount of food as in the first two weeks of treatment.

Weekly body weights were measured and body compositions were monitored at different time point with an Echo MRI Body Composition Analyzer. The mice were euthanized after 8 weeks of treatment.

RNA Analysis

RNA was extracted from the liver for RT-PCR analysis of murine FGFR4 expression. The primer probe set mFGFR4_LTS00702 was used to analyze mRNA levels. The results indicated that treatment with ISIS 446259 reduced murine FGFR4 levels by 83%.

Body Weight and Body Composition Analysis

Weekly body weights were measured and are presented in Table 47. Body fat content data is presented in Table 48, expressed as percent of the corresponding body weight. Lean body mass was presented in Table 49, expressed in grams. The data indicates calorie restriction significantly lowered body weight and total body fat content. Treatment with ISIS 446259 further lowered both body weight and fat content, but had no effect on body lean mass. Treatment with ISIS 141923 had no further effect. Hence, antisense inhibition of FGFR4 expression has a beneficial effect on body weight and body fat content in subjects suffering from obesity in addition to effects seen by caloric restriction alone.

TABLE 47

Weekly body weights (g)

| | Calorie-restricted | Week 0 | Week 2 | Week 4 | Week 6 | Week 8 |
|---|---|---|---|---|---|---|
| PBS | No | 48.7 | 49.9 | 51 | 53.4 | 52.5 |
| PBS | Yes | 49.7 | 50.7 | 46.9 | 46.9 | 46.2 |
| ISIS 141923 | Yes | 49.6 | 50.5 | 46.9 | 46.1 | 44.5 |
| ISIS 446259 | Yes | 49.4 | 49.4 | 45.2 | 43.8 | 39.7 |

TABLE 48

Body fat content (% body weight)

| | Calorie-restricted | Week 0 | Week 2 | Week 5 | Week 8 |
|---|---|---|---|---|---|
| PBS | No | 41 | 43 | 43 | 42 |
| PBS | Yes | 41 | 43 | 41 | 39 |
| ISIS 141923 | Yes | 40 | 40 | 37 | 35 |
| ISIS 446259 | Yes | 41 | 41 | 35 | 30 |

TABLE 49

Lean body mass (g)

| | Calorie-restricted | Week 0 | Week 2 | Week 5 | Week 8 |
|---|---|---|---|---|---|
| PBS | No | 26 | 24 | 26 | 27 |
| PBS | Yes | 26 | 25 | 25 | 25 |
| ISIS 141923 | Yes | 27 | 26 | 25 | 26 |
| ISIS 446259 | Yes | 26 | 25 | 25 | 25 |

Plasma Lipid Analysis

To evaluate the effect of ISIS oligonucleotides on cholesterol and triglyceride metabolism, plasma levels of each were measured at the end of the treatment period. The mice were euthanized and blood was collected via cardiac puncture. The lipid levels were measured using an automated clinical chemistry analyzer (Hitachi Olympus AU400e, Melville, N.Y.). Results are presented in Table 50, expressed as mg/dL. The results indicate that treatment with ISIS 446259 reduced both cholesterol and triglyceride levels in the mice. Therefore, antisense inhibition of FGFR4 had a beneficial effect on the lipid profile and may be used to reduce adiposity in obese subjects.

TABLE 50

Cholesterol and lipid levels (mg/dL)

|  | Calorie-restricted | Cholesterol | Triglycerides |
|---|---|---|---|
| PBS | No | 270 | 137 |
| PBS | Yes | 240 | 128 |
| ISIS 141923 | Yes | 222 | 113 |
| ISIS 446259 | Yes | 181 | 84 |

Example 18

In Vivo Effect of Antisense Inhibition of Murine FGFR4 on FGF15 Levels in DIO Mice The effect of ISIS 393250 and ISIS 446259 on FGF15 levels in DIO mice was evaluated.

Treatment

Male 6 week-old C57BL/6 mice (Jackson Laboratories) were fed with 58 kcal % high-fat diet Research diet D12330) ad lib for 3.5 months to induce obesity. A group of C57BL/6 mice were fed normal Purina mouse chow and served as the naïve control. The DIO mice were divided into groups based on body weight and body fat content. The first group of DIO mice was treated with 25 mg/kg ISIS 393250 administered subcutaneously twice weekly for 4 weeks. The second group of DIO mice was treated with 25 mg/kg ISIS 446259 administered subcutaneously twice weekly for 4 weeks. The third group of DIO mice was treated with 25 mg/kg control oligonucleotide, ISIS 141923 administered subcutaneously twice weekly for 4 weeks. A control group of DIO mice was treated with PBS administered subcutaneously twice weekly for 4 weeks. The mice were euthanized after 4 weeks of treatment.

FGF15 Levels

FGF15 is the rodent equivalent of FGF19 (Wright, T. J. et al., Dev. Biol. 269: 264-275, 2004), and is therefore important for the reduction of adiposity and improvement of insulin sensitivity in mice.

RNA was extracted from liver and ileum. Liver RNA was analyzed by RT-PCR analysis for FGFR4 mRNA levels using primer probe set mFGFR4_LTS00702. Ileum RNA was analyzed by RT-PCR analysis for FGF15 levels using primer probe set mFgf15_LTS00635 (forward sequence GACCAAAACGAACGAAATTTGTT, designated herein as SEQ ID NO: 342; reverse sequence ACGTCCTTGATGGCAATCG, designated herein as SEQ ID NO: 343; probe sequence AATTCCGCGCGGTCGCTCTG, designated herein as SEQ ID NO: 344). The results are presented in Table 51 and demonstrate that treatment with either antisense oligonucleotide significantly decreases FGFR4 mRNA levels and also significantly enhances FGF15 expression levels.

Plasma samples of the mice group were also analyzed at weeks 2 and 4 for FGF15 protein levels with ELISA using an anti-FGF15 antibody (Santa Cruz Biotechnology Inc). The results are presented in Table 52 and demonstrate that antisense inhibition of FGFR4 results in enhanced plasma levels of FGF15.

TABLE 51

FGFR4 and FGF15 mRNA levels relative to control

| ISIS No | Liver FGFR4 (% inhibition) | Ileum FGF15 (% expression) |
|---|---|---|
| 141923 | 14 | 92 |
| 393250 | 96 | 1117 |
| 446259 | 94 | 707 |
| C57BL/6 control | 0 | 25 |

TABLE 52

FGF15 plasma levels at week 2 and 4 (ng/ml)

|  | Week 2 | Week 4 |
|---|---|---|
| PBS | 0.13 | 0.13 |
| ISIS 141923 | 0.12 | 0.14 |
| ISIS 393250 | 0.69 | 0.96 |
| ISIS 446259 | 0.18 | 0.25 |
| C57BL/6 control | 0.1 | 0.12 |

Example 19

In Vivo Effect of Antisense Inhibition of Murine FGFR4 on FGF15 Levels in C57BL/6 Mice The effect of ISIS 393250 on FGF15 levels in C57BL/6 mice was evaluated.

Treatment

Male 6 week-old C57BL/6 mice (Jackson Laboratories) were fed normal Purina mouse chow. The mice were randomly divided into 3 groups. The first group of mice was treated with 50 mg/kg ISIS 393250 administered subcutaneously twice weekly for 5.5 weeks. The second group of mice was treated with 50 mg/kg control oligonucleotide, ISIS 141923 administered subcutaneously twice weekly for 5.5 weeks. A control group of mice was treated with PBS administered subcutaneously twice weekly for 5.5 weeks.

FGFR4 Levels

RNA was extracted from liver and RNA was analyzed by RT-PCR analysis for FGFR4 mRNA levels using primer probe set mFGFR4_LTS00702. The results are presented in Table 53 and demonstrate that treatment with ISIS 393250 significantly decreases FGFR4 mRNA levels

TABLE 53

FGFR4 mRNA inhibition levels (%)

| ISIS No | % |
|---|---|
| 141923 | 0 |
| 393250 | 79 |

FGF15 Levels

Plasma samples of the mice group were analyzed for FGF15 protein levels using with ELISA using an anti-FGF15 antibody (Santa Cruz Biotechnology Inc). The results are presented in Table 54 and demonstrate that antisense inhibition of FGFR4 results in enhanced plasma levels of FGF15.

TABLE 54

FGF15 plasma levels at day 16

| | ng/mL |
|---|---|
| PBS | 0.07 |
| ISIS 141923 | 0.08 |
| ISIS 393250 | 0.28 |

Example 20

In Vivo Effect of Antisense Inhibition of Murine FGFR4 on FGF15 Levels in Ob/Ob Mice Leptin is a hormone produced by fat that regulates appetite. Deficiency of this hormone in both humans and in non-human animals, leads to obesity. ob/ob mice have a mutation in the leptin gene which results in obesity and hyperglycemia. As such, these mice are a useful model for the investigation of obesity and diabetes and related conditions provided herein. These mice models are also useful for testing compounds, compositions and methods designed to treat, prevent or ameliorate such conditions.

In accordance with the present invention, the effects of antisense inhibition of FGFR4 were investigated in the ob/ob mouse model of obesity. Male 12 week old ob/ob (C57B1/6J-Lep$^{ob}$/Lep$^{ob}$) mice were purchased from Jackson Laboratories (Bar Harbor, Me.) and used for the current study.

Treatment

The mice were divided into groups based on body weight and body fat content. The first group of mice was treated with 25 mg/kg ISIS 393250 administered subcutaneously twice weekly for 14 weeks. The second group of mice was treated with 25 mg/kg control oligonucleotide, ISIS 141923 administered subcutaneously twice weekly for 14 weeks. A control group of mice was treated with PBS administered subcutaneously twice weekly for 14 weeks.

FGFR4 Levels

RNA was extracted from liver and RNA was analyzed by RT-PCR analysis for FGFR4 mRNA levels using primer probe set mFGFR4_LTS00702. The results are presented in Table 55 and demonstrate that treatment with ISIS 393250 significantly decreases FGFR4 mRNA levels

TABLE 55

FGFR4 mRNA inhibition levels (%)

| ISIS No | % |
|---|---|
| 141923 | 0 |
| 393250 | 89 |

FGF15 Levels

Plasma samples of the mice group were analyzed for FGF15 protein levels using with ELISA using an anti-FGF15 antibody (Santa Cruz Biotechnology Inc). The results are presented in Table 56 and demonstrate that antisense inhibition of FGFR4 results in enhanced plasma levels of FGF15.

TABLE 56

FGF15 plasma levels at week 4 and 8 (ng/mL)

| | Week 4 | Week 8 |
|---|---|---|
| PBS | 0.5 | 1.2 |
| ISIS 141923 | 0.8 | 0.5 |
| ISIS 393250 | 4.2 | 4.2 |

Example 21

Effect of Antisense Inhibition of Murine FGFR4 in Monkey Primary Hepatocytes

The effect of antisense inhibition of FGFR4 with ISIS 299004 on fatty acid oxidation in monkey hepatocytes was evaluated. AICAR was used as a positive control.

Treatment

Primary hepatocytes purchased from APL/Lovelace In Vitro Enterprises and cultured in William E medium. The cells were seeded at a density of 1 million cells per 25 ml flask. After 4-5 hrs of culture, the cells were treated with 30 nM of ISIS 299004 or 1000 μM AICAR for 18 hrs. A control set of cells was treated with PBS. FGFR4 levels were measured using the primer probe set cynoFGFR4_MGB_LTS00689 (forward sequence GCAC-CAGGGATGAGCTTGAC, designated herein as SEQ ID NO: 348; reverse sequence CCAAGTCTCCCACTTTC-CAGTT, designated herein as SEQ ID NO: 349; probe sequence AAGAGCCTGACTCCAGT, designated herein as SEQ ID NO: 350). Treatment with ISIS 299004 reduced FGFR4 levels by 83%.

For evaluation of fatty acid oxidation, the cells were placed in low glucose media containing $^{1-14c}$Oleic acid and BSA, and the culture flasks were capped with a rubber stopper containing a hanging reservoir bucket. The cells were then incubated at 37° C. under 5% $CO_2$ for 1.5 hrs. Following incubation, 200 μl of 1M hyamine hydroxide (a $^{14}CO_2$ trapping agent) was added to the reservoir bucket and 1 ml of 10% perchloric acid solution was added to the cells. The flasks were transferred to a 37° C. shaking incubator for 40 min. Upon completion of the incubation, the hanging bucket reservoir containing the hyamine hydroxide was separated from the flask and placed in scintillation fluid overnight, and read in the scintillation counter the next day. Bradford-based protein measurements were conducted on an equal number of primary monkey hepatocytes, by using the DC™ Biorad protein assay kit (Bearden, J. Biochem. Biophys. Acta. 533: 525. 1978). The values obtained from the protein readout was used for normalization of the $CO_2$ production counted by the scintillation counter. The results are presented in Table 57 and indicate that antisense inhibition of FGFR4 increased fatty acid oxidation in primary hepatocytes. Five independent fatty acid oxidation experiments were conducted, which demonstrated a similar trend on the results.

TABLE 57

$CO_2$ production (% of the control)

| | $CO_2$ |
|---|---|
| ISIS 141923 | +2 |
| ISIS 299004 | +48 |
| AICAR | +44 |

What is claimed:

1. A single-stranded oligonucleotide consisting of 20 linked nucleosides having a nucleobase sequence consisting of the sequence recited in SEQ ID NO: 16, wherein the oligonucleotide comprises
   a gap segment consisting of ten linked deoxynucleosides;
   a 5' wing segment consisting of five linked nucleosides; and
   a 3' wing segment consisting of five linked nucleosides;
   wherein the gap segment is positioned between the 5' wing segment and the 3' wing segment; wherein each nucleoside of each wing segment comprises a 2'-O-methoxyethyl sugar; wherein each internucleoside linkage is a phosphorothioate linkage; and wherein each cytosine is a 5-methylcytosine.

2. A composition comprising the compound of claim 1 or salt thereof and a pharmaceutically acceptable carrier or diluent.

3. A method of treating or preventing a metabolic disease in a human comprising administering to the human a therapeutically effective amount of the compound of claim 1, thereby treating or preventing the metabolic disease.

4. The method of claim 3, wherein the metabolic disease is obesity.

5. The method of claim 3, wherein administering the compound reduces at least one of insulin resistance, glucose levels, fat mass, fat pad weight, adipose tissue size and weight, body fat, body weight or a combination thereof.

6. The method of claim 3, wherein administering the compound increases metabolic rate.

7. The method of claim 3, comprising co-administering the compound and a second agent.

8. The method of claim 7, wherein the compound and the second agent are administered concomitantly.

9. The method of claim 4, wherein administering the compound treats obesity in the human.

* * * * *

SEQUENCE LISTING

<160> NUMBER OF SEQ ID NOS: 350

<210> SEQ ID NO 1
<211> LENGTH: 3040
<212> TYPE: DNA
<213> ORGANISM: Homo sapiens
<220> FEATURE:
<221> NAME/KEY: CDS
<222> LOCATION: (168)...(2576)

<400> SEQUENCE: 1

```
ctcgctcccg gccgaggagc gctcgggctg tctgcggacc ctgccgcgtg caggggtcgc      60
ggccggctgg agctgggagt gaggcggcgg aggagccagg tgaggaggag ccaggaaggc     120
agttggtggg aagtccagct tgggtccctg agagctgtga aaggag atg cgg ctg        176
                                                  Met Arg Leu
                                                    1 ctg ctg gcc ctg ttg ggg gtc ctg ctg agt gtg cct ggg cct cca gtc      224
Leu Leu Ala Leu Leu Gly Val Leu Leu Ser Val Pro Gly Pro Pro Val
      5                  10                  15 ttg tcc ctg gag gcc tct gag gaa gtg gag ctt gag ccc tgc ctg gct      272
Leu Ser Leu Glu Ala Ser Glu Glu Val Glu Leu Glu Pro Cys Leu Ala
 20                  25                  30                  35 ccc agc ctg gag cag caa gag cag gag ctg aca gta gcc ctt ggg cag      320
Pro Ser Leu Glu Gln Gln Glu Gln Glu Leu Thr Val Ala Leu Gly Gln
                 40                  45                  50 cct gtg cgt ctg tgc tgt ggg cgg gct gag cgt ggt ggc cac tgg tac      368
Pro Val Arg Leu Cys Cys Gly Arg Ala Glu Arg Gly Gly His Trp Tyr
             55                  60                  65 aag gag ggc agt cgc ctg gca cct gct ggc cgt gta cgg ggc tgg agg      416
Lys Glu Gly Ser Arg Leu Ala Pro Ala Gly Arg Val Arg Gly Trp Arg
         70                  75                  80 ggc cgc cta gag att gcc agc ttc cta cct gag gat gct ggc cgc tac      464
Gly Arg Leu Glu Ile Ala Ser Phe Leu Pro Glu Asp Ala Gly Arg Tyr
     85                  90                  95 ctc tgc ctg gca cga ggc tcc atg atc gtc ctg cag aat ctc acc ttg      512
Leu Cys Leu Ala Arg Gly Ser Met Ile Val Leu Gln Asn Leu Thr Leu
100                 105                 110                 115 att aca ggt gac tcc ttg acc tcc agc aac gat gat gag gac ccc aag      560
Ile Thr Gly Asp Ser Leu Thr Ser Ser Asn Asp Asp Glu Asp Pro Lys
                120                 125                 130 tcc cat agg gac ccc tcg aat agg cac agt tac ccc cag caa gca ccc      608
Ser His Arg Asp Pro Ser Asn Arg His Ser Tyr Pro Gln Gln Ala Pro
            135                 140                 145 tac tgg aca cac ccc cag cgc atg gag aag aaa ctg cat gca gta cct      656
Tyr Trp Thr His Pro Gln Arg Met Glu Lys Lys Leu His Ala Val Pro
        150                 155                 160 gcg ggg aac acc gtc aag ttc cgc tgt cca gct gca ggc aac ccc acg      704
Ala Gly Asn Thr Val Lys Phe Arg Cys Pro Ala Ala Gly Asn Pro Thr
    165                 170                 175 ccc acc atc cgc tgg ctt aag gat gga cag gcc ttt cat ggg gag aac      752
Pro Thr Ile Arg Trp Leu Lys Asp Gly Gln Ala Phe His Gly Glu Asn
180                 185                 190                 195 cgc att gga ggc att cgg ctg cgc cat cag cac tgg agt ctc gtg atg      800
Arg Ile Gly Gly Ile Arg Leu Arg His Gln His Trp Ser Leu Val Met
                200                 205                 210 gag agc gtg gtg ccc tcg gac cgc ggc aca tac acc tgc ctg gta gag      848
Glu Ser Val Val Pro Ser Asp Arg Gly Thr Tyr Thr Cys Leu Val Glu
            215                 220                 225 aac gct gtg ggc agc atc cgc tat aac tac ctg cta gat gtg ctg gag      896
Asn Ala Val Gly Ser Ile Arg Tyr Asn Tyr Leu Leu Asp Val Leu Glu
```

|    |    |    |    |    |    |    |    |    |    |    |    |    |    |    |    |      |
|----|----|----|----|----|----|----|----|----|----|----|----|----|----|----|----|------|
|    |    |    |    |230 |    |    |    |235 |    |    |    |240 |    |    |    |      |
|cgg |tcc |ccg |cac |cgg |ccc |atc |ctg |cag |gcc |ggg |ctc |ccg |gcc |aac |acc | 944  |
|Arg |Ser |Pro |His |Arg |Pro |Ile |Leu |Gln |Ala |Gly |Leu |Pro |Ala |Asn |Thr |      |
|    |245 |    |    |    |250 |    |    |    |255 |    |    |    |    |    |    |      |
|aca |gcc |gtg |gtg |ggc |agc |gac |gtg |gag |ctg |ctg |tgc |aag |gtg |tac |agc | 992  |
|Thr |Ala |Val |Val |Gly |Ser |Asp |Val |Glu |Leu |Leu |Cys |Lys |Val |Tyr |Ser |      |
|260 |    |    |    |    |265 |    |    |    |    |270 |    |    |    |    |275 |      |
|gat |gcc |cag |ccc |cac |atc |cag |tgg |ctg |aag |cac |atc |gtc |atc |aac |ggc | 1040 |
|Asp |Ala |Gln |Pro |His |Ile |Gln |Trp |Leu |Lys |His |Ile |Val |Ile |Asn |Gly |      |
|    |    |    |    |280 |    |    |    |    |285 |    |    |    |    |290 |    |      |
|agc |agc |ttc |gga |gcc |gac |ggt |ttc |ccc |tat |gtg |caa |gtc |cta |aag |act | 1088 |
|Ser |Ser |Phe |Gly |Ala |Asp |Gly |Phe |Pro |Tyr |Val |Gln |Val |Leu |Lys |Thr |      |
|    |    |295 |    |    |    |    |300 |    |    |    |    |305 |    |    |    |      |
|gca |gac |atc |aat |agc |tca |gag |gtg |gag |gtc |ctg |tac |ctg |cgg |aac |gtg | 1136 |
|Ala |Asp |Ile |Asn |Ser |Ser |Glu |Val |Glu |Val |Leu |Tyr |Leu |Arg |Asn |Val |      |
|    |    |310 |    |    |    |    |315 |    |    |    |    |320 |    |    |    |      |
|tca |gcc |gag |gac |gca |ggc |gag |tac |acc |tgc |ctc |gca |ggc |aat |tcc |atc | 1184 |
|Ser |Ala |Glu |Asp |Ala |Gly |Glu |Tyr |Thr |Cys |Leu |Ala |Gly |Asn |Ser |Ile |      |
|325 |    |    |    |    |330 |    |    |    |    |335 |    |    |    |    |    |      |
|ggc |ctc |tcc |tac |cag |tct |gcc |tgg |ctc |acg |gtg |ctg |cca |gag |gag |gac | 1232 |
|Gly |Leu |Ser |Tyr |Gln |Ser |Ala |Trp |Leu |Thr |Val |Leu |Pro |Glu |Glu |Asp |      |
|340 |    |    |    |    |345 |    |    |    |    |350 |    |    |    |    |355 |      |
|ccc |aca |tgg |acc |gca |gca |gcg |ccc |gag |gcc |agg |tat |acg |gac |atc |atc | 1280 |
|Pro |Thr |Trp |Thr |Ala |Ala |Ala |Pro |Glu |Ala |Arg |Tyr |Thr |Asp |Ile |Ile |      |
|    |    |    |    |360 |    |    |    |    |365 |    |    |    |    |370 |    |      |
|ctg |tac |gcg |tcg |ggc |tcc |ctg |gcc |ttg |gct |gtg |ctc |ctg |ctg |ctg |gcc | 1328 |
|Leu |Tyr |Ala |Ser |Gly |Ser |Leu |Ala |Leu |Ala |Val |Leu |Leu |Leu |Leu |Ala |      |
|    |    |375 |    |    |    |    |380 |    |    |    |    |385 |    |    |    |      |
|ggg |ctg |tat |cga |ggg |cag |gcg |ctc |cac |ggc |cgg |cac |ccc |cgc |ccg |ccc | 1376 |
|Gly |Leu |Tyr |Arg |Gly |Gln |Ala |Leu |His |Gly |Arg |His |Pro |Arg |Pro |Pro |      |
|    |    |390 |    |    |    |    |395 |    |    |    |    |400 |    |    |    |      |
|gcc |act |gtg |cag |aag |ctc |tcc |cgc |ttc |cct |ctg |gcc |cga |cag |ttc |tcc | 1424 |
|Ala |Thr |Val |Gln |Lys |Leu |Ser |Arg |Phe |Pro |Leu |Ala |Arg |Gln |Phe |Ser |      |
|405 |    |    |    |    |410 |    |    |    |    |415 |    |    |    |    |    |      |
|ctg |gag |tca |ggc |tct |tcc |ggc |aag |tca |agc |tca |tcc |ctg |gta |cga |ggc | 1472 |
|Leu |Glu |Ser |Gly |Ser |Ser |Gly |Lys |Ser |Ser |Ser |Ser |Leu |Val |Arg |Gly |      |
|420 |    |    |    |    |425 |    |    |    |    |430 |    |    |    |    |435 |      |
|gtg |cgt |ctc |tcc |tcc |agc |ggc |ccc |gcc |ttg |ctc |gcc |ggc |ctc |gtg |agt | 1520 |
|Val |Arg |Leu |Ser |Ser |Ser |Gly |Pro |Ala |Leu |Leu |Ala |Gly |Leu |Val |Ser |      |
|    |    |    |    |440 |    |    |    |    |445 |    |    |    |    |450 |    |      |
|cta |gat |cta |cct |ctc |gac |cca |cta |tgg |gag |ttc |ccc |cgg |gac |agg |ctg | 1568 |
|Leu |Asp |Leu |Pro |Leu |Asp |Pro |Leu |Trp |Glu |Phe |Pro |Arg |Asp |Arg |Leu |      |
|    |    |    |    |455 |    |    |    |    |460 |    |    |    |    |465 |    |      |
|gtg |ctt |ggg |aag |ccc |cta |ggc |gag |ggc |tgc |ttt |ggc |cag |gta |gta |cgt | 1616 |
|Val |Leu |Gly |Lys |Pro |Leu |Gly |Glu |Gly |Cys |Phe |Gly |Gln |Val |Val |Arg |      |
|    |    |470 |    |    |    |    |475 |    |    |    |    |480 |    |    |    |      |
|gca |gag |gcc |ttt |ggc |atg |gac |cct |gcc |cgg |cct |gac |caa |gcc |agc |act | 1664 |
|Ala |Glu |Ala |Phe |Gly |Met |Asp |Pro |Ala |Arg |Pro |Asp |Gln |Ala |Ser |Thr |      |
|485 |    |    |    |    |490 |    |    |    |    |495 |    |    |    |    |    |      |
|gtg |gcc |gtc |aag |atg |ctc |aaa |gac |aac |gcc |tct |gac |aag |gac |ctg |gcc | 1712 |
|Val |Ala |Val |Lys |Met |Leu |Lys |Asp |Asn |Ala |Ser |Asp |Lys |Asp |Leu |Ala |      |
|500 |    |    |    |    |505 |    |    |    |    |510 |    |    |    |    |515 |      |
|gac |ctg |gtc |tcg |gag |atg |gag |gtg |atg |aag |ctg |atc |ggc |cga |cac |aag | 1760 |
|Asp |Leu |Val |Ser |Glu |Met |Glu |Val |Met |Lys |Leu |Ile |Gly |Arg |His |Lys |      |
|    |    |    |    |520 |    |    |    |    |525 |    |    |    |    |530 |    |      |
|aac |atc |atc |aac |ctg |ctt |ggt |gtc |tgc |acc |cag |gaa |ggg |ccc |ctg |tac | 1808 |
|Asn |Ile |Ile |Asn |Leu |Leu |Gly |Val |Cys |Thr |Gln |Glu |Gly |Pro |Leu |Tyr |      |
|    |    |535 |    |    |    |    |540 |    |    |    |    |545 |    |    |    |      |
|gtg |atc |gtg |gag |tgc |gcc |gcc |aag |gga |aac |ctg |cgg |gag |ttc |ctg |cgg | 1856 |

```
Val Ile Val Glu Cys Ala Ala Lys Gly Asn Leu Arg Glu Phe Leu Arg
            550                 555                 560 gcc cgg cgc ccc cca ggc ccc gac ctc agc ccc gac ggt cct cgg agc    1904
Ala Arg Arg Pro Pro Gly Pro Asp Leu Ser Pro Asp Gly Pro Arg Ser
565                 570                 575 agt gag ggg ccg ctc tcc ttc cca gtc ctg gtc tcc tgc gcc tac cag    1952
Ser Glu Gly Pro Leu Ser Phe Pro Val Leu Val Ser Cys Ala Tyr Gln
580                 585                 590                 595 gtg gcc cga ggc atg cag tat ctg gag tcc cgg aag tgt atc cac cgg    2000
Val Ala Arg Gly Met Gln Tyr Leu Glu Ser Arg Lys Cys Ile His Arg
            600                 605                 610 gac ctg gct gcc cgc aat gtg ctg gtg act gag gac aat gtg atg aag    2048
Asp Leu Ala Ala Arg Asn Val Leu Val Thr Glu Asp Asn Val Met Lys
            615                 620                 625 att gct gac ttt ggg ctg gcc cgc ggc gtc cac cac att gac tac tat    2096
Ile Ala Asp Phe Gly Leu Ala Arg Gly Val His His Ile Asp Tyr Tyr
            630                 635                 640 aag aaa acc agc aac ggc cgc ctg cct gtg aag tgg atg gcg ccc gag    2144
Lys Lys Thr Ser Asn Gly Arg Leu Pro Val Lys Trp Met Ala Pro Glu
645                 650                 655 gcc ttg ttt gac cgg gtg tac aca cac cag agt gac gtg tgg tct ttt    2192
Ala Leu Phe Asp Arg Val Tyr Thr His Gln Ser Asp Val Trp Ser Phe
660                 665                 670                 675 ggg atc ctg cta tgg gag atc ttc acc ctc ggg ggc tcc ccg tat cct    2240
Gly Ile Leu Leu Trp Glu Ile Phe Thr Leu Gly Gly Ser Pro Tyr Pro
            680                 685                 690 ggc atc ccg gtg gag gag ctg ttc tcg ctg ctg cgg gag gga cat cgg    2288
Gly Ile Pro Val Glu Glu Leu Phe Ser Leu Leu Arg Glu Gly His Arg
            695                 700                 705 atg gac cga ccc cca cac tgc ccc cca gag ctg tac ggg ctg atg cgt    2336
Met Asp Arg Pro Pro His Cys Pro Pro Glu Leu Tyr Gly Leu Met Arg
            710                 715                 720 gag tgc tgg cac gca gcg ccc tcc cag agg cct acc ttc aag cag ctg    2384
Glu Cys Trp His Ala Ala Pro Ser Gln Arg Pro Thr Phe Lys Gln Leu
725                 730                 735 gtg gag gcg ctg gac aag gtc ctg ctg gcc gtc tct gag gag tac ctc    2432
Val Glu Ala Leu Asp Lys Val Leu Leu Ala Val Ser Glu Glu Tyr Leu
740                 745                 750                 755 gac ctc cgc ctg acc ttc gga ccc tat tcc ccc tct ggt ggg gac gcc    2480
Asp Leu Arg Leu Thr Phe Gly Pro Tyr Ser Pro Ser Gly Gly Asp Ala
            760                 765                 770 agc agc acc tgc tcc tcc agc gat tct gtc ttc agc cac gac ccc ctg    2528
Ser Ser Thr Cys Ser Ser Ser Asp Ser Val Phe Ser His Asp Pro Leu
            775                 780                 785 cca ttg gga tcc agc tcc ttc ccc ttc ggg tct ggg gtg cag aca tga    2576
Pro Leu Gly Ser Ser Ser Phe Pro Phe Gly Ser Gly Val Gln Thr
            790                 795                 800 gcaaggctca aggctgtgca ggcacatagg ctggtggcct gggccttgg ggctcagcca    2636 cagcctgaca cagtgctcga ccttgatagc atggggcccc tggcccagag ttgctgtgcc    2696
gtgtccaagg gccgtgccct tgcccttgga gctgccgtgc ctgtgtcctg atggcccaaa    2756
tgtcagggtt ctgctcggct tcttggacct tggcgcttag tccccatccc gggtttggct    2816
gagcctggct ggagagctgc tatgctaaac ctcctgcctc ccaataccag caggaggttc    2876
tgggcctctg aaccccttt ccccacacct ccccctgctg ctgctgcccc agcgtcttga    2936
cgggagcatt ggcccctgag cccagagaag ctggaagcct gccgaaaaca ggagcaaatg    2996
gcgttttata aattatttt ttgaaataaa aaaaaaaaaa aaaa                       3040
```

```
<210> SEQ ID NO 2
<211> LENGTH: 12196
<212> TYPE: DNA
<213> ORGANISM: Homo sapiens

<400> SEQUENCE: 2
tgagggagca aaggaaggg gttctcctat ccgctgcacg gcactgcgca gaagacaggg      60
gagccaggca ttccctgaag ggtgaaaagc aaggagtaga gctgggtagt agactagaat    120
ttaggagcct ggcctggggc ctgggtgggg cgaaagaggc ggagcctgaa tggggtgtgt    180
ataggggggt tgcgtgtagg ggtgtgtgta taggctgggg cggggtcccg ggagtgggct    240
gactgggtcg ggggcggggc tctccaggtg ggcggggatc ttggccaccc ctggccacac    300
ctctctccgg ctcgagctgg tctaggcggg gcgggcccga ggggtgtgg caggaggtgg    360 gcgggcccgg gtggggggg gggggcgtg aaggagggg cgggcccgag caggaggggg      420
cgggcccgag gggcggggtg ggacaggagg tgggccgctc gcggccacgc cgccgtcgcg    480
ggtacattcc tcgctcccgg ccgaggagcg ctcgggctgt ctgcggaccc tgccgcgtgc    540
aggggtcgcg gccggctgga ctgggagtg aggcggcgga ggagccaggt gaggaggagc    600
caggtgagca ggaccctgtg ctgggcgcgg agtcacgcag gctcgaggtg agccggaacc    660
cttgtgggcc cgggctgcgc tcccagccgc caggggcga gaggcggcgg ggctacgggg    720
actgcccctc ccggcgcagg ggacctgggc gtccgccggg cggcagggg tggaggggc     780 ggtaaatcag taacccgcag tgcacacagg gccttttgtc ccgctccgtc caaagagcac    840 cccgccgcg gagctggtta ctcattgccc accgaggcgg gggcaggctg gcctgtgca     900 gctaccctcg ggacccattg attcgcacct ccccccaggc tggcccggca agggtgggg    960 aggacaagcg cgcttgtccc tgcggctgtc ttcgcgccgg cggcagagat gagggacctg   1020
aggccccgaa aagttcagtc acttagtgcc cgggggcctc cagcgcgagt gcgggaggct   1080
gaaggagaac ccaggactgt ctgatgccta aggcaggccc tccattccca cgtgggggt    1140 ggtcggtcag cggtcagcag ccatgggtga ctcgactaag gactctgata tcagggcagc   1200
ctggggtagg aataaaactcc ccgggcctcc ccacccactc ccagcccaag ctgtgtaccc   1260
aaagagctgc cctccctgcc aagccgagct tggtagggag ttttaccaag gaggatccga   1320
ctggattcga gagttgaggt gggccagaga cagcagtatc tgagtcaggt agagaagagc   1380 aatgagggc acagagggat gggcaagaga gcacatgtgc ccagttttga aagccaatgg    1440
cttcagcgct cctgaagggg cagacggtgt gaccaaagag ataggcagcg gcagagaggg   1500
agccctagga tgttgagctg gatcctgctg ggcacaggta gccattaagg gcttgcaagc   1560 tgggggcat gacatggcag acttgcaggt ttttttgttt gtttttttat tttatttttat  1620 ttttttattt tgtttttttt gagacggagt ctcactctgt cgcccaggct ggagtgcagt   1680
ggcgcgatct cggctcactg caagctccgc ctcccgggtt cgcgccattc tcctgcctca   1740
gcctcccgag tagctgggac tacaggcgcc cgccaccgcg cccggctaat ttttttgtatt  1800 tttagtagag acggggtttc accgtgttag ccaggatgtt ctcgatctcc tgacctcgtg   1860
atccgcccac ctcggcctcc caaagtgctg ggattacagg tgtgaaccat cgcgcccagc   1920
cgacttgtag ttttttaaaa ctctgctgga agatgaaggt tgaagagccg agggagagga   1980
tgtttccaga ggcccatgca agagatggca atgacctgcc ttgagaaggg gcaggggaag   2040
ccagatggac tggaagtgga gtggcagtga ccaaggagga ggaggtgtga taggcttccc   2100
acgcagggta gatccagaga caccagtgcc acccataggc ccctaggact gcagtggtca   2160
```

```
ccgattccctt tgtcccagct gagactcagt tctgagtgtt ctatttgggg gaacagaggc    2220
gtccttggta gcatttggaa gaggatagcc agctggggtg tgtgtacatc acagcctgac    2280
agtaacagca tccgaaccag aggtgactgg ctaagggcag acccagggca acaggttaac    2340
cgttctaggg ccgggcacag ggaggagaac attccaacac tctgcgtgcc gacgcacgtt    2400
ctctctttta tcctcaaaac agtcctatga ggatagtaag ccagagagag acagagacaa    2460
ggaattacaa gttggtgaga gtcaggattt gaacttggct ctggcagatg gaaaattagg    2520
gtctgtattc tttacaaaac cgtgtgtgcc tcagatggag ttggtgcata acaagcagag    2580
gtatccaggg tcgcggtcct gcttgccacg aagggggccg ccttgtcagt tgtgaccacc    2640
cagccctgga aatgtcagta atgctgtaag gagtggggat cggatcagat gccatccaga    2700
tgctgaagtt tgaccttgtg tcatttttca ctttcttttt tggctcttct gcaatcaatt    2760
catttattta gcaaaaaaga aattatgtgt gccgagagca tgcagaagat atgtctccgt    2820
tctctgcttc cctccaaaaa agaatcccaa aactgctttc tgtgaacgtg tgccagggtc    2880
ccagcaggac tcagggagag caggaagccc agcccagacc ccttgcacaa cctaccgtgg    2940
ggaggcctta ggctctggct actacagagc tggttccagt ctgcactgcc acagcctggc    3000
cagggacttg gacacatctg ctggccactt cctgtctcag tttccttatc tgcaaaataa    3060
gggaaaagcc cccacaaagg tgcacgtgta gcaggagctc ttttccctcc ctattttagg    3120
aaggcagttg gtgggaagtc cagcttgggt ccctgagagc tgtgagaagg agatgcggct    3180
gctgctggcc ctgttggggg tcctgctgag tgtgcctggg cctccagtct tgtccctgga    3240
ggcctctgag gaagtggagc ttggtatggc ttctgaggtg ggagagggtg gcagggggtgg    3300 gaagagtggg caccaggagg gggctgctgg gctgagcaaa gctggaaagg atccttgccc    3360
aggccctgag aaggtggcgg cagggcaggg ctcaaccact gagactcagt cagtgcctgg    3420
cttccagcaa gcattcatct atcactgtgt ctgcgagaga ggactggcct tgcagggcgc    3480
agggccctaa gctgggctgc agagctggtg gtgagctcct tacctgggtg tgtgtgcgtg    3540
tgtgtgtgtg ttctgtgcac tgggtgtgtg acctaggagg tccaggcagc atgtgtggta    3600
taagcattat gagggtgata tgccccggtg cagcatgacc ctgtatgtgg caccaacagc    3660
atgtgccttg tgtgtgtgtg tgtccgtatg tgtgtgtgtg tatgcgtgtg tgtgtgtgtg    3720
tgtgtcttgg ccactgtcgt gtgcactaaa tgctgtgtgt gtgacatgcc caagagtgt    3780 ggcatttgcc ctgggtgtgg catccgcagc atgtggctgt gtgggtgtca aggagtggtg    3840
gctccttcag catgcgttgc aaagtgcttg tgccctgcat gtgcggtgtg ttctttgtac    3900
acaggaggct gcctcagatg gggctgcggg gtctgctgac ctctgccctc tgcccacaga    3960
gccctgcctg gctcccagcc tggagcagca agagcaggag ctgacagtag cccttgggca    4020
gcctgtgcgt ctgtgctgtg ggcgggctga gcgtggtggc cactggtaca aggagggcag    4080
tcgcctggca cctgctggcc gtgtacgggg ctggaggggc cgcctagaga ttgccagctt    4140
cctacctgag gatgctggcc gctacctctg cctggcacga ggctccatga tcgtcctgca    4200
gaatctcacc ttgattacag gtggtaagag actctagcag gggagtgaagg gatgcctggg    4260 gagacagacc tgcccctctt ggaccttaga tgcttccctc tgtccctgat gtagactcct    4320
tgacctccag caacgatgat gaggacccca gtcccatag ggaccctcg aataggcaca    4380 gttaccccca gcaaggtcag taggtctcca aggacttgtg tccccgctgc tgctcatctg    4440
atcactgaga agaggaggcc tgtgtgggaa cacacggtca ttctaggggc cttcccctgc    4500
```

```
cctccagcac cctactggac acaccccag cgcatggaga agaaactgca tgcagtacct    4560
gcggggaaca ccgtcaagtt ccgctgtcca gctgcaggca accccacgcc caccatccgc    4620
tggcttaagg atggacaggc ctttcatggg gagaaccgca ttggaggcat tcgggtgagt    4680
ctctgggttc caagaccgtc tgctccccca ttttcattcc ttcatcagtc ccctcatacc    4740
tacaagcata cctataaatc aatcgaatga gtgaagcgat tgcggggccc cggaaggagc    4800
cctggactgt ggacctgggc agctctggtt ccccttctgc tactctctgg caagtgactt    4860
aacctctcag cctcagcaac tccatttgta aagggagaag aatcactgac tggttggtct    4920
gcataagcct tagcatctca tcgtcttgat gagaccctgc agggtcggct ccatgctgtc    4980
atgaggcaac tgagtctcag agaaggcaag ggttggctca agtagcaca gctagggaga      5040
gggagagcta aaattccaaa ggctcaaacc caaggctcaa gcgccctggg gagcctactc    5100
ctttgtgcca tagtccttgg cctgggcctg atgttctcag gcctagaga gcttgacaag      5160
agccctgtgg gcaggatgag gatctagcct cctggtcctc tggccccctt ggtggacatg    5220
gtccggtggt cccggacact ctctctgcct gcagctgcgc catcagcact ggagtctcgt    5280
gatggagagc gtggtgccct cggaccgcgg cacatacacc tgcctggtag agaacgctgt    5340
gggcagcatc cgctataact acctgctaga tgtgctgggt gagcgcgggg ctgggaacag    5400
gggaggcctg acccattttg gctcagttg tgccctcttg gtggggtcta gtctggcagg      5460
caggatggac tcagatgagt caggcagctt ggtgagcagg tgggtcaggg gaaagcacag    5520
gggttagtgt ggggctggag gagcagaggt ctgccaagag gaaaaacaag aaggacatcc    5580
aggcagaggg cgcagcccga gcggagggcc tgagtataac aaacgccctg cacttgcagg    5640
ccagcatatt cgtagggcgt ggcgtttata tggggagcca ggtggtggag ggttttgaat    5700
gctaggctga gatgttgtcc ttgacccgaa gcaatagga gccagggaag gtttaagcag      5760
ggtaagcagg agacagacaa gaagctgcag aaaggtccct cccttgaact tgaggaaggc    5820
tggagggagg caaacagggt gcttctatgg gtgccggtgg tcagggttga ctgtctcgcc    5880
cggtccccag agcggtcccc gcaccggccc atcctgcagg ccgggctccc ggccaacacc    5940
acagccgtgt gggcagcga cgtggagctg ctgtgcaagg tgtacagcga tgcccagccc     6000
cacatccagt ggctgaagca catcgtcatc aacggcagca gcttcggagc cgacggtttc    6060
ccctatgtgc aagtcctaaa ggtaaaaggt gcaccctgct gcagcctggg ccccattctt    6120
ctcccacctt gggttggggg gctccccagc ttccctgttg gccacagtgt ggccccaggc    6180
cctgctgtga ccccagagca tgtccccac cccagactgc agacatcaat agctcagagg      6240
tggaggtcct gtacctgcgg aacgtgtcag ccgaggacgc aggcgagtac acctgcctcg    6300
caggcaattc catcggcctc tcctaccagt ctgcctggct cacggtgctg ccaggtgagc    6360
acctgaaggg ccaggagatg ctgcgagatg cccctctggg ccagcagtgg gggctgtggc    6420
ctgttgggtg gtcagtctct gttggcctgt gggtctggc ctgggggca gtgtgtggat      6480
ttgtgggttt gagctgtatg acagcccctc tgtgcctctc cacacgtggc cgtccatgtg    6540
accgtctgct gaggtgtggg tgcctgggac tgggcataac tacagcttcc tccgtgtgtg    6600
tccccacata tgttgggagc tgggagggac tgagttaggg tgcacgggc ggccagtctc      6660
accactgacc agtttgtctg tctgtgtgtg tccatgtgcg agggcagagg aggacccac      6720
atggaccgca gcagcgcccg aggccaggta tacggacatc atcctgtacg cgtcgggctc    6780
cctggccttg gctgtgctcc tgctgctggc cgggctgtat cgaggcagg cgctccacgg      6840
ccggcacccc cgcccgcccg ccactgtgca gaagctctcc cgcttccctc tggcccgaca    6900
```

```
ggtactgggc gcatccccca cctcacatgt gacagcctga ctccagcagg cagaaccaag   6960
tctcccactt tgcagttctc cctggagtca ggctcttccg gcaagtcaag ctcatccctg   7020
gtacgaggcg tgcgtctctc ctccagcggc cccgccttgc tcgccggcct cgtgagtcta   7080
gatctacctc tcgacccact atgggagttc ccccggggaca ggtgcgctga gctgtgtggg   7140
ggcagggacg cgggcgccgg gttgcagccc gccctccgca ggagtgactc ggaggtctga   7200
ggctggactt tctccatctc caggctggtg cttgggaagc cctaggcga gggctgcttt   7260
ggccaggtag tacgtgcaga ggcctttggc atggaccctg cccggcctga ccaagccagc   7320
actgtggccg tcaagatgct caaaggtgag tgtggcccgg tgtggtggct cacacctgta   7380
acgccagcac tttaggaggc tgagggtggg aggatcgctt gaatccagga attcgaggcc   7440
agcctgggca acatggcaag acttcatctc tacaaaaaaa aaataagaaa attagttggg   7500
tgtggtggtg tgtgccttta gtctcagtta ctagggaggc tgaggcagga ggatcccttg   7560
aatccaggag ttgaggttg cagggagcca tgatcacgcc actgtattcc agcctgggca   7620
acacagtgag accctatctg aaaaaataaa taaataaata aaataaaag gtgaacgtgg   7680
cagcctggag gaggtgctat ggcattggga ctaatagaag gggctcacgg tgccaccagg   7740
tgagccctgg agctgggaga ggctgtggga tcccacccctt aaacctgcaa ttcacctctg   7800
ctcctgaccc tggcaagtga cttctgagcc tcagttttcc cttgtgtcat atggggtaga   7860
taacagtccc tactcccagc ccaaggattg tggaaagtgc ctggctcata gtcagggctc   7920
aataaatctt caccactggg gtgatgatga tgagaagaat ttggtgtgac aggcttgata   7980
tcctgtgtca gcattagtct gtgtcagctt tgacttcaca tctccttgtc agcctcacag   8040
gccctctacc tccttcctta tggttccccc cagacacacc ctcagcctcc cttggaccct   8100
ccctaggtct gccccccacg tccactgctg taggaggaca gcccttctgc ttgcacccag   8160
gcccagcccc ggggtgctct tgctgggcac tcctgcaccc cacccatcag ggcctctcct   8220
tgcagttccc cagcccctc tgcaagaatg gcctccactg ctcttctgct cctcccctcc   8280
tctctacaca gctggggcca cctggtgctc cctgggaggc agggattgag aaatgcacat   8340
tgtgtcattg gcccagggcc acaggtcagc cccaggggct cagccagaga agccaaagca   8400
gccttcttcc caagctcccc ggctgcaccc ggcctgccgc cagctccctg aattcccagg   8460
ccagttggaa gccaggccct ggtcaaacag accccagggc gccagcctgc tttccgcacc   8520
cagaagctct gaccccatgc ggggactacc gctgacccct ccagcggcag cttccttcct   8580
tccttcctgc tccgagctct tcccctctct cctgtgtcct gggcctgccc gctggaaggc   8640
ctgcctctta gatccttgat acagttgcat ccttgcaact gctgtgacag gcagggtgtg   8700
acccactgct ctgtttccca caagacgaac ctgaggttca gagacgctag gagactttt   8760
caaggccaca cagcctagca aggattcagc cctagaccta cgtagccctg gtccagtgct   8820
gcttgtcctg cacctgcctc tgcatgctcc ctcgtgcagt tggagggcag cctcttcacc   8880
ccgtctgctg cccttacaga caacgcctct gacaaggacc tggccgacct ggtctcggag   8940
atggaggtga tgaagctgat cggccgacac aagaacatca tcaacctgct tggtgtctgc   9000
acccaggaag gtggggccga ggcggggctg gctgcacggg ccgttagggt gcagagccaa   9060
agctttggca gcctctccac gctccctcca ctccctctgc agggcccctg tacgtgatcg   9120
tggagtgcgc cgccaaggga aacctgcggg agttcctgcg ggcccggcgc ccccaggcc   9180
ccgacctcag ccccgacggt cctcggagca gtgagggcc gctctccttc ccagtcctgg   9240
```

```
tctcctgcgc ctaccaggtg gcccgaggca tgcagtatct ggagtcccgg aaggtacagg   9300
cgctagggct ctgagcccct ctcagtctct ccagctccac tctcaggcct gtggcattca   9360
atgtcccgac ttctccctct ctgctctttt tcatgacccc acctcagtgt ccccaggcat   9420
tcacgctttc ctgcattccc cactcgttcc tcacccttcc ccagagggga gaggggacgc   9480
aggagaaggc actccccgtt tctaaacctt gacctcctcc tctgtaaagt gggtggaggg   9540
cccctgcccc cgggcctgct gggggtggt gtgtgctcaa ctccaggcca ggtgtcctga   9600
ggcacccaag cccccgctcc ctgcagtgta tccaccggga cctggctgcc cgcaatgtgc   9660
tggtgactga ggacaatgtg atgaagattg ctgactttgg gctggcccgc ggcgtccacc   9720
acattgacta ctataagaaa accagcaacg tgagggagat ggggcagaac tggatggggg   9780
tggaggggca ctgggcccgg ggtggcaggc acgaggacct gtgggactct gcactgaggc   9840
cctctctccc ctccagggcc gcctgcctgt gaagtggatg gcgcccgagg ccttgtttga   9900
ccgggtgtac acacaccaga gtgacgtgtg agtcctgccg gcggtcactg tcctacccca   9960
caaaaagggc aaggcactgc ccaaagtcac gtggccccag gagtcatgcg ctcgagggct  10020
ccttcagatt tggtctggga cccgagtggg cccagactcc aggaggagcc cattccccaa  10080
cagctgtggt gggtcatgtc tgtggggtcc cccgtcctag ccccggtcgt cgggagggcg  10140
ctgagccaca ctgagccctg gccctacctc caggtggtct tttgggatcc tgctatggga  10200
gatcttcacc ctcgggggct ccccgtatcc tggcatcccg gtggaggagc tgttctcgct  10260
gctgcgggag ggacatcgga tggaccgacc cccacactgc cccccagagc tgtgaggcct  10320
caccctgccc tcgaccccac tttccagtcc tcctcctcct ctgccctgac catggcctca  10380
gggtgtgtcc cggccagaag gacaacacta caacaactc ctcgtcctcc tcctcctctt  10440
cctcttcctc ctcctcctct tcctcctcct cctcttcctc ctcctcttcc tcctcctcct  10500
cttcctcctc ctcctcttcc tccttctcct cctgctcctc ttcctcctcc ttctcttcct  10560
cctcctcctc ttcctcctcc tcctcttcct cctcctcctc ttcctccttc tcctcctgct  10620
cctcttcctc ctccttctct tcctcctcct tctcttcctc ctcctcctcc tgctcctctt  10680
cctcctcctc ctcttcctcc tcctcagcct agtggagtgt cctggcctgg cttctactga  10740
tgaccctcct atccctcatc aaactcccca ccaaactcct ccccacccag agaacccccg  10800
gtcctccct tcctcctgaa ggcctgaggc tccctgtgac cctccgcccc acctctcgca  10860
ggtacgggct gatgcgtgag tgctggcacg cagcgccctc ccagaggcct accttcaagc  10920
agctggtgga ggcgctggac aaggtcctgc tggccgtctc tgaggaggta cagcccctcc  10980
cacccaccac ctccctctgc ctgctcccct ccaggcctca tctggcctga ccgcgtggac  11040
atgcgccccg tccatcccg ggcgctgcag aggctgacca gctccgttcc ccacagtacc  11100
tcgacctccg cctgaccttc ggaccctatt cccctctgg tggggacgcc agcagcacct  11160
gctcctccag cgattctgtc ttcagccacg acccctgcc attgggatcc agctccttcc  11220
ccttcgggtc tggggtgcag acatgagcaa ggctcaaggc tgtgcaggca cataggctgg  11280
tggccttggg ccttggggct cagccacagc ctgacacagt gctcgacctt gatagcatgg  11340
ggcccctggc ccagagttgc tgtgcgtgt ccaaggccg tgcccttgcc cttggagctg  11400
ccgtgcctgt gtcctgatgg cccaaatgtc agggttctgc tcggcttctt ggaccttggc  11460
gcttagtccc catcccgggt ttggctgagc ctggctggag agctgctatg ctaaacctcc  11520
tgcctcccaa taccagcagg aggttctggg cctctgaacc cccttttcccc acacctcccc  11580
ctgctgctgc tgccccagcg tcttgacggg agcattggcc cctgagccca gagaagctgg  11640
```

```
aagcctgccg aaaacaggag caaatggcgt tttataaatt attttttttga aataaagctc   11700 tgtgtgcctg ggtcttccct gagcaacatg gagtgggggtg aggtggaggg atccctccag   11760
cagagttctg cctacaggac acggactgag ggcactggac caggccatgg gctccgccac   11820
ctccactgcc ccaggagcca gtgtgtgcct atctgggtcc gcctgtccca ccagcccat    11880 cttgtgtctg cgacagtgtg aatgagtatt aatgggctga gtccgcattg cactatacac   11940
ggtgggactc ctgtaccctc tgcacatgtg tgtgtgtgca tgtgtgccct gcagctgtcc   12000
ccaagggagc tggcagcccc cctcccccat ctgctcagca ttaaccaagc tgaccgttaa   12060
cacagcatga aaatctgaga gccagcctta ggccgcggcc cgctcccacg ctctgccggc   12120
tcaggctggg ggcttgtgga ggccatgccc gccccgccct ggccagtctc ccgggcagca   12180
gctggttgcc gcccgc                                                    12196

<210> SEQ ID NO 3
<211> LENGTH: 5192
<212> TYPE: DNA
<213> ORGANISM: Homo sapiens

<400> SEQUENCE: 3
ccatgacctg ccttgagaag gggcagggga agccagatgg actggaagtg gagtggcagt     60
gaccaaggag gaggaggtgt gataggcttc ccacgcaggg tagatccaga gacaccagtg    120
ccacccatag gcccctagga ctgcagtggt cacccgattc ctttgtccca gctgagactc    180
agttctgagt gttctatttt ggggaacaga ggcgtccttg gtagcatttg gaagaggata    240
gccagctggg gtgtgtgtac atcacagcct gacagtaaca gcatccgaac cagaggtgac    300
tggctaaggg cagacccagg gcaacaggtt aaccgttcta gggccgggca cagggaggag    360
aacattccaa cactctgtgt gcccagtgcc gacgcacgtt ctctctttta tcctcaaaac    420
agtcctatga ggatataagc cagagagaga cagagacaag gaattacaag ttggtgagag    480
tcaggatttg aacttggctc tggcagatgg aaaattaggg tctgtattct ttacaaaacc    540
gtgtgtgcct cagatggagt tggtgcataa caagcagagg tatccagggt cgcggtcctg    600
cttgccacgg aaggggccgc cttgtcagtt gtgaccaccc agccctggaa atgtcagtaa    660
tgctgtaagg agtggggatc ggatcagatg ccatccagat gctgaagttt gaccttgtgt    720 cattttttcac tttctttttt ggctcttctg caatcaattc atttatttag caaaaagaa    780 attatgtgtg ccgagagcat gcagaagata tgtctccgtt ctctgcttcc ctccaaaaaa    840
gaatcccaaa actgctttct gtgaacgtgt gccagggtcc cagcaggact cagggagagc    900
aggaagccca gcccagaccc cttgcacaac ctaccgtggg gaggccttag gctctggcta    960
ctacagagct ggttccagtc tgcactgcca cagcctggcc agggacttgg acacatctgc   1020
tggccacttc ctgtctcagt ttccttatct gcaaaataag ggaaaagccc ccacaaaggt   1080
gcacgtgtag caggagctct tttccctccc tattttagga aggcagttgg tgggaagtcc   1140
agcttgggtc cctgagagct gtgagaagga gatgcggctg ctgctggccc tgttgggggt   1200
cctgctgagt gtgcctgggc ctccagtctt gtccctggag gcctctgagg aagtggagct   1260
tggtatggct tctgaggtgg gagagggtgg caggggtggg aagagtgggc accaggaggg   1320
ggctgctggg ctgagcaaag ctggaaagga tccttgccca ggccctgaga aggtggcggc   1380
agggcagggc tcaaccactg agactcagtc agtgcctggc ttccagcaag cattcatcta   1440
tcactgtgtc tgcgagagag gactggcctt gcagggcgca gggccctaag ctgggctgca   1500
```

```
gagctggtgg tgagctcctt gcctgggtgt gtgtgcgtgt gtgtgtgtgt tctgtgcact    1560
gggtgtgtga cctaggaggt ccaggcagca tgtgtggtat aagcattatg agggtgatat    1620
gccccggtgc agcatgaccc tgtatgtggc accaacagca tgtgccttgt gtgtgtgtgt    1680
gtccgtatgt gtgtgtgtgt atgcgtgtgt gtgtgtgtgt gtgtgtgtct tggccactgt    1740
catgtgcact aaatgctgtg tgtgtgacat gccccaagag tgtggcattt gccctgggtg    1800
tggcatccgc agcatgtggc tgtgtgggtg tcaaggagtg gtggctcctt cagcatgcgt    1860
tgcgaagtgc ttgtgccctg catgtgcggt gtgttctctg tacacaggag gctgcctcag    1920
atggggctgc ggggtctgct gacctctgcc ctctgcccac agagccctgc ctggctccca    1980
gcctggagca gcaagagcag gagctgacag tagcccttgg gcagcctgtg cggctgtgct    2040
gtgggcgggc tgagcgtggt ggccactggt acaaggaggg cagtcgcctg cacctgctg     2100 gccgtgtacg gggctggagg ggccgcctag agattgccag cttcctacct gaggatgctg    2160
gccgctacct ctgcctggca cgaggctcca tgatcgtcct gcagaatctc accttgatta    2220
caggtgactc cttgacctcc agcaacgatg atgaggaccc aagtcccat agggacctct     2280 cgaataggca cagttacccc cagcaaggtc agtaggtctc caaggacttg tgtcccccgct   2340 gctgctcatc tgatcactga aagaggagg cctgtgtggg aacacacggt cattctaggg     2400
gccttcccct gccctccagc accctactgg acacacccc agcgcatgga aagaaactg      2460 catgcagtac ctgcgcggaa caccgtcaag ttccgctgtc cagctgcagg caaccccacg    2520
cccaccatcc gctggcttaa ggatggacag gcctttcatg gggagaaccg cattggaggc    2580
attcggctgc gccatcagca ctggagtctc gtgatggaga gcgtggtgcc ctcggaccgc    2640
ggcacataca cctgcctggt agagaacgct gtgggcagca tccgttataa ctacctgcta    2700
gatgtgctgg agcggtcccc gcaccggccc atcctgcagg ccgggctccc ggccaacacc    2760
acagccgtgg tgggcagcga cgtggagctg ctgtgcaagg tgtacagcga tgcccagccc    2820
cacatccagt ggctgaagca catcgtcatc aacggcagca gcttcggagc cgacggtttc    2880
ccctatgtgc aagtcctaaa gactgcagac atcaatagct cagaggtgga ggtcctgtac    2940
ctgcggaacg tgtcagccga ggacgcaggc gagtacacct gcctcgcagg caattccatc    3000
ggcctctcct accagtctgc ctggctcacg gtgctgccag gtgagcacct gaagggccag    3060
gagatgctgc gagatgcccc tctgggccag cagtgggggc tgtggcctgt tgggtggtca    3120
gtctctgttg gcctgtgggg tctggcctgg ggggcagtgt gtggatttgt gggtttgagc    3180
tgtatgacag cccctctgtg cctctccaca cgtggccgtc catgtgaccg tctgctgagg    3240
tgtgggtgcc tgggactggg cataactaca gcttcctccg tgtgtgtccc cacatatgtt    3300
gggagctggg agggactgag ttagggtgca cggggcggcc agtctcacca ctgaccagtt    3360
tgtctgtctg tgtgtgtcca tgtgcgaggg cagaggagga ccccacatgg accgcagcag    3420
cgcccgaggc caggtatacg gacatcatcc tgtacgcgtc gggctccctg gccttggctg    3480
tgctcctgct gctggccagg ctgtatcgag ggcaggcgct ccacggccgg cacccccgcc    3540
cgcccgccac tgtgcagaag ctctcccgct tccctctggc ccgacagttc ccctggagt     3600 caggctcttc cggcaagtca agctcatccc tggtacgagg cgtgcgtctc tcctccagcg    3660
gccccgcctt gctcgccggc ctcgtgagtc tagatctacc tctcgaccca ctatgggagt    3720
tcccccggga caggctggtg cttgggaagc cctaggcga gggctgcttt ggccaggtag     3780
tacgtgcaga ggcctttggc atggaccctg cccggcctga ccaagccagc actgtggccg    3840
tcaagatgct caaagacaac gcctctgaca aggacctggc cgacctggtc tcggagatgg    3900
```

-continued

```
aggtgatgaa gctgatcggc cgacacaaga acatcatcaa cctgcttggt gtctgcaccc    3960
aggaagggcc cctgtacgtg atcgtggagt gcgccgccaa gggaaacctg cgggagttcc    4020
tgcgggcccg cgcccccca ggccccgacc tcagccccga cggtcctcgg agcagtgagg     4080
ggccgctctc cttcccagtc ctggtctcct gcgcctacca ggtggcccga ggcatgcagt    4140
atctggagtc ccggaagtgt atccaccggg acctggctgc ccgcaatgtg ctggtgactg    4200
aggacaatgt gatgaagatt gctgactttg gctggcccg cggcgtccac cacattgact     4260
actataagaa aaccagcaac ggccgcctgc ctgtgaagtg gatggcgccc gaggccttgt    4320
ttgaccgggt gtacacacac cagagtgacg tgtggtcttt tgggatcctg ctatgggaga    4380
tcttcacccct cggggctcc ccgtatcctg gcatcccggt ggaggagctg ttctcgctgc    4440
tgcgggaggg acatcggatg gaccgacccc cacactgccc cccagagctg tacgggctga    4500
tgcgtgagtg ctggcacgca gcgccctccc agaggcctac cttcaagcag ctggtggagg    4560
cgctggacaa ggtcctgctg gccgtctctg aggagtacct cgacctccgc ctgaccttcg    4620
gaccctattc cccctctggt ggggacgcca gcagcacctg ctcctccagc gattctgtct    4680
tcagccacga ccccctgcca ttgggatcca gctccttccc cttcgggtct ggggtgcaga    4740
catgagcaag gctcaaggct gtgcaggcac ataggctggt ggccttgggc cttgggctc     4800
agccacagcc tgacacagtg ctcgaccttg atagcatggg gccctggcc cagagttgct     4860
gtgccgtgtc caagggccgt gcccttgccc ttggagctgc cgtgcctgtg tcctgatggc    4920
ccaaatgtca gggttctgct cggcttcttg gaccttggcg cttagtcccc atcccgggtt    4980
tggctgagcc tggctggaga gctgctatgc taaacctcct gcctcccaat accagcagga    5040
ggttctgggc ctctgaaccc cctttcccca cacctccccc tgctgctgct gccccagcgt    5100
cttgacggga gcattggccc ctgagcccag agaagctgga agcctgccga aaacaggagc    5160
aaatggcgtt ttataaatta tttttttgaa at                                  5192
```

```
<210> SEQ ID NO 4
<211> LENGTH: 2807
<212> TYPE: DNA
<213> ORGANISM: Homo sapiens
<220> FEATURE:
<221> NAME/KEY: CDS
<222> LOCATION: (54)...(2342)

<400> SEQUENCE: 4
```

| | | |
|---|---|---|
| gaaggcagtt ggtgggaagt ccagcttggg tccctgagag ctgtgagaag gag atg<br>                                                                                                                Met<br>                                                                                                                1 | | 56 |

```
cgg ctg ctg ctg gcc ctg ttg ggg gtc ctg ctg agt gtg cct ggg cct     104
Arg Leu Leu Leu Ala Leu Leu Gly Val Leu Leu Ser Val Pro Gly Pro
          5                  10                  15 cca gtc ttg tcc ctg gag gcc tct gag gaa gtg gag ctt gag ccc tgc     152
Pro Val Leu Ser Leu Glu Ala Ser Glu Glu Val Glu Leu Glu Pro Cys
     20                  25                  30 ctg gct ccc agc ctg gag cag caa gag cag gag ctg aca gta gcc ctt    200
Leu Ala Pro Ser Leu Glu Gln Gln Glu Gln Glu Leu Thr Val Ala Leu
 35                  40                  45 ggg cag cct gtg cgt ctg tgc tgt ggg cgg gct gag cgt ggt ggc cac    248
Gly Gln Pro Val Arg Leu Cys Cys Gly Arg Ala Glu Arg Gly Gly His
 50                  55                  60                  65 tgg tac aag gag ggc agt cgc ctg gca cct gct ggc cgt gta cgg ggc    296
Trp Tyr Lys Glu Gly Ser Arg Leu Ala Pro Ala Gly Arg Val Arg Gly
                 70                  75                  80
```

```
tgg agg ggc cgc cta gag att gcc agc ttc cta cct gag gat gct ggc    344
Trp Arg Gly Arg Leu Glu Ile Ala Ser Phe Leu Pro Glu Asp Ala Gly
             85                  90                  95 cgc tac ctc tgc ctg gca cga ggc tcc atg atc gtc ctg cag aat ctc    392
Arg Tyr Leu Cys Leu Ala Arg Gly Ser Met Ile Val Leu Gln Asn Leu
            100                 105                 110 acc ttg att aca ggt gac tcc ttg acc tcc agc aac gat gat gag gac    440
Thr Leu Ile Thr Gly Asp Ser Leu Thr Ser Ser Asn Asp Asp Glu Asp
        115                 120                 125 ccc aag tcc cat agg gac ccc tcg aat agg cac agt tac ccc cag caa    488
Pro Lys Ser His Arg Asp Pro Ser Asn Arg His Ser Tyr Pro Gln Gln
130             135                 140                 145 gca ccc tac tgg aca cac ccc cag cgc atg gag aag aaa ctg cat gca    536
Ala Pro Tyr Trp Thr His Pro Gln Arg Met Glu Lys Lys Leu His Ala
                    150                 155                 160 gta cct gcg ggg aac acc gtc aag ttc cgc tgt cca gct gca ggc aac    584
Val Pro Ala Gly Asn Thr Val Lys Phe Arg Cys Pro Ala Ala Gly Asn
                165                 170                 175 ccc acg ccc acc atc cgc tgg ctt aag gat gga cag gcc ttt cat ggg    632
Pro Thr Pro Thr Ile Arg Trp Leu Lys Asp Gly Gln Ala Phe His Gly
            180                 185                 190 gag aac cgc att gga ggc att cgg ctg cgc cat cag cac tgg agt ctc    680
Glu Asn Arg Ile Gly Gly Ile Arg Leu Arg His Gln His Trp Ser Leu
        195                 200                 205 gtg atg gag agc gtg gtg ccc tcg gac cgc ggc aca tac acc tgc ctg    728
Val Met Glu Ser Val Val Pro Ser Asp Arg Gly Thr Tyr Thr Cys Leu
210                 215                 220                 225 gta gag aac gct gtg ggc agc atc cgc tat aac tac ctg cta gat gtg    776
Val Glu Asn Ala Val Gly Ser Ile Arg Tyr Asn Tyr Leu Leu Asp Val
                230                 235                 240 ctg gag cgg tcc ccg cac cgg ccc atc ctg cag gcc ggg ctc ccg gcc    824
Leu Glu Arg Ser Pro His Arg Pro Ile Leu Gln Ala Gly Leu Pro Ala
            245                 250                 255 aac acc aca gcc gtg gtg ggc agc gac gtg gag ctg ctg tgc aag gtg    872
Asn Thr Thr Ala Val Val Gly Ser Asp Val Glu Leu Leu Cys Lys Val
        260                 265                 270 tac agc gat gcc cag ccc cac atc cag tgg ctg aag cac atc gtc atc    920
Tyr Ser Asp Ala Gln Pro His Ile Gln Trp Leu Lys His Ile Val Ile
275                 280                 285 aac ggc agc agc ttc gga gcc gac ggt ttc ccc tat gtg caa gtc cta    968
Asn Gly Ser Ser Phe Gly Ala Asp Gly Phe Pro Tyr Val Gln Val Leu
290                 295                 300                 305 aag act gca gac atc aat agc tca gag gtg gag gtc ctg tac ctg cgg   1016
Lys Thr Ala Asp Ile Asn Ser Ser Glu Val Glu Val Leu Tyr Leu Arg
                310                 315                 320 aac gtg tca gcc gag gac gca ggc gag tac acc tgc ctc gca ggc aat   1064
Asn Val Ser Ala Glu Asp Ala Gly Glu Tyr Thr Cys Leu Ala Gly Asn
            325                 330                 335 tcc atc ggc ctc tcc tac cag tct gcc tgg ctc acg gtg ctg cca ggt   1112
Ser Ile Gly Leu Ser Tyr Gln Ser Ala Trp Leu Thr Val Leu Pro Gly
        340                 345                 350 act ggg cgc atc ccc cac ctc aca tgt gac agc ctg act cca gca ggc   1160
Thr Gly Arg Ile Pro His Leu Thr Cys Asp Ser Leu Thr Pro Ala Gly
355                 360                 365 aga acc aag tct ccc act ttg cag ttc tcc ctg gag tca ggc tct tcc   1208
Arg Thr Lys Ser Pro Thr Leu Gln Phe Ser Leu Glu Ser Gly Ser Ser
370                 375                 380                 385 ggc aag tca agc tca tcc ctg gta cga ggc gtg cgt ctc tcc tcc agc   1256
Gly Lys Ser Ser Ser Ser Leu Val Arg Gly Val Arg Leu Ser Ser Ser
```

-continued

```
                     390                 395                 400
ggc ccc gcc ttg ctc gcc ggc ctc gtg agt cta gat cta cct ctc gac    1304
Gly Pro Ala Leu Leu Ala Gly Leu Val Ser Leu Asp Leu Pro Leu Asp
        405                 410                 415 cca cta tgg gag ttc ccc cgg gac agg ctg gtg ctt ggg aag ccc cta    1352
Pro Leu Trp Glu Phe Pro Arg Asp Arg Leu Val Leu Gly Lys Pro Leu
    420                 425                 430 ggc gag ggc tgc ttt ggc cag gta gta cgt gca gag gcc ttt ggc atg    1400
Gly Glu Gly Cys Phe Gly Gln Val Val Arg Ala Glu Ala Phe Gly Met
435                 440                 445 gac cct gcc cgg cct gac caa gcc agc act gtg gcc gtc aag atg ctc    1448
Asp Pro Ala Arg Pro Asp Gln Ala Ser Thr Val Ala Val Lys Met Leu
450                 455                 460                 465 aaa gac aac gcc tct gac aag gac ctg gcc gac ctg gtc tcg gag atg    1496
Lys Asp Asn Ala Ser Asp Lys Asp Leu Ala Asp Leu Val Ser Glu Met
                470                 475                 480 gag gtg atg aag ctg atc ggc cga cac aag aac atc atc aac ctg ctt    1544
Glu Val Met Lys Leu Ile Gly Arg His Lys Asn Ile Ile Asn Leu Leu
            485                 490                 495 ggt gtc tgc acc cag gaa ggg ccc ctg tac gtg atc gtg gag tgc gcc    1592
Gly Val Cys Thr Gln Glu Gly Pro Leu Tyr Val Ile Val Glu Cys Ala
        500                 505                 510 gcc aag gga aac ctg cgg gag ttc ctg cgg gcc cgg cgc ccc cca ggc    1640
Ala Lys Gly Asn Leu Arg Glu Phe Leu Arg Ala Arg Arg Pro Pro Gly
    515                 520                 525 ccc gac ctc agc ccc gac ggt cct cgg agc agt gag ggg ccg ctc tcc    1688
Pro Asp Leu Ser Pro Asp Gly Pro Arg Ser Ser Glu Gly Pro Leu Ser
530                 535                 540                 545 ttc cca gtc ctg gtc tcc tgc gcc tac cag gtg gcc cga ggc atg cag    1736
Phe Pro Val Leu Val Ser Cys Ala Tyr Gln Val Ala Arg Gly Met Gln
                550                 555                 560 tat ctg gag tcc cgg aag tgt atc cac cgg gac ctg gct gcc cgc aat    1784
Tyr Leu Glu Ser Arg Lys Cys Ile His Arg Asp Leu Ala Ala Arg Asn
            565                 570                 575 gtg ctg gtg act gag gac aat gtg atg aag att gct gac ttt ggg ctg    1832
Val Leu Val Thr Glu Asp Asn Val Met Lys Ile Ala Asp Phe Gly Leu
        580                 585                 590 gcc cgc ggc gtc cac cac att gac tac tat aag aaa acc agc aac ggc    1880
Ala Arg Gly Val His His Ile Asp Tyr Tyr Lys Lys Thr Ser Asn Gly
    595                 600                 605 cgc ctg cct gtg aag tgg atg gcg ccc gag gcc ttg ttt gac cgg gtg    1928
Arg Leu Pro Val Lys Trp Met Ala Pro Glu Ala Leu Phe Asp Arg Val
610                 615                 620                 625 tac aca cac cag agt gac gtg tgg tct ttt ggg atc ctg cta tgg gag    1976
Tyr Thr His Gln Ser Asp Val Trp Ser Phe Gly Ile Leu Leu Trp Glu
                630                 635                 640 atc ttc acc ctc ggg ggc tcc ccg tat cct ggc atc ccg gtg gag gag    2024
Ile Phe Thr Leu Gly Gly Ser Pro Tyr Pro Gly Ile Pro Val Glu Glu
            645                 650                 655 ctg ttc tcg ctg ctg cgg gag gga cat cgg atg gac cga ccc cac        2072
Leu Phe Ser Leu Leu Arg Glu Gly His Arg Met Asp Arg Pro His
        660                 665                 670 tgc ccc cca gag ctg tac ggg ctg atg cgt gag tgc tgg cac gca gcg    2120
Cys Pro Pro Glu Leu Tyr Gly Leu Met Arg Glu Cys Trp His Ala Ala
    675                 680                 685 ccc tcc cag agg cct acc ttc aag cag ctg gtg gag gcg ctg gac aag    2168
Pro Ser Gln Arg Pro Thr Phe Lys Gln Leu Val Glu Ala Leu Asp Lys
690                 695                 700                 705 gtc ctg ctg gcc gtc tct gag gag tac ctc gac ctc cgc ctg acc ttc    2216
Val Leu Leu Ala Val Ser Glu Glu Tyr Leu Asp Leu Arg Leu Thr Phe
```

|  |  |  |  |  |  |  |  |  |  |  |  |
|---|---|---|---|---|---|---|---|---|---|---|---|
| Val | Leu | Leu | Ala | Val | Ser | Glu | Glu | Tyr | Leu | Asp | Leu | Arg | Leu | Thr | Phe |
|  |  |  |  | 710 |  |  |  | 715 |  |  |  | 720 |

| gga | ccc | tat | tcc | ccc | tct | ggt | ggg | gac | gcc | agc | agc | acc | tgc | tcc | tcc | 2264 |
|---|---|---|---|---|---|---|---|---|---|---|---|---|---|---|---|---|
| Gly | Pro | Tyr | Ser | Pro | Ser | Gly | Gly | Asp | Ala | Ser | Ser | Thr | Cys | Ser | Ser |  |
|  |  | 725 |  |  |  |  | 730 |  |  |  |  | 735 |

| agc | gat | tct | gtc | ttc | agc | cac | gac | ccc | ctg | cca | ttg | gga | tcc | agc | tcc | 2312 |
|---|---|---|---|---|---|---|---|---|---|---|---|---|---|---|---|---|
| Ser | Asp | Ser | Val | Phe | Ser | His | Asp | Pro | Leu | Pro | Leu | Gly | Ser | Ser | Ser |  |
|  | 740 |  |  |  |  | 745 |  |  |  |  | 750 |

| ttc | ccc | ttc | ggg | tct | ggg | gtg | cag | aca | tga | gcaaggctca | aggctgtgca | 2362 |
|---|---|---|---|---|---|---|---|---|---|---|---|---|
| Phe | Pro | Phe | Gly | Ser | Gly | Val | Gln | Thr |
|  | 755 |  |  |  | 760 |

```
ggcacatagg ctggtggcct tgggccttgg ggctcagcca cagcctgaca cagtgctcga    2422
ccttgatagc atgggccccc tgcccagag ttgctgtgcc gtgtccaagg gccgtgccct     2482
tgcccttgga gctgccgtgc ctgtgtcctg atggcccaaa tgtcagggtt ctgctcggct    2542
tcttggacct tggcgcttag tccccatccc gggtttggct gagcctggct ggagagctgc    2602
tatgctaaac ctcctgcctc ccaataccag caggaggttc tgggcctctg aaccccettt    2662 ccccacacct cccctgctg ctgctgcccc agcgtcttga cgggagcatt ggccctgag     2722 cccagagaag ctggaagcct gccgaaaaca ggagcaaatg gcgttttata aattatttt     2782 ttgaaataaa aaaaaaaaa aaaaa                                          2807
```

<210> SEQ ID NO 5
<211> LENGTH: 15001
<212> TYPE: DNA
<213> ORGANISM: Macaca mulatta
<220> FEATURE:
<221> NAME/KEY: misc_feature
<222> LOCATION: (1)...(15001)
<223> OTHER INFORMATION: n = A,T,C or G

<400> SEQUENCE: 5

```
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnnnn nnnnnnnnnn nnnnnnnnnn nnnnnnnnnn     780
nnnnnnnnnn nnnnnnnnnn nnnnnnnnnn nnnnnnnnnn nnnnnnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
nnnnnnnnnn nnnnnnnnnn nnnnnnnnnn nnnnnnnnnn nnnnnnnnnn nnnnnnnnnn    1020
nnnnnnnnnn nnnnnnnnnn nnnnnnnnnn nnnnnnnnnn nnnnnnnnnn nnnnnnnnnn    1080
```

```
nnnnnnnnnn nnnnnnnnnn nnnnnnnnnn nnnnnnnnnn nnnnnnnnnn nnnnnnnnnn    1140
nnnnnnnnnn nnnnnnnnnn nnnnnnnnnn nnnnnnnnnn nnnnnnnnnn nnnnnnnnnn    1200
nnnnnnnnnn nnnnnnnnnn nnnnnnnnnn nnnnnnnnnn nnnnnnnnnn nnnnnnnnnn    1260
nnnnnnnnnn nnnnnnnnnn nnnnnnnnnn nnnnnnnnnn nnnnnnnnnn nnnnnnnnnn    1320
nnnnnnnnnn nnnnnnnnnn nnnnnnnnnn nnnnnnnnnn nnnnnnnnnn nnnnnnnnnn    1380
nnnnnnnnnn nnnnnnnnnn nnnnnnnnnn nnnnnnnnnn nnnnnnnnnn nnnnnnnnnn    1440
nnnnnnnnnn nnnnnnnnnn nnnnnnnnnn nnnnnnnnnn nnnnnnnnnn nnnnnnnnnn    1500
nnnnnnnnnn nnnnnnnnnn nnnnnnnnnn nnnnnnnnnn nnnnnnnnnn nnnnnnnnnn    1560
nnnnnnnnnn nnnnnnnnnn nnnnnnnnnn nnnnnnnnnn nnnnnnnnnn nnnnnnnnnn    1620
nnnnnnnnnn nnnnnnnnnn nnnnnnnnnn nnnnnnnnnn nnnnnnnnnn nnnnnnnnnn    1680
nnnnnnnnnn nnnnnnnnnn nnnnnnnnnn nnnnnnnnnn nnnnnnnnnn nnnnnnnnnn    1740
nnnnnnnnnn nnnnnnnnnn nnnnnnnnnn nnnnnnnnnn nnnnnnnnnn nnnnnnnnnn    1800
nnnnnnnnnn nnnnnnnnnn nnnnnnnnnn nnnnnnnnnn nnnnnnnnnn nnnnnnnnnn    1860
nnnnnnnnnn nnnnnnnnnn nnnnnnnnnn nnnnnnnnnn nnnnnnnnnn nnnnnnnnnn    1920
nnnnnnnnnn nnnnnnnnnn nnnnnnnnnn nnnnnnnnnn nnnnnnnnnn nnnnnnnnnn    1980
nnnnnnnnnn nnnnnnnnnn nnnnnnnnnn nnnnnnnnnn nnnnnnnnnn nnnnnnnnnn    2040
nnnnnnnnnn nnnnnnnnnn nnnnnnnnnn nnnnnnnnnn nnnnnnnnnn nnnnnnnnnn    2100
nnnnnnnnnn nnnnnnnnnn nnnnnnnnnn nnnnnnnnnn nnnnnnnnnn nnnnnnnnnn    2160
nnnnnnnnnn nnnnnnnnnn nnnnnnnnnn nnnnnnnnnn nnnnnnnnnn nnnnnnnnnn    2220
nnnnnnnnnn nnnnnnnnnn nnnnnnnnnn nnnnnnnnnn nnnnnnnnnn nnnnnnnnnn    2280
nnnnnnnnnn nnnnnnnnnn nnnnnnnnnn nnnnnnnnnn nnnnnnnnnn nnnnnnnnnn    2340
nnnnnnnnnn nnnnnnnnnn nnnnnnnnnn nnnnnnnnnn nnnnnnnnnn nnnnnnnnnn    2400
nggcgggggc aggctggccc tgtgcagcta ccctcgggac ccattgattc gcacctcccc    2460
ccaggctggc ccggcaaggg tgggggagga caagcttgtc cctgcggctg tcttcgcgcc    2520
ggcggcagag atgagggagc tgaggccccg aaagtttcag tcacttagcg cccgggggcc    2580
tccaccgcga gtgcggagg ctgtctgatg cctaaggcag gccctctgtt cccacgtgtg     2640
gggtggtcgg tcagcggtca gcagccacgg gtgacttttc cacggactct gatatcaggg    2700
cagcctgggg taggaataaa atccccgggc ctccccagcc actcccagcc caagctgtgt    2760
actcaaagag ctgccctccc tgccaagccg agcttggtag ggggttttac caaggggggat   2820
ccaactggat ttgagagttg aagtggcctc agagacagca gtatctgagt caagtagaga    2880
agaggaatgg ggggcacaga gggatgggca agagagcata tgtgaccagt tttgagagcc    2940
aatggcttca gcgttcctga agggacagac ggtgtgacca aagagatagg cagcggaaca    3000
gagggagccc taggatgctg agctgaatcc tgctgggcac aggtaaccat taagggcttg    3060
caagctgggg gcatgacatg gcagacttgt agtcttttaa aactctgctg gaagatgaag    3120
gttgaagagc ccagggagag gatgtttcca aaggcccatg caagagatgg ccatgacctg    3180
ccctgagtca gggcagggga agccagatgg actggaagtg gagtggcagt gaccaagggt    3240
aaggaggtgt gataggcttc ccacacaggg tagatccaga gacaccagtg ccacccatag    3300
gccctagga ctgcagtgat cacagtattc ctttgtccca gctgagactc ggttctgagt     3360
gttctgtttt ggggaacaga ggtgtccttg gtagcatttg aagaggata gccagctggg     3420
gtgtgtgtac atcacagcct gacagtaaca gcacccgaac cagaggtgac tggctgaggg    3480
```

```
cagacccagg gcaacaggtg aacagttcta gggccgggca cagggagaag aacattccaa    3540
cactctgtgt gcccagtgcc gatgcacgtt gtctctttta tcctcaaaac agtcctatga    3600
ggatagtaac ccagagagag acagagacaa ggaattacaa gttgatgaga gtcgggattt    3660
gaacttggct ctggtggatg gataattacg gtctgtattc tttacaaaac cgtgtgtacc    3720
tcggatggag ttggtgcatg acaagcagag gtattcaggg atgcggtcct gcttgccacg    3780
gaaggagctg ccttgtcagt ggtgggcgcc cagctctgga atgtcagta atgctataag     3840 gagtggggat tggatcagat aacatccaga tgctgaagtt tggccttgta tcattttca     3900 ctttgttttt tggctcttcg gcaatcaatt catttattca gcaaaaaata aattacgtgt    3960
gccaagagca tgcagaagat agtctccgtt ctctgcttcc ctccaagaaa agaatcccaa    4020
aactgctttc tgtgaacgtg tgccagggtc ccagcaggac tcaaggagag caggaagccc    4080
agcccagacc ccttgcacaa cctactgtag gaaggcgtca ggctctggct acagcagagc    4140
tggttccagt ctgcactgcc acagcctggc caggacttg  gacacatcta ctggccactt    4200
cctgtctccg tttcctcatc tgcaaaataa gggaaagccc ccgcaaaggt gcatgtggag    4260
caggagctct ttttccccccc tattctagga aggcagttgg tgggaagtcc agcctgggcc    4320
cctgagagct gcgggaagga gatgcggctg ctgtcggccc tcttgggggt cctgctgagt    4380
gtgcctgggc ctccagtctt gtccctggag gcctcggagg aagtggagct gggtatggct    4440 tctgagggg gagagggtgg caggggtggg aagagtgggc accaggaggg ggctgctggg     4500
ctgagcaaag ctggaaagga tccttgccca ggccctgaga agtggcagc agggcagggc     4560 tcaaccactg agactcagtc agtgcctggc ttccagcaag catccatgta tctctgtgtc    4620
tgcgagagag gactggcctc gcagggtgca gggccctaag ctgggccgca gagctggtgg    4680
tgagctcctt gcctgggtgt gtgcgcgcgc gtgtgtgtgt gtgtgttctg tgcactggat    4740
gtgtgaccta ggaggtccag gcagcatgtg tggtgtatgc attatgaggg tgatatgccc    4800
cagtgcagca tgaccctgta tatggcaccg atagcatgtg ccgtgtgtgt gtgtgtccat    4860
gtgtgtgtgt gtgtgtgtct tggccagtgt catgtgcact aaatgctgtg tgcgtgacat    4920
gccccaagag tgtggcattt gccctgggtg tggcatccgc agcatgtggc tgtgcgggtg    4980
tcaaggagcg gtggctcctc cagcatgcgt cgcgaggtgc ttgtgccctg catgtgtggc    5040
gtgttctctg tacgcaggag gctgcctcag atggggctgc ggggtctgct gacctctgcc    5100
ctctgcccac agagccctgc ctggctccca gcatggagca gcaagagcag gagctgacag    5160
tagcccttgg gcagcctgtg cggctgtgct gtgggcgggc tgagcgtggt ggccactggt    5220
acaaggaggg cagtcgcctg gcacctgctg gccgtgtacg gggctggagg ggccgcctag    5280
agattgccag cttcctacct gaggatgctg gccgctatct ctgcctggcc cgagcctcca    5340
tgatcgtcct gcaaaatctc accttgacta tagatggtaa gacactctag cagttaaggg    5400
atgcctgggg agagagacct gccctcccg gacctcagat gcctccctct gtccttgatg     5460
tagactcctt gacctccagc aacgatgatg aggaccccca gtcccatagg gactcctcga    5520
atgggcacat ttaccccccag caaggtgagt ataagtcttc aaggacttgt gtccccgctg    5580
ctcatttaat cactgagaag aagaggtctg tgtgggaaca cacggtcatt ctaagggcct    5640
tcctctcccc tccagcaccc tactggacac accccccagcg catggagaag aaactgcatg    5700
cagtaccggc tggaacacc gtcaagttcc gctgtccggc tgcaggcaac cccacgccca    5760
ccatccgctg gcttaaggat ggacaggcct ttcatgggga gaaccgcatt ggaggcattc    5820
```

```
gggtgagtct ctgggttcca agaccgtctg ctgcctcatt ctcattcctt cctcagtccc    5880
ctcatgccta caagcacacc tatacatcca ttgaatgagg aaagcaattg cagggtccca    5940
gaaggagccc tggactgtgg acctgggcag ctctggttcc tcttctgcta ctctctggca    6000
agtgacttaa cctcacagcc ttagcaactc catttgtaaa gtgagaagaa tcacggactg    6060
gttggtctca gtaagcctta gcatctcatc atcttgatga gaccctgcag agtcggctcc    6120
atgctgtcat aaggcaactg agtctcgag aaggcaaggg ctggctcaga gtggcacagc    6180
cagggagagg gagagctaaa attcaaaagg ctcaaaccca aggcttaagc actctgggga    6240
gccttctcct ttgtcccata gtccttggcc tggccctgat gttctcgggg cctagagagc    6300
ttgagaagag tcctgtgggc aggatgagga tctagccccc tggtcctctg gccccttgg     6360 tggacatggt ctggtggtcc tggacactcc ctctgcctgc agctgcgcca ccagcactgg    6420
agtctcgtga tggagagcgt ggtgccctcg gaccgcggca catacacttg cctggtggag    6480
aacgctgtgg gcatcatccg ctataactac ctgctggatg tgctgggtga gtgcggggcc    6540
ggaaacgggg gaggcctgac ccatcctggg ctcagtcgtg ccctccggtg gggtctagtc    6600
tggcgggcag gatggactca gatgagtcaa gcagctcggt gaccaggcgg tcaggggaaa    6660
gcacaggggt tagtgtgggg ctggaggagc agggctctgc caagaggaaa aacaagaagg    6720
acagccaggc aaagggcgca gcctgagctg caggcctgag tataacgaat gccgtgcact    6780
tgcaggccag cgtattcgga gatgtggctt ttatatgggg agccaggtgg tggagggttt    6840
tgagtgctag gctgaaacgt ccttgacccg aagcaatgag gagccaggga aggttgaaac    6900
agggtaagca ggagacggac aagaagctgc agaaaggtcc ttcccttgaa cctgaggaag    6960
gctggaggga ggcaaacagg tgcttctatg ggtgccagtg atgagggttg actaccttgc    7020
ctggtcccca gagcggtccc cgcaccggcc catcctgcag gctgggctcc cggccaacac    7080
cacagccgtg gtgggcagtg acgtggagct gctgtgcaag gtgtacagcg atgcccagcc    7140
ccacatccag tggctgaagc acatcgtcat caacggcagc agcttcgggg ccgacggctt    7200
cccctatgtg caagtcctga aggtgcaccg tgctccagcc tgggcccac tcttctccca     7260 cccaggattg ggggctccct agcttccctg ttgatcacag tgtggcccca ggccctgctg    7320
tgaccccaga gtatgtcccc ctccccagac tgcagacatc aatagctcag aggtggaggt    7380
cctgtacctg cggaacgtgt cagccgagga cgcaggcgag tacacctgcc ttgcaggcaa    7440
ttccatcggc ctctcctacc agtctgcctg gctcacggtg ctgccaggta agcacctgca    7500
gggccagaat atgctgcgag atgccctct gggccagcag tggggctgt ggtctgttgg      7560 gtggtcagtc tctgttggct tgtggggtct gccctcgggg gcagtgtgtg gatttgtgag    7620
tttgagctgt atggcagccc ctctgtgcct gtccacgtgt ggctgtccat gtgaccctct    7680
gctgagctat gggactgggc ataactacag cttcctccgt gtgtgtcccc acatatgctg    7740
ggagctggga gggactgagt tagggcacat ggggaggcca gtcttaccac tgaccacttg    7800
gtctgtctgt gtatgttcat gtgcgagggc agaggaggac ctcacatgga ccgcagcaac    7860
gcccgaggcc aggtatacgg acgtcatcct gtacgcgtcg ggctccctgg ccttggctgt    7920
gctcctgctg ctggccgggc tgtatcgagg gcaggcgctc cacggccggc accccgccc    7980 acccgccacc gtgcagaagc tctcccgctt ccctctggcc cgacaggtac tgggcgcatc    8040
ccccacctcg catgtggcag cctgactcca gcaggcagaa ccaagtctcc cactttgcag    8100
ttctccctgg agtcaggctc ttccagcaag tcaagctcat ccctggtgcg aggcgtgcgt    8160
ctctcctcca gcggccccgc cttgctcgcc ggcctcgtga gtctagacct acctctcgac    8220
```

-continued

```
ccactgtggg agttccccg ggacaggtgc gctgagctgt gtgggggcag ggacacaggt      8280
gccaggtcgc agcctgccct cagcaggagt gactcggagg tctgaggcat ggactttctc      8340
catctccagg ctggtgcttg ggaagcccct gggcgagggc tgctttggac aggtagtacg      8400
tgcagaggcc tttggcatgg accctgcccg gcctgaccaa gccagtactg tggctgtcaa      8460
gatgctcaaa ggtgagtgtg acccagcgtg gtggctcaca cctgtaatgc cagcactttg      8520
ggagaccgag gtgggaggat cacttgaatc caggagttcg aggccaacct gggcaacatg      8580
gcgagacttc atctctaaaa aaaaaaataa gaaaattagt tgggtgtggt ggtgtgtgcc      8640
tttagtccca gttactagga aggctgaggc aggaggatcc cttgaaccca ggagttggag      8700
gttgcagtga gccatgatca cgccactgta ttccaacttg gcaacagag tgaaaccta      8760
tctgaaaaaa aaaaaagaaa taaaagtaaa aggtgaatgt ggcagcctgg aggaggtgct      8820
atggcattgg gactaataga aggggatcac agtgctaccg ggtgagccct ggagctggga      8880
gaggctgtgg gatcccacct ttaaacctgc agttcagctc tgctcctgac cctggcaagt      8940
gacttctgag cctcagtttt ccctcgtgtc atatgggta aataacagtc cctactccca      9000
gcccagggac tgtggaaagt gcctggctca tagtcagccc tcaacaaatc gtcaccattg      9060
gggtgacgat gatgagaagg atttggtgtg acaggcttga tatcctctgt cagcgtcagt      9120
ctgtgtcagc cttgacttca cctcttctca gcctcacagg ccctcccccg ccttccctgt      9180
ggttcccccc agacacaccc tcagcctccc tgggaccctc cctaggtcca tcccgcgtcc      9240
actgctctag gaggacagcc cttctgcttg cacccagtcc cagccccgag ggtgctcttg      9300
ccaggcactc ccgtaccccg cccatcaggt cctctcgttg cagttcccca gcgcccctg      9360
caagaatggc ctcaactgct cttctgctcc tcccctcctc tctacacagc tggggccacc      9420
tggtgctccc tgggaggcag ggattgagaa atgtgcattg tgacattgcc gtgtgtgggt      9480
ggggagtgtt acatcactgg cccagggcca caggtcagcc ccaggggccc agccagagaa      9540
gccagagcag ccttcttccc aagctccctg gctgcgccct gcctgccgcc ggctccctga      9600
attcccaggc cagttggacg ccaggccctg gtcaaacaga ccccagggtg ccagcctgct      9660
ttccgctccc agaagctctg accccatgta gggactaccg ctaacccctc cagaggcagc      9720
ttccttcctg ctccgagctc ttcccctctc tcctgttcc tggacctgcc cactggaagg      9780
cctgcctctc agatccttga tatagttgca tccttgcaac tgctgtgaca ggtagggtgt      9840
gacccactgc tctgtttccc acaagacgac cctgaggttc agagacacta agagactttt      9900
tcaaggccac acagactagc aaggaatcag ccctagacct acgtagccct ggtccagtgc      9960
tcctcgccct gccctgcct ctacctcgcc ctgcccctgc ctctgcctcg ccctgcccct     10020
gccctctgcc tcgccctgcc cctgcctctg cctgttccct catgtagttg gagagcagcc     10080
tcttcacccc atctgctgcc cttacagaca acgcctctga caaggacctg gctgacctgg     10140
tctcggagat ggaggtgatg aagctgattg gccgacacaa gaacatcatc aacctgctgg     10200
gtgtctgcac ccaggaaggt ggggccaagg cggggccggc tgcatgggcc gttagggtac     10260
agagccaaag ctgtggcagt ctctccgagc tccctccact ccctctgtag ggccctgta     10320
tgtaatcgtg gagtgcgctg ccaagggaaa ccttcgggag ttcctgcggg ccggcgccc     10380
cccgggccct gacctcagcc cggacggtcc tcagagcagt gagggccac tcgccttccc     10440
agtcctggtc tcctgcgcct accaggtggc ccgaggcatg cagtatctgg agtcccggaa     10500
ggtacaggcg gtagggctct gggcccctct cgatctctcc agctccactc tctcaggcct     10560
```

```
gtggcattaa atgtccccaa cttcttcctt tctgctcttt tcatgaccc cacctcagtg    10620 tccccaggca ttcatgcttt cctgccttcc ccacttgttc ctcacacttc cctagaaggg    10680 agagggaga ggggagaggg gagaggggac acaggagagg gcgttcccca tttctaaacc    10740
ttgaccacct cctctgtaaa gtgggtggag ggccctgcc cctgggcctg ctgggggtg    10800 gtgtgtgctc agctcaaggt caggtgtcct gatgcaccca agcccccact ccctgcagtg    10860
tatccaccgg gacctggctg cccgcaatgt gctggtgacg gaggacaatg tgatgaagat    10920
agctgacttt gggctggccc gtggcatcca ccacattgac tactataaga aaaccagcaa    10980
cgtgagggag acggggcaga actgatgggg agtggagggg ggctgggcct ggggtggcag    11040
gcatgggaac tcgtgggact ctgcactgag gccctccctc ccctccaggg ccgcctgcct    11100
gtcaagtgga tggcgcccga ggccttgttt gaccgagtgt acacacacca gagtgacgtg    11160
tgagtcctgc cagcggtcac tgtcctaccc cacaaaaagg gcaaggcact gcccaaagtc    11220
acatggcccc aggaggcctg cgctccaggg ctccttcaga tttgttctgg gatccgagtg    11280
ggaccacact ccaggaggag cccactcccc accagctggg gtgggtcatg cctgtggggt    11340
cccccgtcct agccctggtc ttagggaggg cgctgggcca cactgagccc tggccctgcc    11400
tccaggtggt cttttggggt cctgctgtgg gagatcttca ccctcggggg ctccccgtat    11460
cctggcatcc cggtggagga gctgttctca ctgctgcggg agggacatcg gatggaccga    11520
cccccacact gccccccaga gctgtgaggc ctcatcctgc cctcgacccc cactttccag    11580
tcctcctcct ctgccctgac cttggcctca gggtttgtgc cggccagaag gacaacacta    11640
acaacaactc ctcctcctct tcctcctcct cctctcctct tcctcctcct cctcctcctc    11700
tcctcctcct cctctttctc ctccttctcc tcctcctctt cctcttcctg ctcctcagcc    11760
tagtggatcg tcctggcctg gcttccactg atgacccgc ctatccctca tcaaactccc    11820
tactcagaga accccggtc ctcccttcc tcctgaaggc ctgaggctcc ctatgacctt    11880
ctggcccacc tctcccaggt acgggctgat gcgtgagtgc tggcatgcag cacctccca    11940 gaggcccacc ttcaagcagc tggtggaggc gctggacaag gtcttactgg ccgtctctga    12000
ggaggtacag ccccctccca cccaccacct ccctctgcct gctcccctcc aggcctcgtc    12060
tggcctgacc gcgtggacat gcgccccgtc ccatcctggg cactgcagag gctgaccggc    12120
tccgttcccc acagtacctc gacctccgcc tgacttcgg accctattcc cctgctggtg    12180
gggacaccag cagcacctgc tcctccagtg actccgtctt cagccacgac cccctgccac    12240
tgggatccga ctccttcccc tttgggtctg ggtgcagac atgagtaagg ctcaaggctg    12300
tgcaggcaca taaactagtg gccttgggcc ttggggctca gccacagcct ggcacagtgc    12360
ttgaccttgg cagcacgggg tccctggccc agagtgctgt cccaggtctc tggttctgct    12420
ttgggtaggt cccttcttgg tcctggagtt cgtaaaggct tcctgctctg gccttgggtt    12480
cccaacctac agctcaactc aaatctcaag gccgtgccct tgcccttggc gctgcagtgc    12540
ctgtgtcctg atgggccaaa cgtcagggtt ctgctcggcc cttggacctt ggcgctcagc    12600
ccccacctca ggtttggctg agcctggctg gagagctgct atgctaaatc tcctgcctcc    12660
caataccagc aggggttca gggctctga acccccttc cccacacctc ccctgctgc    12720 ttgccccagc gtcttgatgg gagcgtcggc ccctgagccc agagaagctg gaagcccgcc    12780
aaaaacagga gcaaatggcg ttctataaat tatttttttg aaataaagct ctgtgtgcct    12840
aggtcttccc tgagcaacat ggaggggagt gggatggagg gatcccccca ggagagagtt    12900
ctgcctgcag gacacggact gagggcgctg gaccaggccg tgggctctgc cacctcccct    12960
```

```
gccccgggag ccagggtgtg cctgtcttgg tccgccggtc ccaccagcac catcttgtgt   13020
cggtgacagt gtgaatgagt gttaatgggc tgagtccgca ttgcaccatc tacagtggga   13080
ctcctgtgcc ctctgcacat gtgtgtgtgc gtgtgtgccc tgcagctgtc cccggggag    13140 caggcagccc cctcccccat ctgctcagca ttaaccaagc tgaccgttaa cacagcatga   13200
aaatctgaaa gccagcctta ggccacggcc tgctcccacg ctctgcctgc tcaggctggg   13260
ggcttgtggg ggccatgccc gccccaccct ggccaatctc ccaggcagca gctggttgcc   13320
gcccgcctgg gctgcagctg tccctgcctg cctggtcttc cactggggac ccgtcacagc   13380
cctgtaccca gagcccctca gagggagcag cttctcaggg ctctgagcct ggagccttcc   13440
ctggccccat cctggcatgt actgctactc cccagcccct gagtgggcca tggggggcct   13500
aggcatggtg tctgacacag cgcttggcac tctcctgcct tttcctacag gcctcaggct   13560
gggacagaac tgcccaacca ggacagcctt tatggaggcc actgggattg cccccatctg   13620
cccccaggga gtggtggctg aaaactctcc acatagcctc tccggctgac agtctcccac   13680
acagaactca tcctccccc agagcggcgc ctcctccagc gcaggctccg gggagtcacc    13740
tgaccacttc cctcaagaac ctcgttccag gccgggcacg gcggctcacg cctgtaatcc   13800
cagcagtttg gaaggccgag gaggacgcat cacctgaggt taggaattcg agaccagcct   13860
ggacaacatg tgaagccct gtctctacta aaaatacaaa aattagcctg gcgtagtggg    13920
ctgcactgta gtcccagcta ctcaggaggc tgaggcagga gaatcacttg aatccgggag   13980
gtgagggttg cagtgaaccg agattgtgcc agcctgggct aaggagcaag gctctgtctc   14040
aaaaaaaaaa aaaaaagaa ccctattccc taaagtgctt ccagggtcca gccatggctc    14100
ctgaggccag cactgccacc tctctgatga tcactgtcct tgcccatgag tagggtgcgc   14160
ctgtcccgcc tgcctcctgg ggcttagggt ttaggacgaa gcgaagcaca gtgcagatgc   14220
acataggctt gggggagggc gtaccctact tttgctccct ccctgcagg tggctccaga    14280 ggcagcttcc aaaggcggac tgctcgcaaa gaccccctct aactcctgaa agcccccaga   14340
ctgactttct ttttccttcc ttcctccttc cttccctccc tccctccctt cttccctccc   14400
tcccttcctt tctttctttc tgtcttttgt tctttcgttc tttcattcgt tcgttctttt   14460
tctttctctt tctctctctc tctttcgctc tctcttcttc tttctcttc tctctttctc     14520 ttttccttcc ttccttcctt ccttccttcc tctcttctc tctctctctt ctttatttct    14580
ttccttcttt cttcttttt ttttttga cacaggtct tgatctattg accagattgg       14640
agtgcagtga cgccatgatc atggctctgc tgcctcaaac tcctgggctc aagcaatcct   14700
cccacctcag cctgccaagt gcataggact acaggtgcat gccaccacac atggataatt   14760
attttttatt tttgtagag atggggtttt gctatgttgt ccaagctggt ctcaaactcc    14820
tggcctcaag caatcctccc accttggcct cccaaagctc ccaaacccccg gacattctga  14880 ctgagcctca ctctacaatg tatagcctcc cattgggggt cactgtccac tgactgtgtc   14940
cacctgtcca gccaatcaca ggagaagcag atcccttgga cttgaccttg ggaaggagag   15000
g                                                                   15001

<210> SEQ ID NO 6
<211> LENGTH: 3323
<212> TYPE: DNA
<213> ORGANISM: Mus musculus
<220> FEATURE:
<221> NAME/KEY: CDS
<222> LOCATION: (350)...(2749)
```

<400> SEQUENCE: 6

```
cccacgcgtc cggaacgact gagactgggc gatccagtcc caacgggag ctcccgcact        60 agggtaccgg gctgacattt gccgggtctc ggaccacgcc tctcagatca gaagtggtcc      120
aggaggggcg gagtccgagg tgggcggggc aggaggggc agccccccgc cacgctgcag       180
ttgcagggac attcctggct cttcggcccg ggcggagga gctccgggcg gtgagtgtg        240 ccagccctgc cgggatcgtg acccgcgcgc gcggagccg gcggcggag gagccaggaa        300 ggtggtcagt gggaagtctg gccctgatcc tgagatcagc tggaaggaa atg tgg ctg     358
                                                       Met Trp Leu
                                                         1
```

| | | | | | | | | | | | | | | | | |
|---|---|---|---|---|---|---|---|---|---|---|---|---|---|---|---|---|
| ctc | ttg | gcc | ctg | ttg | agc | atc | ttt | cag | ggg | aca | cca | gct | ttg | tcc | ctt | 406 |
| Leu | Leu | Ala | Leu | Leu | Ser | Ile | Phe | Gln | Gly | Thr | Pro | Ala | Leu | Ser | Leu | |
| | 5 | | | | 10 | | | | | 15 | | | | | | |
| gag | gcc | tct | gag | gaa | atg | gag | cag | gag | ccc | tgc | cta | gcc | cca | atc | ctg | 454 |
| Glu | Ala | Ser | Glu | Glu | Met | Glu | Gln | Glu | Pro | Cys | Leu | Ala | Pro | Ile | Leu | |
| 20 | | | | | 25 | | | | | 30 | | | | | 35 | |
| gag | cag | caa | gag | cag | gtg | ttg | acg | gtg | gcc | ctg | ggg | cag | cct | gtg | agg | 502 |
| Glu | Gln | Gln | Glu | Gln | Val | Leu | Thr | Val | Ala | Leu | Gly | Gln | Pro | Val | Arg | |
| | | | 40 | | | | | 45 | | | | | 50 | | | |
| ctg | tgc | tgt | ggg | cgc | acc | gag | cgt | ggt | cgt | cac | tgg | tac | aaa | gag | ggc | 550 |
| Leu | Cys | Cys | Gly | Arg | Thr | Glu | Arg | Gly | Arg | His | Trp | Tyr | Lys | Glu | Gly | |
| | | 55 | | | | | 60 | | | | | 65 | | | | |
| agc | cgc | cta | gca | tct | gct | ggg | cga | gta | cgg | ggt | tgg | aga | ggc | cgc | ctg | 598 |
| Ser | Arg | Leu | Ala | Ser | Ala | Gly | Arg | Val | Arg | Gly | Trp | Arg | Gly | Arg | Leu | |
| | 70 | | | | | 75 | | | | | 80 | | | | | |
| gag | atc | gcc | agc | ttc | ctt | cct | gag | gat | gct | ggc | cga | tac | ctc | tgc | ctg | 646 |
| Glu | Ile | Ala | Ser | Phe | Leu | Pro | Glu | Asp | Ala | Gly | Arg | Tyr | Leu | Cys | Leu | |
| 85 | | | | | 90 | | | | | 95 | | | | | | |
| gcc | cgt | ggc | tcc | atg | acc | gtc | gta | cac | aat | ctt | acg | ttg | ctt | atg | gat | 694 |
| Ala | Arg | Gly | Ser | Met | Thr | Val | Val | His | Asn | Leu | Thr | Leu | Leu | Met | Asp | |
| 100 | | | | | 105 | | | | | 110 | | | | | 115 | |
| gac | tcc | tta | acc | tcc | atc | agt | aat | gat | gaa | gac | ccc | aag | aca | ctc | agc | 742 |
| Asp | Ser | Leu | Thr | Ser | Ile | Ser | Asn | Asp | Glu | Asp | Pro | Lys | Thr | Leu | Ser | |
| | | | | 120 | | | | | 125 | | | | | 130 | | |
| agc | tcc | tcg | agt | ggt | cat | gtc | tac | cca | cag | caa | gca | ccc | tac | tgg | aca | 790 |
| Ser | Ser | Ser | Ser | Gly | His | Val | Tyr | Pro | Gln | Gln | Ala | Pro | Tyr | Trp | Thr | |
| | | | 135 | | | | | 140 | | | | | 145 | | | |
| cac | ccc | caa | cgc | atg | gag | aag | aaa | ctg | cat | gca | gtg | cct | gcc | ggg | aat | 838 |
| His | Pro | Gln | Arg | Met | Glu | Lys | Lys | Leu | His | Ala | Val | Pro | Ala | Gly | Asn | |
| | | 150 | | | | | 155 | | | | | 160 | | | | |
| act | gtc | aaa | ttc | cgc | tgt | cca | gct | gca | ggg | aac | ccc | atg | cct | acc | atc | 886 |
| Thr | Val | Lys | Phe | Arg | Cys | Pro | Ala | Ala | Gly | Asn | Pro | Met | Pro | Thr | Ile | |
| | 165 | | | | | 170 | | | | | 175 | | | | | |
| cac | tgg | ctc | aag | gat | gga | cag | gcc | ttc | cac | ggg | gag | aat | cgt | att | gga | 934 |
| His | Trp | Leu | Lys | Asp | Gly | Gln | Ala | Phe | His | Gly | Glu | Asn | Arg | Ile | Gly | |
| 180 | | | | | 185 | | | | | 190 | | | | | 195 | |
| ggc | att | cgg | ctg | cgc | cac | caa | cac | tgg | agc | ctg | gtg | atg | gaa | agt | gtg | 982 |
| Gly | Ile | Arg | Leu | Arg | His | Gln | His | Trp | Ser | Leu | Val | Met | Glu | Ser | Val | |
| | | | | 200 | | | | | 205 | | | | | 210 | | |
| gta | ccc | tcg | gac | cgt | ggc | aca | tac | aca | tgc | ctt | gtg | gag | aac | tct | ctg | 1030 |
| Val | Pro | Ser | Asp | Arg | Gly | Thr | Tyr | Thr | Cys | Leu | Val | Glu | Asn | Ser | Leu | |
| | | | 215 | | | | | 220 | | | | | 225 | | | |
| ggt | agc | att | cgc | tac | agc | tat | ctc | ctg | gat | gtg | ctg | gag | cgg | tcc | ccg | 1078 |
| Gly | Ser | Ile | Arg | Tyr | Ser | Tyr | Leu | Leu | Asp | Val | Leu | Glu | Arg | Ser | Pro | |
| | | | 230 | | | | | 235 | | | | | 240 | | | |
| cac | cgg | ccc | atc | ctg | cag | gcg | ggg | ctc | cca | gcc | aac | acc | aca | gct | gtg | 1126 |
| His | Arg | Pro | Ile | Leu | Gln | Ala | Gly | Leu | Pro | Ala | Asn | Thr | Thr | Ala | Val | |

```
                245                 250                 255
gtt ggc agc gat gtg gag cta ctc tgc aag gtg tac agc gac gcc cag    1174
Val Gly Ser Asp Val Glu Leu Leu Cys Lys Val Tyr Ser Asp Ala Gln
260                 265                 270                 275 ccc cac ata cag tgg ctg aaa cac gtc gtc atc aac ggc agc agc ttc    1222
Pro His Ile Gln Trp Leu Lys His Val Val Ile Asn Gly Ser Ser Phe
                280                 285                 290 ggc gcc gac ggt ttc ccc tac gta caa gtc ctg aag aca aca gac atc    1270
Gly Ala Asp Gly Phe Pro Tyr Val Gln Val Leu Lys Thr Thr Asp Ile
            295                 300                 305 aat agc tcg gag gta gag gtc ttg tat ctg agg aac gtg tcc gct gag    1318
Asn Ser Ser Glu Val Glu Val Leu Tyr Leu Arg Asn Val Ser Ala Glu
310                 315                 320 gat gca gga gag tat acc tgt ctg gcg ggc aac tcc atc ggc ctt tcc    1366
Asp Ala Gly Glu Tyr Thr Cys Leu Ala Gly Asn Ser Ile Gly Leu Ser
325                 330                 335 tac cag tca gcg tgg ctc acg gtg ctg cca gag gaa gac ctc acg tgg    1414
Tyr Gln Ser Ala Trp Leu Thr Val Leu Pro Glu Glu Asp Leu Thr Trp
340                 345                 350                 355 aca aca gca acc cct gag gcc aga tac aca gat atc atc ctg tat gta    1462
Thr Thr Ala Thr Pro Glu Ala Arg Tyr Thr Asp Ile Ile Leu Tyr Val
                360                 365                 370 tca ggc tca ctg gtt ctg ctt gtc ctg ctg ctg gcc ggg gtg tat        1510
Ser Gly Ser Leu Val Leu Leu Val Leu Leu Leu Ala Gly Val Tyr
            375                 380                 385 cat cgg caa gtc atc cgt ggc cac tac tct cgc cag cct gtc act ata    1558
His Arg Gln Val Ile Arg Gly His Tyr Ser Arg Gln Pro Val Thr Ile
                390                 395                 400 caa aag ctg tcc cgt ttc cct ttg gcc cga cag ttc tct ttg gag tcg    1606
Gln Lys Leu Ser Arg Phe Pro Leu Ala Arg Gln Phe Ser Leu Glu Ser
            405                 410                 415 agg tcc tct ggc aag tca agt ttg tcc ctg gtg cga ggt gtc cgt ctc    1654
Arg Ser Ser Gly Lys Ser Ser Leu Ser Leu Val Arg Gly Val Arg Leu
420                 425                 430                 435 tcc tcc agc ggc ccg ccc ttg ctc acg ggc ctt gtg aat cta gac ctg    1702
Ser Ser Ser Gly Pro Pro Leu Leu Thr Gly Leu Val Asn Leu Asp Leu
                440                 445                 450 cct ctc gat ccg ctt tgg gaa ttc ccc cgg gac agg ttg gtg ctc gga    1750
Pro Leu Asp Pro Leu Trp Glu Phe Pro Arg Asp Arg Leu Val Leu Gly
            455                 460                 465 aag ccc ctg ggt gag ggc tgc ttt ggg caa gtg gtt cgt gca gag gcc    1798
Lys Pro Leu Gly Glu Gly Cys Phe Gly Gln Val Val Arg Ala Glu Ala
                470                 475                 480 ttt ggt atg gat ccc tcc cgg ccc gac caa acc agc acc gtg gct gtg    1846
Phe Gly Met Asp Pro Ser Arg Pro Asp Gln Thr Ser Thr Val Ala Val
            485                 490                 495 aag atg ctg aaa gac aat gcc tcc gac aag gat ttg gca gac ctg gtc    1894
Lys Met Leu Lys Asp Asn Ala Ser Asp Lys Asp Leu Ala Asp Leu Val
500                 505                 510                 515 tcc gag atg gag gtg atg aag cta atc gga aga cac aag aac atc atc    1942
Ser Glu Met Glu Val Met Lys Leu Ile Gly Arg His Lys Asn Ile Ile
                520                 525                 530 aac ctg ctg ggt gtc tgc act cag gaa ggg ccc ctg tac gtg att gtg    1990
Asn Leu Leu Gly Val Cys Thr Gln Glu Gly Pro Leu Tyr Val Ile Val
            535                 540                 545 gaa tgt gcc gcc aag gga aat ctt cgg gaa ttc ctc cgt gcc cgg cgc    2038
Glu Cys Ala Ala Lys Gly Asn Leu Arg Glu Phe Leu Arg Ala Arg Arg
                550                 555                 560 ccc cca ggc cct gat ctc agc cct gat gga cct cgg agc agc gaa gga    2086
```

```
Pro Pro Gly Pro Asp Leu Ser Pro Asp Gly Pro Arg Ser Ser Glu Gly
        565                 570                 575 cca ctc tcc ttc ccg gcc cta gtc tcc tgt gcc tac cag gtg gcc cga       2134
Pro Leu Ser Phe Pro Ala Leu Val Ser Cys Ala Tyr Gln Val Ala Arg
580                 585                 590                 595 ggc atg cag tat ctg gag tct cgg aag tgc atc cac cgg gac ctg gct       2182
Gly Met Gln Tyr Leu Glu Ser Arg Lys Cys Ile His Arg Asp Leu Ala
                    600                 605                 610 gcc cga aat gtg ctg gtg acc gag gat gat gtg atg aag atc gct gac       2230
Ala Arg Asn Val Leu Val Thr Glu Asp Asp Val Met Lys Ile Ala Asp
                615                 620                 625 ttt ggg ctg gca cgt ggt gtc cac cac att gac tac tat aag aaa acc       2278
Phe Gly Leu Ala Arg Gly Val His His Ile Asp Tyr Tyr Lys Lys Thr
            630                 635                 640 agc aac ggc cgc ctg cca gtc aaa tgg atg gct cca gag gcg ttg ttc       2326
Ser Asn Gly Arg Leu Pro Val Lys Trp Met Ala Pro Glu Ala Leu Phe
        645                 650                 655 gac cgt gtg tac aca cac cag agt gac gtg tgg tct ttc ggg atc ctg       2374
Asp Arg Val Tyr Thr His Gln Ser Asp Val Trp Ser Phe Gly Ile Leu
660                 665                 670                 675 ctg tgg gaa atc ttc acc ctc ggg ggc tcc cca tac cct ggc att ccg       2422
Leu Trp Glu Ile Phe Thr Leu Gly Gly Ser Pro Tyr Pro Gly Ile Pro
                    680                 685                 690 gtg gag gag ctc ttc tca ctg ctg cga gag ggg cac agg atg gag cgg       2470
Val Glu Glu Leu Phe Ser Leu Leu Arg Glu Gly His Arg Met Glu Arg
                695                 700                 705 ccc cca aac tgc ccc tca gag ctg tat ggg cta atg agg gag tgc tgg       2518
Pro Pro Asn Cys Pro Ser Glu Leu Tyr Gly Leu Met Arg Glu Cys Trp
            710                 715                 720 cac gca gtc cca tct cag agg cct act ttt aag cag ctg gtg gaa gct       2566
His Ala Val Pro Ser Gln Arg Pro Thr Phe Lys Gln Leu Val Glu Ala
        725                 730                 735 ctg gac aag gtc ctg ctg gct gtc tct gaa gag tac ctt gac ctc cgc       2614
Leu Asp Lys Val Leu Leu Ala Val Ser Glu Glu Tyr Leu Asp Leu Arg
740                 745                 750                 755 ctg acc ttt gga ccc ttt tct ccc tcc aat ggg gat gcc agc agc acc       2662
Leu Thr Phe Gly Pro Phe Ser Pro Ser Asn Gly Asp Ala Ser Ser Thr
                    760                 765                 770 tgc tcc tcc agt gac tcg gtt ttc agc cac gac cct ttg ccc ctc gag       2710
Cys Ser Ser Ser Asp Ser Val Phe Ser His Asp Pro Leu Pro Leu Glu
                775                 780                 785 cca agc ccc ttc cct ttc tct gac tcg cag acg aca tga gccggggagc        2759
Pro Ser Pro Phe Pro Phe Ser Asp Ser Gln Thr Thr
            790                 795 agcaatttg tatgggctac gcggcccatg gccgtgggtc tcctcgctga gctgcaacct      2819
gatgcatcga catttaatgt tggcagtgtc aggcctctga cttgagacta ctgctgtcgc     2879
agatcctctc tctggccctg ttttggggag ggccattctt ggtcctaagg ttcatagttg     2939
aggccttctg ttccagcctt atgctcccat ctcagagttc aactctcatc tcaagatcat     2999
ggccttgccc ttggactcat cctcagagaa gttaagcatt aaggccttgg cacgcagcct     3059
ccgtctccgg ggctctccgg gcctagctgc aaaacttatg ctctaaacat ttctagttcc     3119
cccaaacaac ctagaggcct tgggacttca catccccag cacacaagcc tcaccacccc      3179
ctgccatccc ccctccattg cttgttccag catcttggtg aaaggggcat cagctctggt     3239
gtccctgaga gacgggaagc ctgtgggaac gacagaagaa catggcattt ttataaatta     3299 ttttttttgaa aaaaaaaaa aaaa                                            3323
```

```
<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
ggcacactca gcaggacccc                                                    20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
aggctgccca agggctactg                                                    20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
gtccagtagg gtgcttgctg                                                    20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
cccatgaaag gcctgtccat                                                    20

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
gcgcagccga atgcctccaa                                                    20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
tctccatcac gagactccag                                                    20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 13
tacaccttgc acagcagctc                                               20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
gctgctgccg ttgatgacga                                               20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
ccgaagctgc tgccgttgat                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
gcacactcag caggaccccc                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
aggcacactc agcaggaccc                                               20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
caggcacact cagcaggacc                                               20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
cccaggcaca ctcagcagga                                               20

<210> SEQ ID NO 20
```

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
gcccaggcac actcagcagg                                            20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
ggcccaggca cactcagcag                                            20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
gaggcccagg cacactcagc                                            20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
tggaggccca ggcacactca                                            20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
ctggaggccc aggcacactc                                            20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
gactggaggc ccaggcacac                                            20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26
```
ctgtcagctc ctgctcttgc                                        20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
ctactgtcag ctcctgctct                                        20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
gctactgtca gctcctgctc                                        20

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
ggctactgtc agctcctgct                                        20

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
gggctactgt cagctcctgc                                        20

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 31
gcccaagggc tactgtcagc                                        20

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32
cgcacaggct gcccaagggc                                        20

<210> SEQ ID NO 33
<211> LENGTH: 20
<212> TYPE: DNA

```
<213> ORGANISM: Artificial Sequence
<220> FEATURE:
<223> OTHER INFORMATION: Synthetic oligonucleotide

<400> SEQUENCE: 33
gctcagcccg cccacagcac                                            20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
caccacgctc agcccgccca                                            20

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 35
ccaccacgct cagcccgccc                                            20

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 36
gccaccacgc tcagcccgcc                                            20

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
ggccaccacg ctcagcccgc                                            20

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
accagtggcc accacgctca                                            20

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
gtaccagtgg ccaccacgct                                            20
```

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 40
tgtaccagtg gccaccacgc                                               20

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
ctccttgtac cagtggccac                                               20

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42
cctccttgta ccagtggcca                                               20

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 43
ccctccttgt accagtggcc                                               20

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 44
ccaggcgact gccctccttg                                               20

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 45
gccaggcgac tgccctcctt                                               20

<210> SEQ ID NO 46
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 46
tgccaggcga ctgccctcct                                                    20

<210> SEQ ID NO 47
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 47
gtgccaggcg actgccctcc                                                    20

<210> SEQ ID NO 48
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 48
ggtgccaggc gactgccctc                                                    20

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 49
ccgtacacgg ccagcaggtg                                                    20

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 50
cccgtacacg gccagcaggt                                                    20

<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 51
agccccgtac acggccagca                                                    20

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 52
cctccagccc cgtacacggc                                                    20

```
<210> SEQ ID NO 53
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 53
ccctccagcc ccgtacacgg                                              20

<210> SEQ ID NO 54
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 54
ggcggcccct ccagccccgt                                              20

<210> SEQ ID NO 55
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 55
gcaatctcta ggcggcccct                                              20

<210> SEQ ID NO 56
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 56
ggcaatctct aggcggcccc                                              20

<210> SEQ ID NO 57
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 57
tggcaatctc taggcggccc                                              20

<210> SEQ ID NO 58
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 58
cctcaggtag gaagctggca                                              20

<210> SEQ ID NO 59
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 59
tcctcaggta ggaagctggc                                               20

<210> SEQ ID NO 60
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 60
agcggccagc atcctcaggt                                               20

<210> SEQ ID NO 61
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 61
tagcggccag catcctcagg                                               20

<210> SEQ ID NO 62
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 62
gtgtccagta gggtgcttgc                                               20

<210> SEQ ID NO 63
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 63
gtgtgtccag tagggtgctt                                               20

<210> SEQ ID NO 64
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 64
agtttcttct ccatgcgctg                                               20

<210> SEQ ID NO 65
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 65
gcctgtccat ccttaagcca                                               20

<210> SEQ ID NO 66
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 66
ttctccccat gaaaggcctg                                                    20

<210> SEQ ID NO 67
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 67
ggttctcccc atgaaaggcc                                                    20

<210> SEQ ID NO 68
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 68
ctccatcacg agactccagt                                                    20

<210> SEQ ID NO 69
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 69
gctctccatc acgagactcc                                                    20

<210> SEQ ID NO 70
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 70
cgctctccat cacgagactc                                                    20

<210> SEQ ID NO 71
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 71
acgctctcca tcacgagact                                                    20

<210> SEQ ID NO 72
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 72
```
cacgctctcc atcacgagac                                              20

<210> SEQ ID NO 73
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 73
ccacgctctc catcacgaga                                              20

<210> SEQ ID NO 74
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 74
acaccttgca cagcagctcc                                              20

<210> SEQ ID NO 75
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 75
gtacaccttg cacagcagct                                              20

<210> SEQ ID NO 76
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 76
gccgttgatg acgatgtgct                                              20

<210> SEQ ID NO 77
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 77
gctgccgttg atgacgatgt                                              20

<210> SEQ ID NO 78
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 78
tgctgccgtt gatgacgatg                                              20

<210> SEQ ID NO 79
<211> LENGTH: 20
<212> TYPE: DNA
<213> ORGANISM: Artificial Sequence

```
<220> FEATURE:
<223> OTHER INFORMATION: Synthetic oligonucleotide

<400> SEQUENCE: 79
ctgctgccgt tgatgacgat                                               20

<210> SEQ ID NO 80
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 80
agctgctgcc gttgatgacg                                               20

<210> SEQ ID NO 81
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 81
aagctgctgc cgttgatgac                                               20

<210> SEQ ID NO 82
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 82
cgaagctgct gccgttgatg                                               20

<210> SEQ ID NO 83
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 83
gctattgatg tctgcagtct                                               20

<210> SEQ ID NO 84
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 84
agctattgat gtctgcagtc                                               20

<210> SEQ ID NO 85
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 85
gagctattga tgtctgcagt                                               20
```

<210> SEQ ID NO 86
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 86
cctccacctc tgagctattg     20

<210> SEQ ID NO 87
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 87
acctccacct ctgagctatt     20

<210> SEQ ID NO 88
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 88
gacctccacc tctgagctat     20

<210> SEQ ID NO 89
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 89
ggacctccac ctctgagcta     20

<210> SEQ ID NO 90
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 90
aggacctcca cctctgagct     20

<210> SEQ ID NO 91
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 91
caggacctcc acctctgagc     20

<210> SEQ ID NO 92
<211> LENGTH: 20
<212> TYPE: DNA
<213> ORGANISM: Artificial Sequence
<220> FEATURE:
<223> OTHER INFORMATION: Synthetic oligonucleotide

```
<400> SEQUENCE: 92
acaggacctc cacctctgag                                              20

<210> SEQ ID NO 93
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 93
gtacaggacc tccacctctg                                              20

<210> SEQ ID NO 94
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 94
ggtacaggac ctccacctct                                              20

<210> SEQ ID NO 95
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 95
ccgcaggtac aggacctcca                                              20

<210> SEQ ID NO 96
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 96
tccgcaggta caggacctcc                                              20

<210> SEQ ID NO 97
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 97
cgttccgcag gtacaggacc                                              20

<210> SEQ ID NO 98
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 98
gcagactggt aggagaggcc                                              20

<210> SEQ ID NO 99
```

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 99
ggcagactgg taggagaggc                                            20

<210> SEQ ID NO 100
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 100
ggtcctcctc tggcagcacc                                            20

<210> SEQ ID NO 101
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 101
gcaggagcac agccaaggcc                                            20

<210> SEQ ID NO 102
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 102
gcctgccctc gatacagccc                                            20

<210> SEQ ID NO 103
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 103
gcctgactcc agggagaact                                            20

<210> SEQ ID NO 104
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 104
gagcctgact ccagggagaa                                            20

<210> SEQ ID NO 105
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 105
```
ggaggagaga cgcacgcctc                                        20

<210> SEQ ID NO 106
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 106
tggaggagag acgcacgcct                                        20

<210> SEQ ID NO 107
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 107
ctggaggaga gacgcacgcc                                        20

<210> SEQ ID NO 108
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 108
gactcacgag gccggcgagc                                        20

<210> SEQ ID NO 109
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 109
ctagactcac gaggccggcg                                        20

<210> SEQ ID NO 110
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 110
cccaagcacc agcctgtccc                                        20

<210> SEQ ID NO 111
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 111
tcccaagcac cagcctgtcc                                        20

<210> SEQ ID NO 112
<211> LENGTH: 20
<212> TYPE: DNA

```
<213> ORGANISM: Artificial Sequence
<220> FEATURE:
<223> OTHER INFORMATION: Synthetic oligonucleotide

<400> SEQUENCE: 112
gcttcccaag caccagcctg                                              20

<210> SEQ ID NO 113
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 113
gggcttccca agcaccagcc                                              20

<210> SEQ ID NO 114
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 114
ccatgccaaa ggcctctgca                                              20

<210> SEQ ID NO 115
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 115
gtccatgcca aaggcctctg                                              20

<210> SEQ ID NO 116
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 116
ggtccatgcc aaaggcctct                                              20

<210> SEQ ID NO 117
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 117
cagcagccgc atctccttct                                              20

<210> SEQ ID NO 118
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 118
gctgaagaca gaatcgctgg                                              20
```

<210> SEQ ID NO 119
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 119
cagcactcac gcatcagccc					20

<210> SEQ ID NO 120
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 120
ccagcactca cgcatcagcc					20

<210> SEQ ID NO 121
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 121
gggtccgaag gtcaggcgga					20

<210> SEQ ID NO 122
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 122
agggtccgaa ggtcaggcgg					20

<210> SEQ ID NO 123
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 123
atagggtccg aaggtcaggc					20

<210> SEQ ID NO 124
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 124
ggaatagggt ccgaaggtca					20

<210> SEQ ID NO 125
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 125
gtgcctgcac agccttgagc                                               20

<210> SEQ ID NO 126
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 126
tctccagcca ggctcagcca                                               20

<210> SEQ ID NO 127
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 127
cagctctcca gccaggctca                                               20

<210> SEQ ID NO 128
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 128
gcagctctcc agccaggctc                                               20

<210> SEQ ID NO 129
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 129
agcagctctc cagccaggct                                               20

<210> SEQ ID NO 130
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 130
tagcagctct ccagccaggc                                               20

<210> SEQ ID NO 131
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 131
gcatagcagc tctccagcca                                               20

<210> SEQ ID NO 132
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 132
agcatagcag ctctccagcc                                               20

<210> SEQ ID NO 133
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 133
tagcatagca gctctccagc                                               20

<210> SEQ ID NO 134
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 134
ttagcatagc agctctccag                                               20

<210> SEQ ID NO 135
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 135
ccagcttctc tgggctcagg                                               20

<210> SEQ ID NO 136
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 136
tccagcttct ctgggctcag                                               20

<210> SEQ ID NO 137
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 137
ttccagcttc tctgggctca                                               20

<210> SEQ ID NO 138
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 138
cttccagctt ctctgggctc                                                        20

<210> SEQ ID NO 139
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 139
gcttccagct tctctgggct                                                        20

<210> SEQ ID NO 140
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 140
ggcttccagc ttctctgggc                                                        20

<210> SEQ ID NO 141
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 141
acgccatttg ctcctgtttt                                                        20

<210> SEQ ID NO 142
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 142
tgcgaatcaa tgggtcccga                                                        20

<210> SEQ ID NO 143
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 143
ggtgcgaatc aatgggtccc                                                        20

<210> SEQ ID NO 144
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 144
ccgccggcgc gaagacagcc                                                        20

<210> SEQ ID NO 145
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 145
catctctgcc gccggcgcga                                           20

<210> SEQ ID NO 146
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 146
ctgaccgctg accgaccacc                                           20

<210> SEQ ID NO 147
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 147
gctgctgacc gctgaccgac                                           20

<210> SEQ ID NO 148
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 148
ctgccctgat atcagagtcc                                           20

<210> SEQ ID NO 149
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 149
ggctgccctg atatcagagt                                           20

<210> SEQ ID NO 150
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 150
ctcagatact gctgtctctg                                           20

<210> SEQ ID NO 151
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 151
```
tgcccatccc tctgtgcccc                                            20

<210> SEQ ID NO 152
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 152
tgctctcttg cccatccctc                                            20

<210> SEQ ID NO 153
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 153
ctctttggtc acaccgtctg                                            20

<210> SEQ ID NO 154
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 154
atctctttgg tcacaccgtc                                            20

<210> SEQ ID NO 155
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 155
ctatctcttt ggtcacaccg                                            20

<210> SEQ ID NO 156
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 156
gcctatctct ttggtcacac                                            20

<210> SEQ ID NO 157
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 157
cgctgcctat ctctttggtc                                            20

<210> SEQ ID NO 158
<211> LENGTH: 20
<212> TYPE: DNA
<213> ORGANISM: Artificial Sequence -continued
<220> FEATURE:
<223> OTHER INFORMATION: Synthetic oligonucleotide

<400> SEQUENCE: 158
agcttgcaag cccttaatgg                                               20

<210> SEQ ID NO 159
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 159
ccagcttgca agcccttaat                                               20

<210> SEQ ID NO 160
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 160
accttcatct tccagcagag                                               20

<210> SEQ ID NO 161
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 161
caaccttcat cttccagcag                                               20

<210> SEQ ID NO 162
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 162
ttcaaccttc atcttccagc                                               20

<210> SEQ ID NO 163
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 163
cagctttgct cagcccagca                                               20

<210> SEQ ID NO 164
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 164
tccagctttg ctcagcccag                                               20

<210> SEQ ID NO 165
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 165
tttccagctt tgctcagccc                                                      20

<210> SEQ ID NO 166
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 166
cctttccagc tttgctcagc                                                      20

<210> SEQ ID NO 167
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 167
ccaggtccac agtccagggc                                                      20

<210> SEQ ID NO 168
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 168
acttgccaga gagtagcaga                                                      20

<210> SEQ ID NO 169
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 169
gccatagcac ctcctccagg                                                      20

<210> SEQ ID NO 170
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 170
cccaatgcca tagcacctcc                                                      20

<210> SEQ ID NO 171
<211> LENGTH: 20
<212> TYPE: DNA
<213> ORGANISM: Artificial Sequence
<220> FEATURE:
<223> OTHER INFORMATION: Synthetic oligonucleotide

```
<400> SEQUENCE: 171
gtcccaatgc catagcacct                                               20

<210> SEQ ID NO 172
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 172
tagtcccaat gccatagcac                                               20

<210> SEQ ID NO 173
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 173
ttctattagt cccaatgcca                                               20

<210> SEQ ID NO 174
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 174
gtcacttgcc agggtcagga                                               20

<210> SEQ ID NO 175
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 175
gctcagaagt cacttgccag                                               20

<210> SEQ ID NO 176
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 176
gtccatctgg cttcccctgc                                               20

<210> SEQ ID NO 177
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 177
cagtccatct ggcttcccct                                               20

<210> SEQ ID NO 178
```

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 178
ccactccact tccagtccat                                               20

<210> SEQ ID NO 179
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 179
tgccactcca cttccagtcc                                               20

<210> SEQ ID NO 180
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 180
ggtcactgcc actccacttc                                               20

<210> SEQ ID NO 181
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 181
ccttggtcac tgccactcca                                               20

<210> SEQ ID NO 182
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 182
ggaagcctat cacacctcct                                               20

<210> SEQ ID NO 183
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 183
gtgtctctgg atctaccctg                                               20

<210> SEQ ID NO 184
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 184
```
tggtgtctct ggatctaccc                                           20

<210> SEQ ID NO 185
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 185
actggtgtct ctggatctac                                           20

<210> SEQ ID NO 186
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 186
gcactggtgt ctctggatct                                           20

<210> SEQ ID NO 187
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 187
tggcactggt gtctctggat                                           20

<210> SEQ ID NO 188
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 188
ggtggcactg gtgtctctgg                                           20

<210> SEQ ID NO 189
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 189
tgggtggcac tggtgtctct                                           20

<210> SEQ ID NO 190
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 190
tatgggtggc actggtgtct                                           20

<210> SEQ ID NO 191
<211> LENGTH: 20
<212> TYPE: DNA

```
<213> ORGANISM: Artificial Sequence
<220> FEATURE:
<223> OTHER INFORMATION: Synthetic oligonucleotide

<400> SEQUENCE: 191
ggcctatggg tggcactggt                                              20

<210> SEQ ID NO 192
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 192
gtcaggctgt gatgtacaca                                              20

<210> SEQ ID NO 193
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 193
tgctgttact gtcaggctgt                                              20

<210> SEQ ID NO 194
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 194
gccagtcacc tctggttcgg                                              20

<210> SEQ ID NO 195
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 195
agcagttttg ggattctttt                                              20

<210> SEQ ID NO 196
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 196
aaagcagttt tgggattctt                                              20

<210> SEQ ID NO 197
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 197
tccaagtccc tggccaggct                                              20
```

<210> SEQ ID NO 198
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 198
atcctttcca gctttgctca                                                   20

<210> SEQ ID NO 199
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 199
ggatcctttc cagctttgct                                                   20

<210> SEQ ID NO 200
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 200
aaggatcctt tccagctttg                                                   20

<210> SEQ ID NO 201
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 201
gcaaggatcc tttccagctt                                                   20

<210> SEQ ID NO 202
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 202
gggcaaggat cctttccagc                                                   20

<210> SEQ ID NO 203
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 203
ctgggcaagg atcctttcca                                                   20

<210> SEQ ID NO 204
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 204
gcctgggcaa ggatcctttc               20

<210> SEQ ID NO 205
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 205
gtggttgagc cctgccctgc               20

<210> SEQ ID NO 206
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 206
gtctcagtgg ttgagccctg               20

<210> SEQ ID NO 207
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 207
ctgactgagt ctcagtggtt               20

<210> SEQ ID NO 208
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 208
ggcactgact gagtctcagt               20

<210> SEQ ID NO 209
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 209
caggcactga ctgagtctca               20

<210> SEQ ID NO 210
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 210
aagccaggca ctgactgagt               20

```
<210> SEQ ID NO 211
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 211
ctggaagcca ggcactgact                                                    20

<210> SEQ ID NO 212
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 212
gcttgctgga agccaggcac                                                    20

<210> SEQ ID NO 213
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 213
atgcttgctg gaagccaggc                                                    20

<210> SEQ ID NO 214
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 214
gtcctctctc gcagacacag                                                    20

<210> SEQ ID NO 215
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 215
cagtcctctc tcgcagacac                                                    20

<210> SEQ ID NO 216
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 216
gccagtcctc tctcgcagac                                                    20

<210> SEQ ID NO 217
<211> LENGTH: 20
<212> TYPE: DNA
<213> ORGANISM: Artificial Sequence
<220> FEATURE:
<223> OTHER INFORMATION: Synthetic oligonucleotide
```

<400> SEQUENCE: 217
aggccagtcc tctctcgcag						20

<210> SEQ ID NO 218
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 218
gagctcacca ccagctctgc						20

<210> SEQ ID NO 219
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 219
gctgcctgga cctcctaggt						20

<210> SEQ ID NO 220
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 220
atgctgcctg gacctcctag						20

<210> SEQ ID NO 221
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 221
acatgctgcc tggacctcct						20

<210> SEQ ID NO 222
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 222
acacatgctg cctggacctc						20

<210> SEQ ID NO 223
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 223
ccacacatgc tgcctggacc						20

<210> SEQ ID NO 224
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 224
gcaaatgcca cactcttggg                                          20

<210> SEQ ID NO 225
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 225
gggcaaatgc cacactcttg                                          20

<210> SEQ ID NO 226
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 226
cagggcaaat gccacactct                                          20

<210> SEQ ID NO 227
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 227
cccagggcaa atgccacact                                          20

<210> SEQ ID NO 228
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 228
cacccagggc aaatgccaca                                          20

<210> SEQ ID NO 229
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 229
gccacaccca gggcaaatgc                                          20

<210> SEQ ID NO 230
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 230
```
ggatgccaca cccagggcaa                                          20

<210> SEQ ID NO 231
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 231
gcggatgcca cacccagggc                                          20

<210> SEQ ID NO 232
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 232
ctgcggatgc cacacccagg                                          20

<210> SEQ ID NO 233
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 233
gccacatgct gcggatgcca                                          20

<210> SEQ ID NO 234
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 234
ggacttccca ccaactgcct                                          20

<210> SEQ ID NO 235
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 235
gctggacttc ccaccaactg                                          20

<210> SEQ ID NO 236
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 236
caaggagctc accaccagct                                          20

<210> SEQ ID NO 237
<211> LENGTH: 20
<212> TYPE: DNA
<213> ORGANISM: Artificial Sequence

```
<220> FEATURE:
<223> OTHER INFORMATION: Synthetic oligonucleotide

<400> SEQUENCE: 237
ggcaaggagc tcaccaccag                                              20

<210> SEQ ID NO 238
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 238
caggcaagga gctcaccacc                                              20

<210> SEQ ID NO 239
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 239
tggacttccc accaactgcc                                              20

<210> SEQ ID NO 240
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 240
cactggtgtc tctggatcta                                              20

<210> SEQ ID NO 241
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 241
ggcactggtg tctctggatc                                              20

<210> SEQ ID NO 242
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 242
gtggcactgg tgtctctgga                                              20

<210> SEQ ID NO 243
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 243
gggtggcact ggtgtctctg                                              20
```

```
<210> SEQ ID NO 244
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 244
gatcctttcc agctttgctc                                              20

<210> SEQ ID NO 245
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 245
aggatccttt ccagctttgc                                              20

<210> SEQ ID NO 246
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 246
caaggatcct ttccagcttt                                              20

<210> SEQ ID NO 247
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 247
ggcaaggatc ctttccagct                                              20

<210> SEQ ID NO 248
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 248
tgggcaagga tcctttccag                                              20

<210> SEQ ID NO 249
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 249
tgactgagtc tcagtggttg                                              20

<210> SEQ ID NO 250
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 250
actgactgag tctcagtggt                                               20

<210> SEQ ID NO 251
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 251
gcactgactg agtctcagtg                                               20

<210> SEQ ID NO 252
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 252
aggcactgac tgagtctcag                                               20

<210> SEQ ID NO 253
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 253
tgcttgctgg aagccaggca                                               20

<210> SEQ ID NO 254
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 254
agtcctctct cgcagacaca                                               20

<210> SEQ ID NO 255
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 255
ccagtcctct ctcgcagaca                                               20

<210> SEQ ID NO 256
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 256
ggccagtcct ctctcgcaga                                               20

<210> SEQ ID NO 257
```

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 257
aaggagctca ccaccagctc                                              20

<210> SEQ ID NO 258
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 258
gcaaggagct caccaccagc                                              20

<210> SEQ ID NO 259
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 259
ctgcctggac ctcctaggtc                                              20

<210> SEQ ID NO 260
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 260
tgctgcctgg acctcctagg                                              20

<210> SEQ ID NO 261
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 261
catgctgcct ggacctccta                                              20

<210> SEQ ID NO 262
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 262
cacatgctgc ctggacctcc                                              20

<210> SEQ ID NO 263
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 263
```
cacacatgct gcctggacct                                              20

<210> SEQ ID NO 264
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 264
accacacatg ctgcctggac                                              20

<210> SEQ ID NO 265
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 265
ccagggcaaa tgccacactc                                              20

<210> SEQ ID NO 266
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 266
acccagggca aatgccacac                                              20

<210> SEQ ID NO 267
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 267
tgccacaccc agggcaaatg                                              20

<210> SEQ ID NO 268
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 268
cggatgccac acccagggca                                              20

<210> SEQ ID NO 269
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 269
tgcggatgcc acacccaggg                                              20

<210> SEQ ID NO 270
<211> LENGTH: 20
<212> TYPE: DNA

```
<213> ORGANISM: Artificial Sequence
<220> FEATURE:
<223> OTHER INFORMATION: Synthetic oligonucleotide

<400> SEQUENCE: 270
agccacatgc tgcggatgcc                                                 20

<210> SEQ ID NO 271
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 271
gctctcttgc ccatccctct                                                 20

<210> SEQ ID NO 272
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 272
tctctttggt cacaccgtct                                                 20

<210> SEQ ID NO 273
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 273
tatctctttg gtcacaccgt                                                 20

<210> SEQ ID NO 274
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 274
cctatctctt tggtcacacc                                                 20

<210> SEQ ID NO 275
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 275
tgcctatctc tttggtcaca                                                 20

<210> SEQ ID NO 276
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 276
tcaaccttca tcttccagca                                                 20
```

<210> SEQ ID NO 277
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 277
agctttgctc agcccagcag                                          20

<210> SEQ ID NO 278
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 278
ccagctttgc tcagcccagc                                          20

<210> SEQ ID NO 279
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 279
ttccagcttt gctcagccca                                          20

<210> SEQ ID NO 280
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 280
tcacttgcca gggtcaggag                                          20

<210> SEQ ID NO 281
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 281
agtcacttgc cagggtcagg                                          20

<210> SEQ ID NO 282
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 282
ctttggtcac accgtct                                             17

<210> SEQ ID NO 283
<211> LENGTH: 17
<212> TYPE: DNA
<213> ORGANISM: Artificial Sequence
<220> FEATURE:

<223> OTHER INFORMATION: Synthetic oligonucleotide

<400> SEQUENCE: 283
tctttggtca caccgtc                                                      17

<210> SEQ ID NO 284
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 284
ctctttggtc acaccgt                                                      17

<210> SEQ ID NO 285
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 285
tctctttggt cacaccg                                                      17

<210> SEQ ID NO 286
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 286
gctttgctca gcccagc                                                      17

<210> SEQ ID NO 287
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 287
cagctttgct cagccca                                                      17

<210> SEQ ID NO 288
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 288
ccagctttgc tcagccc                                                      17

<210> SEQ ID NO 289
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 289
gcagccgcat ctccttc                                                      17

```
<210> SEQ ID NO 290
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 290
gcacactcag caggacc                                                    17

<210> SEQ ID NO 291
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 291
ggcacactca gcaggac                                                    17

<210> SEQ ID NO 292
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 292
ccagtggcca ccacgct                                                    17

<210> SEQ ID NO 293
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 293
aggcgactgc cctcctt                                                    17

<210> SEQ ID NO 294
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 294
caggcgactg ccctcct                                                    17

<210> SEQ ID NO 295
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 295
gtgtccagta gggtgct                                                    17

<210> SEQ ID NO 296
<211> LENGTH: 17
<212> TYPE: DNA
<213> ORGANISM: Artificial Sequence
<220> FEATURE:
<223> OTHER INFORMATION: Synthetic oligonucleotide
```

<400> SEQUENCE: 296
cagctctcca gccaggc                                                17

<210> SEQ ID NO 297
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 297
gcttctctgg gctcagg                                                17

<210> SEQ ID NO 298
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 298
agcttctctg ggctcag                                                17

<210> SEQ ID NO 299
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 299
cagcttctct gggctca                                                17

<210> SEQ ID NO 300
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 300
ccagcttctc tgggctc                                                17

<210> SEQ ID NO 301
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 301
tccagcttct ctgggct                                                17

<210> SEQ ID NO 302
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 302
ttccagcttc tctgggc                                                17

<210> SEQ ID NO 303
<211> LENGTH: 17

```
<212> TYPE: DNA
<213> ORGANISM: Artificial Sequence
<220> FEATURE:
<223> OTHER INFORMATION: Synthetic oligonucleotide

<400> SEQUENCE: 303
gcttccagct tctctgg                                                    17

<210> SEQ ID NO 304
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 304
ccatttgctc ctgtttt                                                    17

<210> SEQ ID NO 305
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 305
gccatttgct cctgttt                                                    17

<210> SEQ ID NO 306
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 306
cgccatttgc tcctgtt                                                    17

<210> SEQ ID NO 307
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 307
gcactggtgt ctctgga                                                    17

<210> SEQ ID NO 308
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 308
ggcactggtg tctctgg                                                    17

<210> SEQ ID NO 309
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 309
```
tggcactggt gtctctg					17

<210> SEQ ID NO 310
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 310
gtggcactgg tgtctct					17

<210> SEQ ID NO 311
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 311
gactgagtct cagtggt					17

<210> SEQ ID NO 312
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 312
cttgctggaa gccaggc					17

<210> SEQ ID NO 313
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 313
gcttgctgga agccagg					17

<210> SEQ ID NO 314
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 314
cctctctcgc agacaca					17

<210> SEQ ID NO 315
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 315
gccagtcctc tctcgca					17

<210> SEQ ID NO 316
<211> LENGTH: 17
<212> TYPE: DNA
<213> ORGANISM: Artificial Sequence

```
<220> FEATURE:
<223> OTHER INFORMATION: Synthetic oligonucleotide

<400> SEQUENCE: 316
ggccagtcct ctctcgc                                                        17

<210> SEQ ID NO 317
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 317
gcctggacct cctaggt                                                        17

<210> SEQ ID NO 318
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 318
tgcctggacc tcctagg                                                        17

<210> SEQ ID NO 319
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 319
ctgcctggac ctcctag                                                        17

<210> SEQ ID NO 320
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 320
gctgcctgga cctccta                                                        17

<210> SEQ ID NO 321
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 321
tgctgcctgg acctcct                                                        17

<210> SEQ ID NO 322
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 322
atgctgcctg gacctcc                                                        17
```

<210> SEQ ID NO 323
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 323
gcgtttgctc ttcttcttgc gtttttt                                27

<210> SEQ ID NO 324
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 324
gccacatttc cttccagctg                                        20

<210> SEQ ID NO 325
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 325
ccttccctga aggttcctcc                                        20

<210> SEQ ID NO 326
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 326
tccatttcct cagaggcctc                                        20

<210> SEQ ID NO 327
<211> LENGTH: 19
<212> TYPE: DNA
<213> ORGANISM: Artificial Sequence
<220> FEATURE:
<223> OTHER INFORMATION: Primer

<400> SEQUENCE: 327
tcatcaacgg cagcagctt                                         19

<210> SEQ ID NO 328
<211> LENGTH: 26
<212> TYPE: DNA
<213> ORGANISM: Artificial Sequence
<220> FEATURE:
<223> OTHER INFORMATION: Primer

<400> SEQUENCE: 328
agctattgat gtctgcagtc tttagg                                 26

<210> SEQ ID NO 329
<211> LENGTH: 24
<212> TYPE: DNA
<213> ORGANISM: Artificial Sequence
<220> FEATURE:
<223> OTHER INFORMATION: Probe

<400> SEQUENCE: 329
agccgacggt ttcccctatg tgca                                              24

<210> SEQ ID NO 330
<211> LENGTH: 18
<212> TYPE: DNA
<213> ORGANISM: Artificial Sequence
<220> FEATURE:
<223> OTHER INFORMATION: Primer

<400> SEQUENCE: 330
ttgctgtgcc gtgtccaa                                                     18

<210> SEQ ID NO 331
<211> LENGTH: 20
<212> TYPE: DNA
<213> ORGANISM: Artificial Sequence
<220> FEATURE:
<223> OTHER INFORMATION: Primer

<400> SEQUENCE: 331
tccaagaagc cgagcagaac                                                   20

<210> SEQ ID NO 332
<211> LENGTH: 23
<212> TYPE: DNA
<213> ORGANISM: Artificial Sequence
<220> FEATURE:
<223> OTHER INFORMATION: Probe

<400> SEQUENCE: 332
agctgccgtg cctgtgtcct gat                                               23

<210> SEQ ID NO 333
<211> LENGTH: 19
<212> TYPE: DNA
<213> ORGANISM: Artificial Sequence
<220> FEATURE:
<223> OTHER INFORMATION: Primer

<400> SEQUENCE: 333
tcatcaacgg cagcagctt                                                    19

<210> SEQ ID NO 334
<211> LENGTH: 25
<212> TYPE: DNA
<213> ORGANISM: Artificial Sequence
<220> FEATURE:
<223> OTHER INFORMATION: Primer

<400> SEQUENCE: 334
tgagctattg atgtctgcag tcttc                                             25

<210> SEQ ID NO 335
<211> LENGTH: 22
<212> TYPE: DNA
<213> ORGANISM: Artificial Sequence
<220> FEATURE:
<223> OTHER INFORMATION: Probe

<400> SEQUENCE: 335
ccgacggctt ccccctatgtg ca                                               22

<210> SEQ ID NO 336

```
<211> LENGTH: 20
<212> TYPE: DNA
<213> ORGANISM: Artificial Sequence
<220> FEATURE:
<223> OTHER INFORMATION: Primer

<400> SEQUENCE: 336
ccccatgtgg gaattgatct                                              20

<210> SEQ ID NO 337
<211> LENGTH: 22
<212> TYPE: DNA
<213> ORGANISM: Artificial Sequence
<220> FEATURE:
<223> OTHER INFORMATION: Primer

<400> SEQUENCE: 337
catgcctgct tcagtcagtt ct                                           22

<210> SEQ ID NO 338
<211> LENGTH: 23
<212> TYPE: DNA
<213> ORGANISM: Artificial Sequence
<220> FEATURE:
<223> OTHER INFORMATION: Probe

<400> SEQUENCE: 338
tttgcccttc ccaaacccct cca                                          23

<210> SEQ ID NO 339
<211> LENGTH: 24
<212> TYPE: DNA
<213> ORGANISM: Artificial Sequence
<220> FEATURE:
<223> OTHER INFORMATION: Primer

<400> SEQUENCE: 339
ccctgaggcc agatacacag atat                                         24

<210> SEQ ID NO 340
<211> LENGTH: 21
<212> TYPE: DNA
<213> ORGANISM: Artificial Sequence
<220> FEATURE:
<223> OTHER INFORMATION: Primer

<400> SEQUENCE: 340
acggatgact tgccgatgat a                                            21

<210> SEQ ID NO 341
<211> LENGTH: 27
<212> TYPE: DNA
<213> ORGANISM: Artificial Sequence
<220> FEATURE:
<223> OTHER INFORMATION: Probe

<400> SEQUENCE: 341
ctcactggtt ctgcttgtgc tcctgct                                      27

<210> SEQ ID NO 342
<211> LENGTH: 23
<212> TYPE: DNA
<213> ORGANISM: Artificial Sequence
<220> FEATURE:
<223> OTHER INFORMATION: Primer

<400> SEQUENCE: 342
```

```
gaccaaaacg aacgaaattt gtt                                               23

<210> SEQ ID NO 343
<211> LENGTH: 19
<212> TYPE: DNA
<213> ORGANISM: Artificial Sequence
<220> FEATURE:
<223> OTHER INFORMATION: Primer

<400> SEQUENCE: 343
acgtccttga tggcaatcg                                                    19

<210> SEQ ID NO 344
<211> LENGTH: 20
<212> TYPE: DNA
<213> ORGANISM: Artificial Sequence
<220> FEATURE:
<223> OTHER INFORMATION: Probe

<400> SEQUENCE: 344
aattccgcgc ggtcgctctg                                                   20

<210> SEQ ID NO 345
<211> LENGTH: 1809
<212> TYPE: DNA
<213> ORGANISM: Mus musculus
<220> FEATURE:
<221> NAME/KEY: CDS
<222> LOCATION: (148)...(804)

<400> SEQUENCE: 345
ctgtcggagc agtaactctg tgcgccccac gccacaagcg cccagttgct ttgtgggttg       60
tgcctgccct cgcgcctgcaa cttgagtccc cgccgcatcg cagtctccgc gccacctttg     120
taacggcctt caggaccccg aggtgtc atg gcg aga aag tgg aac ggg cgt gcg      174
                                Met Ala Arg Lys Trp Asn Gly Arg Ala
                                  1               5 gtg gcc cga gcc ctg gtc ctg gcc act ctg tgg ctg gct gtg tct ggg        222
Val Ala Arg Ala Leu Val Leu Ala Thr Leu Trp Leu Ala Val Ser Gly
 10                  15                  20                  25 cgt ccc ctg gct cag caa tcc cag tct gtg tca gat gaa gat cca ctc        270
Arg Pro Leu Ala Gln Gln Ser Gln Ser Val Ser Asp Glu Asp Pro Leu
                 30                  35                  40 ttt ctc tac ggc tgg ggc aag att acc cgc ctg cag tac ctg tac tcc        318
Phe Leu Tyr Gly Trp Gly Lys Ile Thr Arg Leu Gln Tyr Leu Tyr Ser
             45                  50                  55 gct ggt ccc tat gtc tcc aac tgc ttc ctc cga atc cgg agc gac ggc        366
Ala Gly Pro Tyr Val Ser Asn Cys Phe Leu Arg Ile Arg Ser Asp Gly
         60                  65                  70 tct gtg gac tgc gag gag gac caa aac gaa cga aat ttg ttg gaa ttc        414
Ser Val Asp Cys Glu Glu Asp Gln Asn Glu Arg Asn Leu Leu Glu Phe
     75                  80                  85 cgc gcg gtc gct ctg aag acg att gcc atc aag gac gtc agc agc gtg        462
Arg Ala Val Ala Leu Lys Thr Ile Ala Ile Lys Asp Val Ser Ser Val
 90                  95                 100                 105 cgg tac ctc tgc atg agc gcg gac ggc aag ata tac ggg ctg att cgc        510
Arg Tyr Leu Cys Met Ser Ala Asp Gly Lys Ile Tyr Gly Leu Ile Arg
                110                 115                 120 tac tcg gag gaa gac tgt acc ttc agg gag gaa atg gac tgt tta ggc        558
Tyr Ser Glu Glu Asp Cys Thr Phe Arg Glu Glu Met Asp Cys Leu Gly
            125                 130                 135 tac aac cag tac aga tcc atg aag cac cat ctc cat atc atc ttc atc        606
```

```
                Tyr Asn Gln Tyr Arg Ser Met Lys His His Leu His Ile Ile Phe Ile
                            140                 145                 150 cag gcc aag ccc aga gaa cag ctc cag gac cag aaa ccc tca aac ttt        654
Gln Ala Lys Pro Arg Glu Gln Leu Gln Asp Gln Lys Pro Ser Asn Phe
            155                 160                 165 atc ccc gtg ttt cac cgc tcc ttc ttt gaa acc ggg gac cag ctg agg        702
Ile Pro Val Phe His Arg Ser Phe Phe Glu Thr Gly Asp Gln Leu Arg
170                 175                 180                 185 tct aaa atg ttc tcc ctg ccc ctg gag agt gac agc atg gat ccg ttc        750
Ser Lys Met Phe Ser Leu Pro Leu Glu Ser Asp Ser Met Asp Pro Phe
                190                 195                 200 agg atg gtg gag gat gta gac cac cta gtg aag agt ccc agc ttc cag        798
Arg Met Val Glu Asp Val Asp His Leu Val Lys Ser Pro Ser Phe Gln
            205                 210                 215 aaa tga caggattccg acaggatgga gaaaacccca aggtcccgtg aacttccccc         854
Lys ttaggaagct gtacatattc taagtctcac atggaccctg ttgtgttagt ggctagactt      914
gatcatgaac ttaagttgac aacctgcctg gctgccatcg gagccccact gactttggag      974
gctgctgata tgtgcctaag ttactccagt tctgtttgaa tacctccact aatagggaac     1034
ttactcctgt gaaacattct tagttttgag ccaaatctgt gacttggatg gttttagcga     1094
ggaagccaga aggtatgaag tcaaatgata aaattcatgt atagaaagtg ggctctaaaa     1154
tatatattcc ctatatggat ctcatgggat cttagcttgc cccccaaatg tctcctggcc     1214
agaactaact ggggttacaa acttggaaca aaggacagcc tagaaaactt tgggagcctt     1274
gaaggatggt cttaggatta cgaattccag ctgactacga agcttccccc ttttccactt     1334
ataaatgtca gatggaagtg acccttagct gagtgcatag ccaagctgcc acttaggccc     1394
caggagcttg tctctgtccc atgacccag atttccagga cctggatctt ctcctctgac      1454
cttccccaga gttcacctgg gctctccaac cccagagcag gtagcttatg agccatccag     1514
ttgtgtcccc agctcctggc tctcagttct ggtcaccaaa cattgtgaat caacgtgtct     1574
gctgcctgtg tcaacctgga cccctcattt acaaacaaga ttaggaagcc caaattctc     1634 cagtggcagc tggggaactg tggagtcctt tccccggcac ttacgtggca gcatgatatt    1694
tataagtaat ttattgtgtg tgtgtcttct attttcttac tttatttatg ccccagatca    1754
tatttatgta catgacttgt tttctacatt aaaaaggagt tggtttgtat caaaa         1809
```

<210> SEQ ID NO 346
<211> LENGTH: 2442
<212> TYPE: DNA
<213> ORGANISM: Macaca mulatta
<220> FEATURE:
<221> NAME/KEY: CDS
<222> LOCATION: (1)...(651)

<400> SEQUENCE: 346

```
tgg gag aac ctg aga cgg tcg gaa ctg cgg ggg gaa att cta ttg gac         48
Trp Glu Asn Leu Arg Arg Ser Glu Leu Arg Gly Glu Ile Leu Leu Asp
1               5                   10                  15 ggc ttt gac gtc aga tgt gct ggg ctg gga aag tcg ggg gag gga gtg         96
Gly Phe Asp Val Arg Cys Ala Gly Leu Gly Lys Ser Gly Glu Gly Val
                20                  25                  30 cga gtg gcc ttt taa ggg gaa gga ccc taa ggc cga ggt gag gct ttt        144
Arg Val Ala Phe     Gly Glu Gly Pro     Gly Arg Gly Glu Ala Phe
            35                  40                  45 acc gac tag agg gtg aag gag gca aaa ctc ggt gcc ccc aaa cct ctg        192
Thr Asp     Arg Val Lys Glu Ala Lys Leu Gly Ala Pro Lys Pro Leu
```

|  |  |  |  |  |  |  |  |  |  |  |  |  |  |  |  |
|---|---|---|---|---|---|---|---|---|---|---|---|---|---|---|---|
|  |  |  | 50 |  |  |  | 55 |  |  |  | 60 |  |  |  |  |
| acc | ccg | ggg | ttc | ctg | acc | ccg | ccc | ctg | ctg | gtg | ccc | cat | gcc | gag | cgc | 240 |
| Thr | Pro | Gly | Phe | Leu | Thr | Pro | Pro | Leu | Leu | Val | Pro | His | Ala | Glu | Arg |  |
|  |  |  | 65 |  |  |  | 70 |  |  |  | 75 |  |  |  |  |  |
| atc | cac | tgg | gag | ccc | gac | gcc | tgg | ggg | agg | ggc | ccc | agt | tgt | cga | ttg | 288 |
| Ile | His | Trp | Glu | Pro | Asp | Ala | Trp | Gly | Arg | Gly | Pro | Ser | Cys | Arg | Leu |  |
|  |  | 80 |  |  |  |  | 85 |  |  |  |  | 90 |  |  |  |  |
| ctt | tgc | aaa | atc | aaa | ctc | tcc | cag | cca | aga | acc | tcg | ggg | ccg | ctg | cgc | 336 |
| Leu | Cys | Lys | Ile | Lys | Leu | Ser | Gln | Pro | Arg | Thr | Ser | Gly | Pro | Leu | Arg |  |
|  | 95 |  |  |  |  | 100 |  |  |  |  | 105 |  |  |  |  |  |
| ggt | ggg | gag | gag | ttc | ccc | gaa | acc | cgg | ccg | cta | aac | gag | gcc | tcc | tcc | 384 |
| Gly | Gly | Glu | Glu | Phe | Pro | Glu | Thr | Arg | Pro | Leu | Asn | Glu | Ala | Ser | Ser |  |
| 110 |  |  |  |  | 115 |  |  |  |  | 120 |  |  |  |  | 125 |  |
| tcc | cgc | aga | tcc | gaa | cgg | cct | ggg | cgg | ggt | cac | ccc | ggc | tgg | gac | aag | 432 |
| Ser | Arg | Arg | Ser | Glu | Arg | Pro | Gly | Arg | Gly | His | Pro | Gly | Trp | Asp | Lys |  |
|  |  |  | 130 |  |  |  |  | 135 |  |  |  |  | 140 |  |  |  |
| aag | ccg | ccg | cct | gcc | tgc | ccg | ggc | ccg | ggg | agg | ggg | ctg | ggg | ccg | gag | 480 |
| Lys | Pro | Pro | Pro | Ala | Cys | Pro | Gly | Pro | Gly | Arg | Gly | Leu | Gly | Pro | Glu |  |
|  |  |  | 145 |  |  |  |  | 150 |  |  |  |  | 155 |  |  |  |
| gcg | ggg | tgt | gag | tgg | gtg | tgt | gcg | ggg | ggc | gga | ggc | ttg | atg | caa | tcc | 528 |
| Ala | Gly | Cys | Glu | Trp | Val | Cys | Ala | Gly | Gly | Gly | Gly | Leu | Met | Gln | Ser |  |
|  |  | 160 |  |  |  |  | 165 |  |  |  |  | 170 |  |  |  |  |
| cga | taa | gaa | atg | ctc | ggg | tgt | ctt | ggg | cac | cta | ccc | gcg | ggg | ccc | gta | 576 |
| Arg |  | Glu | Met | Leu | Gly | Cys | Leu | Gly | His | Leu | Pro | Ala | Gly | Pro | Val |  |
|  |  | 175 |  |  |  |  | 180 |  |  |  |  | 185 |  |  |  |  |
| agg | cgc | tac | tat | ata | agg | ttg | ccg | gcc | cgg | agc | cgc | cgc | gcc | gtc | gga | 624 |
| Arg | Arg | Tyr | Tyr | Ile | Arg | Leu | Pro | Ala | Arg | Ser | Arg | Arg | Ala | Val | Gly |  |
|  | 190 |  |  |  |  | 195 |  |  |  |  | 200 |  |  |  |  |  |
| gca | gga | gcg | ctg | cgt | cca | gga | tcg | agg | gccacggcca | tcccaatccg |  |  |  |  |  | 671 |
| Ala | Gly | Ala | Leu | Arg | Pro | Gly | Ser | Arg |  |  |  |  |  |  |  |  |
| 205 |  |  |  |  | 210 |  |  |  |  |  |  |  |  |  |  |  |

```
gcactcacag ccccgcagcg catcccggtc gccgcccagc ctcccgcacc cccatcgccg      731
gaactgcgcc gagagcccca gggaggtgcc atgaggagcg ggtgtgtggt ggtccacgcc      791
tggatcctgg ccagcctctg gctggccgtg gccgggcgtc ccctcgcctt ctcggacgcg      851
gggccccacg tgcactacgg ctggggcgac cccatccgcc tgcggcacct gtacacctcc      911
ggcccccatg ggctctccag ctgcttcctg cgcatccgca ccgacggcgt cgtggactgc      971
gcgcggggcc aaagcgcgca cagtttgctg gagatcaagg cagtagctct gcggaccgtg     1031
gccatcaagg gcgtgcacag cgtgcggtac ctctgcatgg gcgccgacgg caagatgcag     1091
gggctgcttc agtactcaga ggaagactgt gctttcgagg aggagatccg ccctgatggc     1151
tacaatgtat accgatccga gaagcaccgc ctcccggtct ctctgagcag tgccaaacag     1211
aggcagctgt acaagaacag aggctttctt ccgctctctc atttcctacc catgctgccc     1271
atggcccag aggagcctga ggacctcagg gccacttgg aatctgacat gttctcttcg       1331
cccctggaga ctgacagcat ggacccattt gggcttgtca ccggactgga ggcggtgagg     1391
agtcccagct ttgagaaata actgaggcca tgcccgggcc tcttcactgc tgccaggggc     1451
tgtggtacct gcagagtgga ggccgtgctt ctacaagagc agtcccgagt ccacgttctg     1511
tttagcttta ggaagaaaca tctagaagtt gtacatattc agagttttcc attggccgtg     1571
ccagtttcta gccaatagac ttgtctgatc ataacattgt aagcttgtag cttgcccagc     1631
tgctgcccgg gccccattc tgctccctcg aggttgctgg acaagctgct gtgctgtctc      1691
agtcctgctt gaatacctcc actgatgggg aactcacttc ctttggaaaa attcttatgt     1751
caagctgaaa ttctctaatt tttttttctc atcacttccc caggagcagc cggaagatag     1811
```

```
gcagtggttt aaatttcagg aacaggtgat ccactctgta aaacagcacg tacatttcac    1871
tcaaccccat gtgggaattg atctatatct acttccaggg accgtttgcc cttcccaaac    1931
ccctccaggc cagaactgac tgaagcaggc atggcccaag aggcttcagg agtaggggaa    1991
gcccagagcc ccactccagc cctgggacat cttgagaatt ccccctgagg ccagttctgt    2051
catggatgct gtcctgagaa taacttgctg tccccggtgt cacctgcttc cacccccag    2111 cccaccagcc ctctgcccac ctcacatgtc tccccatgga ttggggcttc ccaggccccc    2171
catcttatgt caacctgcac ttctcgttca aaaatcagga aagaaaaga tttgaagacc    2231 ccaagtcttg tcaataactt gcggtgtgga agcagcgggg gaagacttag aaccctttcc    2291
ccagcactta gttttccaac atgatattta tgagtaattt attttgatat gtacatctct    2351
tattttctta cattatttat gcccccaaat tatatttatg tatgtaagtg aggtttgttt    2411
tgtacattaa aatggagttt gtttgtatga a                                  2442

<210> SEQ ID NO 347
<211> LENGTH: 651
<212> TYPE: DNA
<213> ORGANISM: Homo sapiens
<220> FEATURE:
<221> NAME/KEY: CDS
<222> LOCATION: (1)...(651)

<400> SEQUENCE: 347 atg cgg agc ggg tgt gtg gtg gtc cac gta tgg atc ctg gcc ggc ctc     48
Met Arg Ser Gly Cys Val Val Val His Val Trp Ile Leu Ala Gly Leu
 1               5                  10                  15 tgg ctg gcc gtg gcc ggg cgc ccc ctc gcc ttc tcg gac gcg ggg ccc     96
Trp Leu Ala Val Ala Gly Arg Pro Leu Ala Phe Ser Asp Ala Gly Pro
             20                  25                  30 cac gtg cac tac ggc tgg ggc gac ccc atc cgc ctg cgg cac ctg tac    144
His Val His Tyr Gly Trp Gly Asp Pro Ile Arg Leu Arg His Leu Tyr
         35                  40                  45 acc tcc ggc ccc cac ggg ctc tcc agc tgc ttc ctg cgc atc cgt gcc    192
Thr Ser Gly Pro His Gly Leu Ser Ser Cys Phe Leu Arg Ile Arg Ala
     50                  55                  60 gac ggc gtc gtg gac tgc gcg cgg ggc cag agc gcg cac agt ttg ctg    240
Asp Gly Val Val Asp Cys Ala Arg Gly Gln Ser Ala His Ser Leu Leu
 65                  70                  75                  80 gag atc aag gca gtc gct ctg cgg acc gtg gcc atc aag ggc gtg cac    288
Glu Ile Lys Ala Val Ala Leu Arg Thr Val Ala Ile Lys Gly Val His
                 85                  90                  95 agc gtg cgg tac ctc tgc atg ggc gcc gac ggc aag atg cag ggg ctg    336
Ser Val Arg Tyr Leu Cys Met Gly Ala Asp Gly Lys Met Gln Gly Leu
            100                 105                 110 ctt cag tac tcg gag gaa gac tgt gct ttc gag gag gag atc cgc cca    384
Leu Gln Tyr Ser Glu Glu Asp Cys Ala Phe Glu Glu Glu Ile Arg Pro
        115                 120                 125 gat ggc tac aat gtg tac cga tcc gag aag cac cgc ctc ccg gtc tcc    432
Asp Gly Tyr Asn Val Tyr Arg Ser Glu Lys His Arg Leu Pro Val Ser
    130                 135                 140 ctg agc agt gcc aaa cag cgg cag ctg tac aag aac aga ggc ttt ctt    480
Leu Ser Ser Ala Lys Gln Arg Gln Leu Tyr Lys Asn Arg Gly Phe Leu
145                 150                 155                 160 cca ctc tct cat ttc ctg ccc atg ctg ccc atg gtc cca gag gag cct    528
Pro Leu Ser His Phe Leu Pro Met Leu Pro Met Val Pro Glu Glu Pro
                165                 170                 175 gag gac ctc agg ggc cac ttg gaa tct gac atg ttc tct tcg ccc ctg    576
Glu Asp Leu Arg Gly His Leu Glu Ser Asp Met Phe Ser Ser Pro Leu
```

```
                Glu Asp Leu Arg Gly His Leu Glu Ser Asp Met Phe Ser Ser Pro Leu
                                180                 185                 190 gag acc gac agc atg gac cca ttt ggg ctt gtc acc gga ctg gag gcc              624
Glu Thr Asp Ser Met Asp Pro Phe Gly Leu Val Thr Gly Leu Glu Ala
        195                 200                 205 gtg agg agt ccc agc ttt gag aag taa                                          651
Val Arg Ser Pro Ser Phe Glu Lys
    210                 215

<210> SEQ ID NO 348
<211> LENGTH: 20
<212> TYPE: DNA
<213> ORGANISM: Artificial Sequence
<220> FEATURE:
<223> OTHER INFORMATION: Primer

<400> SEQUENCE: 348
gcaccaggga tgagcttgac                                                         20

<210> SEQ ID NO 349
<211> LENGTH: 22
<212> TYPE: DNA
<213> ORGANISM: Artificial Sequence
<220> FEATURE:
<223> OTHER INFORMATION: Primer

<400> SEQUENCE: 349
ccaagtctcc cactttccag tt                                                      22

<210> SEQ ID NO 350
<211> LENGTH: 17
<212> TYPE: DNA
<213> ORGANISM: Artificial Sequence
<220> FEATURE:
<223> OTHER INFORMATION: Probe

<400> SEQUENCE: 350
aagagcctga ctccagt                                                            17
```